United States Patent [19]
Calabretta et al.

[11] Patent Number: 5,734,039
[45] Date of Patent: Mar. 31, 1998

[54] ANTISENSE OLIGONUCLEOTIDES TARGETING COOPERATING ONCOGENES

[75] Inventors: Bruno Calabretta; Tomasz Skorski, both of Philadelphia, Pa.

[73] Assignee: Thomas Jefferson University, Philadelphia, Pa.

[21] Appl. No.: 306,691

[22] Filed: Sep. 15, 1994

[51] Int. Cl.$^6$ .................................... C07H 21/04
[52] U.S. Cl. .................................... 536/24.5; 514/44
[58] Field of Search ................... 435/91.1, 91.21, 435/91.41, 172.3, 320.1; 536/23.1, 24.5, 22.1; 514/44; 935/34

[56] References Cited

PUBLICATIONS

Morishita et al. (1994) J. Clin. Invest. 93:1458–1464.
Morishita et al. (1993) Proc. Natl. Acad. Sci. USA 90:8474–8478.
Genesis Report–Rx (1994) 3.
Hunter (1991) Cell 64:249–270.
Tidd et al. (1988) Anti–Cancer Drug Des. 3:117–127.
Amini et al. (1986) Mol. Cell. Bio. 6:2305–2316.
Heikkila et al. (1987) Nature 328:445–449.
Szczylik et al. (1991) Science 253:562–565.

*Primary Examiner*—David Guzo
*Assistant Examiner*—Robert Schwartzman
*Attorney, Agent, or Firm*—Seidel, Gonda, LaVorgna & Monaco, PC

[57] ABSTRACT

Therapeutic combinations of two or more antisense oligonucleotides are provided. At least one first antisense oligonucleotide specific for a cytoplasmic oncogene or proto-oncogene and at least one second antisense oligonucleotide specific for a nuclear oncogene or proto-oncogene are combined for treatment of a neoplastic disease. The first antisense oligonucleotide may be specific for, e.g., a ras or raf gene, or an oncogene which codes for a protein tyrosine kinase. The nuclear gene-targeting antisense oligonucleotide preferably may be specific for a nuclear oncogene or proto-oncogene which encodes a transcriptional factor. The combined oligonucleotides have enhanced activity against neoplastic disease.

12 Claims, 7 Drawing Sheets

SEQUENCE LISTING ( 1 ) GENERAL INFORMATION:

( i i i ) NUMBER OF SEQUENCES: 55

( 2 ) INFORMATION FOR SEQ ID NO:1:

( i ) SEQUENCE CHARACTERISTICS:
( A ) LENGTH: 26 Nucleotides
( B ) TYPE: nucleic acid
( C ) STRANDEDNESS: single stranded
( D ) TOPOLOGY: linear ( x i ) SEQUENCE DESCRIPTION: SEQ ID NO:1:

CGCTGAAGGG CTTCTTCCTT ATTGAT    26

( 2 ) INFORMATION FOR SEQ ID NO:2:

( i ) SEQUENCE CHARACTERISTICS:
        ( A ) LENGTH: 26 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:2:

ATCAATAAGG AAGAAGCCCT TCAGCG    26

( 2 ) INFORMATION FOR SEQ ID NO:3:

( i ) SEQUENCE CHARACTERISTICS:
        ( A ) LENGTH: 26 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:3:

TTGGTGAAGC TAACGTTGAG GGGCAT    26

( 2 ) INFORMATION FOR SEQ ID NO:4:

( i ) SEQUENCE CHARACTERISTICS:
        ( A ) LENGTH: 26 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:4:

ATGCCCCTCA ACGTTAGCTT CACCAA    26

( 2 ) INFORMATION FOR SEQ ID NO:5:

( i ) SEQUENCE CHARACTERISTICS:
        ( A ) LENGTH: 26 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:5:

GGTGAGGGAG CGGGAGGCGG TCACAT    26

( 2 ) INFORMATION FOR SEQ ID NO:6:

( i ) SEQUENCE CHARACTERISTICS:
        ( A ) LENGTH: 26 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:6:

ATGTGACCGC CTCCCGCTCC CTCACC    26

( 2 ) INFORMATION FOR SEQ ID NO:7:

( i ) SEQUENCE CHARACTERISTICS:
        ( A ) LENGTH: 24 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:7:

CACCACCAGT TTGTACTCAG TCAT    24

( 2 ) INFORMATION FOR SEQ ID NO:8:

( i ) SEQUENCE CHARACTERISTICS:
      ( A ) LENGTH: 24 Nucleotides
      ( B ) TYPE: nucleic acid
      ( C ) STRANDEDNESS: single stranded
      ( D ) TOPOLOGY: linear ( x i ) SEQUENCE DESCRIPTION: SEQ ID NO:8:

ATGACTGAGT ACAAACTGGT GGTG     24

( 2 ) INFORMATION FOR SEQ ID NO:9:

( i ) SEQUENCE CHARACTERISTICS:
      ( A ) LENGTH: 24 Nucleotides
      ( B ) TYPE: nucleic acid
      ( C ) STRANDEDNESS: single stranded
      ( D ) TOPOLOGY: linear ( x i ) SEQUENCE DESCRIPTION: SEQ ID NO:9:

TACCACAAGT TTATATTCAG TCAT     24

( 2 ) INFORMATION FOR SEQ ID NO:10:

( i ) SEQUENCE CHARACTERISTICS:
      ( A ) LENGTH: 24 Nucleotides
      ( B ) TYPE: nucleic acid
      ( C ) STRANDEDNESS: single stranded
      ( D ) TOPOLOGY: linear ( x i ) SEQUENCE DESCRIPTION: SEQ ID NO:10:

ATGACTGAAT ATAAACTTGT GGTA     24

( 2 ) INFORMATION FOR SEQ ID NO:11:

( i ) SEQUENCE CHARACTERISTICS:
      ( A ) LENGTH: 24 Nucleotides
      ( B ) TYPE: nucleic acid
      ( C ) STRANDEDNESS: single stranded
      ( D ) TOPOLOGY: linear ( x i ) SEQUENCE DESCRIPTION: SEQ ID NO:11:

CACCACCAGC TTATATTCCG TCAT     24

( 2 ) INFORMATION FOR SEQ ID NO:12:

( i ) SEQUENCE CHARACTERISTICS:
      ( A ) LENGTH: 24 Nucleotides
      ( B ) TYPE: nucleic acid
      ( C ) STRANDEDNESS: single stranded
      ( D ) TOPOLOGY: linear ( x i ) SEQUENCE DESCRIPTION: SEQ ID NO:12:

ATGACGGAAT ATAAGCTGGT GGTG     24

( 2 ) INFORMATION FOR SEQ ID NO:13:

( i ) SEQUENCE CHARACTERISTICS:
      ( A ) LENGTH: 3622 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:13:

CCCGGGGAGG GGACCGGGGA ACAGAGGGCC GAGAGGCGTG CGGCAGGGGG GAGGGTAGGA     60

GAAAGAAGGG CCCGACTGTA GGAGGGCAGC GGAGCATTAC CTCATCCCGT GAGCCTCCGC    120

GGGCCCAGAG AAGAATCTTC TAGGGTGGAG TCTCCATGGT GACGGGCGGG CCCGCCCCCC    180

```
TGAGAGCGAC GCGAGCCAAT GGGAAGGCCT TGGGGTGACA TCATGGGCTA TTTTTAGGGG    240
TTGACTGGTA GCAGATAAGT GTTGAGCTCG GGCTGGATAA GGGCTCAGAG TTGCACTGAG    300
TGTGGCTGAA GCAGCGAGGC GGGAGTGGAG GTGCGCGGAG TCAGGCAGAC AGACAGACAC    360
AGCCAGCCAG CCAGGTCGGC AGTATAGTCC GAACTGCAAA TCTTATTTTC TTTTCACCTT    420
CTCTCTAACT GCCCAGAGCT AGCGCCTGTG GCTCCGGGC TGGTGGTTCG GGAGTGTCCA     480
GAGAGCCTTG TCTCCAGCCG GCCCCGGGAG GAGAGCCCTG CTGCCCAGGC GCTGTTGACA    540
GCGGCGGAAA GCAGCGGTAC CCCACGCGCC CGCCGGGGGA CGTCGGCGAG CGGCTGCAGC    600
AGCAAAGAAC TTTCCCGGCG GGAGGACCG GAGACAAGTG GCAGAGTCCC GGAGCGAACT     660
TTTGCAAGCC TTTCCTGCGT CTTAGGCTTC TCCACGGCGG TAAAGACCAG AAGGCGGCGG    720
AGAGCCACGC AAGAGAAGAA GGACGTGCGC TCAGCTTCGC TCGCACCGGT TGTTGAACTT    780
GGGCGAGCGC GAGCCGCGGC TGCCGGGCGC CCCCTCCCCC TAGCAGCGGA GGAGGGGACA    840
AGTCGTCGGA GTCCGGGCGG CCAAGACCCG CCGCCGGCCG GCCACTGCAG GGTCCGCACT    900
GATCCGCTCC GCGGGGAGAG CCGCTGCTCT GGGAAGTGAG TTCGCCTGCG GACTCCGAGG    960
AACCGCTGCG CCCGAAGAGC GCTCAGTGAG TGACCGCGAC TTTTCAAAGC CGGGTAGCGC   1020
GCGCGAGTCG ACAAGTAAGA GTGCGGGAGG CATCTTAATT AACCCTGCGC TCCCTGGAGC   1080
GAGCTGGTGA GGAGGGCGCA GCGGGACGA CAGCCAGCGG GTGCGTGCGC TCTTAGAGAA    1140
ACTTTCCCTG TCAAGGCTC CGGGGGCGC GGGTGTCCCC CGCTTGCCAG AGCCCTGTTG     1200
CGGCCCCGAA ACTTGTGCGC GCACGCCAAA CTAACCTCAC GTGAAGTGAC GGACTGTTCT   1260
ATGACTGCAA AGATGGAAAC GACCTTCTAT GACGATGCCC TCAACGCCTC GTTCCTCCCG   1320
TCCGAGAGCG GACCTTATGG CTACAGTAAC CCCAAGATCC TGAAACAGAG CATGACCCTG   1380
AACCTGGCCG ACCCAGTGGG GAGCCTGAAG CCGCACCTCC GCGCCAAGAA CTCGGACCTC   1440
CTCACCTCGC CCGACGTGGG GCTGCTCAAG CTGGCGTCGC CCGAGCTGGA GCGCCTGATA   1500
ATCCAGTCCA GCAACGGGCA CATCACCACC ACGCCGACCC CACCCAGTT CCTGTGCCCC    1560
AAGAACGTGA CAGATGAGCA GGAGGGGTTC GCCGAGGGCT TCGTGCGCGC CCTGGCCGAA   1620
CTGCACAGCC AGAACACGCT GCCCAGCGTC ACGTCGGCGG CGCAGCCGGT CAACGGGGCA   1680
GGCATGGTGG CTCCCGCGGT AGCCTCGGTG GCAGGGGGCA GCGGCAGCGG CGGCTTCAGC   1740
GCCAGCCTGC ACAGCGAGCC GCCGGTCTAC GCAAACCTCA GCAACTTCAA CCCAGGCGCG   1800
CTGAGCAGCG GCGGCGGGGC GCCCTCCTAC GGCGCGGCCG GCCTGGCCTT TCCCGCGCAA   1860
CCCCAGCAGC AGCAGCAGCC GCCGCACCAC CTGCCCCAGC AGATGCCCGT GCAGCACCCG   1920
CGGCTGCAGG CCCTGAAGGA GGAGCCTCAG ACAGTGCCCG AGATGCCCGG CGAGACACCG   1980
CCCCTGTCCC CCATCGACAT GGAGTCCCAG GAGCGGATCA AGGCGGAGAG GAAGCGCATG   2040
AGGAACCGCA TCGCTGCCTC CAAGTGCCGA AAAAGGAAGC TGGAGAGAAT CGCCCGGCTG   2100
GAGGAAAAAG TGAAAACCTT GAAAGCTCAG AACTCGGAGC TGGCGTCCAC GGCCAACATG   2160
CTCAGGGAAC AGGTGGCACA GCTTAAACAG AAAGTCATGA ACCACGTTAA CAGTGGGTGC   2220
CAACTCATGC TAACGCAGCA GTTGCAAACA TTTTGAAGAG AGACCGTCGG GGGCTGAGGG   2280
GCAACGAAGA AAAAAAATAA CACAGAGAGA CAGACTTGAG AACTTGACAA GTTGCGACGG   2340
AGAGAAAAAA GAAGTGTCCG AGAACTAAAG CCAAGGGTAT CCAAGTTGGA CTGGGTTCGG   2400
TCTGACGGCG CCCCCAGTGT GCACGAGTGG GAAGGACTTG GTCGCGCCCT CCCTTGGCGT   2460
GGAGCCAGGG AGCGGCCGCC TGCGGGCTGC CCCGCTTTGC GGACGGGCTG TCCCCGCGCG   2520
AACGGAACGT TGGACTTTCG TTAACATTGA CCAAGAACTG CATGGACCTA ACATTCGATC   2580
```

| | | | | | | |
|---|---|---|---|---|---|---|
| TCATTCAGTA | TTAAAGGGGG | GAGGGGGAGG | GGGTTACAAA | CTGCAATAGA | GACTGTAGAT | 2640 |
| TGCTTCTGTA | GTACTCCTTA | AGAACACAAA | GCGGGGGAG | GGTTGGGGAG | GGGCGGCAGG | 2700 |
| AGGGAGGTTT | GTGAGAGCGA | GGCTGAGCCT | ACAGATGAAC | TCTTTCTGGC | CTGCTTTCGT | 2760 |
| TAACTGTGTA | TGTACATATA | TATATTTTTT | AATTTGATTA | AAGCTGATTA | CTGTCAATAA | 2820 |
| ACAGCTTCAT | GCCTTTGTAA | GTTATTTCTT | GTTTGTTTGT | TTGGGTATCC | TGCCCAGTGT | 2880 |
| TGTTTGTAAA | TAAGAGATTT | GGAGCACTCT | GAGTTACCA | TTTGTAATAA | AGTATATAAT | 2940 |
| TTTTTATGT | TTTGTTTCTG | AAAATTCCAG | AAAGGATATT | TAAGAAAATA | CAATAAACTA | 3000 |
| TTGGAAAGTA | CTCCCCTAAC | CTCTTTTCTG | CATCATCTGT | AGATCCTAGT | CTATCTAGGT | 3060 |
| GGAGTTGAAA | GAGTTAAGAA | TGCTCGATAA | AATCACTCTC | AGTGCTTCTT | ACTATTAAGC | 3120 |
| AGTAAAAACT | GTTCTCTATT | AGACTTAGAA | ATAAATGTAC | CTGATGTACC | TGATGCTATG | 3180 |
| TCAGGCTTCA | TACTCCACGC | TCCCCCAGCG | TATCTATATG | GAATTGCTTA | CCAAAGGCTA | 3240 |
| GTGCGATGTT | TCAGGAGGCT | GGAGGAAGGG | GGGTTGCAGT | GGAGAGGGAC | AGCCCACTGA | 3300 |
| GAAGTCAAAC | ATTTCAAAGT | TTGGATTGCA | TCAAGTGGCA | TGTGCTGTGA | CCATTTATAA | 3360 |
| TGTTAGAAAT | TTTACAATAG | GTGCTTATTC | TCAAAGCAGG | AATTGGTGGC | AGATTTTACA | 3420 |
| AAAGATGTAT | CCTTCCAATT | TGGAATCTTC | TCTTTGACAA | TTCCTAGATA | AAAAGATGGC | 3480 |
| CTTTGTCTTA | TGAATATTTA | TAACAGCATT | CTGTCACAAT | AAATGTATTC | AAATACCAAT | 3540 |
| AACAGATCTT | GAATTGCTTC | CCTTTACTAC | TTTTTGTTC | CCAAGTTATA | TACTGAAGTT | 3600 |
| TTTATTTTTA | GTTGCTGAGG | TT | | | | 3622 |

( 2 ) INFORMATION FOR SEQ ID NO:14:

( i ) SEQUENCE CHARACTERISTICS:
        ( A ) LENGTH: 6453 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

| | | | | | | |
|---|---|---|---|---|---|---|
| GGATCCCAGC | CTTTCCCCAG | CCCGTAGCCC | CGGGACCTCC | GCGGTGGGCG | GCGCCGCGCT | 60 |
| GCCGGCGCAG | GGAGGGCCTC | TGGTGCACCG | GCACCGCTGA | GTCGGGTTCT | CTCGCCGGCC | 120 |
| TGTTCCCGGG | AGAGCCCGGG | GCCCTGCTCG | GAGATGCCGC | CCCGGGCCCC | CAGACACCGG | 180 |
| CTCCCTGGCC | TTCCTCGAGC | AACCCCGAGC | TCGGCTCCGG | TCTCCAGCCA | AGCCCAACCC | 240 |
| CGAGAGGCCG | CGGCCCTACT | GGCTCCGCCT | CCCGCGTTGC | TCCCGGAAGC | CCGCCCGAC | 300 |
| CGCGGCTCCT | GACAGACGGG | CCGCTCAGCC | AACCGGGGTG | GGGCGGGGCC | CGATGGCGCG | 360 |
| CAGCCAATGG | TAGGCCGCGC | CTGGCAGACG | GACGGGCGCG | GGGCGGGGCG | TGCGCAGGCC | 420 |
| CGCCCGAGTC | TCCGCCGCCC | GTGCCCTGCG | CCCGCAACCC | GAGCCGCACC | CGCCGCGGAC | 480 |
| GGAGCCCATG | CGCGGGGCGA | ACCGCGCGCC | CCGCCCCCG | CCCCGCCCCG | GCCTCGGCCC | 540 |
| CGGCCCTGGC | CCCGGGGGCA | GTCGCGCCTG | TGAACGGTGA | GTGCGGGCAG | GGATCGGCCG | 600 |
| GGCCGCGCGC | CCTCCTCGCC | CCCAGGCGGC | AGCAATACGC | GCGGCGCGGG | CCGGGGGCGC | 660 |
| GGGGCCGGCG | GGCGTAAGCG | GCGGCGGCGG | CGGCGGGTGG | GTGGGCCGG | GCGGGGCCCG | 720 |
| CGGGCACAGG | TGAGCGGGCG | TCGGGGGCTG | CGGCGGGCGG | GGGCCCCTTC | CTCCCTGGGG | 780 |
| CCTGCGGGAA | TCCGGGCCCC | ACCCGTGGCC | TCGCGCTGGG | CACGGTCCCC | ACGCCGGCGT | 840 |
| ACCCGGGAGC | CTCGGGCCCG | GCGCCCTCAC | ACCCGGGGGC | GTCTGGGAGG | AGGCGGCCGC | 900 |
| GGCCACGGCA | CGCCCGGGCA | CCCCCGATTC | AGCATCACAG | GTCGCGGACC | AGGCCGGGGG | 960 |

| | | | | | |
|---|---|---|---|---|---|
| CCTCAGCCCC | AGTGCCTTTT | CCCTCTCCGG | GTCTCCCGCG | CCGCTTCTCG | GCCCCTTCCT | 1020 |
| GTCGCTCAGT | CCCTGCTTCC | CAGGAGCTCC | TCTGTCTTCT | CCAGCTTTCT | GTGGCTGAAA | 1080 |
| GATGCCCCCG | GTTCCCGCC | GGGGGTGCGG | GGCGCTGCCC | GGGTCTGCCC | TCCCCTCGGC | 1140 |
| GGCGCCTAGT | ACGCAGTAGG | CGCTCAGCAA | ATACTTGTCG | GAGGCACCAG | CGCCGCGGGG | 1200 |
| CCTGCAGGCT | GGCACTAGCC | TGCCCGGGCA | CGCCGTGGCG | CGCTCCGCCG | TGGCCAGACC | 1260 |
| TGTTCTGGAG | GACGGTAACC | TCAGCCCTCG | GGCGCCTCCC | TTTAGCCTTT | CTGCCGACCC | 1320 |
| AGCAGCTTCT | AATTTGGGTG | CGTGGTTGAG | AGCGCTCAGC | TGTCAGCCCT | GCCTTTGAGG | 1380 |
| GCTGGGTCCC | TTTTCCCATC | ACTGGGTCAT | TAAGAGCAAG | TGGGGGCGAG | GCGACAGCCC | 1440 |
| TCCCGCACGC | TGGGTTGCAG | CTGCACAGGT | AGGCACGCTG | CAGTCCTTGC | TGCCTGGCGT | 1500 |
| TGGGGCCCAG | GGACCGCTGT | GGGTTTGCCC | TTCAGATGGC | CCTGCCAGCA | GCTGCCCTGT | 1560 |
| GGGGCCTGGG | GCTGGGCCTG | GCCTGGCTG | AGCAGGGCCC | TCCTTGGCAG | GTGGGGCAGG | 1620 |
| AGACCCTGTA | GGAGGACCCC | GGGCCGCAGG | CCCCTGAGGA | GCGATGACGG | AATATAAGCT | 1680 |
| GGTGGTGGTG | GGCGCCGGCG | GTGTGGGCAA | GAGTGCGCTG | ACCATCCAGC | TGATCCAGAA | 1740 |
| CCATTTTGTG | GACGAATACG | ACCCCACTAT | AGAGGTGAGC | CTAGCGCCGC | CGTCCAGGTG | 1800 |
| CCAGCAGCTG | CTGCGGGCGA | GCCCAGGACA | CAGCCAGGAT | AGGGCTGGCT | GCAGCCCCTG | 1860 |
| GTCCCTGCA | TGGTGCTGTG | GCCCTGTCTC | CTGCTTCCTC | TAGAGGAGGG | GAGTCCCTCG | 1920 |
| TCTCAGCACC | CCAGGAGAGG | AGGGGGCATG | AGGGGCATGA | GAGGTACCAG | GGAGAGGCTG | 1980 |
| GCTGTGTGAA | CTCCCCCCAC | GGAAGGTCCT | GAGGGGGTCC | CTGAGCCCTG | TCCTCCTGCA | 2040 |
| GGATTCCTAC | CGGAAGCAGG | TGGTCATTGA | TGGGGAGACG | TGCCTGTTGG | ACATCCTGGA | 2100 |
| TACCGCCGGC | CAGGAGGAGT | ACAGCGCCAT | GCGGGACCAG | TACATGCGCA | CCGGGGAGGG | 2160 |
| CTTCCTGTGT | GTGTTTGCCA | TCAACAACAC | CAAGTCTTTT | GAGGACATCC | ACCAGTACAG | 2220 |
| GTGAACCCCG | TGAGGCTGGC | CCGGGAGCCC | ACGCCGCACA | GGTGGGGCCA | GGCCGGCTGC | 2280 |
| GTCCAGGCAG | GGGCCTCCTG | TCCTCTCTGC | GCATGTCCTG | GATGCCGCTG | CGCCTGCAGC | 2340 |
| CCCCGTAGCC | AGCTCTCGCT | TTCCACCTCT | CAGGGAGCAG | ATCAAACGGG | TGAAGGACTC | 2400 |
| GGATGACGTG | CCCATGGTGC | TGGTGGGGAA | CAAGTGTGAC | CTGGCTGCAC | GCACTGTGGA | 2460 |
| ATCTCGGCAG | GCTCAGGACC | TCGCCCGAAG | CTACGGCATC | CCCTACATCG | AGACCTCGGC | 2520 |
| CAAGACCCGG | CAGGTGAGGC | AGCTCTCCAC | CCCACAGCTA | GCCAGGGACC | CGCCCCGCCC | 2580 |
| CGCCCCAGCC | AGGGAGCAGC | ACTCACTGAC | CCTCTCCCTT | GACACAGGGC | AGCCGCTCTG | 2640 |
| GCTCTAGCTC | CAGCTCCGGG | ACCCTCTGGG | ACCCCCGGG | ACCCATGTGA | CCCAGCGGCC | 2700 |
| CCTCGCACTG | TAGGTCTCCC | GGGACGGCAG | GGCAGTGAGG | GAGGCGAGGG | CCGGGGTCTG | 2760 |
| GGCTCACGCC | CTGCAGTCCT | GGGCCGACAC | AGCTCCGGGG | AAGGCGGAGG | TCCTTGGGGA | 2820 |
| GAGCTGCCCT | GAGCCAGGCC | GGAGCGGTGA | CCCTGGGGCC | CGGCCCTCT | TGTCCCAGA | 2880 |
| GTGTCCCACG | GCACCTGTT | GGTTCTGAGT | CTTAGTGGGG | CTACTGGGGA | CACGGGCCGT | 2940 |
| AGCTGAGTCG | AGAGCTGGGT | GCAGGTGGT | CAAACCCTGG | CCAGACCTGG | AGTTCAGGAG | 3000 |
| GGCCCCGGGC | CACCCTGACC | TTTGAGGGGC | TGCTGTAGCA | TGATGCGGGT | GGCCCTGGGC | 3060 |
| ACTTCGAGAT | GGCCAGAGTC | CAGCTTCCCG | TGTGTGTGGT | GGGCCTGGGG | AAGTGGCTGG | 3120 |
| TGGAGTCGGG | AGCTTCGGGC | CAGGCAAGGC | TTGATCCCAC | AGCAGGGAGC | CCCTCACCCA | 3180 |
| GGCAGGCGGC | CACAGGCCGG | TCCCTCCTGA | TCCCATCCCT | CCTTTCCCAG | GGAGTGGAGG | 3240 |
| ATGCCTTCTA | CACGTTGGTG | CGTGAGATCC | GGCAGCACAA | GCTGCGGAAG | CTGAACCCTC | 3300 |
| CTGATGAGAG | TGGCCCCGGC | TGCATGAGCT | GCAAGTGTGT | GCTCTCCTGA | CGCAGGTGAG | 3360 |

```
GGGGACTCCC  AGGGCGGCCG  CCACGCCCAC  CGGATGACCC  CGGCTCCCCG  CCCCTGCCGG  3420
TCTCCTGGCC  TGCGGTCAGC  AGCCTCCCTT  GTGCCCCGCC  CAGCACAAGC  TCAGGACATG  3480
GAGGTGCCGG  ATGCAGGAAG  GAGGTGCAGA  CGGAAGGAGG  AGGAAGGAAG  GACGGAAGCA  3540
AGGAAGGAAG  GAAGGGCTGC  TGGAGCCCAG  TCACCCCGGG  ACCGTGGGCC  GAGGTGACTG  3600
CAGACCCTCC  CAGGGAGGCT  GTGCACAGAC  TGTCTTGAAC  ATCCAAATG   CCACCGGAAC  3660
CCCAGCCCTT  AGCTCCCTC   CCAGGCCTCT  GTGGGCCCTT  GTCGGGCACA  GATGGGATCA  3720
CAGTAAATTA  TTGGATGGTC  TTGATCTTGG  TTTTCGGCTG  AGGGTGGGAC  ACGGTGCGCG  3780
TGTGGCCTGG  CATGAGGTAT  GTCGGAACCT  CAGGCCTGTC  CAGCCCTGGG  CTCTCCATAG  3840
CCTTTGGGAG  GGGGAGGTTG  GGAGAGGCCG  GTCAGGGGTC  TGGGCTGTGG  TGCTCTCTCC  3900
TCCCGCCTGC  CCCAGTGTCC  ACGGCTTCTG  GCAGAGAGCT  CTGGACAAGC  AGGCAGATCA  3960
TAAGGACAGA  GAGCTTACTG  TGCTTCTACC  AACTAGGAGG  GCGTCCTGGT  CCTCCAGAGG  4020
GAGGTGGTTT  CAGGGGTTGG  GGATCTGTGC  CGGTGGCTCT  GGTCTCTGCT  GGGAGCCTTC  4080
TTGGCGGTGA  GAGGCATCAC  CTTTCCTGAC  TTGCTCCCAG  CGTGAAATGC  ACCTGCCAAG  4140
AATGGCAGAC  ATAGGGACCC  CGCCTCCTGG  GCCTTCACAT  GCCCAGTTTT  CTTCGGCTCT  4200
GTGGCCTGAA  GCGGTCTGTG  GACCTTGGAA  GTAGGGCTCC  AGCACCGACT  GGCCTCAGGC  4260
CTCTGCCTCA  TTGGTGGTCG  GGTAGCGGCC  AGTAGGGCGT  GGGAGCCTGG  CCATCCCTGC  4320
CTCCTGGAGT  GGACGAGGTT  GGCAGCTGGT  CCGTCTGCTC  CTGCCCCACT  CTCCCCGCC   4380
CCTGCCCTCA  CCCTACCCTT  GCCCCACGCC  TGCCTCATGG  CTGGTTGCTC  TTGGAGCCTG  4440
GTAGTGTCAC  TGGCTCAGCC  TTGCTGGGTA  TACACAGGCT  CTGCCACCCA  CTCTGCTCCA  4500
AGGGGCTTGC  CCTGCCTTGG  GCCAAGTTCT  AGGTCTGGCC  ACAGCCACAG  ACAGCTCAGT  4560
CCCCTGTGTG  GTCATCCTGG  CTTCTGCTGG  GGGCCCACAG  CGCCCTGGT   GCCCTCCCC   4620
TCCCAGGGCC  CGGGTTGAGG  CTGGGCCAGG  CCCTCTGGGA  CGGGGACTTG  TGCCCTGTCA  4680
GGGTTCCCTA  TCCCTGAGGT  TGGGGAGAG   CTAGCAGGGC  ATGCCGCTGG  CTGGCCAGGG  4740
CTGCAGGGAC  ACTCCCCCTT  TTGTCCAGGG  AATACCACAC  TCGCCCTTCT  CTCCAGCGAA  4800
CACCACACTC  GCCCTTCTCT  CCAGGGGACG  CCACACTCCC  CCTTCTGTCC  AGGGGACGCC  4860
ACACTCCCCC  TTCTCTCCAG  GGGACGCCAC  ACTCGCCCTT  CTCTCCAGGG  GACGCCACAC  4920
TCGCCCTTCT  CTCCAGGGGA  CGCCACACTC  GCCCTTCTGT  CCAGGGGACG  CCACACTCGC  4980
CCTTCTCTCC  AGGGGACGCC  ACACTCGCCC  TTCTCTCCAG  GGGACGCCAC  ACTCCCCCTT  5040
CTGTCCAGGG  GACGCCACAC  TCCCCCTTCT  CTCCAGGGGA  CGCCACACTC  CCCCTTCTCT  5100
CCAGGGGACG  CCACACTCGC  CCTTCTCTCC  AGGGGACGCC  ACACTCCCCC  TTCTGTCCAG  5160
GGGACGCCAC  ACTCGCCCTT  CTCTCCAGGG  GACGCCACAC  TCGCCCTTCT  CTCCAGGGGA  5220
CGCCACACTC  CCCCTTCTCT  CCAGGGGACG  CCACACTCCC  CCTTCTCTCC  AGGGGACGCC  5280
ACACTCCCCC  TTCTGTCCAG  GGGACGCCAC  ACTCGCCCTT  CTCTCCAGGG  GACGCCACAC  5340
TCCCCCTTCT  CTCCAGGGGA  CGCCACACTC  CCCCTTCTCT  CCAGGGGACG  CCACACTCCC  5400
CCTTCTGTCC  AGGGGACGCC  ACACTCGCCC  TTCTCTCCAG  GGGACGCCAC  ACTCGCCCTT  5460
CTCTCCAGGG  GACGCCACAC  TCGCCCTTCT  CTCCAGGGA   CGCCACACTT  GCCCTTCTGT  5520
CCAGGGAATG  CCACACTCCC  CCTTCTCCCC  AGCAGCCTCC  GAGTGACCAG  CTTCCCCATC  5580
GATAGACTTC  CCGAGGCCAG  GAGCCCTCTA  GGGCTGCCGG  GTGCCACCCT  GGCTCCTTCC  5640
ACACCGTGCT  GGTCACTGCC  TGCTGGGGGC  GTCAGATGCA  GGTGACCCTG  TGCAGGAGGT  5700
ATCTCTGGAC  CTGCCTCTTG  GTCATTACGG  GGCTGGGCAG  GGCCTGGTAT  CAGGGCCCCG  5760
```

-continued

| | | | | | |
|---|---|---|---|---|---|
|CTGGGGTTGC|AGGGCTGGGC|CTGTGCTGTG|GTCCTGGGGT|GTCCAGGACA|GACGTGGAGG|5820|
|GGTCAGGGCC|CAGCACCCCT|GCTCCATGCT|GAACTGTGGG|AAGCATCCAG|GTCCCTGGGT|5880|
|GGCTTCAACA|GGAGTTCCAG|CACGGGAACC|ACTGGACAAC|CTGGGGTGTG|TCCTGATCTG|5940|
|GGGACAGGCC|AGCCACACCC|CGAGTCCTAG|GGACTCCAGA|GAGCAGCCCA|CTGCCCTGGG|6000|
|CTCCACGGAA|GCCCCTCAT|GCCGCTAGGC|CTTGGCCTCG|GGACAGCCC|AGCTAGGCCA|6060|
|GTGTGTGGCA|GGACCAGGCC|CCCATGTGGG|AGCTGACCCC|TTGGGATTCT|GGAGCTGTGC|6120|
|TGATGGGCAG|GGGAGAGCCA|GCTCCTCCCC|TTGAGGGAGG|GTCTTGATGC|CTGGGGTTAC|6180|
|CCGCAGAGGC|CTGGGTGCCG|GGACGCTCCC|CGGTTTGGCT|GAAAGGAAAG|CAGATGTGGT|6240|
|CAGCTTCTCC|ACTGAGCCCA|TCTGGTCTTC|CCGGGGCTGG|GCCCCATAGA|TCTGGGTCCC|6300|
|TGTGTGGCCC|CCCTGGTCTG|ATGCCGAGGA|TACCCCTGCA|AACTGCCAAT|CCCAGAGGAC|6360|
|AAGACTGGGA|AGTCCCTGCA|GGGAGAGCCC|ATCCCCGCAC|CCTGACCCAC|AAGAGGGACT|6420|
|CCTGCTGCCC|ACCAGGCATC|CCTCCAGGGA|TCC|||6453|

( 2 ) INFORMATION FOR SEQ ID NO:15:

( i ) SEQUENCE CHARACTERISTICS:
        ( A ) LENGTH: 5775 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
|TCCTAGGCGG|CGGCCGCGGC|GGCGGAGGCA|GCAGCGGCGG|CGGCAGTGGC|GGCGGCGAAG|60|
|GTGGCGGCGG|CTCGGCCAGT|ACTCCCGGCC|CCGCCATTT|CGGACTGGGA|GCGAGCGCGG|120|
|CGCAGGCACT|GAAGGCGGCG|GCGGGGCCAG|AGGCTCAGCG|GCTCCAGGT|GCGGGAGAGA|180|
|GGCCTGCTGA|AAATGACTGA|ATATAAACTT|GTGGTAGTTG|GAGCTTGTGG|CGTAGGCAAG|240|
|AGTGCCTTGA|CGATACAGCT|AATTCAGAAT|CATTTGTGG|ACGAATATGA|TCCAACAATA|300|
|GAGGATTCCT|ACAGGAAGCA|AGTAGTAATT|GATGGAGAAA|CCTGTCTCTT|GGATATTCTC|360|
|GACACAGCAG|GTCAAGAGGA|GTACAGTGCA|ATGAGGGACC|AGTACATGAG|GACTGGGGAG|420|
|GGCTTTCTTT|GTGTATTTGC|CATAAATAAT|ACTAAATCAT|TTGAAGATAT|TCACCATTAT|480|
|AGAGAACAAA|TTAAAAGAGT|TAAGGACTCT|GAAGATGTAC|CTATGGTCCT|AGTAGGAAAT|540|
|AAATGTGATT|TGCCTTCTAG|AACAGTAGAC|ACAAAACAGG|CTCAGGACTT|AGCAAGAAGT|600|
|TATGGAATTC|CTTTTATTGA|AACATCAGCA|AAGACAAGAC|AGGGTGTTGA|TGATGCCTTC|660|
|TATACATTAG|TTCGAGAAAT|TCGAAAACAT|AAAGAAAAGA|TGAGCAAAGA|TGGTAAAAAG|720|
|AAGAAAAAGA|AGTCAAAGAC|AAAGTGTGTA|ATTATGTAAA|TACAATTTGT|ACTTTTTTCT|780|
|TAAGGCATAC|TAGTACAAGT|GGTAATTTTT|GTACATTACA|CTAAATTATT|AGCATTTGTT|840|
|TTAGCATTAC|CTAATTTTTT|TCCTGCTCCA|TGCAGACTGT|TAGCTTTTAC|CTTAAATGCT|900|
|TATTTTAAAA|TGACAGTGGA|AGTTTTTTTT|TCCTCGAAGT|GCCAGTATTC|CCAGAGTTTT|960|
|GGTTTTTGAA|CTAGCAATGC|CTGTGAAAAA|GAAACTGAAT|ACCTAAGATT|TCTGTCTTGG|1020|
|GGTTTTTGGT|GCATGCAGTT|GATTACTTCT|TATTTTCTT|ACCAAGTGTG|AATGTTGGTG|1080|
|TGAAACAAAT|TAATGAAGCT|TTTGAATCAT|CCCTATTCTG|TGTTTATCT|AGTCACATAA|1140|
|ATGGATTAAT|TACTAATTTC|AGTTGAGACC|TTCTAATTGG|TTTTACTGA|AACATTGAGG|1200|
|GACACAAATT|TATGGGCTTC|CTGATGATGA|TTCTTCTAGG|CATCATGTCC|TATAGTTTGT|1260|
|CATCCCTGAT|GAATGTAAAG|TTACACTGTT|CACAAAGGTT|TTGTCTCCTT|TCCACTGCTA|1320|

```
TTAGTCATGG TCACTCTCCC CAAAATATTA TATTTTTTCT ATAAAAGAA  AAAAATGGAA    1380
AAAAATTACA AGGCAATGGA AACTATTATA AGGCCATTTC CTTTTCACAT TAGATAAATT    1440
ACTATAAAGA CTCCTAATAG CTTTTTCCTG TTAAGGCAGA CCCAGTATGA ATGGGATTAT    1500
TATAGCAACC ATTTGGGGC  TATATTTACA TGCTACTAAA TTTTTATAAT AATTGAAAAG    1560
ATTTTAACAA GTATAAAAAA ATTCTCATAG GAATTAAATG TAGTCTCCCT GTGTCAGACT    1620
GCTCTTTCAT AGTATAACTT TAAATCTTTT CTTCAACTTG AGTCTTGAA  GATAGTTTTA    1680
ATTCTGCTTG TGACATTAAA AGATTATTTG GGCCAGTTAT AGCTTATTAG GTGTTGAAGA    1740
GACCAAGGTT GCAAGCCAGG CCCTGTGTGA ACCTTGAGCT TCATAGAGA  GTTTCACAGC    1800
ATGGACTGTG TGCCCCACGG TCATCCGAGT GGTTGTACGA TGCATTGGTT AGTCAAAAAT    1860
GGGGAGGGAC TAGGGCAGTT TGGATAGCTC AACAAGATAC AATCTCACTC TGTGGTGGTC    1920
CTGCTGACAA ATCAAGAGCA TTGCTTTTGT TTCTTAAGAA AACAAACTCT TTTTTAAAAA    1980
TTACTTTTAA ATATTAACTC AAAAGTTGAG ATTTTGGGGT GGTGGTGTGC CAAGACATTA    2040
ATTTTTTTTT TAAACAATGA AGTGAAAAAG TTTTACAATC TCTAGGTTTG GCTAGTTCTC    2100
TTAACACTGG TTAAATTAAC ATTGCATAAA CACTTTTCAA GTCTGATCCA TATTTAATAA    2160
TGCTTTAAAA TAAAAATAAA AACAATCCTT TTGATAAATT TAAAATGTTA CTTATTTTAA    2220
AATAAATGAA GTGAGATGGC ATGGTGAGGT GAAAGTATCA CTGGACTAGG TTGTTGGTGA    2280
CTTAGGTTCT AGATAGGTGT CTTTTAGGAC TCTGATTTTG AGGACATCAC TTACTATCCA    2340
TTTCTTCATG TTAAAAGAAG TCATCTCAAA CTCTTAGTTT TTTTTTTTA  CACTATGTGA    2400
TTTATATTCC ATTTACATAA GGATACACTT ATTTGTCAAG CTCAGCACAA TCTGTAAATT    2460
TTTAACCTAT GTTACACCAT CTTCAGTGCC AGTCTTGGGC AAAATTGTGC AAGAGGTGAA    2520
GTTTATATTT GAATATCCAT TCTCGTTTTA GGACTCTTCT TCCATATTAG TGTCATCTTG    2580
CCTCCCTACC TTCCACATGC CCCATGACTT GATGCAGTTT TAATACTTGT AATTCCCCTA    2640
ACCATAAGAT TTACTGCTGC TGTGGATATC TCCATGAAGT TTTCCCACTG AGTCACATCA    2700
GAAATGCCCT ACATCTTATT TTCCTCAGGG CTCAAGAGAA TCTGACAGAT ACCATAAAGG    2760
GATTTGACCT AATCACTAAT TTTCAGGTGG TGGCTGATGC TTTGAACATC TCTTTGCTGC    2820
CCAATCCATT AGCGACAGTA GGATTTTTCA ACCCTGGTAT GAATAGACAG AACCCTATCC    2880
AGTGGAAGGA GAATTTAATA AAGATAGTGC AGAAAGAATT CCTTAGGTAA TCTATAACTA    2940
GGACTACTCC TGGTAACAGT AATACATTCC ATTGTTTTAG TAACCAGAAA TCTTCATGCA    3000
ATGAAAAATA CTTTAATTCA TGAAGCTTAC TTTTTTTTTT TTGGTGTCAG AGTCTCGCTC    3060
TTGTCACCCA GGCTGGAATG CAGTGGCGCC ATCTCAGCTC ACTGCAACCT TCCATCTTCC    3120
CAGGTTCAAG CGATTCTCGT GCCTCGGCCT CCTGAGTAGC TGGGATTACA GGCGTGTGCA    3180
CTACACTCAA CTAATTTTTG TATTTTTAGG AGAGACGGGG TTTCACCTGT TGGCCAGGCT    3240
GGTCTCGAAC TCCTGACCTC AAGTGATTCA CCCACCTTGG CCTCATAAAC CTGTTTTGCA    3300
GAACTCATTT ATTCAGCAAA TATTTATTGA GTGCCTACCA GATGCCAGTC ACCGCACAAG    3360
GCACTGGGTA TATGGTATCC CCAAACAAGA GACATAATCC CGGTCCTTAG GTACTGCTAG    3420
TGTGGTCTGT AATATCTTAC TAAGGCCTTT GGTATACGAC CCAGAGATAA CACGATGCGT    3480
ATTTAGTTT  TGCAAGAAG  GGGTTTGGTC TCTGTGCCAG CTCTATAATT GTTTGCTAC     3540
GATTCCACTG AAACTCTTCG ATCAAGCTAC TTTATGTAAA TCACTTCATT GTTTTAAGG     3600
AATAAACTTG ATTATATTGT TTTTTATTT  GGCATAACTG TGATTCTTTT AGGACAATTA    3660
CTGTACACAT TAAGGTGTAT GTCAGATATT CATATTGACC CAAATGTGTA ATATTCCAGT    3720
```

-continued

```
TTTCTCTGCA TAAGTAATTA AAATATACTT AAAAATTAAT AGTTTTATCT GGGTACAAAT    3780
AAACAGTGCC TGAACTAGTT CACAGACAAG GGAACTTCT ATGTAAAAAT CACTATGATT     3840
TCTGAATTGC TATGTGAAAC TACAGATCTT TGGAACACTG TTTAGGTAGG GTGTTAAGAC    3900
TTGACACAGT ACCTCGTTTC TACACAGAGA AAGAAATGGC CATACTTCAG GAACTGCAGT    3960
GCTTATGAGG GGATATTTAG GCCTCTTGAA TTTTGATGT AGATGGGCAT TTTTTAAGG      4020
TAGTGGTTAA TTACCTTTAT GTGAACTTTG AATGGTTTAA CAAAAGATTT GTTTTGTAG     4080
AGATTTTAAA GGGGAGAAT TCTAGAAATA AATGTTACCT AATTATTCA GCCTAAAGA       4140
CAAAAATCCT TGTTGAAGTT TTTTAAAAA AAGACTAAAT TACATAGACT TAGGCATTAA     4200
CATGTTTGTG GAAGAATATA GCAGACGTAT ATTGTATCAT TTGAGTGAAT GTTCCCAAGT    4260
AGGCATTCTA GGCTCTATTT AACTGAGTCA CACTGCATAG GAATTTAGAA CCTAACTTTT    4320
ATAGGTTATC AAAACTGTTG TCACCATTGC ACAATTTGT CCTAATATAT ACATAGAAAC     4380
TTTGTGGGGC ATGTTAAGTT ACAGTTTGCA CAAGTTCATC TCATTTGTAT TCCATTGATT    4440
TTTTTTTTTC TTCTAAACAT TTTTCTTCA AAACAGTATA TATAACTTTT TTAGGGGAT      4500
TTTTTTTAGA CAGCAAAAAA CTATCTGAAG ATTTCCATTT GTCAAAAGT AATGATTTCT     4560
TGATAATTGT GTAGTGAATG TTTTTAGAA CCCAGCAGTT ACCTTGAAAG CTGAATTTAT     4620
ATTAGTAAC TTCTGTGTTA ATACTGGATA GCATGAATTC TGCATTGAGA AACTGAATAG     4680
CTGTCATAAA ATGCTTCTT TCCTAAAGAA AGATACTCAC ATGAGTTCTT GAAGAATAGT     4740
CATAACTAGA TTAAGATCTG TGTTTAGTT TAATAGTTTG AAGTGCCTGT TTGGGATAAT     4800
GATAGGTAAT TTAGATGAAT TTAGGGGAAA AAAAAGTTAT CTGCAGTTAT GTTGAGGGCC    4860
CATCTCTCCC CCCACACCCC CACAGAGCTA ACTGGGTTAC AGTGTTTAT CCGAAAGTTT     4920
CCAATTCCAC TGTCTTGTGT TTTCATGTTG AAAATACTTT TGCATTTTC CTTTGAGTGC     4980
CAATTTCTTA CTAGTACTAT TTCTTAATGT AACATGTTTA CCTGGCCTGT CTTTTAACTA    5040
TTTTTGTATA GTGTAAACTG AAACATGCAC ATTTTGTACA TTGTGCTTTC TTTTGTGGGT    5100
CATATGCAGT GTGATCCAGT TGTTTTCCAT CATTTGGTTG CGCTGACCTA GGAATGTTGG    5160
TCATATCAAA CATTAAAAAT GACCACTCTT TTAATGAAAT TAACTTTTAA ATGTTTATAG    5220
GAGTATGTGC TGTGAAGTGA TCTAAAATTT GTAATATTTT TGTCATGAAC TGTACTACTC    5280
CTAATTATTG TAATGTAATA AAAATAGTTA CAGTGACTAT GAGTGTGTAT TTATTCATGC    5340
AAATTTGAAC TGTTTGCCCC GAAATGGATA TGGATACTTT ATAAGCCATA GACACTATAG    5400
TATACCAGTG AATCTTTTAT GCAGCTTGTT AGAAGTATCC TTTTATTTC TAAAGGTGC      5460
TGTGGATATT ATGTAAAGGC GTGTTTGCTT AAACAATTTT CCATATTTAG AAGTAGATGC    5520
AAAACAAATC TGCCTTTATG ACAAAAAAAT AGGATAACAT TATTTATTTA TTTCCTTTTA    5580
TCAATAAGGT AATTGATACA CAACAGGTGA CTTGGTTTTA GGCCCAAAGG TAGCAGCAGC    5640
AACATTAATA ATGGAAATAA TTGAATAGTT AGTTATGTAT GTTAATGCCA GTCACCAGCA    5700
GGCTATTTCA AGGTCAGAAG TAATGACTCC ATACATATTA TTTATTTCTA TAACTACATT    5760
TAAATCATTA CCAGG                                                    5775
```

( 2 ) INFORMATION FOR SEQ ID NO:16:

( i ) SEQUENCE CHARACTERISTICS:
      ( A ) LENGTH: 2436 base pairs
      ( B ) TYPE: nucleic acid
      ( C ) STRANDEDNESS: double
      ( D ) TOPOLOGY: linear (x i) SEQUENCE DESCRIPTION: SEQ ID NO:16:

| | | | | | | |
|---|---|---|---|---|---|---|
| CTGCAGCTTC | TAGGACCCGG | TTTCTTTTAC | TGATTTAAAA | ACAAAACAAA | AAAAAATAAA | 60 |
| AAAGTTGTGC | CTGAAATGAA | TCTTGTTTTT | TTTTATAAG | TAGCCGCCTG | GTTACTGTGT | 120 |
| CCTGTAAAAT | ACAGACATTG | ACCCTTGGTG | TAGCTTCTGT | TCAACTTTAT | ATCACGGGAA | 180 |
| TGGATGGGTC | TGATTTCTTG | GCCCTCTTCT | TGAATTGGCC | ATATACAGGG | TCCCTGGCCA | 240 |
| GTGGACTGAA | GGCTTTGTCT | AAGATGACAA | GGGTCAGCTC | AGGGGATGTG | GGGGAGGGCG | 300 |
| GTTTTATCTT | CCCCCTTGTC | GTTGAGGTT | TTGATCTCTG | GGTAAAGAGG | CCGTTATCT | 360 |
| TTGTAAACAC | GAAACATTTT | TGCTTTCTCC | AGTTTCTGT | TAATGGCGAA | AGAATGGAAG | 420 |
| CGAATAAAGT | TTACTGATT | TTTGAGACAC | TAGCACCTAG | CGCTTTCATT | ATTGAAACGT | 480 |
| CCCGTGTGGG | AGGGGCGGGT | CTGGGTGCGG | CTGCCGCATG | ACTCGTGGTT | CGGAGGCCCA | 540 |
| CGTGGCCGGG | GCGGGGACTC | AGGCGCCTGG | CAGCCGACTG | ATTACGTAGC | GGGCGGGGCC | 600 |
| GGAAGTGCCG | CTCCTTGGTG | GGGGCTGTTC | ATGGCGGTTC | CGGGTCTCC | AACATTTTC | 660 |
| CCGGTCTGTG | GTCCTAAATC | TGTCCAAAGC | AGAGGCAGTG | GAGCTTGAGG | TTCTTGCTGG | 720 |
| TGTGAAATGA | CTGAGTACAA | ACTGGTGGTG | GTTGGAGCAG | GTGGTGTTGG | GAAAAGCGCA | 780 |
| CTGACAATCC | AGCTAATCCA | GAACCACTTT | GTAGATGAAT | ATGATCCCAC | CATAGAGGAT | 840 |
| TCTTACAGAA | AACAAGTGGT | TATAGATGGT | GAAACCTGTT | TGTTGGACAT | ACTGGATACA | 900 |
| GCTGGACAAG | AAGAGTACAG | TGCCATGAGA | GACCAATACA | TGAGGACAGG | CGAAGGCTTC | 960 |
| CTCTGTGTAT | TTGCCATCAA | TAATAGCAAG | TCATTGCGG | ATATTAACCT | CTACAGGGAG | 1020 |
| CAGATTAAGC | GAGTAAAAGA | CTCGGATGAT | GTACCTATGG | TGCTAGTGGG | AAACAAGTGT | 1080 |
| GATTTGCCAA | CAAGGACAGT | TGATACAAAA | CAAGCCCACG | AACTGGCCAA | GAGTTACGGG | 1140 |
| ATTCCATTCA | TTGAAACCTC | AGCCAAGACC | AGACAGGGTG | TTGAAGATGC | TTTTTACACA | 1200 |
| CTGGTAAGAG | AAATACGCCA | GTACCGAATG | AAAAAACTCA | ACAGCAGTGA | TGATGGGACT | 1260 |
| CAGGGTTGTA | TGGGATTGCC | ATGTGTGGTG | ATGTAACAAG | ATACTTTTAA | AGTTTTGTCA | 1320 |
| GAAAAGAGCC | ACTTTCAAGC | TGCACTGACA | CCCTGGTCCT | GACTTCCTGG | AGGAGAAGTA | 1380 |
| TTCCTGTTGC | TGTCTTCAGT | CTCACAGAGA | AGCTCCTGCT | ACTTCCCCAG | CTCTCAGTAG | 1440 |
| TTTAGTACAA | TAATCTCTAT | TTGAGAAGTT | CTCAGAATAA | CTACCTCCTC | ACTTGGCTGT | 1500 |
| CTGACCAGAG | AATGCACCTC | TTGTTACTCC | CTGTTATTTT | TCTGCCCTGG | GTTCTTCCAC | 1560 |
| AGCACAAACA | CACCTCAACA | CACCTCTGCC | ACCCCAGGTT | TTTCATCTGA | AAAGCAGTTC | 1620 |
| ATGTCTGAAA | CAGAGAACCA | AACCGCAAAC | GTGAAATTCT | ATTGAAAACA | GTGTCTTGAG | 1680 |
| CTCTAAAGTA | GCAACTGCTG | GTGATTTTTT | TTTTCTTTTT | ACTGTTGAAC | TTAGAACTAT | 1740 |
| GCCTAATTTT | TGGAGAAATG | TCATAAATTA | CTGTTTTGCC | AAGAATATAG | TTATTATTGC | 1800 |
| TGTTTGGTTT | GTTTATAATG | TTATCGGCTC | TATTCTCTAA | ACTGGCATCT | GCTCTAGATT | 1860 |
| CATAAATACA | AAAATGAATA | CTGAATTTTG | AGTCTATCCT | AGTCTTCACA | ACTTTGACGT | 1920 |
| AATTAAATCC | AACTTTTCAC | AGTGAAGTGC | CTTTTTCCTA | GAAGTGGTTT | GTAGACTCCT | 1980 |
| TTATAATATT | TCAGTGGAAT | AGATGTCTCA | AAAATCCTTA | TGCATGAAAT | GAATGTCTGA | 2040 |
| GATACGTCTG | TGACTTATCT | ACCATTGAAG | GAAAGCTATA | TCTATTTGAG | AGCAGATGCC | 2100 |
| ATTTTGTACA | TGTATGAAAT | TGGTTTTCCA | GAGGCCTGTT | TTGGGGCTTT | CCCAGGAGAA | 2160 |
| AGATGAAACT | GAAAGCATAT | GAATAATTTC | ACTTAATAAT | TTTACCTAA | TCTCCACTTT | 2220 |
| TTTCATAGGT | TACTACCTAT | ACAATGTATG | TAATTTGTTT | CCCCTAGCTT | ACTGATAAAC | 2280 |
| CTAATATTCA | ATGAACTTCC | ATTTGTATTC | AAATTGTGT | CATACCAGAA | AGCTCTACAT | 2340 |

```
TTGCAGATGT  TCAAATATTG  TAAAACTTTG  GTGCATTGTT  ATTTAATAGC  TGTGATCAGT    2400

GATTTTCAAA  CCTCAAATAT  AGTATATTAA  CAAATT                                2436
```

( 2 ) INFORMATION FOR SEQ ID NO:17:

( i ) SEQUENCE CHARACTERISTICS:
        ( A ) LENGTH: 2977 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
CCGAATGTGA  CCGCCTCCCG  CTCCCTCACC  CGCCGCGGGG  AGGAGGAGCG  GGCGAGAAGC      60

TGCCGCCGAA  CGACAGGACG  TTGGGGCGGC  CTGGCTCCCT  CAGGTTTAAG  AATTGTTTAA     120

GCTGCATCAA  TGGAGCACAT  ACAGGGAGCT  TGGAAGACGA  TCAGCAATGG  TTTTGGATTC     180

AAAGATGCCG  TGTTGATGG   CTCCAGCTGC  ATCTCTCCTA  CAATAGTTCA  GCAGTTTGGC     240

TATCAGCGCC  GGGCATCAGA  TGATGGCAAA  CTCACAGATC  CTTCTAAGAC  AAGCAACACT     300

ATCCGTGTTT  TCTTGCCGAA  CAAGCAAAGA  ACAGTGGTCA  ATGTGCGAAA  TGGAATGAGC     360

TTGCATGACT  GCCTTATGAA  AGCACTCAAG  GTGAGGGGCC  TGCAACCAGA  GTGCTGTGCA     420

GTGTTCAGAC  TTCTCCACGA  ACACAAAGGT  AAAAAGCAC   GCTTAGATTG  GAATACTGAT     480

GCTGCGTCTT  TGATTGGAGA  AGAACTTCAA  GTAGATTTCC  TGGATCATGT  TCCCCTCACA     540

ACACACAACT  TTGCTCGGAA  GACGTTCCTG  AAGCTTGCCT  TCTGTGACAT  CTGTCAGAAA     600

TTCCTGCTCA  ATGGATTTCG  ATGTCAGACT  TGTGGCTACA  AATTTCATGA  GCACTGTAGC     660

ACCAAAGTAC  CTACTATGTG  TGTGGACTGG  AGTAACATCA  GACAACTCTT  ATTGTTTCCA     720

AATTCCACTA  TTGGTGATAG  TGGAGTCCCA  GCACTACCTT  CTTTGACTAT  GCGTCGTATG     780

CGAGAGTCTG  TTTCCAGGAT  GCCTGTTAGT  TCTCAGCACA  GATATTCTAC  ACCTCACGCC     840

TTCACCTTTA  ACACCTCCAG  TCCCTCATCT  GAAGGTTCCC  TCTCCAGAG   GCAGAGGTCG     900

ACATCCACAC  CTAATGTCCA  CATGGTCAGC  ACCACGCTGC  CTGTGGACAG  CAGGATGATT     960

GAGGATGCAA  TTCGAAGTCA  CAGCGAATCA  GCCTCACCTT  CAGCCCTGTC  CAGTAGCCCC    1020

AACAATCTGA  GCCCAACAGG  CTGGTCACAG  CCGAAAACCC  CCGTGCCAGC  ACAAAGAGAG    1080

CGGGCACCAG  TATCTGGGAC  CCAGGAGAAA  AACAAAATTA  GGCCTCGTGG  ACAGAGAGAT    1140

TCAAGCTATT  ATTGGGAAAT  AGAAGCCAGT  GAAGTGATGC  TGTCCACTCG  GATTGGGTCA    1200

GGCTCTTTTG  GAACTGTTTA  TAAGGGTAAA  TGGCACGGAG  ATGTTGCAGT  AAAGATCCTA    1260

AAGGTTGTCG  ACCCAACCCC  AGAGCAATTC  CAGGCCTTCA  GGAATGAGGT  GGCTGTTCTG    1320

CGCAAAACAC  GGCATGTGAA  CATTCTGCTT  TTCATGGGGT  ACATGACAAA  GGACAACCTG    1380

GCAATTGTGA  CCCAGTGGTG  CGAGGGCAGC  AGCCTCTACA  ACACCTGCA   TGTCCAGGAG    1440

ACCAAGTTTC  AGATGTTCCA  GCTAATTGAC  ATTGCCCGGC  AGACGGCTCA  GGGAATGGAC    1500

TATTTGCATG  CAAAGAACAT  CATCCATAGA  GACATGAAAT  CCAACAATAT  ATTTCTCCAT    1560

GAAGGCTTAA  CAGTGAAAAT  TGGAGATTTT  GGTTTGGCAA  CAGTAAAGTC  ACGCTGGAGT    1620

GGTTCTCAGC  AGGTTGAACA  ACCTACTGGC  TCTGTCCTCT  GGATGGCCCC  AGAGGTGATC    1680

CGAATGCAGG  ATAACAACCC  ATTCAGTTTC  CAGTCGGATG  TCTACTCCTA  TGGCATCGTA    1740

TTGTATGAAC  TGATGACGGG  GGAGCTTCCT  TATTCTCACA  TCAACAACCG  AGATCAGATC    1800

ATCTTCATGG  TGGGCCGAGG  ATATGCCTCC  CCAGATCTTA  GTAAGCTATA  TAAGAACTGC    1860

CCCAAAGCAA  TGAAGAGGCT  GGTAGCTGAC  TGTGTGAAGA  AAGTAAAGGA  AGAGAGGCCT    1920

CTTTTTCCCC  AGATCCTGTC  TTCCATTGAG  CTGCTCCAAC  ACTCTCTACC  GAAGATCAAC    1980
```

| | | | | | | |
|---|---|---|---|---|---|---|
| CGGAGCGCTT | CCGAGCCATC | CTTGCATCGG | GCAGCCCACA | CTGAGGATAT | CAATGCTTGC | 2040 |
| ACGCTGACCA | CGTCCCCGAG | GCTGCCTGTC | TTCTAGTTGA | CTTTGCACCT | GTCTTCAGGC | 2100 |
| TGCCAGGGGA | GGAGGAGAAG | CCAGCAGGCA | CCACTTTTCT | GCTCCCTTTC | TCCAGAGGCA | 2160 |
| GAACACATGT | TTTCAGAGAA | GCTCTGCTAA | GGACCTTCTA | GACTGCTCAC | AGGGCCTTAA | 2220 |
| CTTCATGTTG | CCTTCTTTTC | TATCCCTTTG | GGCCCTGGGA | GAAGGAAGCC | ATTTGCAGTG | 2280 |
| CTGGTGTGTC | CTGCTCCCTC | CCCACATTCC | CCATGCTCAA | GGCCCAGCCT | TCTGTAGATG | 2340 |
| CGCAAGTGGA | TGTTGATGGT | AGTACAAAAA | GCAGGGCCC | AGCCCCAGCT | GTTGGCTACA | 2400 |
| TGAGTATTTA | GAGGAAGTAA | GGTAGCAGGC | AGTCCAGCCC | TGATGTGGAG | ACACATGGGA | 2460 |
| TTTTGGAAAT | CAGCTTCTGG | AGGAATGCAT | GTCACAGGCG | GGACTTTCTT | CAGAGAGTGG | 2520 |
| TGCAGCGCCA | GACATTTGC | ACATAAGGCA | CCAAACAGCC | CAGGACTGCC | GAGACTCTGG | 2580 |
| CCGCCCGAAG | GAGCCTGCTT | TGGTACTATG | GAACTTTTCT | TAGGGACAC | GTCCTCCTTT | 2640 |
| CACAGCTTCT | AAGGTGTCCA | GTGCATTGGG | ATGGTTTTCC | AGGCAAGGCA | CTCGGCCAAT | 2700 |
| CCGCATCTCA | GCCCTCTCAG | GAGCAGTCTT | CCATCATGCT | GAATTTTGTC | TTCCAGGAGC | 2760 |
| TGCCCCTATG | GGGCGGGCCG | CAGGGCCAGC | CTGTTTCTCT | AACAAACAAA | CAAACAAACA | 2820 |
| GCCTTGTTTC | TCTAGTCACA | TCATGTGTAT | ACAAGGAAGC | CAGGAATACA | GGTTTTCTTG | 2880 |
| ATGATTTGGG | TTTTAATTTT | GTTTTATTG | CACCTGACAA | AATACAGTTA | TCTGATGGTC | 2940 |
| CCTCAATTAT | GTTATTTAA | TAAAATAAAT | TAAATTT | | | 2977 |

( 2 ) INFORMATION FOR SEQ ID NO:18:

( i ) SEQUENCE CHARACTERISTICS:
        ( A ) LENGTH: 2517 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

| | | | | | | |
|---|---|---|---|---|---|---|
| GGAATTCCGT | GGCCGGGACT | TTGCAGGCAG | CGGCGGCCGG | GGGCGGAGCG | GGATCGAGCC | 60 |
| CTCGCCGAGG | CCTGCCGCCA | TGGGCCCGCG | CCGCCGCCGC | CGCCTGTCAC | CCGGGCCGCG | 120 |
| CGGGCCGTGA | GCGTCATGGC | CTTGGCCGGG | GCCCTGCGG | GCGGCCCATG | CGCGCCGGCG | 180 |
| CTGGAGGCCC | TGCTCGGGGC | CGGCGCGCTG | CGGCTGCTCG | ACTCCTCGCA | GATCGTCATC | 240 |
| ATCTCCGCCG | CGCAGGACGC | CAGCGCCCCG | CCGGCTCCCA | CCGGCCCCGC | GGCGCCCGCC | 300 |
| GCCGGCCCCT | GCGACCCTGA | CCTGCTGCTC | TTCGCCACAC | CGCAGGCGCC | CGGCCCACA | 360 |
| CCCAGTGCGC | CGCGGCCCGC | GCTCGGCCGC | CCGCCGGTGA | AGCGGAGGCT | GGACCTGGAA | 420 |
| ACTGACCATC | AGTACCTGGC | CGAGAGCAGT | GGGCCAGCTC | GGGGCAGAGG | CCGCCATCCA | 480 |
| GGAAAAGGTG | TGAAATCCCC | GGGGGAGAAG | TCACGCTATG | AGACCTCACT | GAATCTGACC | 540 |
| ACCAAGCGCT | TCCTGGAGCT | GCTGAGCCAC | TCGGCTGACG | GTGTCGTCGA | CCTGAACTGG | 600 |
| GCTGCCGAGG | TGCTGAAGGT | GCAGAAGCGG | CGCATCTATG | ACATCACCAA | CGTCCTTGAG | 660 |
| GGCATCCAGC | TCATTGCCAA | GAAGTCCAAG | AACCACATCC | AGTGGCTGGG | CAGCCACACC | 720 |
| ACAGTGGGCG | TCGGCGGACG | GCTTGAGGGG | TTGACCCAGG | ACCTCCGACA | GCTGCAGGAG | 780 |
| AGCGAGCAGC | AGCTGGACCA | CCTGATGAAT | ATCTGTACTA | CGCAGCTGCG | CCTGCTCTCC | 840 |
| GAGGACACTG | ACAGCCAGCG | CCTGGCCTAC | GTGACGTGTC | AGGACCTTCG | TAGCATTGCA | 900 |
| GACCCTGCAG | AGCAGATGGT | TATGGTGATC | AAAGCCCCTC | CTGAGACCCA | GCTCCAAGCC | 960 |
| GTGGACTCTT | CGGAGAACTT | TCAGATCTCC | CTTAAGAGCA | ACAAGGCCC | GATCGATGTT | 1020 |

-continued

| | | | | | |
|---|---|---|---|---|---|
| TTCCTGTGCC | CTGAGGAGAC | CGTAGGTGGG | ATCAGCCCTG | GGAAGACCCC | ATCCCAGGAG | 1080 |
| GTCACTTCTG | AGGAGGAGAA | CAGGGCCACT | GACTCTGCCA | CCATAGTGTC | ACCACCACCA | 1140 |
| TCATCTCCCC | CCTCATCCCT | CACCACAGAT | CCCAGCCAGT | CTCTACTCAG | CCTGGAGCAA | 1200 |
| GAACCGCTGT | TGTCCCGGAT | GGGCAGCCTG | CGGGCTCCCG | TGGACGAGGA | CCGCCTGTCC | 1260 |
| CCGCTGGTGG | CGGCCGACTC | GCTCCTGGAG | CATGTGCGGG | AGGACTTCTC | CGGCCTCCTC | 1320 |
| CCTGAGGAGT | TCATCAGCCT | TTCCCCACCC | CACGAGGCCC | TCGACTACCA | CTTCGGCCTC | 1380 |
| GAGGAGGGCG | AGGGCATCAG | AGACCTCTTC | GACTGTGACT | TGGGGACCT | CACCCCCTG | 1440 |
| GATTTCTGAC | AGGGCTTGGA | GGGACCAGGG | TTTCCAGAGT | AGCTCACCTT | GTCTCTGCAG | 1500 |
| CCCTGGAGCC | CCCTGTCCCT | GGCCGTCCTC | CCAGCCTGTT | TGGAAACATT | TAATTTATAC | 1560 |
| CCCTCTCCTC | TGTCTCCAGA | AGCTTCTAGC | TCTGGGGTCT | GGCTACCGCT | AGGAGGCTGA | 1620 |
| GCAAGCCAGG | AAGGGAAGGA | GTCTGTGTGG | TGTGTATGTG | CATGCAGCCT | ACACCCACAC | 1680 |
| GTGTGTACCG | GGGGTGAATG | TGTGTGAGCA | TGTGTGTGT | CATGTACCGG | GGAATGAAGG | 1740 |
| TGAACATACA | CCTCTGTGTG | TGCACTGCAG | ACACGCCCCA | GTGTGTCCAC | ATGTGTGTGC | 1800 |
| ATGAGTCCAT | CTCTGCGCGT | GGGGGGGCTC | TAACTGCACT | TTCGGCCCTT | TTGCTCGTGG | 1860 |
| GGTCCCACAA | GGCCCAGGGC | AGTGCCTGCT | CCCAGAATCT | GGTGCTCTGA | CCAGGCCAGG | 1920 |
| TGGGGAGGCT | TTGGCTGGCT | GGGCGTGTAG | GACGGTGAGA | GCACTTCTGT | CTTAAAGGTT | 1980 |
| TTTTCTGATT | GAAGCTTTAA | TGGAGCGTTA | TTTATTTATC | GAGGCCTCTT | TGGTGAGCCT | 2040 |
| GGGGAATCAG | CAAAAGGGGA | GGAGGGGTGT | GGGGTTGATA | CCCCAACTCC | CTCTACCCTT | 2100 |
| GAGCAAGGGC | AGGGGTCCCT | GAGCTGTTCT | TCTGCCCCAT | ACTGAAGGAA | CTGAGGCCTG | 2160 |
| GGTGATTTAT | TTATTGGGAA | AGTGAGGGAG | GGAGACAGAC | TGACTGACAG | CCATGGGTGG | 2220 |
| TCAGATGGTG | GGGTGGGCCC | TCTCCAGGGG | GCCAGTTCAG | GGCCAGCTG | CCCCCAGGA | 2280 |
| TGGATATGAG | ATGGGAGAGG | TGAGTGGGGG | ACCTTCACTG | ATGTGGGCAG | GAGGGGTGGT | 2340 |
| GAAGGCCTCC | CCCAGCCCAG | ACCCTGTGGT | CCCTCCTGCA | GTGTCTGAAG | CGCCTGCCTC | 2400 |
| CCCACTGCTC | TGCCCCACCC | TCCAATCTGC | ACTTTGATTT | GCTTCCTAAC | AGCTCTGTTC | 2460 |
| CCTCCTGCTT | TGGTTTTAAT | AAATATTTTG | ATGACGTTAA | AAAAGGAAT | TCGATAT | 2517 |

( 2 ) INFORMATION FOR SEQ ID NO:19:

( i ) SEQUENCE CHARACTERISTICS:
        ( A ) LENGTH: 35100 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:19:

| | | | | | |
|---|---|---|---|---|---|
| AATTCACCAG | TGAAGCCATC | TGGTCCTGGG | CTTTGCTTTG | TCGGAGGTT | TTTGATTACT | 60 |
| GATTAAATTT | CTTTTCTTGT | TATAGGTTTA | TTTGGATTTT | CTTTTTCTTC | TTGAGTCAGC | 120 |
| TTTGATTGAC | ATTCATGATT | GCTAAAGGTT | CAAAACACTT | TTCTGAAAAA | GAAAGTACAT | 180 |
| ATATACACTC | ATAAATATAC | ATACAAACAC | ACACATACAC | ACCACACACA | CACCTGAGTA | 240 |
| CACGGGAATG | ATCATTTTCC | TGGATCAATG | TTATATCAGG | ATTTTCAAT | TCAAGAAGG | 300 |
| AACTTTAGGC | TGGGTATAGT | GGCTCATACC | TATAATCCCA | GTACTTTGGG | AAGCCAAGGT | 360 |
| ATGCGAATCA | CTTGAGCTCA | GGGGTTTGAG | ACCAGCCTGG | ACAACATGGT | GAAACCCCAT | 420 |
| GTCTACCAAA | AATACAGAAA | TTTGCTAGGA | ATGGTGGCAC | ATGCCCTGT | AGTCCCAACT | 480 |
| ACTCAGGAGG | ATGAGGTAGG | AGGATGGCTT | GAGTCCGGGA | GGTGGAGGTT | GCAGTGAGCC | 540 |
| GAGATCACAC | TACTGCACTC | CAGCCTGGGT | GACAGAACCA | AACCCTGTCT | CAGAAAAAAA | 600 |

| | | | | | | |
|---|---|---|---|---|---|---|
| AAAAGAAAAA | AAGAAGAAGA | AATGACCATG | TTCTTTAGAG | ATAAGAAGTA | AAATACTAAG | 660 |
| CGAATCAACT | AAAAGAGGTA | AAAGCAATTG | CCTCCAGGAA | AAGAGGGAGC | AAAGGAATGC | 720 |
| TATATATTTT | AAGAATTATG | CAGAACAATT | AGATTCTTTG | TAAAAATAAA | TAAACAATGT | 780 |
| AAGTAACGCA | CAAAAGATAG | TTTTATAACC | AGACTGCTGG | GATCCAAATC | CTATCTCCAC | 840 |
| CATTTGGTAG | CTGTTTGACT | ATGGACAAGC | TTAAGGCACT | TGATCTCTCT | GAGCTTTAGT | 900 |
| TTTCCCATCT | GTGAAATGAG | AATGACAATA | GTACTTACCT | ACATAAAGTT | TTGCAGTACT | 960 |
| AAAGGAGACA | GTGAATGTAA | AAGGTTTGGC | TAGTAAATGT | CCTGTAAAAG | GAAGCTTATT | 1020 |
| GCCAATATTA | TCAGGCTCTC | CCAGACCAAC | CTGTATACAG | GAAGAAAACA | AACTCCGTTT | 1080 |
| CTCCTATAGT | CTCACAACAC | AAAATACTTC | TGACCCCAGA | TGTAGAGGAT | GGGGCATATT | 1140 |
| TCCCCATACA | CCAAGCAATC | AACCAATTGT | TCAGATTCTG | CAGCAGACAC | GAATCTGGTG | 1200 |
| CCCTCCGATT | CAATTTGAAC | ACTATATTTA | CCTAGAGATA | ACGTCAGATC | TCACAGCTTG | 1260 |
| AAGGCTTGAG | CCAGGAGTTT | GAGGCTGCAG | TGAGCTATGA | TCGAGCCACA | GAGCTCCAGC | 1320 |
| CTGGGCAACA | GAGTGAAACT | GCGTCTCTAA | AATAATAATA | ATAAATTTTT | AAAAGATATG | 1380 |
| CATTACTTTG | GAGATTCCAA | GGATTTAGG | AGTTGTAAGC | CAGGACATCA | GGGTAAAGAA | 1440 |
| AAAATATATA | TGTCACAATA | TCATGCAACC | TAACTTCTCT | TTGGGATCTG | CCAGAGCCAC | 1500 |
| CTGATCACTC | TGAAGACCCT | CATTTGTGCT | ACTGACTAAC | GGTCTGGCTG | CTCTTGGACA | 1560 |
| TGTCTCTTCT | CCCAAGACCC | CTTGAAGATG | GCTTAGAAG | GCCCCAAAC | TTAGCTAGCT | 1620 |
| CCCCCCAAGC | TCAGGCTGGC | CCTGCCCCAG | ACTGCGACCC | CTCCCTCTTG | GGTTCAAGGC | 1680 |
| TTTGTTTTCT | TCTTAAAGAC | CCAAGATTTC | CAAACTCTGT | GGTTGCCTTG | CCTAGCTAAA | 1740 |
| AGGGGAAGAA | GAGGATCAGC | CCAAGGAGGA | GGAAGAGGAA | AACAAGACAA | ACAGCCAGTG | 1800 |
| CAGAGGAGAG | GAACGTGTGT | CCAGTGTCCC | GATCCCTGCG | GAGCTAGTAG | CTGAGAGCTC | 1860 |
| TGTGCCCTGG | GCACCTTGCA | GCCCTGCACC | TGCCTGCCAC | TTCCCCACCG | AGGCCATGGG | 1920 |
| CCCAGGAGTT | CTGCTGCTCC | TGCTGGTGGC | CACAGCTTGG | CATGGTAAGA | GCAGAACGGG | 1980 |
| GGGTGGGGGA | CTTTGTTGGG | GTGTGATGGA | GAAGACCCCT | GTGAAAGGAT | TCAGTCCTTG | 2040 |
| CCCCTCACTG | GGTGTCCTCA | GGCTGTTTTA | GTCTCCCCAA | CACTGGACTG | CAGGCTTGTG | 2100 |
| GGTATCTGCT | TTGGAGAGGT | AGTGGGGTGA | AAAGAGATGG | GTGTGGTGGA | ACTGGTCCAC | 2160 |
| CTGGTGCTGT | GGATCTGTCC | CAGCTCTGCC | AGCGACTCAC | TGTGTGTCCT | GAGCAAGCCT | 2220 |
| CTGATACTCT | TGAGGCTTCA | GTGTCCACTT | CTATTCAATT | GCAGGTGTTG | GGGCAGGGG | 2280 |
| GACAGTGATA | GACTAGACCA | GAGCAGTGCT | TTTCATACTT | TCCTGTGCAT | ACAAGTTACC | 2340 |
| TGAGGATTTT | GTTACAATGC | AGATTCAGAC | TCAGTCGGTC | TCAGGTGCGA | CCTGAGATTC | 2400 |
| TGTATATCCA | ACACACTCCT | GGGAGATGTG | AGATGCCGGC | ACTGCTGGTC | CAGACCTACA | 2460 |
| CTGAGTTGGG | AGGACCTGGA | GAGCTCCTGA | TGGCTCTGGC | AGCTCTGCCA | GCCTGTGATT | 2520 |
| CGATGATTCT | ATGCAAGATC | TGATTTGGAA | GGGCCTGATA | GGGGTGGTGG | TTCTTCCTTG | 2580 |
| GGTGGCTTGT | GTAAGGGTC | AGAGGGGAGA | GACAAGAGGT | TGGCCTCTCT | GGCCCAGGGC | 2640 |
| TCAGGAGAGG | GGAATTCGGG | GTGAAATAGG | TATAGGGCTA | GAGGAGGGAT | TGGGAAGAGG | 2700 |
| CCAGTGAGGG | TCTCCTGGAC | CAGAGCCCTC | CCAGACACAG | GCTGCCAAGT | CTCAGGAGGT | 2760 |
| CCCCAGGCTG | TAGCAGTTCT | GCAGAATTTC | CATCTGGGAG | GGAACATGAC | TAGAGGTGAG | 2820 |
| GGGCTGCTGT | GCTTGGCTTG | TTGGCCCAAC | AAACACATTT | CTATTGCCTG | CTTATTCAAA | 2880 |
| GGGACCTTGG | GGGAGGATGG | GGATTGAAGG | GGAGAAAGGA | CAGCCTCATA | CTGGCCTCTT | 2940 |
| CACAGAAGGA | CCCTAAGGCC | GTGGCGCTTC | TGGTCCCTGA | TGAGGAGGAG | ATGGCCCACT | 3000 |

```
GACCATCCTT CTCTGGCCCA GGCAATCACA CTGAGCTTGA GTATTTGGGT TTTTTTTTTT    3060
TTTTTCCTGA GACAGAGTCT CTCTCTGTCA CCAGGCTGGA GTACAGTGGC ACAATCTCGG    3120
CTCACTGCAA CCTCCACCTC CCGGGTTCAA GTGTTTCTCC TGTCTCAGCC TCCCAAGCTG    3180
GGATTACAGG CATACACCAT CATGACTGGC TAATTTTGT ATTTTAGTA GAGATGGGAT      3240
TTCACCATGT TGGCCAAGCT GGTCTCGAAC TCCTGACCTC AGGTGATCCA CCTGCCTTGG    3300
CCTCCCAAAG TGTTGGGATT ACTGGTGTGA GTCACGGCGC CGGCCTGGA CTTCTTATTT     3360
TGCAATGTAA CTTACATGCA GTAGAAAGCA CAGGTTCTTA AGTTCAATGA GGTCTGACAA    3420
ATGCACACAC AGTGTACCCG CCACCCCCTT CATCTCAGAG AGTCCCACAG GTTGATTTC     3480
ACTGCCTTGT CCTATCCTTA CACCCACAAC CTGCCTGTGG GGCAAAAACG GAAAAGTATC    3540
TGAGCCAGGT CTCAATTTAA TTTTATTTTT TTTATTGAGA TGGAGTCTTG TGGCCAGGCA    3600
TGGTGGCTCA CACCTGTAAT CCCAGCACTC TGGGAGGCCG AGGCGGGTGG ATCACAAGAT    3660
CAGGAGTTTC AGACCAGCCT CGCCAATATG GTGAAGCCCC CTCTCTACTA AAAATACAA     3720
AAATTAGCCG GGTGTGGTGG TGGGTTCCTG TAGTTCCAGC TACTCAGGAG GCTGAGGTGG    3780
GAGAATCACT TGAACCCGGG AGGCAGAGGT TGCAGTGAGC TGAGATCATG CCACTGCACT    3840
CCAGCCTAGG CGACAGAGCA AGACTCCATC TCCTTCCTTT CTTTCTTCCT TCCTTCCTTC    3900
CTTCCTTCCT TCCTTCCTTC CTTCCTTCCT TCCTTCCTTC CTTCCTTCTT TCTTTCTTTC    3960
TTTCTTTCTT TCTTTCTTTC TTTCTTTCTT TCTTTTTTCT ATCTTTTTGA GACCGAGTCT    4020
TGCTCTGTTG CCCAGGCTGG AGTGCAATGG CATGGATCTC GGCTCACTGC AACCTCCGCC    4080
TCCGGGGTTC AAGCAATTCT GCCACTCCTG AGTAGCTGTG ATTACTGGTG CCTGCCACCA    4140
CACCCAGCTA ATTTTTTTAT TTTTGGTAGA GACAGGGTTT TATCATGCTG GCCATGCTGG    4200
TCTCGAACTC CTGAACTCAA GCGATCCCCC TGCCTTGGCG TCCCAAAGTG CTGGGATTAC    4260
AGGCATGAGC CACTGTGCCT GGCTTCAATC AATTTAGAAG TTTATTTTGC CAAGGTTAAG    4320
GACATGCTGG CGAGAAAAAA ACATGGAGTC ACAAAAACAT TCTGTGGTCT GTGCCATTCT    4380
GGATGAATTC GAGGGCTTTA ATATTTAAAG GGGAAAGTGG GCTGGAGGGG AAAAGGGGAG    4440
GTTGTGGTAA TCCACATGTT GCAAAAGAAA AGCAGCAGGT AGGGGAACAG TCAATTATCT    4500
CGGTTCAGTA AATTGGCTCT TTACATAGGG AAAGTGAACA TAGAGGAGCT GCCTGTGGGA    4560
TATTTTACCT TTTATCTGTC GCTATCTGCT TAGGAATAAA AGGCAAGGCA GCTTCTTGCA    4620
TGACTCAGTT TCCAGCTTGA TTTTTCCTTT TGGCAGAGTG AATTAGGGTC CCAAGTTTTT    4680
ATTTTCCCTT CACAGGGGCA TGGTGTGTGG GAGGGGGGCC AGATGGTTTT CCAGGGTCCA    4740
GTCCCAAGAG AAAGAAGAGA TGGGGAGGCT GGAAACCTAA GTTTCAGCC CAACAGACCA     4800
ATGATGAGTG GATGAGGGGC CACTGTGAGG AGACTGGGGA TGGTATTGGA GGACCCTAGA    4860
GAGAGAGGGG GGCTCTCTCT TCATTACTGC GATGAGATCC TGGGCTGAAG AGGGGCTGTG    4920
TCCAGCCTTA GTGTGCAGTG TGTGTGTGTG TGTGTGTGTG TGTGTGTGTG TGTGTGTGTG    4980
TGTGTGTGTT GGGAGAGAAG AGTAGAGATT GGGGCACATT CTGGAAGTGA TGAGGGAGGG    5040
GCTTCCAGGC AAGTGGGAGC TAGTGGAGAG GTGTGGGGCA TGGGAGAAT TGGGAGTGG      5100
AGATGAGAGG GGGGAAGAAT GGACAGGCAC AGAAGGGGAC CTCAGTTAAT GTTCATAAGC    5160
CCATGCCCCC ACCCCGAGGA GGATGGGGGC CAAGCCGGCT TCCTTCCCTG CTAGCCAAGC    5220
CAGCAGGGGA AGTTGGCTGC GGAAGTTGCG GGTATCAGCC TTATCCTGCG TGAATACCTG    5280
GGACAATAGG ATAGGACAAA ATAGGGCAGA CACCGCTCCC TGACCACATT TCCTGGAGGC    5340
CAAGGCAGGG TCTAGAGAGA CAGGCTGGGG GAAGGGATGG GAGAAGCCCA CTGTAAGGTG    5400
```

```
TGAGGCAGGT GTAAAAAAGG AACAAATGGA ATCACAGAAT CCAAGGTTAA AATCTTGAGC        5460
GATCAGAGTT GGCCCAGAAG GGACATTAGA AATGTAGCAA TTAAAGCAGG TGCCCAGGGC        5520
AGGAGTAGTT CTATACATCA TCTCACTCAA CCTTCAGCTG AAGTTTTGG GGTGGGAGCT         5580
GGGATTATTC CCATCAGACA GAAGAATAGC CTGAGGCTCA AAGAGGTTAA GAAACTAACC        5640
CAGCTGGTAA GGGAAGAACC AAGATCCAAA CCCAAGTTGG TGTGAGCCCA CACTCCAAGC        5700
TGTTTCCTGC TATAAACCC CGGCCTGGGG GCCCTAGATT GCTGCAGCAG TGATAGGGCA         5760
GCCCCAGCTC TGTTGAGATT TGCTAAAAAG GCTGCTAGAA ATGACACTTG TCCCTCTTCC        5820
TGGCAGTTGC ACTGCATAGG AGGGCTACAA CCCCAGGTGG CAGGCTTGGC AGTATTCACA        5880
ATTCACTCAA TCCCGTTTGC TGATCAGAGT CTTGGGGAGA AGGGATGCAC ATTCTGATGA        5940
ATACAAAATC AAAACGTGAA TTAAGCCATC CTGAAAGGAC TTGAGAGAGG AAACCTTTCC        6000
AATTCTGGGC TCTATGGTGG GGCAGGGGA ATTTCCATTT CAAGGGGGTT TGCAGAGAAC         6060
AATGGAGATA CCCTGAATTC ACCGAAAGCC CTCGGGGTGG CCTGTCATTG TGCCCCCATC        6120
ACTGGGAAGA GGAAGGGCCA GAGCTGAGGA GTTGGATGGC CAGGGTCAGC CAGTGGGTCA        6180
GCGTCAGAGC CCAGCCTCAC AGCTGCCCCG CAAGTGGCAC TCCCTCTCCC TGCCTGGAGA        6240
GAGGAGAGTG GCTAGGAGGC TGGGGAAGCA GAAGTGAGAA CATCCCTGTA GAAGGGCCAC        6300
AGGCTGAGCG GAAACCGGGG GCTGAGCCTG ACGCCAACAA TGTGTTTCCG CCCACACAGG        6360
CTGGGGGGCG CCTGGCAGCC CCTCGGAGGC TTGAATCAGC TCTCACTTCC CTCCTTTGCC        6420
CCTATTTTAG GCCCTGGAAA AATGCTGACG CTGCAGAGGC AACGGGCCTT CTTCCCGGAC        6480
AGCCTGATAG GGGTTTCAAG TTCTCTTTTC TCCTTCAAGA AAATTTCCT TAAAAGAGAT         6540
TGGCTTCCCA GTAAACACAG ATGTGTGGGG GTGCCGGGGT GAGCTGCTGG GTGTAGACTA        6600
GGTAATAAAC ATAGTGACTA ACTCTTACTG AGCCATTTAT TTGGTGACAG GTGATGTTCT        6660
AAAGTCTTCC CATGCATTTA AAATGCCTAA CATACCAATG AGTGGGTACG ATGATTGTCC        6720
CTGTTTTATA GGTGGGGAAA CTGAGGCATG GCACCTCCCC ATCCACTGT GCTGCAGACC         6780
AGATGTCCAT TGGTGGGAGC GGGCACACCA GGAGATTCTT GGGACCTCTC TAACTCTGCT        6840
GGGCTAAGAT CCTACATCTC TTTTTTTTC TTTCCCATAT GAATTAAGCT GAGGACTTGG         6900
CCGTGAACAT TCCATTCATT TGTTTCTTCA TTCGGTGGTA GAAATACATC CACTTTGTAC        6960
ACAGGGTTAA AAGAGTCCAT TCCTGGGGAG TAGAAAGATG GCATCACAGC AGGGAAGACT        7020
GAGGCAGGAG GCTGAGGACC CCAGGGGAC AGAGGCCTGG GTGAGAGGCT GAGCAAGCTG         7080
CAAGCCCCCT TTCTCAGAGG AGGGACCTCC TGGACATCAG AGACATCAGT CTGTCCCTGA        7140
GCAGGTTGAG GGTTAGGAGC TGAGCAAATG ACCAGGGGC AGGGCTCGT TCAAGGTGGT          7200
CCCTTGATGG CACAGCACCA TCCCTGCCAA GCTACCACCC ATCTCAGAGT CAGGACGGCC        7260
CAAGGGGCGC ATCCTAGACC TCACTTCTGT CTGCTGTCCC TCTCTCCCAC CAGGTCAGGG        7320
AATCCCAGTG ATAGAGCCCA GTGTCCCCGA GCTGGTCGTG AAGCCAGGAG CAACGGTGAC        7380
CTTGCGATGT GTGGGCAATG GCAGCGTGGA ATGGATGGC CCCCATCAC CTCACTGGAC          7440
CCTGTACTCT GATGGCTCCA GCAGCATCCT CAGCACCAAC AACGCTACCT TCCAAAACAC        7500
GGGGACCTAT CGCTGCACTG AGCCTGGAGA CCCCCTGGGA GGCAGCGCCG CCATCCACCT        7560
CTATGTCAAA GGTGAGGAGT CTGAGCCTCC TCCCAAGAGG CCTGACCCGG CAGGCCCAC         7620
TACAATGGGC CCTAAAATTA ACAATCGTAA CAATTCAGCT CTGCATTTAC TGAGTGCTGG        7680
CTATGAGCAA GGACCTGGAA GAGCTGCTAA TGTAATGCAG TCCTCACAAC AACCCTGCAA        7740
GTCGGGTCTA TGATGATGCA TTTTCTAGAA GTGCAGGGAG GTTATCCAAG GTCACACAGC        7800
```

```
CTCACATAGT GGGACTAGAC TGGAGCCCAG GTGCGCCTGA CTCTGGAGCC ACCACGCTGA    7860
AGCATCCGCT GAACTGTCCT GGCGTGGTGT GACCTCAGAT GAATGATCAG CCTCTCTGAG    7920
CTTCCTTGTC ACCTATGTCC AGGTACTCCT TGGCCCAGTG GAGGGAGGGC AGTTGTAACC    7980
CTGTGCCCTC CTCTACTCTA GACCCTGCCC GGCCCTGGAA CGTGCTAGCA CAGGAGGTGG    8040
TCGTGTTCGA GGACCAGGAC GCACTACTGC CCTGTCTGCT CACAGACCCG GTGCTGGAAG    8100
CAGGCGTCTC GCTGGTGCGT GTGCGTGGCC GGCCCCTCAT GCGCCACACC AACTACTCCT    8160
TCTCGCCCTG GCATGGCTTC ACCATCCACA GGGCCAAGTT CATTCAGAGC CAGGACTATC    8220
AATGCAGTGC CCTGATGGGT GGCAGGAAGG TGATGTCCAT CAGCATCCGG CTGAAAGTGC    8280
AGAAAGGTGC GTGGGGCATG GGACCGGCA GCCAGGCCTG AAGAGTGGGG ACAGAGAGCC    8340
GGCGGCCACA TGGGTGGTGA CTGGGGACTG GGTGTGATGG GGGCAGTGG GATGTCCTCT    8400
TTCTTTCACT TCTTCCCCTC AATGGTTCCA CGATCATCTA TGGGGCAGGA CTGACAAGGT    8460
GTCGGGGCAG GGAGACAAAC CACATGTGAG CAAATAACTC AGTGGGCAAG GTCATCTCAG    8520
GTCATTGGAC ATGCTACAAA AATAAACATT CAACATGGTA GCTGAATAAG GAGTGTGTAG    8580
GGCGGGGAGC CTCACTGAGA AGGAAACACT TTATTAGAGC GGAAATCTGA ATGACATGAA    8640
GAAGGTGGCT GTGCAAAGAT CTGCTTCAGC AGGGGACAG TGAGTACCAA GTGGTGAGGT    8700
GGGACAGGC TCTGAATGTT CTAGGTATGG AAAGAGGACG GAAGCTCAGC CTCAGACATG    8760
GATTTCCCAC TGGGGGCCTG CCTAAGGCCA AGTGCTGGGC ATGTGTAGGA GGGATGCTGA    8820
GCCAAGAGGC AGGGAGGAGA TGGTGGGTGC GTGTGATGGC TCTCGCGGTG GCCAGGTAAC    8880
AGTGGAGGTG GAGTCTCACC CTGCTGGGAT GGCAGGCAGG ATTCTGGTTT CTGGGAGGAC    8940
TGGTGAGAGC AAGCAGGACC CCAGCCTGAG GACCTGGGCT TGAGACAGCA ATCAGTCCCT    9000
GTAACAAGGG CCAGGGTCAG AGTGAAGCAG CTAGCCCAAT GCCACTGGGA TCTGAAGCCA    9060
CTAAACCTGC CTAGGGGGTC AAAGGACCCC AGCTGTGTGG GCAGAGGAGG CCATTAGGGC    9120
TCTTTCCTGG CATTTCATCC TGCAGAGCCC TGGGCTGGCC AAGAGCCAAA GGTCCTGGGC    9180
CCTAGTTCTG CCTTGACCCC CCCTCAGGGA CCTTGGGTGA GTCCTTTCAT GTCCCTGGGC    9240
CTTAGGAATC TGGATTAGAT TATCTTTCAA CAGCAGCAAT GGGCATAAAT ATGAATTCAA    9300
GGCCTACTGT GCATCAGGCA TCTTGCTGGC TGCTGGAATA TTCCTGTCAC GGATTTGACA    9360
TTCGACTAGA GTCTAACTAT TAAATAGAAA GTAAATACAA ATGTGATGAG CAAGAAACCA    9420
AGCTGGGGAG TGGCGGGCAT GGAGGTGCTG GGAGGCTAA TTCATATCAG CTGGTCACAG    9480
AAGCCTTGCT GAGGAATTTT TGAGCTAAAG ATCTGAAGGA TGAACAGC CTCCCATTTG    9540
AAGTGTGGGA GGAAAGGCAT TCCAGGAGGG AAAGGTGGGT GCAAAGGCCC TGTGGTAGGA    9600
AAGAGGTCCA GCGGGCTGCA GTGCAGTGAA CAAGGGGTGG GGTTATCAGG GCGGTCAGAA    9660
ACAGGTTGGG CTGTGGAAGG ACTTTGACTT CTTTTCTGAG AGTAATGGGA AGCCCCAAAT    9720
GTTTACAGAG GAGAGAGGCA TGGTCCCATT TATATTTGTA AGAGGTCACT TTGGTGAAGA    9780
ATCTAGGTGT GGGGGGCTTG GAGGGAGGCA GGGAGGTCTC TGAGGAGGCT GGTGCAGAAG    9840
TCCAGAGTGG AGAATGGTGA CGGGACTGGG GAGGGGTAGA GGTGATGGAG AAAGTAGACT    9900
TTCCAAGGTC TCTTTAGGAC AGGCCTTGCA GTGGGGGAC TGGGAGCATC AAGGCTGCCT    9960
CCCAGGATTT GGGATGGGGC AGTGATGGGG ACCCTGGCCT GTGTGTCCTG GCCCATGGCA   10020
GGGAGGAGAG CAATATCTCT ATCATATTCA GGGAGCCTGG GTGTTCAGGG GTCTCTCCCC   10080
CGGTCTCAGT CATCCCAGGG CCCCCAGCCT TGACACTGGT GCCTGCAGAG CTGGTGCGGA   10140
TTCGAGGGGA GGCTGCCCAG ATCGTGTGCT CAGCCAGCAG CGTTGATGTT AACTTTGATG   10200
```

| | | | | | |
|---|---|---|---|---|---|
| TCTTCCTCCA | ACACAACAAC | ACCAAGGTCA | GTCCCTGCAG | ATCACAAGGT | GAAGTCTGGC | 10260 |
| CATCCTCCCA | GCACACCAGG | TTTCCCATGG | TGGAGTCCTG | GGCCCCCAAC | TCCAAACTGG | 10320 |
| CTGTCTTAGC | TGAAGGCACA | GCTCAGACTC | CAGAGAGGGG | TGCAGACTCA | CCCGAGATCT | 10380 |
| CACTCCCAGT | CAGTAGCTGA | CACAGAATCA | GGACTCATGC | TTGTGCCGCT | GAACTTTGTG | 10440 |
| GGGGTGGGTG | GGGGGAGGTG | GTTCTCTGTC | ACCTTGACAC | ATGGCCTTTG | CCCCAGCCTT | 10500 |
| TAGACAAAAG | CCAGAGGTGA | GCTCACTTCT | GATTAGCAA | GGGTTTCCTA | GCCACCATT | 10560 |
| GAAGCCCAGG | AATATAACAG | CTATTTCAGA | AAGACATTGG | GAGAGAGGGA | GGAGGAGGGA | 10620 |
| GGATTCCAGG | AGGGACTCAC | GTTGGGCTGC | CTCTAAGAGC | CCCCTCCCTT | CCCACTGCAC | 10680 |
| CTGCCGTGTT | CCAGACACAG | CCCTAAGCCA | CTTGCATGCA | TATCTCATTT | ACTCCTCACT | 10740 |
| ACAGTCTTGG | GGCAGGGAGC | CAGTATTAGC | CCCATTTTAC | AAGTGAAGCA | ACAGGCTCAG | 10800 |
| AGGAAAGGCA | GATAGTAATC | CTTAAAGGCT | GAGGATTGGA | ACCCAGATCT | TTCTAATCCC | 10860 |
| TAAACTACCT | TGGTATAACA | TCTCCATTCC | TTCTGGCTGC | AGCTCGCAAT | CCCTCAACAA | 10920 |
| TCTGACTTTC | ATAATAACCG | TTACCAAAAA | GTCCTGACCC | TCAACCTCGA | TCAAGTAGAT | 10980 |
| TTCCAACATG | CCGGCAACTA | CTCCTGCGTG | GCCAGCAACG | TGCAGGGCAA | GCACTCCACC | 11040 |
| TCCATGTTCT | TCCGGGTGGT | AGGTAAGCAT | CAGGGTGGTG | GTGGACAGTC | GGTAGGGATC | 11100 |
| CTGCAGGAGT | GTGAGCAGAA | GGGTTTTGTT | GAGGAAGCTG | ATGTCAGGGA | AGGAGACCTG | 11160 |
| CTGAGGATAT | CTCTGCTGGA | GTTTGTTTAT | CCAAGGCCTG | GCTAAGGAGC | CACTCTCCAG | 11220 |
| GAGCTTTCCC | TTACCCTCTC | CTGGGATCTC | TCTCCATCT | TGGAGCTCTT | ACAGTGCATG | 11280 |
| GCTGCATTGG | GTGCACCTTA | GTGCCATTTT | TTGTTTATTT | GGGGATTGGG | GTCCAGTAGC | 11340 |
| TCCCTACTGG | ACTTCATTTG | TTCATTCTTT | CATGCATTCC | TTTATGGAAA | CATGAAAAGA | 11400 |
| CAATGATCAC | CCAGTGATTA | TGGGGGAAGC | ACAAGGTGTC | CTGGGAACAC | TGAAGAGTCC | 11460 |
| CCCCAACCCA | GGCTTCGAGA | AGGTGGCCTC | TAAACTGGGA | TGGGAAGAAT | GAAGGTGAGT | 11520 |
| TGGCCGGGCA | GAAGGGTGGG | AAAGGAAGGG | GAACAGCGCT | TCTGGCAGAG | GGAGGAACAT | 11580 |
| ATGCAAGGCT | CAAAGGCAAA | GAGAACATAG | ATCATTTGGA | ACACTGAAAG | AACTTGACAA | 11640 |
| CAGCTGGGAT | GTGGAGTGGT | GTGAGGAGTG | GCCACAGGGG | AGCAGAGGAG | GTGGCAGAAG | 11700 |
| CCGGAGGTAA | AGGTGTCTTA | AAGTGAGAAA | GAATAACTGC | ATCTTAACCT | ATTGGGAGGT | 11760 |
| CATTGTAAAG | AGGAGAGTGA | TGGGGTCAGA | TTGTACAGAG | GAGGCACTTC | GTGGTGGTCA | 11820 |
| GGAGCACACA | CTCCAGGGCA | GTGTTCCAAC | CTGAGTCTGC | CAAGGACTAG | CAGGTTGCTA | 11880 |
| ACCACCCTGT | GTCTCAGTTT | TCCTACCTGT | AAAATGAAGA | TATTAACAGT | AACTGCCTTC | 11940 |
| ATAGATAGAA | GATAGATAGA | TTAGATAGAT | AGATAGATAG | ATAGATAGAT | AGATAGATAG | 12000 |
| ATAGATAGAT | AGGAAGTACT | TAGAACAGGG | TCTGACACAG | GAAATGCTGT | CCAAGTGTGC | 12060 |
| ACCAGGAGAT | AGTATCTGAG | AAGGCTCAGT | CTGGCACCAT | GTGGGTTGGG | TGGGAACCTG | 12120 |
| GAGGCTGGAG | AATGGGCTGA | AGATGGCCAG | TGGTGTGTGG | AAGAGTCTGA | GATGCAGGGA | 12180 |
| TGAGGAAGAG | AAAGGAGATA | AGGATGACCT | CCAGGTCTCT | GGCTATGGTG | ATTGGGTGCA | 12240 |
| GGCAGTGGCA | GTCACTGGAC | TCAGACCCTG | AAGCAAGGCA | GCAGCTCATC | GGAGTGTGAG | 12300 |
| CAGGCTCTGA | GACATTTAGG | TCTGGCCGTG | CCTCATGTGT | TGAATGTTAT | GGGAGATGGA | 12360 |
| GGTGGCGAGG | AGCATGAGAA | TCATGAGCAT | CACTGCCCCT | AGAGTATGTG | CAAGGCACTG | 12420 |
| GACTTGCAGC | AGATTGTGAG | CTCTGCTGTG | GACCCCAATC | TGCACTGGGA | GCTTTGGCAG | 12480 |
| GGTAAAGGGG | AAGAAGAGCA | AAAGCACAAG | AATTCAGTTA | CGGCTTCTAA | TCCTGTCTGC | 12540 |
| TTTCTAGTAC | AGGCATACAG | TCATCACTCA | AGAAATGTTT | ATGTTCATTC | ACACTTTGGG | 12600 |

```
CCAGACACTG TTCTAGACAT CGAGGATACA GCTGCAAGTG AAACAGATAC AACAACCCCC  12660
GACTCATGAA GTGTGTGCTC TAGCTGGGAG TGGGCAAGCA ATGAGCCAAG TAAATTATTA  12720
AAAAAACAAA TTATATAGCA TTTGCAGCTT CAGATAGGGT GTTCACCAAG GAAGATCTCA  12780
CTAGAAAGCT GATATTTGAG CAAAGGCTTA AATTGCTGAA GGAGCAAGCC ATGCGGCCAT  12840
TTTGGAGAAG GGAGCTCCAT CCTGCAGCGG GACTGTGCTT GCCATGTTCA GGGGACAAGT  12900
GGGCCAGTGT GGCTGCGGGG AGAGAGTGAG AAAAAAGTG GTCTCAGATG AGGTCAGAGA  12960
GCTAAAGTGG GAAGGTGAGA TGAAAGGAGG CTACCGCAGT GGTCCAGGCT GGAGCTGATG  13020
GTGGGTGGAC TAGAGTGGTA ATGGTGAAGG CAGCAGGAAG TTGTTGGTGT TTGGATGGAT  13080
GAATGGACTA ATGGATGGAT GAATAATAGA TAGATGGATT GTTGAGAGAG ACAGAGAAGA  13140
GAAAAGCCTT GCCCCCAAAA GCTCACAGAC TACTTGGAGA GAGAAGAAAG CTACCTGGAG  13200
GGAGAACCAG ATGCATGAAG CAGTGCAGAT GTGGTGCCTA ATGAGTGTGT AGTCTGGAAG  13260
GGCAGCAAAA GTCGAGTGGA GTGAGAGGTT CCTGTGTCCT GGAGCACTGA GTAGAGACTC  13320
CCTCATGGGG GTGAATCTTA AAGGATAAAG GGGCCTCTAT AATGAAAAGG AGGAGGATGG  13380
GATTTCTGGT AGAGGAAATT GCTTGAGCAA AACCTCCAAG GTTGGAATGA CTATGGTGTG  13440
TTCAGGGATG TTAGCAGACC CAGATGGGTG GAGCGTTGAG TGTGTGTGTG TAGGAAGGAA  13500
GAGGGGAGGT GGCTGGATGA GCACAGTGAG ACCTGATTTG ATTGAGAGCC TTGAACGCCA  13560
CGCTGAATAA TGGAGGCAAT GGGACGCCAT AGAGGGCTTT TGAGTAGACA TATATCAGTG  13620
TAGAAGGGTG AATTTCAGAT TTTTAGACAG AATAGAGTAA GGAGAGGAGC TCTTAGAAAT  13680
CATCTAGTCC AGGGCTTGTG GCAGAGCCCT GAGGTTTTAA GAAGGCATGT CAGGGGCTAC  13740
CATGACAGGC ACGGAGAGGC TGAGTGAATT GGGGTTCTTG CCACAATTCC CTTGCCTGAG  13800
ATTCAACAAG AGCAGCTGTA TTACAATCTG TGCAAAATGT CATTAGGAGA AACTAGTTAG  13860
TAGCTGGGCG TGGTGGCATG CAACTGTTGT CCCAGCTACT CGGGAGGCTG AGGCCGGAGA  13920
ATCGCTTGAA GCTGGGAGGC GGAGGTTGCA GTGAGCAGAG ACTGTGCCAC TGCACTCCAG  13980
CCTGGATGAC AGAGCAAGAC TCTGTTTCAA AAAAAAAAA AAAAAAACT AGTCAGGACT  14040
CTTTCAGATA CAAGTAATAG AAACCAACTC AAACTGGCCT AATTAAAAGG ATTTTTTCC  14100
TTATAGCTAA AAAGCTCATG GATATCAGCT TCAGGAACAC TTGGATCCAG GTGTTCAGCT  14160
GATGCTGGAA AGAATCTATG ACTCCCCAAC TCTCAGCCCT GCCAGGAAGG CTTTCCCCTT  14220
GTAGGACTCC GACTATCCGC CTTGTAGTAT CTGATCCAGC AACACCAGTA AAATGAGGGC  14280
TTCTCTTTTC CCAGAGTCTT AACAAAAATC ATGGAATTGA GTGTTATGGA CTCATGGATT  14340
CATGGTAACC CAAACCAATC ACCGGGCCAG AGGGGACAGA GTACCCTCAC TGGTTGGCCT  14400
GGGTTACACA CCTACTCCAG AGCTATATTT GGAAGCCGCA TTGACTGATT TATGACCAGA  14460
AGAAAGGGAA ATGGATGAGG ACACGTGAAA TTGTGTGTGT ATGTGTGTGT GTGTTTCTT  14520
GCTGCCAAAA ATTTTCAAA AACTTGGAAA ATCACAGATA TATTCAATCT CTTCATTACA  14580
CAAATAAGGA GATGGAGGCA CAAATGGGGA TAGAGGGATT TGCCCAGGTT CTCCTAGGGC  14640
TTCAGTGAGA AAAGTTTTGA TCCAGGGATT CTGAAGGGGG TGGTGAGAAG AGGGGTGTCA  14700
GAGGACCTGT CTTGGGTGGT GGGGACTATG TACCTGTGAC ATAGCTGCTC AGGGACTGGA  14760
TCAATGGGTG GATGACAAAA TGGACAAATA AACAAGGACA TCTTCCCACT AATGCCAGAT  14820
GCTTGTGTGT TCTGCTTTCC AGAGAGTGCC TACTTGAACT TGAGCTCTGA GCAGAACCTC  14880
ATCCAGGAGG TGACCGTGGG GGAGGGGCTC AACCTCAAAG TCATGGTGGA GGCCTACCCA  14940
GGCCTGCAAG GTTTTAACTG GACCTACCTG GGACCCTTTT CTGACCACCA GCCTGAGCCC  15000
```

```
AAGCTTGCTA ATGCTACCAC CAAGGACACA TACAGGTACC ACTTATCAGC TCCCGTCTAC   15060
ACAGCCCGAC AACCAGATGG GGTATGCTTC AGCAAGCATC AGGACGCTTG GCTCATGTCC   15120
CAACCTTGGT GTATGACCTT GAGCAAGTCC CTGCCCCTTT CTGGGCTTCG CTTTCCCTGA   15180
CTTCATGGAA TCCCAATATT GGTCATCTGT GTTGAGATC  TAGATGAAAT TGACCTACCT   15240
CTCCATCCCA CATCCTTGGG ATAGTCAATG CCCCACCCAA GGATTCTACC ATTTCTTGGG   15300
AGTGTGCATT CTCATTGGTC CCTCAAGAAC CCTCAGCCTC ATTCATTTTC CTCTCTTGGG   15360
GCCAATCCAA ATGCAGAAAA CAGCCCCACT CATAGACACA CTCCTGATAA TGACTGCACA   15420
AGTTATCTGC TACATACAAA AGCTTGGAGG GAGGGGAAGA GGGAATTAAG ATCACACAAT   15480
CACAGATACA TGAAATGTTC TTTAAGGAT  TGTGATCACC CAGCCCCAAG AATTTCTCAC   15540
TGGCTGCTCT TCTCTGTAAG CTCAAAACTC TTCCCATGAA GTGCAATCTA TAATAACTCC   15600
ACACCCTCT  TCTTCCGTCT CTCCACTCCC ACAATCCTGT GTATTCCACA CACATTTAG   15660
AAATCTTTTT CCTGTCTGCT TGTGAACTGT GTTCTTGGGG TCTTGCTTTC TCATCCAAAG   15720
TGGCTTAAGC AGGTAGGTTC TAAATAAGAA AGCTTTGTGC CTAAGAGGAA CACTCATACC   15780
AGGTATATCA GGTATTAACT CAGGTATTAA AATAGTTCCT TCTTTTCTTT CTTTTTATTA   15840
TTTTTTTTAG ATGGAGTTTT GCTCTTGTTG CTGGAGTGCA ATGGCACAAT CTCGGCTCAC   15900
TGCAAACTCG GCCTCCCGGG TTCAAGTGAT TCTCCTGCCT CAGCCTCCCG AGTAGCTGGG   15960
ATTACAGATG CCCACCACCA CACCCAGCTA ATTTTTGTAT TTTTAGTAGA GACAGAGTTT   16020
CACCATGTTG GCCAGGCTGG TCTCGAACTC CTGACCTCAG GTGATCTGCC TGCCTCGGCC   16080
TCCCAAGGTG CTAGGATTAC AGGTGTGAGC CATCGTGCCT GGCCTGAAAT AATCATTCAT   16140
ACCCTGCCCT TTCAGAGGGA GACAGTACAG CTTAAGGGCA GCGAATACGT GGTGTGCATG   16200
CCACACTCAC TCTCATTCTT GTTTCTGCAA CTCTGTTCTG CAGAGTGTAG ATGCGGCCTC   16260
AGAGTCCTCC TCAACACAGG TCCCAGGCAG TATTTCCAGC ATAGTTGGCT CATGAGAGAT   16320
CTGTTTGTCA TCCCTGTGTG GATCCCTTAG ACAACTTCAA AACTCTTTGG GATTCTCGTT   16380
CTAGCTCTGG AAGCCCAAAC CTCATTGATT CCCACAATCT GCTTGTCAA  TTGTCAGAAG   16440
CAACAAGGAT GTTTTCTTGT CCTCATCTTC CTCCTCTCAG TTCCCTTCTG GTCCTTTCTG   16500
GCCAGGTCTC TGTCTTCCTC TCATTTAAAG CAGAAGTTCT GAATCTGGAA TGTGTAGGCC   16560
CTTTGGAGGG GGCTGGTCCA TGGATCGGTT TAATGGGTCC ATAAGCCACA GAGACATTGA   16620
GGAAAGGAAC ACGAGATCCC CTAAAACACA GTAGTCTGGG CCCATTCAGC ACAAGGCAGA   16680
CAAGCCTGGA CACCAAACAG CCACAGAATT TTAGTTCATG TGATGGGTTG TTCATAATGG   16740
TGACTTTCAA TTATCCAAAA AAGTCAAATT ATTTTTAGTT AAAGGGGTTA GTTATCTCAA   16800
GAAGTGACCT GGGCAGAGGC CTTGTATATG CCCAGGGTCT GGCTGGATGA GACTGCTCTC   16860
TGAATACCAT AGATTTTAGT CTAGTAGTAG CTGCAGACAT TCCCAAGCA  AGAACTGGCC   16920
ATTTGCTATA ATTTTAAAA  TTTATTTAT  TTGACAGTG  AACTGGGGGA CTTTTAAAA    16980
AATGTATTTA TTACCTAAAA CAACACATGT TCATTATGGA CAAATTGTAA AATAGAGATT   17040
AAAGAAAGAA TAAACAAAA  AATTTCCCAG AATCAGCCAA AGATGATTTT TATTGTTAGT   17100
TTTTGCTCCA GGGCCTTTTC TGTAATAAAG GGTACCATTG AATTGAGTGC CCACAAAGAT   17160
TCAACTTCTG TGTCAAGCAC CCTAAAAAGG TCCTTTAATC CTCAAGCCAA GCCTGTGAAT   17220
TAATAACCAT CGATATCACT CTCACAGCAA AGGAAGTGAG GGATCAGAGA GGTTAAGTAC   17280
TTGTCTAAGA TCACACAGCC AAGAAACAGC AGCACCAGGA CTTGAACCCC AGTCTCTGCA   17340
GCAACATGGC TCAGAACCCA GGGCCCTACA TCCTGCCTCT TGTCTCTTTC TCAGTCCCTC   17400
```

```
TTGGCAAGGT TGGCACTTCA GGGATTTGTA GCAGGGATTG CAGCTTTCAT GAAAGCTTAG    17460
TCCAGTGACA GTGGTCAACG TAGGCGACCT GTGATAGGCC TCCAGCACC  TTGAAGACAT    17520
CACCTCTATT AAACCTCGGG AAAAAAACAC TTTCAGATAA GAAAACCAAC TAAGGAAATG    17580
GGATTGGTGG TTTTTGCATG TCTCAATGGC ACCCTGTCTG AGTATCTGGC TTACCCAAGG    17640
CCGTTGGGCC CTGAATATTT TACCAAAAAT AAAATAAACC CCTTTAAGGC TGTTATCTGA    17700
CTGCAATCCT GGCAGGGGCC ATACTAGGCT GGGGCTCACC AACACCACCT GATTCTCTCC    17760
TGCAGGCACA CCTTCACCCT CTCTCTGCCC CGCCTGAAGC CCTCTGAGGC TGGCCGCTAC    17820
TCCTTCCTGG CCAGAAACCC AGGAGGCTGG AGAGCTCTGA CGTTTGAGCT CACCCTTCGA    17880
TGTGAGTGCT GGGGCCGAGC GCCACCTGGG GCGGAGGCCC TGGGACTGCC TGGAGGGATG    17940
GGGTTGACTG GGCAGGGCA  CAGGGAAGTA GGTACTGGGA GATTGGGAGG TGGCGGGGAA    18000
AGTGTGACTT GGGGCCTCCT CCTTCTTCC  TCAGACCCCC CAGAGGTAAG CGTCATATGG    18060
ACATTCATCA ACGGCTCTGG CACCCTTTTG TGTGCTGCCT CTGGGTACCC CCAGCCCAAC    18120
GTGACATGGC TGCAGTGCAG TGGCCACACT GATAGGTAAG TGGGCTCCAC TCACCTCCCT    18180
CACCTGGGCT CAGGGGCTGG GCACCCTGTG AGTGGGAGGG ACATGCTGGC GCTGGGAACC    18240
CTGAAGCTCT GAGCCACATT CTGCTTTTGC CAGGTGTGAT GAGGCCCAAG TGCTGCAGGT    18300
CTGGGATGAC CCATACCCTG AGGTCCTGAG CCAGGAGCCC TTCCACAAGG TGACGGTGCA    18360
GAGCCTGCTG ACTGTTGAGA CCTTAGAGCA CAACCAAACC TACGAGTGCA GGGCCCACAA    18420
CAGCGTGGGG AGTGGCTCCT GGGCCTTCAT ACCCATCTCT GCAGGTGAGA GGGAGCCTTC    18480
GCACCCGCAC CGCCCCCCCG CCCGCCCCCC GCCCTGCTC  CTTTAGGCGG CTCCTCCCCC    18540
ACCCCCCACC GAGGGAGCTG GGGTTGGCTC CACCTTTGGA GCAGATCCTA GCAGTACCAA    18600
GGTCCACCTC TCTGGGCCAG TCCAAGCCCC TCCTGCCTGG CAGGTCCCCC GAAGCAGTAG    18660
GACGGGGTAG TCTCTGAGAA AGCAGAGAGA AAGCAGCCTG AAGAAACTGG CCCCCACTCT    18720
TGTCCCTGCA CTCTAACTCA TGCATCTATT CACAAGTATG TGCAGGCATT ATGCACCGTG    18780
TGCCAGGGAC GTGCCCTATG CAGGGAAGCA GTGCCTCCCC AGAGCTCAGA GGCTGATGAG    18840
GGAGGCAGGC AATGAGCAAG GAAACAGTCC ATCTCCAGCT CGGGGCCAGC TAAGGACGGC    18900
CTTCTCCAAC TCTCCCCTCT TGCTCCAGAC ACAGTCTATC CATTTGAGGT TGCTGTGCAA    18960
GAGGCTGCCC CGGGGGATGA TGCCCGGCCC TGTGCACAAC ACAGGCTGCC TCTCTGCTTT    19020
ACACAAAGGC TCCTTACCAG CTAGTTCTGT GATTCTCAGA GGCCCACAGC ATCCTCAGGC    19080
TTTTGACAAC CAGGCTCTGG CACCCACTGT GTGCCAGACC CTGGCATCTG CCTGGCTCAG    19140
GGGTGGTCAC TCACGTCCCC AGCTGCTGGC CTTGGAGCAA CTGCTACCAG GGTCCAGCTG    19200
CAAGCAGGAG CCTGCGGCCG CGCTGGGCCT CACTGCTGGA GGTTGTATAT TATAATAAAG    19260
CCAACATTTT GTTGAAGGCT TCTGCTGCGC CAGGCACTGT GTTAAGCTCT TTGTGGGGAT    19320
TATCTCGATT AACTCCTACA AACCTAGGAA ATAAATAGAA TTTTCCCTAG GCTCAATGTC    19380
ACACAGCTCC CAAGTGGCAC AGGTGAAACT TGACTGCAGA TCTAAGTTAC TGATCTGAGC    19440
AAGGAAGTGG AAATTATGTT CTCCAAAACA TCGCTAGAAC TAGTAGTATA GATTCTGGGA    19500
AGAGGAGACT CAGGGGCCAC AAGCCTGGCT TGCTAGACCC TCAGAAGGGC TGTATGATTC    19560
CAAAGGCATG TGGAGAAGCT GCAGGGGAAA TGCAGGAGAG GAAGGTTGCA GTGTGACCTC    19620
CAGAAGGCCT TTCTGAACGA GCTTCCTGGA GGTGTAGTGC ATGCAAGCCA TGGCTGGGCA    19680
CCAGGCCAGG CCGCTGCAGA GAGGTTTCTT GCACTGGCAG AGGGTGAGAC TGCATGACCC    19740
CAGAGGCTCC CTACCCCCAG CCACAGGAGG CTGTGACTCT GGACAGGGTT TGGGGCTGGG    19800
```

```
CATGAGCAGA GCTGAAGAGG CCGTCCTCTC TGCCTTTCTC GGGGAGGGTG TGCAGGAGAG    19860
GCTCCAGAGG CTTCCAGTGG AGGATGCTTC ATTCAGTCAA CAAGCATTTA TTGAGCACCC    19920
ACTGTGTTCC AGGCAGTGTG CAGGCCTGAC CTCAGGGGGC TCGGAGGCAC CCCTGCCTGC    19980
TCACTGCTTT GCTTCATGCC TTCCAGGAGC CCACACGCAT CCCCCGGATG AGTTCCTCTT    20040
CACACCAGTG GTGGTCGCCT GCATGTCCAT CATGGCCTTG CTGCTGCTGC TGCTCCTGCT    20100
GCTATTGTAC AAGTATAAGC AGGTGAGCCG GAGCGGAGTG GGGCTGCCAG GTGCCTGAGT    20160
GAGCCAGATT TGGATGGTAC CCCCAGGCTG CATGGATTCA CCCTTCCTCC TCCTCAGTCA    20220
GTCCATCAGC TAACAGCTCT TTAGTGGGTG CCTACTGTAT GCAACATGA GCCAGCTGCT     20280
GGGTGGCCTC TGAGGCTCTG CCCTAATAGC GTTACTGTC TAGTGCGAGA GACAGGTGCT     20340
AATCAAATAG CCATTAAAGC AAGGGCACAC CTGTAATCCC AGCTACTTGG GAGGTTGAGG    20400
CAGGGGATT GCTTGAGGCC AGGAGTTAGG GACCAGCCTG GGTGATACAG CCAGATCCCA     20460
GCTCAAAAAA CAAACAAAAA GCCGTGAAAG CAAGAGCATG GATTATAGAG TGAGAGGCTA    20520
TGAGGAGAGG AATGGCATTC TGAGGCAGCG CAGCCCTGGG ATCCTGTCTC AGCCCAGGGG    20580
TGTCCTGGCA CCCAGCACGG GGCAGAGGAA ATGGATATAC AAGCGTGGTG TCCCTGGGC     20640
CAGGCCTGAG CCCTGCCCTA AGAAGCACAT GGTCTAGTGA AGACGAGGGC CTGTGACCAT    20700
CATCCTCTTC ATTATTTCAT GTTACTGTCC TATTAGCCAA AGCCACAATT TAGTGCATGT    20760
TGCGTATAGT GTGCTTCCTG TGTCTGCTCA GTATATGACA GTGATTTGAG GGGCATTTTT    20820
CTATAGCATG TTACCTACAT CATCTCATTT AATGCCCTCA GCAACCACTG TATGCAGCTA    20880
GCATTAGTCT ATTTTACAGA GTTGTAAACT GAGGTTCTGA GAGGTTGGGA CAGTTGCCCT    20940
TGTCTACAGC TGGTCAAAGG CAGAGTCTGG TTTTTAACCC TGAAGGAGGA CTCACTCCAA    21000
AGCATGTCCC AATCATTATG TGAAACATTG ACTCATCTTA TTTTACCCTC ACAAGAAGCT    21060
GGAGGCAGGA AGTATACTAG TCAGTATCTT ACCCATCAGG AAGCTGAGGC TCAGCAAGGT    21120
TAAAAAAAAA ACCCCAAGGG GCTGAGGGAT AGGGTTGGCA CTGGGCCCCA GGGGCTTCTG    21180
TCCCTAGAGC CCATGGCCTC CACTGCCTGC CTGCCCACAC AAAGACCATG TGCAATGTGA    21240
TCAGAAGCTG AGAGGACCAG GCCAGAGGGC TGTGGGAGTT CAGAGGTGGA CGGACTTTTC    21300
AGGCTGGTGG GTAAGGGAGA CTGCCTGGAG GAGGTGGCTT GGCATTGGTG GGACGGGCTT    21360
TGGAGGATGA GGATGCAGCA GGGGAGATGA CACTAAGGGA AAGGGTATCT CTGGGGGAGA    21420
GGGCAGAGTG TGCAGAGGTG CAGGTGAGGG AAGGACCAGG GTGGGGCTGG GGGTCTGAAG    21480
GGTTGGACCC CACCCTGTCG GTCCAAGGCC ATCAGTGGGT TTGAACAAGG GAGTGGTGTG    21540
ATCAAGGACT GAATGACCCA TCTTGTGTCC CCTTGGCTAC CTTTCTTCC CCACACCCCT     21600
TGGGCTTTT GTGAGAAGAG GGCTTGAAGT GGGCAGGGTG GAAGGATGT TGGGGAGCC       21660
CCAGGGGCAC ATGGATCGGG ATCTCTACTC CTGCCAGCAC TCAGCATGAG AAGGCTGCTC    21720
TGAGGGCAGC CCCGGTCAAT ACCTCCGGAT CTAGGTCCAG CTCTGACACT GTTTTGCCAT    21780
GTAACCTCAG CTGACTCGCT GTCCTCTCTG GGCCTTAGTT TCCCCTCTTA TACCATGGGT    21840
CTGGGTGTTC TCTAACAGCC CCTCCTCCTC TGACATGCCA AGAGCCCACT GGTGGTCTAG    21900
TTTAAGCACC AGAAACTTGG ACTTCAGTGA ATCTGGGTCC AAATCCTGCC TCTGCCAAGC    21960
TCTGGCTATG GGTGATGAG AAAGTTGGTG TGTCTGAGTC TCTTCTCCAT TTGTAAAATG     22020
GGATCATTAA CAGCCTGTTG TGAGGGATTC CGTACCACAA CGCACATAGA GGACTGAGCG    22080
GGGTGCTGGA CGAGACAGTC TCTGTGATGG GAGCTGCACA CTCTTGTCCC AGGAGGAAGT    22140
TCGTTGGGGA ACCAGAGTTA GCTCATGCCT CTTGGGATGG TGGAAGGAGG GGGAGGTCTG    22200
```

```
AGGTCGGGCA TCATCTCCTT GACTACACAC CCAAAGCGGT TGTTTGGCCC AGCCCACCCA    22260
CCTCCAGGGA CAGGACCTTA CTCACTCTCG GGGCCACCCG TTCCTTCTCT GAGCAGCTCC    22320
AATGTTTGCA AAGTTCTTCC TTACATGGAA CTGAAAACTG CCTCGCAGTG CCCACAGAGC    22380
TGCCAGGACA GTCATGCAGA GATTCCAGAG AAGGGCCTAG GGCCCCCTGC GGCCCTTTCT    22440
GCCTTGGGCT GGCCAGCCCC CTTGGCTGTG GTTAGGAAC  TCTGTATCCC CTCTCCACGG    22500
GACCATTTTT GGAACATGTC ACCTCCACAC TTCCTGTCCA GGAAATTCAG CTGCCCCTGG    22560
AGCCCATGCA AGGCTGCGAG AAGACTTGCA GCTACCCTCC TCCCTACAC  CCATTCACAG    22620
ACCCTTTAGC TCCAGGCCGA GGTGTCCACC CATGGGAGCG GAGGGGCAG  GATGGTCATG    22680
CCCGTGCTAA GTGCCTGCCC TCCCATCCTC CTCTGCCTTG CCCCATGAGG TTCGGAGCCT    22740
TGCCCCTTCA CTGGGGACTC AGCCCAGCCT CTCCTCATTG CCCAGGCCTG GGAAAGAAG    22800
TGGCCTGTCT GTGGGAGTG  TTTGTTCTGC CTCAGGGCTG AATCATCACC TTTCTGTCCC    22860
CCAGAGTGAC CACAAGGGGG GCCGTGGGGG AAGAGAAAAG GCAGGAGTC  AGCAGGCTCC    22920
CCTGGAGGAG GAGGCGCACA GGGAAATGGC TGAGGCAGCA GGGAAGGGAG GGTCCAGGGA    22980
GGCTGCTGGA AAGACTACGA TTCTGGGGGC TGGAACTGAG CTCTGAGGAG CAACAGGAGG    23040
GTCCCCAAAG ATTCCACTGG GAATTGTTCA GATCTCCACC TTCCTGTGAG AACATCCACT    23100
CACCCAGAAC CAGCAGGCCT AGATGGGGAG GGGACCGGGA CTTTGTCTCC ATGCCCCCTT    23160
TGGTGGGGAG GATGGGAGGA AGGGAAGAAG TCAGGGGGTG GGCCTGGGGC TTAGGCCCAT    23220
TGCAAGGAAT GAATGGGGTG ATGTGCTTCA AGCATCTAGC CCAGCGCCCC ACTCCCAGGA    23280
AGAGCTCAGG AAGAACCCGC TGCCATCATG ACAATTACGT CCACCTTCT  CAGGGAGCCT    23340
CGCCCATCCC CACCTCTTGA TCTCTCACTC ATAGTTCTTT GGAAGAGAGG CTGCCTCTGG    23400
GTAGACGCCC ATGAGCCCTT TCCAGGGATG GCACAGGTGC CCTGGGAGGT TTACATGCCC    23460
AGCAGGGGCA GGGGAGGGTT CCTGAGGCAG GCAGAAGGCA GCTTGGTCCG CTTCCAGAAA    23520
TTAGGAGCCT AGGATTCAGA AATCTGAGAA TCCAGCCAAA CCTCCATCCT CCTTGATCCC    23580
CTCCCTTTCA ACAGTGCCCC CTGCCCAGCT GGGGGCAGGG AGGGCTGAC  TCAGCCCAGC    23640
TGCAGAGGGA CAGAGGAACA AGAAGTGGTA AGAAAAAACA GTCTTAGCCA CAGAGGCTCC    23700
TAGAGATGGA AGTGGCCAGG AGAGGCTGAA GAATCCCCTC CTCGCCTTGT TGCTGTCTTT    23760
TGGGCTGGGA AGGCACCCAC GGGCAGGATT TGGATCCTCA GAGGCTTGGG AAGCTCTTCT    23820
CCCTGGGTCC CGTTTCAGAC TCTCTCCCAA GCTATAACGC AGAGGCTCTG AAGTTCACCT    23880
GCAGTCCGCC CTTCCAAATC AGAGCCTGGA AGTTAGTTCC TTCTCATTTC TAATTGCAGT    23940
CTTTTCTCTC TAACTACCAG CTAGAAGTTC TTCCTGATGG TTAGCTGGAA GCTTTCTCCC    24000
TGTCTCTCTC TTTAAAAATG TCCACATTTT ATTTTGATT  CAGGGGATAG ACGTACAGGT    24060
TTGTTGCATG CGTATGTTTC GTGATGCTGA GCTTTGGAAT ATGGATCCCA TCACCTGCTA    24120
CTGAGCATAG CTCCATAGT  TTTTCAACCC TCGCCCGCTT CCACCCTCCC TGCTCTAGTA    24180
GCCCCCAGTG TCTGTTGGTG CCATCTTTAT GCCCATGCAC ACTCAATATT TAGCTCCCAC    24240
TTATAAGTGA GAACATGCGG TATGTAGGTT TTCTGTTTCG GTGTTAATTT GCTTAGGATA    24300
ATGGCCTTCA GCTGCACCAC GTTGCTGCAA AGGACATGAC TGGAATCTTC TCTCTCAACC    24360
AGGACTTGCA GCTAAAGGCC AGCCTCCTCC CTAGCACCGG TCCACACTTC CTTTAAGTTT    24420
CTAGCTCGGG TGCCCAGGGA AGGAGCCCAG CTGCAGGCAC AGCCAAGCTT GTCCATCCC    24480
CAAGGCCTGG CCGGAAAGAG TTGCTCTGCT GACCCAGGGC CTCAGTGTCC TCCACCGCCC    24540
CAGCCCAGCT TCCACTTTCC CCCTCAACTT GGTCTTCCAT CAGCATTTCT TATGGGCAAC    24600
```

```
CCTTAGCATG GTACTCCCCC TCAGCAGCTG ACCCCTGGGC AAGAAACAGG GGCAGCCATT   24660
CCTCCTCCCC ACATCCCAGG GCTTGCCTCC CCTGGCTGGG TGGTAACAGC ATGGAGAGCC   24720
TAAGGAAGGA AATCAGGTCT TTCCAAAGGT GCTGGTCCTC CAGAATCTAT CTAGTGGGCA   24780
GCGTCTCTCT TTCTCTCTCA AAAAGGTAAA GTCAAGGCTG GGTGCGATGG CTCACGCCTA   24840
TAATCCCAGC ACTTTGAGAG GCCAAGGCAG AAGGATTGCT TGAGCCCAGG AGTTTGAGCC   24900
TAGTGAGCTA TGATCGTGCC ACTGCACTCC GGCATGAGTG AAGGAGCAAG ACTCTGTCTC   24960
AAAAAAAAAA AGTCAGATGG CGACTCACCT GTGTCAAACT CTCAGGGTCT CTCACTGCCC   25020
GGCCAGGCAT GGTAGCTCAT GCCTGTAATC CCAGCACTTT GAGAGACCGA GGCAGGCAAA   25080
CTGCTTGAGC TCACGAGTTC AAGACCAGCC TAGGCTGCGA CAAAGCCCCG TCTCTACAAA   25140
AATTAGCCAG GTGTGGTGCC ACATGCTTGT AGTCCCGGCT GCTTGGGAGA CTGAGGTGGG   25200
AGGATTGCTT GAACCTCGGG GGTCGAGGCT GTAGTGAGCC AAGACTGCCC CCACTGCATG   25260
CCAGTCTGGG GGACAGAGAT CCTGTCTTGG AAAAAAAAA ATCCCAAAAG GAACCCACT   25320
CACCTTATCA TAGCCCTCAA GGCCTTCCTG TTTCTGGAAT CTGCCCCCA CTTCCCTCAA   25380
GCCATGATGG CTGCCTTCCT ATAGCTCAAA CTTGCCAGGA TCATTCCCAT GTCAAGCATA   25440
CAGCATTTCC ATGCACTGTT CCTGGAAAAT TCTTCCTCTG ATGGTCACAT GGTGGGCTCT   25500
TTAGGGGCCT TCCCTGACTT ATCTTACTTT ATTTCTTCA TAGCACCACT TGAGAATCTC   25560
CTAGATACAT GTTTATTTGC GTTAATGCC TCTCTCAGCC ACTAGAATGC AAACTCCATG   25620
GAGGGGCAGG GACTTTGTCC TGTTCAACTC TGAATCAGCG GTGCCTGACA CAAATAGATG   25680
TTCAAGAAAG TATGTGGATG GGCTACTATT ATTCAGCCTT AAAAAGGAAG GGAATTCTGA   25740
CCTGTGCTGC AGCATGAATG AACCTTGAAG ACATTATGCT GGGTGAAATA AGGCAATCTC   25800
AATAGACACA TGCTGTGTGA GTCCACTGAG GTGCAGTGCC TAGAGCAGTG CAATTCACAG   25860
AGACAGCAGA ATCATGGTTG CCAGGGGCTG GAGGAGGGAA AGGGGAGTTG CTTTTTAACA   25920
GGAACAGAAT TTCAGTTTTG CAAGATGAAA AGAGCTCTGG AAACTGGTTG CACAAGGTAG   25980
AATGTAATTT ACTTAATACT ACTGAACCAT ACACTTAAAA ATGGTTGAAA TGGTAAATTT   26040
CATGTATGTT TTATCACAAT TAAAATATAT ATATATATTT GGATGGGAGG TTGGGTGGGT   26100
GGATGGATGG GTAGATGGAT GGACAGATGA ACGGATGGAT AAGATCTCAA GTTCCACCCT   26160
CCCTCCTGGC TCAGGAATTA CCAGATTATC AGAGATATCA GGGCCCTCAG AGGTTGTCTT   26220
GTCCAAGGTC TTCAATACAC AAATAGTGAA ACAGGCTTGG AGAAGGGAAG GTCACACAAC   26280
AAGGCAGAGT CAAGCAGGAA CATGCTCTCA GTGCTATGTT CATGAGACGA CCTCTCTCAG   26340
CCCAGAGCAG GCCTTGCCCT GCCTTCTCCC ACTGGGCGCC TTGGGACTGC CCACACCCCT   26400
GCTCTTGGGG GTCAGAAACA AGGTCCAGGA ACTGCCTGCC AGCCCGACT GCCACGTGCT   26460
CCCTTCCTCT TCTGCAGAAG CCCAAGTACC AGGTCCGCTG GAAGATCATC GAGAGCTATG   26520
AGGGCAACAG TTATACTTTC ATCGACCCCA CGCAGCTGCC TTACAACGAG AAGTGGGAGT   26580
TCCCCCGGAA CAACCTGCAG TTTGGTGAGA TGGCAGCTCA TCACTCCACA GCTTCCTATC   26640
ACAGGGCCTG TGGGGGTTGC AGGGAGCCCA TGGGCCCTTG ACAGAGGCC CTTTGGTGCC   26700
CAGGGACTTA AGGGACCTGT GTGCGTGGCA GGTAAGACCC TCGGAGCTGG AGCCTTTGGG   26760
AAGGTGGTGG AGGCCACGGC CTTTGGTCTG GGCAAGGAGG ATGCTGTCCT GAAGGTGGCT   26820
GTGAAGATGC TGAAGTGTGA GTGAGGGGAG GGATGAGGG AAGGGATGGG GGTGGTAGAT   26880
GCTGGGGGTG GGCTGGCCCT GGTGTCACAA GAGGCATCAC ACACATTTCA ACCTGTTGAA   26940
GCCTGGGGGA CAGAGCTCAG GGGTGAGGAC TTGGGTTTTC TTGTGAGCTC CAGGCACCCT   27000
```

| | | | | | |
|---|---|---|---|---|---|
| CTGACTCCCG | GCTCCAAGAA | GGTCTAGGTC | ACCCTTTAGT | TGTGAAGGGG | CTCCTGACTG | 27060 |
| AGCTCCAAAA | AGTCTGGGGG | TGCAGAAAGG | CCACCATGG | CCATGGCCTG | GCCACAGTTT | 27120 |
| GGCTTCCTGT | CACCTGAAGA | CCAGCTCAGT | GACAGGCTCA | TCCCTTCTCT | CTCTCTCTCT | 27180 |
| GCCATCTGTG | TGTCTGCATT | TTTCCTTCTC | CTTCTTTTGG | CTTCTGGTCA | CTCCGGGTCT | 27240 |
| TGGGATATGC | CCTGCTTTCT | CCCCTGGGTC | TCTGCATTTG | GTCCCATGT | ATCTGTGTGG | 27300 |
| TGCTCTCTGT | CCTGCCCTCT | CCCTGTCTTT | GGGACTGTGG | TTCTTCCTCC | CAGCCACGGC | 27360 |
| CCATGCTGAT | GAGAAGGAGG | CCCTCATGTC | CGAGCTGAAG | ATCATGAGCC | ACCTGGGCCA | 27420 |
| GCACGAGAAC | ATCGTCAACC | TTCTGGGAGC | CTGTACCCAT | GGAGGTAAGG | GCCTTGGGGT | 27480 |
| TCCTGGGGCC | AAGGTCTTGG | GGCCTCTGGG | GAATCTCAGG | GCCCCAGGGC | TACCTTGTTC | 27540 |
| CGTCTTCTCC | TTCTCAGGAT | CCTACTGCTC | CAAGTGTCAG | GGGGATCCCG | GTCACAGCAT | 27600 |
| CCCTTAAACT | CCTGGGCCCA | TCTCCTGGAA | TAGTCAGGAG | CTGCACGGGC | AGCTTGAGGT | 27660 |
| ATAAAGAGAG | ACTGATAGGG | AGCATCGGAG | CCCTTGGAGG | AGGAGATGAA | TGTGCAAGCT | 27720 |
| CCTAGGCCCT | GCTTCCAGGG | AGCCGGATCC | TCTGGGTCTG | GAGTGAAGCC | CCCGCCTAC | 27780 |
| CTCTTATGAA | GCTTCCATTC | AAGGATGCTT | GGACACTCTC | CCAGGGCCC | CCAAAGGTGC | 27840 |
| CCCGGGCTTT | GCTGGGACTC | CAAGTGCCCC | ACATCCTCTT | CACTGATAGC | AGCTCTGACC | 27900 |
| TACAGTGAGC | CGCCATAGCT | TTCCTTTGAA | GAAATAATTC | TTGGGCTACA | TTTTTTTTAA | 27960 |
| GGTTGTCTTT | TTTTTTTCAT | TTTTTGTTTT | TTTTTCTTG | AGACGGAGCC | TCACTCTGTC | 28020 |
| ACCCAGGCTG | GAGTGCAGTG | GTGCGATCTC | GGCTCACTGC | AACCTCTGCC | TCCCAGGTTC | 28080 |
| AAGCAATTCT | CCTGCCTCAA | CCTCCTGAGT | AGTTGGAACT | ACAGGCACAT | GCCACCATGC | 28140 |
| CCGGCTGATT | TTTTTGTATT | TTTGTAGAGA | TGGGGTTTCA | CCATGTTAGC | CAGGATGGTC | 28200 |
| TCGATCTCCT | GACCTCGTGA | TCCACCCACC | TTGGCCTCCC | AAAGTGCTGA | GATTACAGGC | 28260 |
| ATGAGCCACC | GTGCCCCGCC | AAAGCCATCT | GTTTTAAACA | AATGGAACTA | CTGAGGCACA | 28320 |
| AGGAAACTTG | CTCACAGAGC | CGAGGTTAGA | ACTCAGCTAT | GCTGAGTCCA | AGTCCAGTGG | 28380 |
| CCTCACTGCC | CCCAGTCTCA | TGCTCCTGTT | CATGGAGGGG | AGCACTCAGC | ACCTCCCTCA | 28440 |
| CCCCACACCC | TTGGCTGCTC | TAGGCCCTGT | ACTGGTCATC | ACGGAGTACT | GTTGCTATGG | 28500 |
| CGACCTGCTC | AACTTTCTGC | GAAGGAAGGC | TGAGGCCATG | CTGGGACCCA | GCCTGAGCCC | 28560 |
| CGGCCAGGAC | CCCGAGGGAG | GCGTCGACTA | TAAGAACATC | CACCTCGAGA | AGAAATATGT | 28620 |
| CCGCAGGTAG | CCCCTGGCAA | AGGACAAGAA | AAAGGCCAGG | TCTGGGAGGC | AGGATCCGAG | 28680 |
| TCTGTCTTCA | AAGCCAGCTC | AGGGTTGGAT | GGCTCATGAA | TGGGTGGCTA | TGCAGCCCTC | 28740 |
| ACCTGCCACC | TGTGTCATGG | GAAGTAGCCA | CCACAGGTTT | TATGGCCATC | TCTTGTTTCT | 28800 |
| CTACTCCTTT | TCCCCTTCAT | TCAACAAATA | TTTGAACACC | TACCGTGTTC | TGGGAGTGTG | 28860 |
| GAGGGCAAAG | ATGGGCAGCT | CATAATCTGG | TGGAGATATG | CATCAATGAA | ATCACCACCC | 28920 |
| AGTGTGTGTA | AAAGATCAAC | CAAGATCTGT | GCCTGGAGCC | CTAGTAAGAG | ATGGGCAGAT | 28980 |
| GTGGCCGGGT | GCAGTGGCTC | ATGCCTGTAA | TCCCAGCACT | TTGGGAGGCT | GAGGCGGGCA | 29040 |
| GATCACCTGA | GGATGGGAGT | TCGAGACCAG | CCTTACCAAC | AAGGTGAAAC | CCCGTCTCTA | 29100 |
| TTAAATATAC | AAAATTAGCC | GGGCGTGGTG | GCGCATGCCT | ATAATCCCAG | CTACTCGGGA | 29160 |
| GGCTGAGGCG | GGAGAATTGC | TTGAACCCAG | GAGGCAGAGG | TTGCTGTGAG | CTGAGATCAC | 29220 |
| ACCATTGCAC | TCCAGCCTGG | GCAACAAGAA | TGAAACTCCG | TCTCAAAAAA | AAGAGAGAT | 29280 |
| GGCTCTGTTG | TCCTGTTGCT | GTGATTCCTG | GAAGCCATCC | AGAACAGAGC | CATCCAACAG | 29340 |
| ACAGAGCCAC | ATGGGGAACC | AAAGAGAGGA | AGTGGGGAGA | TTCATGTCAC | ACATGAGTCA | 29400 |

```
GGGTTAGAGG TGGAGCCTGG ACTAGAATCC TGCTCTCTTG ACTTCCAGTC CAGGAGTCAC    29460
CCAAGCCACA CTGCTGTCCT GGAGGTCTCT GTCTCAGGGG CTTGTGGGGT CAGGACAGGA    29520
TCAGAACAAG AAGGGTGTAC ACTGCGCCCT CATCCTAGAT ACTGTCAGCT GCCACGCCTG    29580
GGGAGGCAAA AGAGAAGGAG GCCATCTCTT CACCCAGGGC CTTAAAAATG GGGCCTGGC     29640
AGCATCACTT CCTCTTCTGA TTCCCTGACA CTTCTATGAG GGTGGCACAC ACTAGGCCTC    29700
TGAAGATCAG ATCAAAATGA GCACCAAAGG AAAGTATTAG CTTCCATCTT CAAATACGCA    29760
GATGGGGAAA GTATTCCCAG AGTGGGTAAT TTCGAGGGCA AATGGCCTGT AAACCAACTC    29820
TGTCAAAGGA TTCCAGGCTG TTAACGAAG CATAGTTTCT ACAAGGGAGC GGAAGGTTTT     29880
TTCGGTTTCT CCTTCTGGGA ACACTAGAAT ATGGACATTG TCAAGGTACA CATCTCTAGC    29940
GCAGAGGGGA CAGGAGGGAG AGAAATCC TATCTGGCTG GAACGTTAGG AGCAGTAGTG      30000
CTTCAGTCTA CAGTAGTGCT TCTCAAATTC TCTACCCCAA GTGTGCTCTC ATAGGCATCT    30060
CTTGAGGACT GTTGGAAGTG CACCACCTCA GGCCCATCCA CCCAGGCCTG CTGATTCAAA    30120
ATCTGCATTG CAGAGATTCC CGGGGTGATT TATCTGCACA TGAGTTGCAG CGTAAGCAGC    30180
ACTGCTCTAG ACCAGTGGGC CTCAGCTTAG GCTGTACTTT GTGATCACCT GGGGAGATTT    30240
AAATCTGTGA ATGACTGTTT TGTCCCTAGA GTTTCTGAAG TATTAGTAAT TAGCCTGATC    30300
CTAAAAGCTC CCGAAGTGAT TTTAATGTGA AGCCAGGGGT GTGAGGCACT GTCCAGAGAA    30360
GAGAGGGCAC AAGGGGCCCT AGAATATGCC CCAATTCTAG TAGGGCTGTT ATGGGAAGA     30420
GGACTCCAAC TTCTCTGTGG CCCTTGAGGG TAGAGCAGGG GCTAGGAGGA AAATCTCAGG    30480
GGTAGATTGG CATTAGGAAC AGTGAAGAAC TTTCTCACAG GCAGAGCTGC CCAAAACCAG    30540
AATGGGTTGT AAGCTCCCTC ACCGGGGACA GCCGAGCAGA GACCAATGCT CACTCAGATG    30600
GAGTGTGGCA GGAGGGTTTC TTATCAGAAA GGGAGGTTCC AGTTGACCAT GGGGTGGTGG    30660
GTGGTCAAGG CCTGAGCTGA GCAGTGCAGT GATGATGACT GACCTCTGCC CCCCAACCCT    30720
CTCTCCTATG TAGGGACAGT GGCTTCTCCA GCCAGGGTGT GGACACCTAT GTGGAGATGA    30780
GGCCTGTCTC CACTTCTTCA AATGACTCCT TCTCTGAGCA AGGTGAGGAG GTCCCAGGGC    30840
CAGGCCCCAT TTGCTTGATA ACAAGGGAAA AGGAGAAGGG GCTGCTGGGG TGAGGGGTGG    30900
GGAGTGTGGC AGGGCTGCCC TGACGCCTCT TCCCACCCTA GACCTGGACA AGGAGGATGG    30960
ACGGCCCCTG GAGCTCCGGG ACCTGCTTCA CTTCTCCAGC CAAGTAGCCC AGGGCATGGC    31020
CTTCCTCGCT TCCAAGAATG TGAGTAGGAA CCTGGCCCTG GCTCATAGCC ACCCAGGTCT    31080
GTGCTCCGGG GAGGCTGGAT GAGTGACGAT GGGGAGGAGG AAACGGGAGC CTGTGAGGGG    31140
GTAGGGGAGG AGACAGAGTA TGAGAGAGTC ATTTGGGCAG CAGCTGCAAG GATGAGTGGG    31200
AGAAAGCTGT GCCCAGGGCT GGAGCTCTGG GGCTGGGCAC CTGTGTCCCC AGCGTGAAGA    31260
TGAGGAAGGG TACCAGGCTT TCTTCATTCG TTTTTACTAA ATAGTGTATG AGAGACAACA    31320
GTTGTCTCTG CTCATAAAGC ACGTGGTCTG GTGGGGATGA TAACGGAAGC TTCCTCAGAA    31380
TTTTGGGGAT ATTAGATAAC GTATAAAGTG CGCTCGGCCT AGGAAGAAGT GCCAGGGAAT    31440
GGGAGCTCTT GCCATCTTCC TTAGAACAGA TTCGGGAGTC AGTGGTTTGA TTGTTGGCTC    31500
TGCCACCTGC TCCGTGACTT TAAGCAACTA TTTAAATTCT GTGCCTCAGT TTCTACACCT    31560
ATAAAAATGG GCATAACGAT TGTTGAAAAG AAAAAGGGTT CAATGTGTGC AGAGTTTAGG    31620
GAAGGGCCTG GCAGATAGCA GCTGCTATGA TCAGAAGTAA CGGTAGGGTT TGGAGACTGC    31680
TCTCTGCACG GAAGCCCTTC GCTTCTGGGG CCTGAGCAGA CCAGTCAGAG GACAAAGGGT    31740
GAGAAGGGCC ATGGCTGCTC AGGGTAATGG GGGTTTCTAA GCATTAAATG ATCAGATCAC    31800
```

-continued

| | | | | | |
|---|---|---|---|---|---|
|GATACACATT|CTCAGATCCT|GGGCCCTGGT|AGAAGGTATA|GACAAGGGTT|TGTGGTAAAG 31860|
|GACCAAAACT|GTTGTTCACT|CCAGCAGGGA|CTCCAAAGCC|ATGTGGGGCC|CTCCCTGCCA 31920|
|TCCTCCTCAC|CTCAGGCTCA|GGTAGGAGAA|GGCCCAAGAC|TAACCCTGCA|GTGCTTTCCC 31980|
|TCAGTGCATC|CACCGGGACG|TGGCAGCGCG|TAACGTGCTG|TTGACCAATG|GTCATGTGGC 32040|
|CAAGATTGGG|GACTTCGGGC|TGGCTAGGGA|CATCATGAAT|GACTCCAACT|ACATTGTCAA 32100|
|GGGCAATGTA|AGTGCTGGGA|GGGCTTGGGT|CAGGCTGGGG|AGGGGGTGAA|GAGTCGGGGC 32160|
|CCAAAATAAC|TGGGGACTGT|CATCCCAGGC|CCGCCTGCCT|GTGAAGTGGA|TGGCCCCAGA 32220|
|GAGCATCTTT|GACTGTGTCT|ACACGGTTCA|GAGCGACGTC|TGGTCCTATG|GCATCCTCCT 32280|
|CTGGGAGATC|TTCTCACTTG|GTGAGCCACT|GGGCCCACTC|CAGGCAGAGC|CTGGGGCTGG 32340|
|CTCCTCTGGT|TGCCCCACTG|GTGGACAAAG|CTGTTTGGTG|CCCAGGACAC|AGCGAGGGTT 32400|
|GGTGAGAGTG|CAGGAATGGG|CAAGGGCTCT|CGAAACCCAG|CATCGTGGCT|CCTGCGGGAC 32460|
|TCGGCAGACC|CTCTGCCCCT|GACAGGCGCT|CCTTTCTGGC|TCTTCCCTCG|TTTGTCTCTG 32520|
|CTCAGTTGCT|GTTACCTGTT|ACCCTCCTTT|GTCACTGTTT|CCCTCCTTTG|TCTGAAATCT 32580|
|ACAGACCCTT|GAAGATGCAG|CTCTCTACTA|CTAGGCTCTA|GTAGAAAGAA|CTGCTATTTC 32640|
|CCGAGGACTA|GGCACAAGGA|CTTGTACTCA|GTTCTTAAAT|ACGCTGCTCC|TATACCCTCA 32700|
|TAACCACCTG|ACTGTCCACA|CTTTAACGAT|ACACAGCTGA|AGCTTGGTC|TGATTCCAAA 32760|
|GCCTGTGCAA|GAATGTTTGG|TGTGATAAGG|CCTGGATAGA|GGCTCACACC|TTCCTAAAGC 32820|
|CTAAGCCTGC|CACACACTGG|CTGGCACACA|GGAAGCACCG|GGTAAGAGTA|GCTGCTGTTG 32880|
|CAGATGTTGT|CAAGTGGGAC|CCTTTAAACC|CAGTCTAAGA|TGTGTGTGGG|TGTGCGGGAA 32940|
|TGGGGAGAAG|ACAATGGGCA|TGGCCTCTTA|CCTGATCTTG|GCCTTTGCAG|GGCTGAATCC 33000|
|CTACCCTGGC|ATCCTGGTGA|ACAGCAAGTT|CTATAAACTG|GTGAAGGATG|GATACCAAAT 33060|
|GGCCCAGCCT|GCATTTGCCC|CAAAGAATAT|GTAAGCGAAG|GGATCCCAGG|GAGGGAAAAG 33120|
|GACACCCCAG|GCTTTCGCTG|GAAAGGGATG|GAAGGCCGTG|TGGCCCTGAT|CTTTCCCTGT 33180|
|CCAAAATGTT|CCAGGGTCAG|ACTTTATCTC|TCCCATAGTG|GACACAACAA|GCCCCTTTTG 33240|
|AGTTCAAGCT|ATGGGGGATG|TTCTCAGAGA|AGCAGCTGTT|CACTAGGGCT|GGTCCTAACC 33300|
|GACCACTTTT|CCTTTTTTTT|TTTTTTTTT|TTTGAGACAG|CATCTTGCTC|TGTAGCCCGG 33360|
|GCTGGAGCGC|AGTGATGTGT|GCAATCATAG|CTCACTGCAG|CCTCAATCTT|CAGGGCTCAA 33420|
|GCAATCCTTT|GGCCTCAGCC|TCCCAAACAG|CTGGGACTAC|AGGTGTGCAC|CACCAAGCCC 33480|
|AGCTATTTTT|AAAAATTTT|TTAGTAGAGA|TGGGATCTCA|CTATGTTGTC|CAGGCTGGTC 33540|
|TGGAACTCCT|GGCCTTATGC|AATCCTCCTG|CATCAACCTC|CCAAAGTGTT|GGGATTACAG 33600|
|GAATGAGCCA|CTGCACCTGT|CCCTAAACAG|ACTTTTAAGA|GATCGTTATT|ACAGTTACCC 33660|
|TGAGGATACC|AAAATGGCCT|CATCTGTCAG|AATGAGGGTG|ATGAGAGTAC|CCTTCTGCAA 33720|
|GGGTTACTGT|GAGGATTAAA|TGGTAAAGCA|TGCCAAGGAC|TTGGCATAGG|TTTTATACTA 33780|
|AACTTACTTT|GACTGGGTTT|GGGGACCTCT|GCTGGGTAGG|TCTCTCTAGG|GGTGTGTGTT 33840|
|AATGGCCCCT|GGACCCTAGG|GAGCTGCCCA|TGGGCATCCT|CTGTCCTATC|TCCCAGATAC 33900|
|AGCATCATGC|AGGCCTGCTG|GGCCTTGGAG|CCCACCCACA|GACCCACCTT|CCAGCAGATC 33960|
|TGCTCCTTCC|TTCAGGAGCA|GGCCCAAGAG|GACAGGAGAG|AGCGGGTGAG|TGGGGTGAGG 34020|
|CTTGGGGTGG|GTGGCCGGTA|AAGCACGTTG|GGCTGGGCCT|GATGGATCTG|GACTGACAGT 34080|
|TTCTGGTCCC|TCCCACCCTC|AGGACTATAC|CAATCTGCCG|AGCAGCAGCA|GAAGCGGTGG 34140|
|CAGCGGCAGC|AGCAGCAGTG|AGCTGGAGGA|GGAGAGCTCT|AGTGAGCACC|TGACCTGCTG 34200|

| | | | | | | |
|---|---|---|---|---|---|---|
| CGAGCAAGGG | GATATCGCCC | AGCCCTTGCT | GCAGCCCAAC | AACTATCAGT | TCTGCTGAGG | 34260 |
| AGTTGACGAC | AGGGAGTACC | ACTCTCCCCT | CCTCCAAACT | TCAACTCCTC | CATGGATGGG | 34320 |
| GCGACACGGG | GAGAACATAC | AAACTCTGCC | TTCGGTCATT | TCACTCAACA | GCTCGGCCCA | 34380 |
| GCTCTGAAAC | TTGGGAAGGT | GAGGGATTCA | GGGGAGGTCA | GAGGATCCCA | CTTCCTGAGC | 34440 |
| ATGGGCCATC | ACTGCCAGTC | AGGGCTGGG | GGCTGAGCCC | TCACCCCCG | CCTCCCCTAC | 34500 |
| TGTTCTCATG | GTGTTGGCCT | CGTGTTTGCT | ATGCCAACTA | GTAGAACCTT | CTTTCCTAAT | 34560 |
| CCCCTTATCT | TCATGGAAAT | GGACTGACTT | TATGCCTATG | AAGTCCCCAG | GAGCTACACT | 34620 |
| GATACTGAGA | AAACCAGGCT | CTTTGGGGCT | AGACAGACTG | GCAGAGAGTG | AGATCTCCCT | 34680 |
| CTCTGAGAGG | AGCAGCAGAT | GCTCACAGAC | CACACTCAGC | TCAGGCCCCT | TGGAGCAGGA | 34740 |
| TGGCTCCTCT | AAGAATCTCA | CAGGACCTCT | TAGTCTCTGC | CCTATACGCC | GCCTTCACTC | 34800 |
| CACAGCCTCA | CCCCTCCCAC | CCCCATACTG | GTACTGCTGT | AATGAGCCAA | GTGGCAGCTA | 34860 |
| AAAGTTGGGG | GTGTTCTGCC | CAGTCCCGTC | ATTCTGGGCT | AGAAGGCAGG | GGACCTTGGC | 34920 |
| ATGTGGCTGG | CCACACCAAG | CAGGAAGCAC | AAACTCCCCC | AAGCTGACTC | ATCCTAACTA | 34980 |
| ACAGTCACGC | CGTGGGATGT | CTCTGTCCAC | ATTAAACTAA | CAGCATTAAT | GCAGTCAGCC | 35040 |
| TCTGGTTCTT | TGTGCCACAT | GAGTACCTGC | AAATTCCCTG | GAACGTCTTT | CTTTCCTTCC | 35100 |

(2) INFORMATION FOR SEQ ID NO:20:

(i) SEQUENCE CHARACTERISTICS:
        (A) LENGTH: 218 base pairs
        (B) TYPE: nucleic acid
        (C) STRANDEDNESS: double
        (D) TOPOLOGY: linear (xi) SEQUENCE DESCRIPTION: SEQ ID NO:20:

| | | | | | | |
|---|---|---|---|---|---|---|
| ATTTATTATT | TTTTGCAGAA | AGAGCACTTC | AAATAATTTA | CAGAACCAGA | ATTTAAGGTG | 60 |
| GAAGATGACA | TTTAATGGAT | CCTGCAGTAG | TGTTTGCACA | TGGAAGTCCA | AAAACCTGAA | 120 |
| AGGAATATTT | CAGTTCAGAG | TAGTAGCTGC | AAATAATCTA | GGGTTTGGTG | AATATAGTGG | 180 |
| AATCAGTGAG | AATATTATAT | TAGTTGGAGG | TATGTTAC | | | 218 |

(2) INFORMATION FOR SEQ ID NO:21:

(i) SEQUENCE CHARACTERISTICS:
        (A) LENGTH: 5084 base pairs
        (B) TYPE: nucleic acid
        (C) STRANDEDNESS: double
        (D) TOPOLOGY: linear (xi) SEQUENCE DESCRIPTION: SEQ ID NO:21:

| | | | | | | |
|---|---|---|---|---|---|---|
| GATCCCATCG | CAGCTACCGC | GATGAGAGGC | GCTCGCGGCG | CCTGGGATTT | TCTCTGCGTT | 60 |
| CTGCTCCTAC | TGCTTCGCGT | CCAGACAGGC | TCTTCTCAAC | CATCTGTGAG | TCCAGGGGAA | 120 |
| CCGTCTCCAC | CATCCATCCA | TCCAGGAAAA | TCAGACTTAA | TAGTCCGCGT | GGGCGACGAG | 180 |
| ATTAGGCTGT | TATGCACTGA | TCCGGGCTTT | GTCAAATGGA | CTTTGAGAT | CCTGGATGAA | 240 |
| ACGAATGAGA | ATAAGCAGAA | TGAATGGATC | ACGGAAAAGG | CAGAAGCCAC | CAACACCGGC | 300 |
| AAATACACGT | GCACCAACAA | ACACGGCTTA | AGCAATTCCA | TTTATGTGTT | TGTTAGAGAT | 360 |
| CCTGCCAAGC | TTTTCCTTGT | TGACCGCTCC | TTGTATGGGA | AAGAAGACAA | CGACACGCTG | 420 |
| GTCCGCTGTC | CTCTCACAGA | CCCAGAAGTG | ACCAATTATT | CCCTCAAGGG | GTGCCAGGGG | 480 |
| AAGCCTCTTC | CCAAGGACTT | GAGGTTTATT | CCTGACCCCA | AGGCGGGCAT | CATGATCAAA | 540 |
| AGTGTGAAAC | GCGCCTACCA | TCGGCTCTGT | CTGCATTGTT | CTGTGGACCA | GGAGGGCAAG | 600 |

```
TCAGTGCTGT CGGAAAAATT CATCCTGAAA GTGAGGCCAG CCTTCAAAGC TGTGCCTGTT      660
GTGTCTGTGT CCAAAGCAAG CTATCTTCTT AGGGAAGGGG AAGAATTCAC AGTGACGTGC      720
ACAATAAAAG ATGTGTCTAG TTCTGTGTAC TCAACGTGGA AAAGAGAAAA CAGTCAGACT      780
AAACTACAGG AGAAATATAA TAGCTGGCAT CACGGTGACT TCAATTATGA ACGTCAGGCA      840
ACGTTGACTA TCAGTTCAGC GAGAGTTAAT GATTCTGGAG TGTTCATGTG TTATGCCAAT      900
AATACTTTTG GATCAGCAAA TGTCACAACA ACCTTGGAAG TAGTAGATAA AGGATTCATT      960
AATATCTTCC CCATGATAAA CACTACAGTA TTTGTAAACG ATGGAGAAAA TGTAGATTTG     1020
ATTGTTGAAT ATGAAGCATT CCCCAAACCT GAACACCAGC AGTGGATCTA TATGAACAGA     1080
ACCTTCACTG ATAAATGGGA AGATTATCCC AAGTCTGAGA ATGAAAGTAA TATCAGATAC     1140
GTAAGTGAAC TTCATCTAAC GAGATTAAAA GGCACCGAAG GAGGCACTTA CACATTCCTA     1200
GTGTCCAATT CTGACGTCAA TGCTGCCATA GCATTTAATG TTTATGTGAA TACAAAACCA     1260
GAAATCCTGA CTTACGACAG GCTCGTGAAT GGCATGCTCC AATGTGTGGC AGCAGGATTC     1320
CCAGAGCCCA CAATAGATTG GTATTTTGT CCAGGAACTG AGCAGAGATG CTCTGCTTCT     1380
GTACTGCCAG TGGATGTGCA GACACTAAAC TCATCTGGGC CACCGTTTGG AAAGCTAGTG     1440
GTTCAGAGTT CTATAGATTC TAGTGCATTC AAGCACAATG GCACGGTTGA ATGTAAGGCT     1500
TACAACGATG TGGGCAAGAC TTCTGCCTAT TTTAACTTTG CATTTAAAGG TAACAACAAA     1560
GAGCAAATCC ATCCCCACAC CCTGTTCACT CCTTTGCTGA TTGGTTTCGT AATCGTAGCT     1620
GGCATGATGT GCATTATTGT GATGATTCTG ACCTACAAAT ATTTACAGAA ACCCATGTAT     1680
GAAGTACAGT GGAAGGTTGT TGAGGAGATA AATGGAAACA ATTATGTTTA CATAGACCCA     1740
ACACAACTTC CTTATGATCA CAAATGGGAG TTTCCCAGAA ACAGGCTGAG TTTTGGGAAA     1800
ACCCTGGGTG CTGGAGCTTT CGGGAAGGTT GTTGAGGCAA CTGCTTATGG CTTAATTAAG     1860
TCAGATGCGG CCATGACTGT CGCTGTAAAG ATGCTCAAGC CGAGTGCCCA TTTGACAGAA     1920
CGGGAAGCCC TCATGTCTGA ACTCAAAGTC CTGAGTTACC TTGGTAATCA CATGAATATT     1980
GTGAATCTAC TTGGAGCCTG CACCATTGGA GGGCCCACCC TGGTCATTAC AGAATATTGT     2040
TGCTATGGTG ATCTTTTGAA TTTTTTGAGA AGAAAACGTG ATTCATTTAT TTGTTCAAAG     2100
CAGGAAGATC ATGCAGAAGC TGCACTTTAT AAGAATCTTC TGCATTCAAA GGAGTCTTCC     2160
TGCAGCGATA GTACTAATGA GTACATGGAC ATGAAACCTG GAGTTTCTTA TGTTGTCCCA     2220
ACCAAGGCCG ACAAAAGGAG ATCTGTGAGA ATAGGCTCAT ACATAGAAAG AGATGTGACT     2280
CCCGCCATCA TGGAGGATGA CGAGTTGGCC CTAGACTTAG AAGACTTGCT GAGCTTTTCT     2340
TACCAGGTGG CAAAGGGCAT GGCTTTCCTC GCCTCCAAGA ATTGTATTCA CAGAGACTTG     2400
GCAGCCAGAA ATATCCTCCT TACTCATGGT CGGATCACAA AGATTTGTGA TTTTGGTCTA     2460
GCCAGAGACA TCAAGAATGA TTCTAATTAT GTGGTTAAAG GAAACGCTCG ACTACCTGTG     2520
AAGTGGATGG CACCTGAAAG CATTTTCAAC TGTGTATACA CGTTTGAAAG TGACGTCTGG     2580
TCCTATGGGA TTTTTCTTTG GGAGCTGTTC TCTTTAGGAA GCAGCCCCTA TCCTGGAATG     2640
CCGGTCGATT CTAAGTTCTA CAAGATGATC AAGGAAGGCT TCCGGATGCT CAGCCCTGAA     2700
CACGCACCTG CTGAAATGTA TGACATAATG AAGACTTGCT GGGATGCAGA TCCCCTAAAA     2760
AGACCAACAT TCAAGCAAAT TGTTCAGCTA ATTGAAGAGC AGATTTCAGA GAGCACCAAT     2820
CATATTTACT CCAACTTAGC AAACTGCAGC CCCAACCGAC AGAAGCCCGT GGTAGACCAT     2880
TCTGTGCGGA TCAATTCTGT CGGCAGCACC GCTTCCTCCT CCCAGCCTCT GCTTGTGCAC     2940
GACGATGTCT GAGCAGAATC AGTGTTTGGG TCACCCCTCC AGGAATGATC TCTTCTTTTG     3000
```

```
GCTTCCATGA TGGTTATTTT CTTTTCTTTC AACTTGCATC CAACTCCAGG ATAGTGGGCA    3060
CCCCACTGCA ATCCTGTCTT TCTGAGCACA CTTTAGTGGC CGATGATTTT TGTCATCAGC    3120
CACCATCCTA TTGCAAAGGT TCCAACTGTA TATATTCCCA ATAGCAACGT AGCTTCTACC    3180
ATGAACAGAA AACATTCTGA TTTGGAAAAA GAGAGGGAGG TATGGACTGG GGCCAGAGT     3240
CCTTTCCAAG GCTTCTCCAA TTCTGCCCAA AAATATGGTT GATAGTTTAC CTGAATAAAT    3300
GGTAGTAATC ACAGTTGGCC TTCAGAACCA TCCATAGTAG TATGATGATA CAAGATTAGA    3360
AGCTGAAAAC CTAAGTCCTT TATGTGGAAA ACAGAACATC ATTAGAACAA GGACAGAGT     3420
ATGAACACCT GGGCTTAAGA AATCTAGTAT TCATGCTGG GAATGAGACA TAGGCCATGA     3480
AAAAAATGAT CCCCAAGTGT GAACAAAAGA TGCTCTTCTG TGGACCACTG CATGAGCTTT    3540
TATACTACCG ACCTGGTTTT TAAATAGAGT TTGCTATTAG AGCATTGAAT GGAGAGAAG     3600
GCCTCCCTAG CCAGCACTTG TATATACGCA TCTATAAATT GTCCGTGTTC ATACATTTGA    3660
GGGGAAAACA CCATAAGGTT TCGTTTCTGT ATACAACCCT GGCATTATGT CCACTGTGTA    3720
TAGAAGTAGA TTAAGAGCCA TATAAGTTTG AAGGAAACAG TTAATACCAT TTTTTAAGGA    3780
AACAATATAA CCACAAAGCA CAGTTTGAAC AAAATCTCCT CTTTTAGCTG ATGAACTTAT    3840
TCTGTAGATT CTGTGGAACA AGCCTATCAG CTTCAGAATG GCATTGTACT CAATGGATTT    3900
GATGCTGTTT GACAAAGTTA CTGATTCACT GCATGGCTCC CACAGGAGTG GGAAAACACT    3960
GCCATCTTAG TTTGGATTCT TATGTAGCAG GAAATAAAGT ATAGGTTTAG CCTCCTTCGC    4020
AGGCATGTCC TGGACACCGG GCCAGTATCT ATATATGTGT ATGTACGTTT GTATGTGTGT    4080
AGACAAATAT TTGGAGGGGT ATTTTGCCC TGAGTCCAAG AGGGTCCTTT AGTACCTGAA     4140
AAGTAACTTG GCTTTCATTA TTAGTACTGC TCTTGTTTCT TTTCACATAG CTGTCTAGAG    4200
TAGCTTACCA GAAGCTTCCA TAGTGGTGCA GAGGAAGTGG AAGGCATCAG TCCCTATGTA    4260
TTTGCAGTTC ACCTGCACTT AAGGCACTCT GTTATTTAGA CTCATCTTAC TGTACCTGTT    4320
CCTTAGACCT TCCATAATGC TACTGTCTCA CTGAAACATT TAAATTTTAC CCTTTAGACT    4380
GTAGCCTGGA TATTATTCTT GTAGTTTACC TCTTTAAAAA CAAAACAAAA CAAAACAAAA    4440
AACTCCCCTT CCTCACTGCC AATATAAAA GGCAAATGTG TACATGGCAG AGTTTGTGTG     4500
TTGTCTTGAA AGATTCAGGT ATGTTGCCTT TATGGTTTCC CCCTTCTACA TTTCTTAGAC    4560
TACATTTAGA GAACTGTGGC CGTTATCTGG AAGTAACCAT TTGCACTGGA GTTCTATGCT    4620
CTCGCACCTT TCCAAAGTTA ACAGATTTTG GGGTTGTGTT GTCACCCAAG AGATTGTTGT    4680
TTGCCATACT TTGTCTGAAA AATTCCTTTG TGTTTCTATT GACTTCAATG ATAGTAAGAA    4740
AAGTGGTTGT TAGTTATAGA TGTCTAGGTA CTTCAGGGGC ACTTCATTGA GAGTTTTGTC    4800
TTGCCATACT TTGTCTGAAA AATTCCTTTG TGTTTCTATT GACTTCAATG ATAGTAAGAA    4860
AAGTGGTTGT TAGTTATAGA TGTCTAGGTA CTTCAGGGGC ACTTCATTGA GAGTTTTGTC    4920
AATGTCTTTT GAATATTCCC AAGCCCATGA GTCCTTGAAA ATATTTTTA TATATACAGT     4980
AACTTTATGT GTAAATACAT AAGCGGCGTA AGTTAAAGG ATGTTGGTGT TCCACGTGTT     5040
TTATTCCTGT ATGTTGTCCA ATTGTTGACA GTTCTGAAGA ATTC                     5084
```

( 2 ) INFORMATION FOR SEQ ID NO:22:

( i ) SEQUENCE CHARACTERISTICS:
        ( A ) LENGTH: 4626 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:22:

| | | | | | |
|---|---|---|---|---|---|
| GAATTCCGCC | CTCGCCGCCC | GCGGCGCCCC | GAGCGCTTTG | TGAGCAGATG | CGGAGCCGAG | 60
| TGGAGGGCGC | GAGCCAGATG | CGGGGCGACA | GCTGACTTGC | TGAGAGGAGG | CGGGGAGGCG | 120
| CGGAGCGCGC | GTGTGGTCCT | TGCGCCGCTG | ACTTCTCCAC | TGGTTCCTGG | GCACCGAAAG | 180
| ATAAACCTCT | CATAATGAAG | GCCCCGCTG | TGCTTGCACC | TGGCATCCTC | GTGCTCCTGT | 240
| TTACCTTGGT | GCAGAGGAGC | AATGGGGAGT | GTAAAGAGGC | ACTAGCAAAG | TCCGAGATGA | 300
| ATGTGAATAT | GAAGTATCAG | CTTCCCAACT | TCACCGCGGA | AACACCCATC | CAGAATGTCA | 360
| TTCTACATGA | GCATCACATT | TTCCTTGGTG | CCACTAACTA | CATTTATGTT | TTAAATGAGG | 420
| AAGACCTTCA | GAAGGTTGCT | GAGTACAAGA | CTGGGCCTGT | GCTGGAACAC | CCAGATTGTT | 480
| TCCCATGTCA | GGACTGCAGC | AGCAAAGCCA | ATTTATCAGG | AGGTGTTTGG | AAAGATAACA | 540
| TCAACATGGC | TCTAGTTGTC | GACACCTACT | ATGATGATCA | ACTCATTAGC | TGTGGCAGCG | 600
| TCAACAGAGG | GACCTGCCAG | CGACATGTCT | TCCCCACAA | TCATACTGCT | GACATACAGT | 660
| CGGAGGTTCA | CTGCATATTC | TCCCCACAGA | TAGAAGAGCC | CAGCCAGTGT | CCTGACTGTG | 720
| TGGTGAGCGC | CCTGGGAGCC | AAAGTCCTTT | CATCTGTAAA | GGACCGGTTC | ATCAACTTCT | 780
| TTGTAGGCAA | TACCATAAAT | TCTTCTTATT | CCCAGATCA | TCCATTGCAT | TCGATATCAG | 840
| TGAGAAGGCT | AAAGGAAACG | AAAGATGGTT | TTATGTTTTT | GACGGACCAG | TCCTACATTG | 900
| ATGTTTTACC | TGAGTTCAGA | GATTCTTACC | CCATTAAGTA | TGTCCATGCC | TTTGAAAGCA | 960
| ACAATTTTAT | TTACTTCTTG | ACGGTCCAAA | GGGAAACTCT | AGATGCTCAG | ACTTTTCACA | 1020
| CAAGAATAAT | CAGGTTCTGT | TCCATAAACT | CTGGATTGCA | TTCCTACATG | GAAATGCCTC | 1080
| TGGAGTGTAT | TCTCACAGAA | AAGAGAAAAA | AGAGATCCAC | AAAGAAGGAA | GTGTTTAATA | 1140
| TACTTCAGGC | TGCGTATGTC | AGCAAGCCTG | GGCCCAGCT | TGCTAGACAA | ATAGGAGCCA | 1200
| GCCTGAATGA | TGACATTCTT | TTCGGGGTGT | TCGCACAAAG | CAAGCCAGAT | TCTGCCGAAC | 1260
| CAATGGATCG | ATCTGCCATG | TGTGCATTCC | CTATCAAATA | TGTCAACGAC | TTCTTCAACA | 1320
| AGATCGTCAA | CAAAAACAAT | GTGAGATGTC | TCCAGCATTT | TTACGGACCC | AATCATGAGC | 1380
| ACTGCTTTAA | TAGGACACTT | CTGAGAAATT | CATCAGGCTG | TGAAGCGCGC | CGTGATGAAT | 1440
| ATCGAACAGA | GTTACCACA | GCTTTGCAGC | GCGTTGACTT | ATTCATGGGT | CAATTCAGCG | 1500
| AAGTCCTCTT | AACATCTATA | TCCACCTTCA | TTAAGGAGA | CCTCACCATA | GCTAATCTTG | 1560
| GGACATCAGA | GGGTCGCTTC | ATGCAGGTTG | TGGTTTCTCG | ATCAGGACCA | TCAACCCCTC | 1620
| ATGTGAATTT | TCTCCTGGAC | TCCCATCCAG | TGTCTCCAGA | AGTGATTGTG | GAGCATACAT | 1680
| TAAACCAAAA | TGGCTACACA | CTGGTTATCA | CTGGGAAGAA | GATCACGAAG | ATCCCATTGA | 1740
| ATGGCTTGGG | CTGCAGACAT | TTCCAGTCCT | GCAGTCAATG | CCTCTCTGCC | CCACCCTTTG | 1800
| TTCAGTGTGG | CTGGTGCCAC | GACAAATGTG | TGCGATCGGA | GGAATGCCTG | AGCGGGACAT | 1860
| GGACTCAACA | GATCTGTCTG | CCTGCAATCT | ACAAGGTTTT | CCCAAATAGT | GCACCCCTTG | 1920
| AAGGAGGGAC | AAGGCTGACC | ATATGTGGCT | GGGACTTTGG | ATTTCGGAGG | AATAATAAAT | 1980
| TTGATTTAAA | GAAAACTAGA | GTTCTCCTTG | GAAATGAGAG | CTGCACCTTG | ACTTTAAGTG | 2040
| AGAGCACGAT | GAATACATTG | AAATGCACAG | TTGGTCCTGC | CATGAATAAG | CATTTCAATA | 2100
| TGTCCATAAT | TATTTCAAAT | GGCCACGGGA | CAACACAATA | CAGTACATTC | TCCTATGTGG | 2160
| ATCCTGTAAT | AACAAGTATT | TCGCCGAAAT | ACGGTCCTAT | GGCTGGTGGC | ACTTTACTTA | 2220
| CTTTAACTGG | AAATTACCTA | AACAGTGGGA | ATTCTAGACA | CATTTCAATT | GGTGGAAAAA | 2280
| CATGTACTTT | AAAAAGTGTG | TCAAACAGTA | TTCTTGAATG | TTATACCCCA | GCCCAAACCA | 2340

-continued

```
TTTCAACTGA GTTTGCTGTT AAATTGAAAA TTGACTTAGC CAACCGAGAG ACAAGCATCT     2400
TCAGTTACCG TGAAGATCCC ATTGTCTATG AAATTCATCC AACCAAATCT TTTATTAGTA     2460
CTTGGTGGAA AGAACCTCTC AACATTGTCA GTTTTCTATT TTGCTTGCC  AGTGGTGGGA     2520
GCACAATAAC AGGTGTTGGG AAAAACCTGA ATTCAGTTAG TGTCCCGAGA ATGGTCATAA     2580
ATGTGCATGA AGCAGGAAGG AACTTACAG  TGGCATGTCA ACATCGCTCT AATTCAGAGA     2640
TAATCTGTTG TACCACTCCT TCCCTGCAAC AGCTGAATCT GCAACTCCCC CTGAAAACCA     2700
AAGCCTTTTT CATGTTAGAT GGGATCCTTT CCAAATACTT TGATCTCATT TATGTACATA     2760
ATCCTGTGTT TAAGCCTTTT GAAAAGCCAG TGATGATCTC AATGGGCAAT GAAAATGTAC     2820
TGGAAATTAA GGGAAATGAT ATTGACCCTG AAGCAGTTAA AGGTGAAGTG TTAAAAGTTG     2880
GAAATAAGAG CTGTGAGAAT ATACACTTAC ATTCTGAAGC CGTTTATGC  ACGGTCCCCA     2940
ATGACCTGCT GAAATTGAAC AGCGAGCTAA ATATAGAGTG GAAGCAAGCA ATTTCTTCAA     3000
CCGTCCTTGG AAAAGTAATA GTTCAACCAG ATCAGAATTT CACAGGATTG ATTGCTGGTG     3060
TTGTCTCAAT ATCAACAGCA CTGTTATTAC TACTTGGGTT TTTCCTGTGG CTGAAAAAGA     3120
GAAAGCAAAT TAAAGATCTG GGCAGTGAAT TAGTTCGCTA CGATGCAAGA GTACACACTC     3180
CTCATTTGGA TAGGCTTGTA AGTGCCCGAA GTGTAAGCCC AACTACAGAA ATGGTTTCAA     3240
ATGAATCTGT AGACTACCGA GCTACTTTTC CAGAAGATCA GTTTCCTAAT TCATCTCAGA     3300
ACGGTTCATG CCGACAAGTG CAGTATCCTC TGACAGACAT GTCCCCATC  CTAACTAGTG     3360
GGGACTCTGA TATATCCAGT CCATTACTGC AAAATACTGT CCACATTGAC CTCAGTGCTC     3420
TAAATCCAGA GCTGGTCCAG GCAGTGCAGC ATGTAGTGAT TGGGCCAGT  AGCCTGATTG     3480
TGCATTTCAA TGAAGTCATA GGAAGAGGGC ATTTTGGTTG TGTATATCAT GGGACTTTGT     3540
TGGACAATGA TGGCAAGAAA ATTCACTGTG CTGTGAAATC CTTGAACAGA ATCACTGACA     3600
TAGGAGAAGT TTCCCAATTT CTGACCGAGG GAATCATCAT GAAAGATTTT AGTCATCCCA     3660
ATGTCCTCTC GCTCCTGGGA ATCTGCCTGC GAAGTGAAGG GTCTCCGCTG GTGGTCCTAC     3720
CATACATGAA ACATGGAGAT CTTCGAAATT TCATTCGAAA TGAGACTCAT AATCCAACTG     3780
TAAAAGATCT TATTGGCTTT GGTCTTCAAG TAGCCAAAGC GATGAAATAT CTTGCAAGCA     3840
AAAAGTTTGT CCACAGAGAC TTGGCTGCAA GAAACTGTAT GCTGGATGAA AAATTCACAG     3900
TCAAGGTTGC TGATTTTGGT CTTGCCAGAG ACATGTATGA TAAAGAATAC TATAGTGTAC     3960
ACAACAAAAC AGGTGCAAAG CTGCCAGTGA AGTGGATGGC TTTGGAAAGT CTGCAAACTC     4020
AAAAGTTTAC CACCAAGTCA GATGTGTGGT CCTTTGGCGT CGTCCTCTGG GAGCTGATGA     4080
CAAGAGGAGC CCCACCTTAT CCTGACGTAA ACACCTTTGA TATAACTGTT TACTTGTTGC     4140
AAGGGAGAAG ACTCCTACAA CCCGAATACT GCCCAGACCC CTTATATGAA GTAATGCTAA     4200
AATGCTGGCA CCCTAAAGCC GAAATGCGCC CATCCTTTTC TGAACTGGTG TCCCGGATAT     4260
CAGCGATCTT CTCTACTTTC ATTGGGGAGC ACTATGTCCA TGTGAACGCT ACTTATGTGA     4320
ACGTAAAATG TGTCGCTCCG TATCCTTCTC TGTTGTCATC AGAAGATAAC GCTGATGATG     4380
AGGTGGACAC ACGACCAGCC TCCTTCTGGG AGACATCATA GTGCTAGTAC TATGTCAAAG     4440
CAACAGTCCA CACTTTGTCC AATGGTTTTT TCACTGCCTG ACCTTTAAAA GGCCATCGAT     4500
ATTCTTTGCT CCTTGCCATA GGACTTGTAT TGTTATTTAA ATTACTGGAT TCTAAGGAAT     4560
TTCTTATCTG ACAGAGCATC AGAACCAGAG GCTTGGTCCC ACAGGCCAGG GACCAATGCG     4620
CTGCAG                                                                4626
```

( 2 ) INFORMATION FOR SEQ ID NO:23:

(i) SEQUENCE CHARACTERISTICS:
    (A) LENGTH: 2301 base pairs
    (B) TYPE: nucleic acid
    (C) STRANDEDNESS: double
    (D) TOPOLOGY: linear (xi) SEQUENCE DESCRIPTION: SEQ ID NO:23:

| | | | | | |
|---|---|---|---|---|---|
| GTCGACCGGA | GGGCAGGAGG | AGCAGGAGGA | GCAGGAGCAG | GAGGAGCAGG | AGGAGCAGGA | 60 |
| GGAGCAGGAG | GAGCAGGAGG | AGCAGGAACA | GGAGGAGGAG | GAGGAGGAGA | AGGAGGAGCA | 120 |
| GGAAGAGCAG | GAGGAGGAGG | AGCAGGAGCA | GGAGGAGCAG | GAGGGAGAGG | AGGCTGCAAC | 180 |
| GCCGAGCGGA | GGAGGCAGGA | ACCGGAGCGC | GAGCAGTAGC | TGGGTGGGCA | CCATGGCTGG | 240 |
| GATCACCACC | ATCGAGGCGG | TGAAGCGCAA | GATCCAGGTT | CTGCAGCAGC | AGGCAGATGA | 300 |
| TGCAGAGGAG | CGAGCTGAGC | GCCTCCAGCG | AGAAGTTGAG | GGAGAAAGGC | GGGCCCGGGA | 360 |
| ACAGGCTGAG | GCTGAGGTGG | CCTCCTTGAA | CCGTAGGATC | CAGCTGGTTG | AAGAAGAGCT | 420 |
| GGACCGTGCT | CAGGAGCGCC | TGGCCACTGC | CCTGCAAAAG | CTGGAAGAAG | CTGAAAAAGC | 480 |
| TGCTGATGAG | AGTGAGAGAG | GTATGAAGGT | TATTGAAAAC | CGGGCCTTAA | AGATGAAGA | 540 |
| AAAGATGGAA | CTCCAGGAAA | TCCAACTCGA | AGAAGCTAAG | CACATTGCAG | AAGAGGCAGA | 600 |
| TAGGAAGTAT | GAAGAGGTGG | CTCGTAAGTT | GGTGATCATT | GAAGGAGACT | GGAACGCAC | 660 |
| AGAGGAACGA | GCTGAGCTGG | CAGAGTCGCG | TTGCCGAGAG | ATGGATGAGC | AGATTAGACT | 720 |
| GATGGACCAG | AACCTGAAGT | GTCTGAGTGC | TGCCGAAGAA | AAGTACTCTC | AAAAAGAAGA | 780 |
| TAAATATGAG | GAAGAAATCA | AGATTCTTAC | TGATAAACTC | AAGGAGGCAG | AGACCCGTGC | 840 |
| TGAGTTTGCT | GAGAGATCGG | TAGCCAAGCT | GGAAAAGACA | ATTGATGACC | TGGAAGACAC | 900 |
| TAACAGCACA | TCTGGAGACC | CGGTGGAGAA | GAAGGACGAA | ACACCTTTTG | GGGTCTCGGT | 960 |
| GGCTGTGGGC | CTGGCCGTCT | TTGCCTGCCT | CTTCCTTTCT | ACGCTGCTCC | TTGTGCTCAA | 1020 |
| CAAATGTGGA | CGGAGAAACA | AGTTTGGGAT | CAACCGCCCG | GCTGTGCTGG | CTCCAGAGGA | 1080 |
| TGGGCTGGCC | ATGTCCTGC | ATTTCATGAC | ATTGGGTGGC | AGCTCCCTGT | CCCCACCGA | 1140 |
| GGGCAAAGGC | TCTGGGCTCC | AAGGCCACAT | CATCGAGAAC | CCACAATACT | TCAGTGATGC | 1200 |
| CTGTGTTCAC | CACATCAAGC | GCCGGGACAT | CGTGCTCAAG | TGGGAGCTGG | GGAGGGCGC | 1260 |
| CTTTGGGAAG | GTCTTCCTTG | CTGAGTGCCA | CAACCTCCTG | CCTGAGCAGG | ACAAGATGCT | 1320 |
| GGTGGCTGTC | AAGGCACTGA | AGGAGGCGTC | CGAGAGTGCT | CGGCAGGACT | TCCAACGTGA | 1380 |
| GGCTGAGCTG | CTCACCATGC | TGCAGCACCA | GCACATCGTG | CGCTTCTTCG | GCGTCTGCAC | 1440 |
| CGAGGGCCGC | CCCCTGCTCA | TGGTCTTCGA | GTATATGCGG | CACGGGACC | TCAACCGCTT | 1500 |
| CCTCCGATCC | CATGGACCCG | ATGCCAAGCT | GCTGGCTGGT | GGGGAGGATG | TGGCTCCAGG | 1560 |
| CCCCCTGGGT | CTGGGGCAGC | TGCTGGCCGT | GGCTAGCCAG | GTCGCTGCGG | GGATGGTGTA | 1620 |
| CCTGGCGGGT | CTGCATTTTG | TGCACCGGGA | CCTGGCCACA | CGCAACTGTC | TAGTGGGCCA | 1680 |
| GGGACTGGTG | GTCAAGATTG | GTGATTTTGG | CATGAGCAGG | GATATCTACA | GCACCGACTA | 1740 |
| TTACCGTGTG | GGAGGCCGCA | CCATGCTGCC | CATTCGCTGG | ATGCCGCCCG | AGAGCATCCT | 1800 |
| GTACCGTAAG | TTCACCACCG | AGAGCGACGT | GTGGAGCTTC | GGCGTGGTGC | TCTGGGAGAT | 1860 |
| CTTCACCTAC | GGCAAGCAGC | CCTGGTACCA | GCTCTCCAAC | ACGGAGGCAA | TCGACTGCAT | 1920 |
| CACGCAGGGA | CGTGAGTTGG | AGCGGCCACG | TGCCTGCCCA | CCAGAGGTCT | ACGCCATCAT | 1980 |
| GCGGGGCTGC | TGGCAGCGGG | AGCCCAGCAA | CGCCACAGCA | TCAAGGATGT | GCACGCCCGG | 2040 |
| CTGCAAGCCC | TGGCCTAGGC | ACCTCCTGTC | TACCTGGATG | TCCTGGGCTA | GGGGCCGGC | 2100 |
| CCAGGGGCTG | GGAGTGGTTA | GCCGGAATAC | TGGGGCCTGC | CCTCAGCATC | CCCCATAGCT | 2160 |

| | | | | | | |
|---|---|---|---|---|---|---|
| CCCAGCAGCC | CCAGGGTGAT | CTCGAAGTAT | CTAATTCGCC | CTCAGCATGT | GGGAAGGGAC | 2220 |
| AGGTGGGGGC | TGGGAGTAGA | GGATGTTCCT | GCTTCTCTAG | GCAAGGTCCC | GTCGTAGCAA | 2280 |
| TTATATTTAT | TATGGGAATT | C | | | | 2301 |

( 2 ) INFORMATION FOR SEQ ID NO:24:

( i ) SEQUENCE CHARACTERISTICS:
        ( A ) LENGTH: 271 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:24:

| | | | | | | |
|---|---|---|---|---|---|---|
| CTGCCAGGAC | CATGGGTAGC | AACAAGAGCA | AGCCCAAGGA | TGCCAGCCAG | CGGCGCCGCA | 60 |
| GCCTGGAGCC | CGCCGAGAAC | GTGCACGGCG | CTGGCGGGGG | CGCTTTCCCC | GCCTCGCAGA | 120 |
| CCCCCAGCAA | GCCAGCCTCG | GCCGACGGCC | ACCGCGGCCC | CAGCGCGGCC | TTCGCCCCCG | 180 |
| CGGCCGCCGA | GCCCAAGCTG | TTCGGAGGCT | TCAACTCCTC | GGACACCGTC | ACCTCCCCGC | 240 |
| AGAGGGCGGG | CCCGCTGGCC | GGTCAGTGCG | C | | | 271 |

( 2 ) INFORMATION FOR SEQ ID NO:25:

( i ) SEQUENCE CHARACTERISTICS:
        ( A ) LENGTH: 118 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:25:

| | | | | | | |
|---|---|---|---|---|---|---|
| CTCTCTGCAG | GTGGAGTGAC | CACCTTTGTG | GCCCTCTATG | ACTATGAGTC | TAGGACGGAG | 60 |
| ACAGACCTGT | CCTTCAAGAA | AGGCGAGCGG | CTCCAGATTG | TCAACAACAC | GTGAGTGC | 118 |

( 2 ) INFORMATION FOR SEQ ID NO:26:

( i ) SEQUENCE CHARACTERISTICS:
        ( A ) LENGTH: 113 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:26:

| | | | | | | |
|---|---|---|---|---|---|---|
| CCTGCTCAGA | GAGGGAGACT | GGTGGCTGGC | CCACTCGCTC | AGCACAGGAC | AGACAGGCTA | 60 |
| CATCCCCAGC | AACTACGTGG | CGCCCTCCGA | CTCCATCCAG | GCTGAGGAGT | TAG | 113 |

( 2 ) INFORMATION FOR SEQ ID NO:27:

( i ) SEQUENCE CHARACTERISTICS:
        ( A ) LENGTH: 115 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:27:

| | | | | | | |
|---|---|---|---|---|---|---|
| CCCCCAGGTG | GTATTTTGGC | AAGATCACCA | GACGGGAGTC | AGAGCGGTTA | CTGCTCAATG | 60 |
| CAGAGAACCC | GAGAGGGACC | TTCCTCGTGC | GAGAAAGTGA | GACCACGAAA | GGTAC | 115 |

( 2 ) INFORMATION FOR SEQ ID NO:28:

( i ) SEQUENCE CHARACTERISTICS:
        ( A ) LENGTH: 164 base pairs
        ( B ) TYPE: nucleic acid
        ( C ) STRANDEDNESS: double ( D ) TOPOLOGY: linear ( x i ) SEQUENCE DESCRIPTION: SEQ ID NO:28:

```
GCCCCGCAGG TGCCTACTGC CTCTCAGTGT CTGACTTCGA CAACGCCAAG GGCCTCAACG      60
TGAAGCACTA CAAGATCCGC AAGCTGGACA GCGGCGGCTT CTACATCACC TCCCGCACCC     120
AGTTCAACAG CCTGCAGCAG CTGGTGGCCT ACTACTCCAG TGAG                      164
```

( 2 ) INFORMATION FOR SEQ ID NO:29:

( i ) SEQUENCE CHARACTERISTICS:
        ( A ) LENGTH: 170 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:29:

```
CCTCCTCAGA ACACGCCGAT GGCCTGTGCC ACCGCCTCAC CACCGTGTGC CCCACGTCCA      60
AGCCGCAGAC TCAGGGCCTG GCCAAGGATG CCTGGGAGAT CCCTCGGGAG TCGCTGCGGC     120
TGGAGGTCAA GCTGGGCCAG GGCTGCTTTG GCGAGGTGTG GATGGGTAAG                170
```

( 2 ) INFORMATION FOR SEQ ID NO:30:

( i ) SEQUENCE CHARACTERISTICS:
        ( A ) LENGTH: 194 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:30:

```
CCTCAACAGG GACCTGGAAC GGTACCACCA GGGTGGCCAT CAAAACCCTG AAGCCTGGCA      60
CGATGTCTCC AGAGGCCTTC CTGCAGGAGG CCCAGGTCAT GAAGAAGCTG AGGCATGAGA     120
AGCTGGTGCA GTTGTATGCT GTGGTTTCAG AGGAGCCCAT TTACATCGTC ACGGAGTACA     180
TGAGCAAGGG TGAG                                                       194
```

( 2 ) INFORMATION FOR SEQ ID NO:31:

( i ) SEQUENCE CHARACTERISTICS:
        ( A ) LENGTH: 91 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:31:

```
TCTGCCCAGG GAGTTTGCTG GACTTTCTCA AGGGGGAGAC AGGCAAGTAC CTGCGGCTGC      60
CTCAGCTGGT GGACATGGCT GCTCAGGTGA G                                     91
```

( 2 ) INFORMATION FOR SEQ ID NO:32:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:32:

```
CTGCAGATCG CCTCAGGCAT GGCGTACGTG GAGCGGATGA ACTACGTCCA CCGGGACCTT      60
CGTGCAGCCA ACATCCTGGT GGGAGAGAAC CTGGTGTGCA AAGTGGCCGA CTTTGGGCTG     120
GCTCGGCTCA TTGAAGACAA TGAGTACACG GCGCGGCAAG GTGGG                     165
```

( 2 ) INFORMATION FOR SEQ ID NO:33:

(i) SEQUENCE CHARACTERISTICS:
    (A) LENGTH: 146 base pairs
    (B) TYPE: nucleic acid
    (C) STRANDEDNESS: double
    (D) TOPOLOGY: linear (xi) SEQUENCE DESCRIPTION: SEQ ID NO:33:

```
TTCCTGCAGG TGCCAAATTC CCCATCAAGT GGACGGCTCC AGAAGCTGCC CTCTATGCC        60
GCTTCACCAT CAAGTCGGAC GTGTGGTCCT TCGGGATCCT GCTGACTGAG CTCACCACAA      120
AGGGACGGGT GCCCTACCCT GGTAAG                                            146
```

(2) INFORMATION FOR SEQ ID NO:34:

(i) SEQUENCE CHARACTERISTICS:
    (A) LENGTH: 255 base pairs
    (B) TYPE: nucleic acid
    (C) STRANDEDNESS: double
    (D) TOPOLOGY: linear (xi) SEQUENCE DESCRIPTION: SEQ ID NO:34:

```
CTGCCACAGG GATGGTGAAC CGCGAGGTGC TGGACCAGGT GGAGCGGGGC TACCGGATGC        60
CCTGCCCGCC GGAGTGTCCC GAGTCCCTGC ACGACCTCAT GTGCCAGTGC TGGCGGAAGG      120
AGCCTGAGGA GCGGCCCACC TTCGAGTACC TGCAGGCCTT CCTGGAGGAC TACTTCACGT      180
CCACCGAGCC CCAGTACCAG CCCGGGGAGA ACCTCTAGGC ACAGGCGGGC CCAGACCGGC      240
TTCTCGGCTT GGATC                                                        255
```

(2) INFORMATION FOR SEQ ID NO:35:

(i) SEQUENCE CHARACTERISTICS:
    (A) LENGTH: 3623 base pairs
    (B) TYPE: nucleic acid
    (C) STRANDEDNESS: double
    (D) TOPOLOGY: linear (xi) SEQUENCE DESCRIPTION: SEQ ID NO:35:

```
CGCGGCCGCC CTGGGCGGGC GCGGGCGGCG GGCGGCGGTG AGGGCGGCCT GCGGGCGGC        60
GCCCGGGGGC CGGGCCGAGC CGGGCCTGAG CCGGGCCCGG ACCGAGCTGG GAGAGGGGCT      120
CCGGCCCGAT CGTTCGCTTG GCGCAAAATG TTGGAGATCT GCCTGAAGCT GGTGGGCTGC      180
AAATCCAAGA AGGGGCTGTC CTCGTCCTCC AGCTGTTATC TGGAAGAAGC CCTTCAGCGG      240
CCAGTAGCAT CTGACTTTGA GCCTCAGGGT CTGAGTGAAG CCGCTCGTTG GAACTCCAAG      300
GAAAACCTTC TCGCTGGACC CAGTGAAAAT GACCCCAACC TTTTCGTTGC ACTGTATGAT      360
TTTGTGGCCA GTGGAGATAA CACTCTAAGC ATAACTAAAG GTGAAAAGCT CCGGGTCTTA      420
GGCTATAATC ACAATGGGGA ATGGTGTGAA GCCCAAACCA AAAATGGCCA AGGCTGGGTC      480
CCAAGCAACT ACATCACGCC AGTCAACAGT CTGGAGAAAC ACTCCTGGTA CCATGGGCCT      540
GTGTCCCGCA ATGCCGCTGA GTATCCGCTG AGCAGCGGGA TCAATGGCAG CTTCTTGGTG      600
CGTGAGAGTG AGAGCAGTCC TAGCCAGAGG TCCATCTCGC TGAGATACGA AGGGAGGGTG      660
TACCATTACA GGATCAACAC TGCTTCTGAT GGCAAGCTCT ACGTCTCCTC CGAGAGCCGC      720
TTCAACACCC TGGCCGAGTT GGTTCATCAT CATTCAACGG TGGCCGACGG GCTCATCACC      780
ACGCTCCATT ATCCAGCCCC AAAGCGCAAC AAGCCCACTG TCTATGGTGT GTCCCCCAAC      840
TACGACAAGT GGGAGATGGA ACGCACGGAC ATCACCATGA AGCACAAGCT GGGCGGGGGC      900
CAGTACGGGG AGGTGTACGA GGGCGTGTGG AAGAAATACA GCCTGACGGT GGCCGTGAAG      960
ACCTTGAAGG AGGACACCAT GGAGGTGGAA GAGTTCTTGA AAGAAGCTGC AGTCATGAAA     1020
```

| | | | | | |
|---|---|---|---|---|---|
| GAGATCAAAC | ACCCTAACCT | AGTGCAGCTC | CTTGGGGTCT | GCACCCGGGA | GCCCCCGTTC | 1080
| TATATCATCA | CTGAGTTCAT | GACCTACGGG | AACCTCCTGG | ACTACCTGAG | GGAGTGCAAC | 1140
| CGGCAGGAGG | TGAACGCCGT | GGTGCTGCTG | TACATGGCCA | CTCAGATCTC | GTCAGCCATG | 1200
| GAGTACCTAG | AGAAGAAAAA | CTTCATCCAC | AGAGATCTTG | CTGCCCGAAA | CTGCCTGGTA | 1260
| GGGGAGAACC | ACTTGGTGAA | GGTAGCTGAT | TTTGGCCTGA | GCAGGTTGAT | GACAGGGGAC | 1320
| ACCTACACAG | CCCATGCTGG | AGCCAAGTTC | CCCATCAAAT | GGACTGCACC | CGAGAGCCTG | 1380
| GCCTACAACA | AGTTCTCCAT | CAAGTCCGAC | GTCTGGGCAT | TTGGAGTATT | GCTTTGGGAA | 1440
| ATTGCTACCT | ATGGCATGTC | CCCTTACCCG | GGAATTGACC | GTTCCAGGT | GTATGAGCTG | 1500
| CTAGAGAAGG | ACTACCGCAT | GAAGCGCCCA | GAAGGCTGCC | CAGAGAAGGT | CTATGAACTC | 1560
| ATGCGAGCAT | GTTGGCAGTG | GAATCCCTCT | GACCGGCCCT | CCTTTGCTGA | AATCCACCAA | 1620
| GCCTTTGAAA | CAATGTTCCA | GGAATCCAGT | ATCTCAGACG | AAGTGGAAAA | GGAGCTGGGG | 1680
| AAACAAGGCG | TCCGTGGGGC | TGTGACTACC | TTGCTGCAGG | CCCCAGAGCT | GCCCACCAAG | 1740
| ACGAGGACCT | CCAGGAGAGC | TGCAGAGCAC | AGAGACACCA | CTGACGTGCC | TGAGATGCCT | 1800
| CACTCCAAGG | GCCAGGGAGA | GAGCGATCCT | CTGGACCATG | AGCCTGCCGT | GTCTCCATTG | 1860
| CTCCCTCGAA | AGAGCGAGG | TCCCCGGAG | GGCGGCCTGA | ATGAAGATGA | GCGCCTTCTC | 1920
| CCCAAAGACA | AAAAGACCAA | CTTGTTCAGC | GCCTTGATCA | AGAAGAAGAA | GAAGACAGCC | 1980
| CCAACCCCTC | CAAACGCAG | CAGCTCCTTC | CGGGAGATGG | ACGGCAGCC | GGAGCGCAGA | 2040
| GGGGCCGGCG | AGGAAGAGGG | CCGAGACATC | AGCAACGGGG | CACTGGCTTT | CACCCCCTTG | 2100
| GACACAGCTG | ACCCAGCCAA | GTCCCCAAAG | CCCAGCAATG | GGCTGGGGT | CCCCAATGGA | 2160
| GCCCTCCGGG | AGTCCGGGGG | CTCAGGCTTC | CGGTCTCCCC | ACCTGTGGAA | GAAGTCCAGC | 2220
| ACGCTGACCA | GCAGCCGCCT | AGCCACCGGC | GAGGAGGAGG | GCGGTGGCAG | CTCCAGCAAG | 2280
| CGCTTCCTGC | GCTCTTGCTC | CGTCTCCTGC | GTTCCCCATG | GGCCAAGGA | CACGGAGTGG | 2340
| AGGTCAGTCA | CGCTGCCTCG | GGACTTGCAG | TCCACGGAA | GACAGTTTGA | CTCGTCCACA | 2400
| TTTGGAGGGC | ACAAAAGTGA | GAAGCCGGCT | CTGCCTCGGA | AGAGGGCAGG | GGAGAACAGG | 2460
| TCTGACCAGG | TGACCCGAGG | CACAGTAACG | CCTCCCCCA | GGCTGGTGAA | AAAGAATGAG | 2520
| GAAGCTGCTG | ATGAGGTCTT | CAAAGACATC | ATGGAGTCCA | GCCCGGGCTC | CAGCCCGCCC | 2580
| AACCTGACTC | CAAAACCCCT | CCGGCGGCAG | GTCACCGTGG | CCCCTGCCTC | GGGCCTCCCC | 2640
| CACAAGGAAG | AAGCCTGGAA | AGGCAGTGCC | TTAGGGACCC | CTGCTGCAGC | TGAGCCAGTG | 2700
| ACCCCCACCA | GCAAAGCAGG | CTCAGGTGCA | CCAAGGGGCA | CCAGCAAGGG | CCCCGCCGAG | 2760
| GAGTCCAGAG | TGAGGAGGCA | CAAGCACTCC | TCTGAGTCGC | CAGGGAGGGA | CAAGGGGAAA | 2820
| TTGTCCAAGC | TCAAACCTGC | CCCGCCGCCC | CCACCAGCAG | CCTCTGCAGG | GAAGGCTGGA | 2880
| GGAAAGCCCT | CGCAGAGGCC | CGGCCAGGAG | GCTGCCGGGG | AGGCAGTCTT | GGGCGCAAAG | 2940
| ACAAAAGCCA | CGAGTCTGGT | TGATGCTGTG | AACAGTGACG | CTGCCAAGCC | CAGCCAGCCG | 3000
| GCAGAGGGCC | TCAAAAAGCC | CGTGCTCCCG | GCCACTCCAA | AGCCACACCC | CGCCAAGCCG | 3060
| TCGGGGACCC | CCATCAGCCC | AGCCCCGTT | CCCCTTTCCA | CGTTGCCATC | AGCATCCTCG | 3120
| GCCTTGGCAG | GGGACCAGCC | GTCTTCCACT | GCCTTCATCC | CTCTCATATC | AACCCGAGTG | 3180
| TCTCTTCGGA | AAACCCGCCA | GCCTCCAGAG | CGGGCCAGCG | GCGCCATCAC | CAAGGGCGTG | 3240
| GTCTTGGACA | GCACCGAGGC | GCTGTGCCTC | GCCATCTCTG | GAACTCCGA | GCAGATGGCC | 3300
| AGCCACAGCG | CAGTGCTGGA | GGCCGGCAAA | AACCTCTACA | CGTTCTGCGT | GAGCTATGTG | 3360
| GATTCCATCC | AGCAAATGAG | GAACAAGTTT | GCCTTCCGAG | AGGCCATCAA | CAAACTGGAG | 3420

| | | | | | | |
|---|---|---|---|---|---|---|
| AATAATCTCC | GGGAGCTTCA | GATCTGCCCG | GCGTCAGCAG | GCAGTGGTCC | GGCGGCCACT | 3480 |
| CAGGACTTCA | GCAAGCTCCT | CAGTTCGGTG | AAGGAAATCA | GTGACATAGT | GCAGAGGTAG | 3540 |
| CAGCAGTCAG | GGGTCAGGTG | TCAGGCCCGT | CGGAGCTGCC | TGCAGCACAT | GCGGGCTCGC | 3600 |
| CCATACCCAT | GACAGTGGCT | GAG | | | | 3623 |

( 2 ) INFORMATION FOR SEQ ID NO:36:

( i ) SEQUENCE CHARACTERISTICS:
        ( A ) LENGTH: 257 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

| | | | | | | |
|---|---|---|---|---|---|---|
| CACAGCATTC | CGCTGACCAT | CAATAAGGAA | GAAGCCCTTC | AGCGGCCAGT | AGCATCTGAC | 60 |
| TTTGAGCCTC | AGGGTCTGAG | TGAAGCCGCT | CGTTGGAACT | CCAAGGAAAA | CCTTCTCGCT | 120 |
| GGACCCAGTG | AAAATGACCC | CAACCTTTTC | GTTGCACTGT | ATGATTTGT | GGCCAGTGGA | 180 |
| GATAACACTC | TAAGCATAAC | TAAAGGTGAA | AAGCTCCGGG | TCTTAGGCTA | TAATCACAAT | 240 |
| GGGGAATGGT | GTGAAGC | | | | | 257 |

( 2 ) INFORMATION FOR SEQ ID NO:37:

( i ) SEQUENCE CHARACTERISTICS:
        ( A ) LENGTH: 266 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

| | | | | | | |
|---|---|---|---|---|---|---|
| GTCATCGTCC | ACTCAGCCAC | TGGATTTAAG | CAGAGTTCAA | AAGCCCTTCA | GCGGCCAGTA | 60 |
| GCATCTGACT | TTGAGCCTCA | GGGTCTGAGT | GAAGCCGCTC | GTTGGAACTC | CAAGGAAAAC | 120 |
| CTTCTCGCTG | ACCCAGTGA | AAATGACCCC | AACCTTTTCG | TTGCACTGTA | TGATTTTGTG | 180 |
| GCCAGTGGAG | ATAACACTCT | AAGCATAACT | AAAGGTGAAA | AGCTCCGGGT | CTTAGGCTAT | 240 |
| AATCACAATG | GGGAATGGTG | TGAAGC | | | | 266 |

( 2 ) INFORMATION FOR SEQ ID NO:38:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

| | | | | | | |
|---|---|---|---|---|---|---|
| GATGGCGAGG | GCGCCTTCCA | TGGAGACGCA | GAAGCCCTTC | AGCGGCCAGT | AGCATCTGAC | 60 |
| TTTGAGCCTC | AGGGTCTGAG | | | | | 80 |

( 2 ) INFORMATION FOR SEQ ID NO:39:

( i ) SEQUENCE CHARACTERISTICS:
        ( A ) LENGTH: 139 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:39:

| | | | | | | |
|---|---|---|---|---|---|---|
| GTTCTGTTCT | GTGCCTACAG | TGAAGGTGAC | TGGTGGGAGG | CTCGGTCTCT | CAGCTCCGGA | 60 |
| AAAACTGGCT | GCATTCCCAG | CAACTACGTG | GCCCCTGTTG | ACTCAATCCA | AGCTGAAGAG | 120 |

TAAGTAGGGA TTGGGGCAA                                                                    139

( 2 ) INFORMATION FOR SEQ ID NO:40:

( i ) SEQUENCE CHARACTERISTICS:
        ( A ) LENGTH: 1804 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:40:

| | | | | | |
|---|---|---|---|---|---|
| GGATCCTCAG | GGGTAACACC | TTTTGGAGGT | GGGCATCTTC | CTCATTCTCA | GTGGTGCCAA | 60
| GTTCATATCC | TGCTGGCTTA | ACACGTGGTG | TTACTATATT | TGTGGCCTTA | TATGATTATG | 120
| AAGCTAGAAC | TACAGAAGAC | CTTTCATTTA | AGAAGGGTGA | AAAATTTCAA | ATAATTAACA | 180
| ATACAGAAGG | AGACTGGTGG | GAAGCAAGAT | CAATCACTAC | AGGAAAGAAT | GGTTATATCC | 240
| TGAGCAGTTA | TGTAGCGCCT | GCAGATTCCA | TTCAGGCAGA | AGAATGGTAT | TTTGGCAAAA | 300
| TGGGGAGAAA | AGATGCTGAA | AGATTACTTC | TGAATCCTGG | AAATTAATGA | GGTATTTTCT | 360
| TAGGAAGAGA | GAGTGAAATG | GCTGGGTGCA | GTGGCTCATG | CCTGTAATCC | CAGCACTTTG | 420
| GGAGGCCGAG | TTGGGCGGAT | CACCTGAGGT | CAGGAGTTCG | AGACTAGCCT | GGCCAACATG | 480
| GTGAAACCCC | ATCTCTACTA | AAAAAAAAG | TACAAAATTA | GCTGGACGTG | GTGGTGAGTG | 540
| CCTGTAATCC | CAGCTACTCA | GGAGGCTGAG | GCAGCAGAAT | CACTTGAACC | TGGGAGGCGG | 600
| AGGTTGCAGT | GAGCTGAGAT | CGCGCCACTG | CACTCCAGCC | TCGGCGACAA | GAGCAAAAAC | 660
| TCCGTCTAAA | AAACAAATAA | GCAAACAGAA | CAAAACAAAA | CAAAAACGAG | AGAGCGAAAC | 720
| TACTAAAGGT | GCTTATTCCC | TCTCTATTCG | TGATTGGGAT | GAGGTAAGGG | GTGACAATGT | 780
| GAAACACCAC | AAAATTAGGA | AACTTGACAA | TGGTAGATAC | TATATCACAA | CCAGAGAACA | 840
| ACTTGATACT | CTGCAGAAAT | TGGCAAAACA | CTACACAGAA | CATGCTGATG | GTTTATGCCA | 900
| CAAGTTAACA | ACTGTGTGTC | CAACTGTGAA | ACCTCAGATT | CAAGGTCTAG | CAAAAGATGC | 960
| TTGGGAAATC | CCTTGATAAT | CTTTGCGACT | AGAGGTTAAA | CTAGGACAAG | GATGTTTTGG | 1020
| CAAAGTGTGG | ATGGGAATAT | GGAATGGAAC | CACAAAAGTA | GCAATCAAAA | CACTAAAACC | 1080
| AGGTACAATG | ATGCCAGAAG | CTTTTCTTCA | AGAAGCTCAG | GTAATGAAAA | AAATAAGACA | 1140
| TGGTAAACTT | GTTCCACTAT | ATGCTGTTGT | TTCTGAAGAG | CCAATTTACA | TTGTCACTGA | 1200
| ATTGATGTCA | AAAGGAAGCT | TATTCAATTT | CCTTAAGGAA | GGAGATGGAA | AGTATTTGAA | 1260
| GCTTCCACAA | ATGGTTGATA | TGCCTGCTCA | GATTGCTGAT | GGTATGGCAT | ATATTAAAAG | 1320
| AATGAACTAT | ATTCACCGAG | ATCTCTGGGC | TGCTAATATT | CTTGTAGGAG | AAAATCTTCT | 1380
| GTGCAAAATA | GCAGATTTTG | GTTAGCAAG | GTTAATTGAA | GACAATGAAT | ACACATCAAG | 1440
| ACAAGGTGCA | GAATTTCCAA | TCAAATGGAC | AGCTCCTGAA | GTTGCACTGT | ATGGTGGGTT | 1500
| TACAATAAAG | TCTGGTGTCT | GCTCATTTGG | AATTCTACAG | ACAGAACTGG | TAACAAAGGG | 1560
| CAGAGTGCCA | TATCCAGGTA | TGGTGAACCA | TGAAATACTG | GAACAGGTGG | AGCGAGGATA | 1620
| CAGGATGCCT | TGCCCTCAGG | GCTGTCCAGA | ATCCTCCAT | GAATTGATGA | ATCTGTGTTG | 1680
| GAAGAAGGAC | CCTGATGAAA | GACCAACATT | TGAATATGTT | CAGTCCTTCT | TGGGAGACTA | 1740
| CTTCACTGCT | ACAGAGCCAT | AGTACCAGCC | AGGAGAAAAC | TTCTAATTCA | AGTAGCCTAT | 1800
| TTTA | | | | | | 1804

( 2 ) INFORMATION FOR SEQ ID NO:41:

( i ) SEQUENCE CHARACTERISTICS:

(A) LENGTH: 8082 base pairs
(B) TYPE: nucleic acid
(C) STRANDEDNESS: double
(D) TOPOLOGY: linear (xi) SEQUENCE DESCRIPTION: SEQ ID NO:41:

| | | | | | | |
|---|---|---|---|---|---|---|
| AGCTTGTTTG | GCCGTTTTAG | GGTTTGTTGG | AATTTTTTTT | TCGTCTATGT | ACTTGTGAAT | 60 |
| TATTTCACGT | TTGCCATTAC | CGGTTCTCCA | TAGGGTGATG | TTCATTAGCA | GTGGTGATAG | 120 |
| GTTAATTTTC | ACCATCTCTT | ATGCGGTTGA | ATAGTCACCT | CTGAACCACT | TTTTCCTCCA | 180 |
| GTAACTCCTC | TTTCTTCGGA | CCTTCTGCAG | CCAACCTGAA | AGAATAACAA | GGAGGTGGCT | 240 |
| GGAAACTTGT | TTTAAGGAAC | CGCCTGTCCT | TCCCCCGCTG | GAAACCTTGC | ACCTCGGACG | 300 |
| CTCCTGCTCC | TGCCCCCACC | TGACCCCGC | CCTCGTTGAC | ATCCAGGCGC | GATGATCTCT | 360 |
| GCTGCCAGTA | GAGGGCACAC | TTACTTTACT | TTCGCAAACC | TGAACGCGGG | TGCTGCCCAG | 420 |
| AGAGGGGGCG | GAGGGAAAGA | CGCTTTGCAG | CAAAATCCAG | CATAGCGATT | GGTTGCTCCC | 480 |
| CGCGTTTGCG | GCAAAGGCCT | GGAGGCAGGA | GTAATTTGCA | ATCCTTAAAG | CTGAATTGTG | 540 |
| CAGTGCATCG | GATTTGGAAG | CTACTATATT | CACTTAACAC | TTGAACGCTG | AGCTGCAAAC | 600 |
| TCAACGGGTA | ATAACCCATC | TTGAACAGCG | TACATGCTAT | ACACACCC | CTTTCCCCCG | 660 |
| AATTGTTTTC | TCTTTTGGAG | GTGGTGGAGG | GAGAGAAAAG | TTTACTTAAA | ATGCCTTTGG | 720 |
| GTGAGGGACC | AAGGATGAGA | AGAATGTTTT | TTGTTTTTCA | TGCCGTGGAA | TAACACAAAA | 780 |
| TAAAAAATCC | CGAGGGAATA | TACATTATAT | ATTAAATATA | GATCATTTCA | GGGAGCAAAC | 840 |
| AAATCATGTG | TGGGGCTGGG | CAACTAGCTG | AGTCGAAGCG | TAAATAAAAT | GTGAATACAC | 900 |
| GTTTGCGGGT | TACATACAGT | GCACTTTCAC | TAGTATTCAG | AAAAAATTGT | GAGTCAGTGA | 960 |
| ACTAGGAAAT | TAATGCCTGG | AAGGCAGCCA | AATTTTAATT | AGCTCAAGAC | TCCCCCCCCC | 1020 |
| CCCCAAAAAA | AGGCACGGAA | GTAATACTCC | TCTCCTCTTC | TTTGATCAGA | ATCGATGCAT | 1080 |
| TTTTTGTGCA | TGACCGCATT | TCCAATAATA | AAAGGGGAAA | GAGGACCTGG | AAAGGAATTA | 1140 |
| AACGTCCGGT | TTGTCCGGGG | AGGAAAGAGT | TAACGGTTTT | TTTCACAAGG | GTCTCTGCTG | 1200 |
| ACTCCCCCGG | CTCGGTCCAC | AAGCTCTCCA | CTTGCCCCTT | TTAGGAAGTC | CGGTCCCGCG | 1260 |
| GTTCGGGTAC | CCCCTGCCCC | TCCCATATTC | TCCCGTCTAG | CACCTTTGAT | TTCTCCCAAA | 1320 |
| CCCGGCAGCC | CGAGACTGTT | GCAAACCGGC | GCCACAGGGC | GCAAAGGGGA | TTTGTCTCTT | 1380 |
| CTGAAACCTG | GCTGAGAAAT | TGGGAACTCC | GTGTGGGAGG | CGTGGGGGTG | GGACGGTGGG | 1440 |
| GTACAGACTG | GCAGAGAGCA | GGCAACCTCC | CTCTCGCCCT | AGCCCAGCTC | TGGAACAGGC | 1500 |
| AGACACATCT | CAGGGCTAAA | CAGACGCCTC | CCGCACGGGG | CCCCACGGAA | GCCTGAGCAG | 1560 |
| GCGGGGCAGG | AGGGGCGGTA | TCTGCTGCTT | TGGCAGCAAA | TTGGGGGACT | CAGTCTGGGT | 1620 |
| GGAAGGTATC | CAATCCAGAT | AGCTGTGCAT | ACATAATGCA | TAATACATGA | CTCCCCCCAA | 1680 |
| CAAATGCAAT | GGGAGTTTAT | TCATAACGCG | CTCTCCAAGT | ATACGTGGCA | ATGCGTTGCT | 1740 |
| GGGTTATTTT | AATCATTCTA | GGCATCGTTT | TCCTCCTTAT | GCCTCTATCA | TTCCTCCCTA | 1800 |
| TCTACACTAA | CATCCCACGC | TCTGAACGCG | CGCCATTAA | TACCCTTCTT | TCCTCCACTC | 1860 |
| TCCCTGGGAC | TCTTGATCAA | AGCGCGGCCC | TTTCCCAGC | CTTAGCGAGG | CGCCCTGCAG | 1920 |
| CCTGGTACGC | GCGTGGCGTG | GCGGTGGGCG | CGCAGTGCGT | TCTCTGTGTG | GAGGGCAGCT | 1980 |
| GTTCCGCCTG | CGATGATTTA | TACTCACAGG | ACAAGGATGC | GGTTTGTCAA | ACAGTACTGC | 2040 |
| TACGGAGGAG | CAGCAGAGAA | AGGGAGAGGG | TTTGAGAGGG | AGCAAAAGAA | AATGGTAGGC | 2100 |
| GCGCGTAGTT | AATTCATGCG | GCTCTCTTAC | TCTGTTTACA | TCCTAGAGCT | AGAGTGCTCG | 2160 |
| GCTGCCCGGC | TGAGTCTCCT | CCCCACCTTC | CCCACCCTCC | CCACCCTCCC | CATAAGCGCC | 2220 |

```
CCTCCCGGGT  TCCCAAAGCA  GAGGGCGTGG  GGGAAAAGAA  AAAAGATCCT  CTCTCGCTAA   2280
TCTCCGCCCA  CCGGCCCTTT  ATAATGCGAG  GGTCTGGACG  GCTGAGGACC  CCCGAGCTGT   2340
GCTGCTCGCG  GCCGCCACCG  CCGGGCCCCG  GCCGTCCCTG  GCTCCCCTCC  TGCCTCGAGA   2400
AGGGCAGGGC  TTCTCAGAGG  CTTGGCGGGA  AAAAGAACGG  AGGGAGGGAT  CGCGCTGAGT   2460
ATAAAAGCCG  GTTTTCGGGG  CTTTATCTAA  CTCGCTGTAG  TAATTCCAGC  GAGAGGCAGA   2520
GGGAGCGAGC  GGGCGGCCGG  CTAGGGTGGA  AGAGCCGGGC  GAGCAGAGCT  GCGCTGCGGG   2580
CGTCCTGGGA  AGGGAGATCC  GGAGCGAATA  GGGGCTTCG   CCTCTGGCCC  AGCCCTCCCG   2640
CTGATCCCCC  AGCCAGCGGT  CCGCAACCCT  TGCCGCATCC  ACGAAACTTT  GCCCATAGCA   2700
GCGGGCGGGC  ACTTTGCACT  GGAACTTACA  ACACCCGAGC  AAGGACGCGA  CTCTCCCGAC   2760
GCGGGAGGC   TATTCTGCCC  ATTTGGGGAC  ACTTCCCCGC  CGCTGCCAGG  ACCCGCTTCT   2820
CTGAAAGGCT  CTCCTTGCAG  CTGCTTAGAC  GCTGGATTTT  TTTCGGGTAG  TGGAAAACCA   2880
GGTAAGCACC  GAAGTCCACT  TGCCTTTTAA  TTTATTTTTT  TATCACTTTA  ATGCTGAGAT   2940
GAGTCGAATG  CCTAAATAGG  GTGTCTTTTC  TCCCATTCCT  GCGCTATTGA  CACTTTCTC   3000
AGAGTAGTTA  TGGTAACTGG  GGCTGGGGTG  GGGGTAATC   CAGAACTGGA  TCGGGGTAAA   3060
GTGACTTGTC  AAGATGGGAG  AGGAGAAGGC  AGAGGGAAAA  CGGGAATGGT  TTTTAAGACT   3120
ACCCTTTCGA  GATTTCTGCC  TTATGAATAT  ATTCACGCTG  ACTCCCGGCC  GGTCGGACAT   3180
TCCTGCTTTA  TTGTGTTAAT  TGCTCTCTGG  GTTTTGGGGG  CTGGGGGTT   GCTTTGCGGT   3240
GGGCAGAAAG  CCCCTTGCAT  CCTGAGCTCC  TTGGAGTAGG  GACCGCATAT  CGCCTGTGTG   3300
AGCCAGATCG  CTCCGCAGCC  GCTGACTTGT  CCCCGTCTCC  GGAGGGCAT   TTAAATTTCG   3360
GCTCACCGCA  TTTCTGACAG  CCGGAGACGG  ACACTGCGGC  GCGTCCCGCC  CGCCTGTCCC   3420
CGCGGCGATT  CCAACCCGCC  CTGATCCTTT  TAAGAAGTTG  GCATTGGCT   TTTTAAAAAG   3480
CAATAATACA  ATTTAAAACC  TGGGTCTCTA  GAGGTGTTAG  GACGTGGTGT  TGGGTAGGCG   3540
CAGGCAGGGG  AAAAGGGAGG  CGAGGATGTG  TCCGATTCTC  CTGGAATCGT  TGACTTGGAA   3600
AAACCAGGGC  GAATCTCCGC  ACCCAGCCCT  GACTCCCTG   CCGCGGCCGC  CCTCGGGTGT   3660
CCTCGCGCCC  GAGATGCGGA  GGAACTGCGA  GGAGCGGGGC  TCTGGGCGGT  TCCAGAACAG   3720
CTGCTACCCT  TGGTGGGGTG  GCTCCGGGGG  AGGTATCGCA  GCGGGTCTC   TGGCGCAGTT   3780
GCATCTCCGT  ATTGAGTGCG  AAGGGAGGTG  CCCCTATTAT  TATTTGACAC  CCCCCTTGTA   3840
TTTATGGAGG  GGTGTTAAAG  CCCGCGGCTG  AGCTCGCCAC  TCCAGCCGGC  GAGAGAAAGA   3900
AGAAAAGCTG  GCAAAAGGAG  TGTTGGACGG  GGGCGGTACT  GGGGGTGGGG  ACGGGGCGG   3960
TGGAGAGGGA  AGGTTGGGAG  GGGCTGCGGT  GCCGGCGGGG  GTAGGAGAGC  GGCTAGGGCG   4020
CGAGTGGGAA  CAGCCGCAGC  GGAGGGGCCC  CGGCGCGGAG  CGGGGTTCAC  GCAGCCGCTA   4080
GCGCCCAGGC  GCCTCTCGCC  TTCTCCTTCA  GGTGGCGCAA  AACTTTGTGC  CTTGGATTTT   4140
GGCAAATTGT  TTTCCTCACC  GCCACCTCCC  GCGGCTTCTT  AAGGGCGCCA  GGGCCGATTT   4200
CGATTCCTCT  GCCGCTGCGG  GGCCGACTCC  CGGGCTTTGC  GCTCCGGGCT  CCCGGGGGAG   4260
CGGGGGCTCG  GCGGGCACCA  AGCCGCTGGT  TCACTAAGTG  CGTCTCCGAG  ATAGCAGGG   4320
ACTGTCCAAA  GGGGGTGAAA  GGGTGCTCCC  TTTATTCCCC  CACCAAGACC  ACCCAGCCGC   4380
TTTAGGGGAT  AGCTCTGCAA  GGGGAGAGGT  TCGGGACTGT  GGCGCGCACT  GCGCGCTGCG   4440
CCAGGTTTCC  GCACCAAGAC  CCCTTTAACT  CAAGACTGCC  TCCCGCTTTG  TGTGCCCCGC   4500
TCCAGCAGCC  TCCCGCGACG  ATGCCCCTCA  ACGTTAGCTT  CACCAACAGG  AACTATGACC   4560
TCGACTACGA  CTCGGTGCAG  CCGTATTTCT  ACTGCGACGA  GGAGGAGAAC  TTCTACCAGC   4620
```

-continued

| | | | | | |
|---|---|---|---|---|---|
| AGCAGCAGCA | GAGCGAGCTG | CAGCCCCCGG | CGCCCAGCGA | GGATATCTGG | AAGAAATTCG | 4680 |
| AGCTGCTGCC | CACCCCGCCC | CTGTCCCCTA | GCCGCCGCTC | CGGGCTCTGC | TCGCCCTCCT | 4740 |
| ACGTTGCGGT | CACACCCTTC | TCCCTTCGGG | GAGACAACGA | CGGCGGTGGC | GGGAGCTTCT | 4800 |
| CCACGGCCGA | CCAGCTGGAG | ATGGTGACCG | AGCTGCTGGG | AGGAGACATG | GTGAACCAGA | 4860 |
| GTTTCATCTG | CGACCCGGAC | GACGAGACCT | TCATCAAAAA | CATCATCATC | CAGGACTGTA | 4920 |
| TGTGGAGCGG | CTTCTCGGCC | GCCGCCAAGC | TCGTCTCAGA | GAAGCTGGCC | TCCTACCAGG | 4980 |
| CTGCGCGCAA | AGACAGCGGC | AGCCCGAACC | CCGCCCGCGG | CCACAGCGTC | TGCTCCACCT | 5040 |
| CCAGCTTGTA | CCTGCAGGAT | CTGAGCGCCG | CCGCCTCAGA | GTGCATCGAC | CCCTCGGTGG | 5100 |
| TCTTCCCCTA | CCCTCTCAAC | GACAGCAGCT | CGCCCAAGTC | CTGCGCCTCG | CAAGACTCCA | 5160 |
| GCGCCTTCTC | TCCGTCCTCG | GATTCTCTGC | TCTCCTCGAC | GGAGTCCTCC | CCGCAGGGCA | 5220 |
| GCCCCGAGCC | CCTGGTGCTC | CATGAGGAGA | CACCGCCCAC | CACCAGCAGC | GACTCTGGTA | 5280 |
| AGCGAAGCCC | GCCAGGCCT | GTCAAAAGTG | GCGGCTGGA | TACCTTTCCC | ATTTTCATTG | 5340 |
| GCAGCTTATT | TAACGGGCCA | CTCTTATTAG | GAAGGAGAGA | TAGCAGATCT | GGAGAGATTT | 5400 |
| GGGAGCTCAT | CACCTCTGAA | ACCTTGGGCT | TTAGCGTTTC | CTCCCATCCC | TTCCCCTTAG | 5460 |
| ACTGCCCATG | TTTGCAGCCC | CCCTCCCCGT | TTGTCTCCCA | CCCCTCAGGA | ATTTCATTTA | 5520 |
| GGTTTTTAAA | CCTTCTGGCT | TATCTTACAA | CTCAATCCAC | TTCTTCTTAC | CTCCCGTTAA | 5580 |
| CATTTTAATT | GCCCTGGGGC | GGGGTGGCAG | GGAGTGTATG | AATGAGGATA | AGAGAGGATT | 5640 |
| GATCTCTGAG | AGTGAATGAA | TTGCTTCCCT | CTTAACTTCC | GAGAAGTGGT | GGGATTTAAT | 5700 |
| GAACTATCTA | CAAAAATGAG | GGGCTGTGTT | TAGAGGCTAG | GCAGGGCCTG | CCTGAGTGCG | 5760 |
| GGAGCCAGTG | AACTGCCTCA | AGAGTGGGTG | GGCTGAGGAG | CTGGGATCTT | CTCAGCCTAT | 5820 |
| TTTGAACACT | GAAAAGCAAA | TCCTTGCCAA | AGTTGGACTT | TTTTTTTTCT | TTTATTCCTT | 5880 |
| CCCCCGCCCT | CTTGGACTTT | TGGCAAAACT | GCAATTTTTT | TTTTTTATT | TTTCATTTCC | 5940 |
| AGTAAAATAG | GGAGTTGCTA | AAGTCATACC | AAGCAATTTG | CAGCTATCAT | TTGCAACACC | 6000 |
| TGAAGTGTTC | TTGGTAAAGT | CCCTCAAAAA | TAGGAGGTGC | TTGGGAATGT | GCTTTGCTTT | 6060 |
| GGGTGTGTCC | AAAGCCTCAT | TAAGTCTTAG | GTAAGAATTG | GCATCAATGT | CCTATCCTGG | 6120 |
| GAAGTTGCAC | TTTTCTTGTC | CATGCCATAA | CCCAGCTGTC | TTTCCCTTTA | TGAGACTCTT | 6180 |
| ACCTTCATGG | TGAGAGGAGT | AAGGGTGGCT | GGCTAGATTG | GTTCTTTTTT | TTTTTTTTC | 6240 |
| CTTTTTTAAG | ACGGAGTCTC | ACTCTGTCAC | TAGGCTGGAG | TGCAGTGGCG | CAATCAACCT | 6300 |
| CCAACCCCCT | GGTTCAAGAG | ATTCTCCTGC | CTCAGCCTCC | CAAGTAGCTG | GGACTACAGG | 6360 |
| TGCACACCAC | CATGCCAGGC | TAATTTTTGT | AATTTTAGTA | GAGATGGGGT | TTCATCGTGT | 6420 |
| TGGCCAGGAT | GGTCTCTCCT | GACCTCACGA | TCCGCCCACC | TCGGCCTCCC | AAAGTGCTGG | 6480 |
| GATTACAGGT | GTGAGCCAGG | GCACCAGGCT | TAGATGTGGC | TCTTTGGGA | GATAATTTTG | 6540 |
| TCCAGAGACC | TTTCTAACGT | ATTCATGCCT | TGTATTTGTA | CAGCATTAAT | CTGGTAATTG | 6600 |
| ATTATTTTAA | TGTAACCTTG | CTAAAGGAGT | GATTTCTATT | TCCTTTCTTA | AAGAGGAGGA | 6660 |
| ACAAGAAGAT | GAGGAAGAAA | TCGATGTTGT | TTCTGTGGAA | AAGAGGCAGG | CTCCTGGCAA | 6720 |
| AAGGTCAGAG | TCTGGATCAC | CTTCTGCTGG | AGGCCACAGC | AAACCTCCTC | ACAGCCCACT | 6780 |
| GGTCCTCAAG | AGGTGCCACG | TCTCCACACA | TCAGCACAAC | TACGCAGCGC | CTCCCTCCAC | 6840 |
| TCGGAAGGAC | TATCCTGCTG | CCAAGAGGGT | CAAGTTGGAC | AGTGTCAGAG | TCCTGAGACA | 6900 |
| GATCAGCAAC | AACCGAAAAT | GCACCAGCCC | CAGGTCCTCG | GACACCGAGG | AGAATGTCAA | 6960 |
| GAGGCGAACA | CACAACGTCT | TGGAGCGCCA | GAGGAGGAAC | GAGCTAAAAC | GGAGCTTTTT | 7020 |

| | | | | | | |
|---|---|---|---|---|---|---|
| TGCCCTGCGT | GACCAGATCC | CGGAGTTGGA | AAACAATGAA | AAGGCCCCCA | AGGTAGTTAT | 7080 |
| CCTTAAAAAA | GCCACAGCAT | ACATCCTGTC | CGTCCAAGCA | GAGGAGCAAA | AGCTCATTTC | 7140 |
| TGAAGAGGAC | TTGTTGCGGA | AACGACGAGA | ACAGTTGAAA | CACAAACTTG | AACAGCTACG | 7200 |
| GAACTCTTGT | GCGTAAGGAA | AAGTAAGGAA | AACGATTCCT | TCTAACAGAA | ATGTCCTGAG | 7260 |
| CAATCACCTA | TGAACTTGTT | TCAAATGCAT | GATCAAATGC | AACCTCACAA | CCTTGGCTGA | 7320 |
| GTCTTGAGAC | TGAAAGATTT | AGCCATAATG | TAAACTGCCT | CAAATTGGAC | TTTGGGCATA | 7380 |
| AAAGAACTTT | TTTATGCTTA | CCATCTTTTT | TTTTCTTTA | ACAGATTTGT | ATTAAGAAT | 7440 |
| TGTTTTTAAA | AAATTTTAAG | ATTTACACAA | TGTTTCTCTG | TAAATATTGC | CATTAAATGT | 7500 |
| AAATAACTTT | AATAAAACGT | TTATAGCAGT | TACACAGAAT | TTCAATCCTA | GTATATAGTA | 7560 |
| CCTAGTATTA | TAGGTACTAT | AAACCCTAAT | TTTTTTATT | TAAGTACATT | TTGCTTTTA | 7620 |
| AAGTTGATTT | TTTTCTATTG | TTTTAGAAA | AAATAAAATA | ACTGGCAAAT | ATATCATTGA | 7680 |
| GCCAAATCTT | AAGTTGTGAA | TGTTTTGTTT | CGTTCTTCC | CCCTCCCAAC | CACCACCATC | 7740 |
| CCTGTTTGTT | TTCATCAATT | GCCCCTTCAG | AGGGCGGTCT | TAAGAAAGGC | AAGAGTTTC | 7800 |
| CTCTGTTGAA | ATGGGTCTGG | GGGCCTTAAG | GTCTTTAAGT | TCTTGGAGGT | TCTAAGATGC | 7860 |
| TTCCTGGAGA | CTATGATAAC | AGCCAGAGTT | GACAGTTAGA | AGGAATGGCA | GAAGGCAGGT | 7920 |
| GAGAAGGTGA | GAGGTAGGCA | AAGGAGATAC | AAGAGGTCAA | AGGTAGCAGT | TAAGTACACA | 7980 |
| AAGAGGCATA | AGGACTGGGG | AGTTGGGAGG | AAGGTGAGGA | AGAAACTCCT | GTTACTTTAG | 8040 |
| TTAACCAGTG | CCAGTCCCCT | GCTCACTCCA | AACCCAGGAA | TT | | 8082 |

( 2 ) INFORMATION FOR SEQ ID NO:42:

( i ) SEQUENCE CHARACTERISTICS:
( A ) LENGTH: 7011 base pairs
( B ) TYPE: nucleic acid
( C ) STRANDEDNESS: single
( D ) TOPOLOGY: linear ( x i ) SEQUENCE DESCRIPTION: SEQ ID NO:42:

| | | | | | | |
|---|---|---|---|---|---|---|
| CGGGCCGCAT | CAGCCCTCCT | CCTGTTTGCG | CTCCCCAGCG | TGCAATTTAT | TTGGGGGGCT | 60 |
| ACCGGGGATT | GAACGGAGCG | GGCGAGCGCT | GCCAGGAGGT | GGGGCCGGCC | CCACCTGTCG | 120 |
| ACTGCCCGTA | GTAGGCAGGG | AGAGGCGGG | GTTTGTCCCA | TAGGGCCCGC | CCCCCAGTCC | 180 |
| CTGGGTCCCG | GGCGCGCGAC | GAGATATAAG | GCAGTCAGGA | AACAATGCGC | CTGCAGCTCG | 240 |
| CGCTCCCGCG | CCGATCCCGA | GAGCGTCCGG | GCCGCCGTGC | GCGAGCGAGG | GAGGGCGCGC | 300 |
| GCGCGGGGGG | GGCGCGCTCG | TGAGTGCGGG | CCGCGCTCTC | GGCGGCGCGC | ATGTGCGTGT | 360 |
| GTGCTGGCTG | CCGGGCTGCC | CCGAGCCGGC | GGGGAGCCGG | TCCGCTCCAG | GTGGCGGGCG | 420 |
| GCTGGAGCGA | GGTGAGGCTG | CGGGTGGCCA | GGGCACGGGC | GCGGGTCCCG | CGGTGCGGGC | 480 |
| TGGCTGCAGG | CTGCCTTCTG | GGCACGGCGC | GCCCCGCCC | GGCCCCGCCG | GGCCCTGGGA | 540 |
| GCTGCGCTCC | GGGCGGCGCT | GGCAAAGTTT | GCTTTGAACT | CGCTGCCCAC | AGTCGGGTCC | 600 |
| GCGCGCTGCG | ATTGGCTTCC | CCTACCACTC | TGACCCGGGG | CCCGGCTTCC | CGGGACGCGA | 660 |
| GGACTGGGCG | CAGGCTGCAA | GCTGGTGGGG | TTGGGGAGGA | ACGAGAGCCC | GGCAGCCGAC | 720 |
| TGTGCCGAGG | GACCCGGGGA | CACCTCCTTC | GCCCGGCCGG | CACCCGGTCA | GCACGTCCCC | 780 |
| CCTTCCCTCC | CGCAGGGAGC | GGACATGGAC | TACGACTCGT | ACCAGCACTA | TTTCTACGAC | 840 |
| TATGACTGCG | GGGAGGATTT | CTACCGCTCC | ACGGCGCCCA | GCGAGGACAT | CTGGAAGAAA | 900 |
| TTCGAGCTGG | TGCCATCGCC | CCCCACGTCG | CCGCCCTGGG | GCTTGGGTCC | CGGCGCAGGG | 960 |

| | | | | | | |
|---|---|---|---|---|---|---|
| GACCCGGCCC | CCGGGATTGG | TCCCCCGGAG | CCGTGGCCCG | GAGGGTGCAC | CGGAGACGAA | 1020 |
| GCGGAATCCC | GGGGCCACTC | GAAAGGCTGG | GGCAGGAACT | ACGCCTCCAT | CATACGCCGT | 1080 |
| GACTGCATGT | GGAGCGGCTT | CTCGGCCCGG | GAACGGCTGG | AGAGAGCTGT | GAGCGACCGG | 1140 |
| CTCGCTCCTG | GCGCGCCCCG | GGGGAACCCG | CCCAAGGCGT | CCGCCGCCCC | GGACTGCACT | 1200 |
| CCCAGCCTCG | AAGCCGGCAA | CCCGGCGCCC | GCCGCCCCCT | GTCCGCTGGG | CGAACCCAAG | 1260 |
| ACCCAGGCCT | GCTCCGGGTC | CGAGAGCCCA | AGCGACTCGG | GTAAGGACCT | CCCCGAGCCA | 1320 |
| TCCAAGAGGG | GGCCACCCCA | TGGGTGGCCA | AAGCTCTGCC | CCTGCCTGAG | GTCAGGCATT | 1380 |
| GGCTCTTCTC | AAGCTCTTGG | GCCATCTCCG | CCTCTCTTTG | GCTGAAGCTG | CCCGTGTAGT | 1440 |
| CCCCAACCGT | GTCTGTCTGG | CACGTGGGTG | TGTTGGTAAA | CAGTTTGGAA | AAGTGGCGTG | 1500 |
| GGAGCCAGCC | TCCCTTTGAT | GATTATTGGA | GCCCAGGGG | ACAAGGGATT | TGAGGTGAGG | 1560 |
| GTTGGCGCTT | AGAGAGGACA | ATACTGGGGT | TGGACTGTAA | GGGATTGAAG | GGGGTACCTT | 1620 |
| AAGAGACACT | CCAAACCTGA | AGTTTTTTTG | CTGCTGCCTC | TTTCCCTAGG | AAACTCACAC | 1680 |
| TCCCCTAGGG | GGAGAAGAAG | CCGAGAGCCT | TTTGTGCAAA | GCCAAAACCT | TCGTCCTTTT | 1740 |
| AAAAACCTAG | GTCTCCAGTT | GGCTTTACTT | TAAAATGCCA | ATAATAAATG | CCCTCTTCTC | 1800 |
| GTGCCTCCCC | ACCACCACTT | ACCACTCGTG | CATCCCTGAG | ACAGGGAGGG | AAGAATGAAC | 1860 |
| ACTCCCCATT | AACAGATGGA | AAAACTGAGG | CTTAGAGATA | GACAATCACT | ACAAGTCAGC | 1920 |
| TCCAGCTTTC | TGCCATCTAG | CCAGCCCCTC | TTCCCCAATG | CTCCATCCCA | ACCAGGCACC | 1980 |
| TCTTCCTTGA | TGTTTGGGGT | CTTTGTGGTA | GCTTATCTTA | GAAGCACTAC | ACCTTGCCTT | 2040 |
| GCTGTTTGTC | CTGAGATGGA | AAAGTGTCCT | TCTTGCTCCC | CCTCAATAGA | TCTCCAGCGT | 2100 |
| CAGCTGCTCC | CTGGCATTCA | ACAAATATTC | ACTGGCCCCT | ACTTGTGGC | AATCTGTGGG | 2160 |
| CTACATGCTG | GGGTCAAGGC | AGTAGAACTC | CAGGCCCTCC | TCTCCCATCC | TTGATGCAAG | 2220 |
| TGCAACCTCG | CTGAGGGCAG | ACTGGGGCAT | CCTGTGCCAC | TAAACTACAT | TGTTCTTATT | 2280 |
| CTGGCATCTT | AGACCTCCAC | ACCCGTGAGA | AATCCTGGAG | AGGGTATTTT | TGTAGAGTGT | 2340 |
| AGACTGTGGC | TAGTGACAAA | TAAATTAGGA | CCAAGAAAGC | TCACTGTAGC | TTTTAGGAAT | 2400 |
| AACTTTTACA | CGACCATTTG | ATAGGGAACT | GGGGAATGGG | GTATGGAAGT | TTTCCTACAC | 2460 |
| TTGAGAGAAA | AAATAGGATA | ACAAAAATTA | AAAGTCTTTT | TTTCCTGGTC | CACTGTGTTA | 2520 |
| AGGTCATTTT | TAACCAGCTT | GCTTTCTACA | CCAAGAGTTT | ATGTTTGTTT | AATGGCTGGA | 2580 |
| AAGAGAATCT | TGAGATCAAA | AAACCAATAA | AGATGTATCT | CTACAACGGC | TGGTGGAGTG | 2640 |
| GTAGAGTGGA | AAGAGCATTG | CTTTGGAAGT | TGGAACATTT | TAGTTTGAGA | TCCAGAACGT | 2700 |
| TACAAAGGTG | ATATGTGGAC | TTCGCTGATC | TGGGCCTCAG | TTTCCCCATT | TGCACACGAT | 2760 |
| GGGGTTGGAC | TTGATTGTCC | TGCTGATGAC | ATTTCCTTGT | CTGGATAGAG | TAAGACACTA | 2820 |
| CTCTCTGAAA | GGGAGAATGG | TGTGCTTAAA | TTATTTCTTT | CTTAGATAGA | ATCTTCCTGA | 2880 |
| GCCACGAGGC | TTAACACTGA | AAATTAAAGG | TTTGGGATGT | AGGAAAGCCT | GCTGAATCAT | 2940 |
| TTTCTAACCT | ACCCTTTAAC | CTGAACCTGT | TTGTGAGCTT | CTAGTTCACT | CACAGGCCAC | 3000 |
| ATGGCCTGGA | ACAAAATGCA | ACAGATTGCA | AACAATGAGG | CGGGGGTGG | GAAAGTGAT | 3060 |
| TGGCAGCAGA | GCTCACCCAA | TAGGGCTAG | GGCTGGGTA | AGACAGAATT | CCAAACACAG | 3120 |
| CGTAATCAGC | CAATCATGGG | CTTTGGGGCC | AGGAGGGCTG | AATGGTCAGG | TTTATTAATG | 3180 |
| GAGAAATAAT | GCGATTGTCC | ACACAATGGA | AGCCTTCCTG | ACAAAGGGGC | TCAAGCTTCC | 3240 |
| TGATATGCAA | AGAAGCTGAG | AACGGAGCTC | TTCCTTTGCC | GAGGCCGAGA | TCCATTAAGG | 3300 |
| TCGGACTTCT | GTGTGGAGGC | TGCAAAATGT | GTGGAGCAGG | AGGAGACTTT | TCTCCCAATT | 3360 |

```
GCCCCTCTCC TGGTTAGGTT AACCTAAGAG ACCTTCAAGC CAGTGAATGA GAAGGGCGTG   3420
TCCAGGTGTC TCCAGGTCTC TGGTGTTATG AGCCCCATAT CTGGGACATT CTGCTGCCCA   3480
GTCTCTGCCT CTGGTGCAGG TAGTTTGGAA ATGGTCGCTT GTACCTTTGT GAAGTTCCTG   3540
CAGCTTCGCC GACCTATGAT TACAAATCTA ACCTTCTAGT CCAGGGAAGG AGGTGGGGCA   3600
GGCGACCTAT AAATGATGGA TGACTTTAGA AACCCATTGA ACCCAGGAGC AAAATGCTCC   3660
TAAGGGAAAC CCTTTCCCTC CCCTCTGTGG GTGAAGAGGG ATGGGTTGTA GCCCTCCCTT   3720
CTCTGAATCT TCAGCTGAAA GGGATGGCAG AATAGAGAGG TGGGGAATA ATAGGATTTA    3780
TAACTTGTGA AAAGTAACAA TTCCCCAAGT GCAGGCTGTG CTGGGCAGGA ACAAAGGGCA   3840
GCTCTGCCCA CAGACCCCTC ATTACAATT CTGATGGGGC ATGAAGAGC CCGACTGGGG     3900
AAGATCTTTA TAGCTAAACT TTGTCCCAGG CCGGTAGCTC TTTCTCTCCA ACCCCTCCGT   3960
GGGGGAGGGG AGAGCCTTTG CAGACTGGGG GCTGTTGGCT TGGGTCTGCC TTTTGTTCTT   4020
ATCTAAGCCT TGCTGTGCAA AAGGAAATTG GAGAATATTT TCCTTCTTGC TAATGTCCCC   4080
TCCTTTCCTT CACTGTGCCC TTACCACATT ACAAATGAAT CAGCTTTCTG CTCACCTCGA   4140
TTTGTATATA TCTAAATTGG AAAAATGTCT CCTACCTTCC CAAGCACCAG CGTAGACAGC   4200
TAAAGCTGTA GGGTCTATGT TTGTGTTTCT CATGGGATGT GTTCTTCTC TTGATCTCTT    4260
TTCTCGGACA GAGAATGAAG AAATTGATGT TGTGACAGTA GAAGAGGC AGTCTCTGGG     4320
TATTCGGAAG CCGGTCACCA TCACGGTGCG AGCAGACCCC CTGGATCCCT GCATGAAGCA   4380
TTTCCACATC TCCATCCATC AGCAACAGCA CAACTATGCT GCCCGTTTTC CTCCAGAAAG   4440
CTGCTCCCAA GAAGAGGCTT CAGAGAGGGG TCCCCAAGAA GAGGTTCTGG AGAGAGATGC   4500
TGCAGGGGAA AAGGAAGATG AGGAGGATGA AGAGATTGTG AGTCCCCAC CTGTAGAAAG    4560
TGAGGCTGCC CAGTCCTGCC ACCCCAAACC TGTCAGTTCT GATACTGAGG ATGTGACCAA   4620
GAGGAAGAAT CACAACTTCC TGGAGCGCAA GAGGCGGAAT GACCTGCGTT CGCGATTCTT   4680
GGCGCTGAGG GACCAGGTGC CCACCCTGGC CAGCTGCTCC AAGGCCCCCA AAGTAGTGAT   4740
CCTAAGCAAG GCCTTGGAAT ACTTGCAAGC CCTGGTGGGG GCTGAGAAGA GGATGGCTAC   4800
AGAGAAAAGA CAGCTCCGAT GCCGGCAGCA GCAGTTGCAG AAAAGAATTG CATACCTCAG   4860
TGGCTACTAA CTGACCAAAA AGCCTGACAG TTCTGTCTTA CGAAGACACA AGTTTATTTT   4920
TTAACCTCCC TCTCCCCTTT AGTAATTTGC ACATTTGGT TATGGTGGGA CAGTCTGGAC    4980
AGTAGATCCC AGAATGCATT GCAGCCGGTG CACACACAAT AAAGGCTTGC ATTCTTGGAA   5040
ACCTTGAAAC CCAGCTCTCC CTCTTCCCTG ACTCATGGGA GTGCTGTATG TTCTCTGGCG   5100
CCTTTGGCTT CCCAGCAGGC AGCTGACTGA GGAGCCTTGG GGTCTGCCTA GCTCACTAGC   5160
TCTGAAGAAA AGGCTGACAG ATGCTATGCA ACAGGTGGTG GATGTTGTCA GGGGCTCCAG   5220
CCTGCATGAA ATCTCACACT CTGCATGAGC TTTAGGCTAG GAAAGGATGC TCCCAACTGG   5280
TGTCTCTGGG GTGATGCAAG GACAGCTGGG CCTGGATGCT CTCCCTGAGG CTCCTTTTTC   5340
CAGAAGACAC ACGAGCTGTC TTGGGTGAAG ACAAGCTTGC AGACTTGATC AACATTGACC   5400
ATTACCTCAC TGTCAGACAC TTTACAGTAG CCAAGGAGTT GGAAACCTTT ATGTATTATG   5460
ATGTTAGCTG ACCCCCTTCC TCCCACTCCC AATGCTGCGA CCCTGGGAAC ACTTAAAAAG   5520
CTTGGCCTCT AGATTCTTTG TCTCAGAGCC CTCTGGGCTC TCTCCTCTGA GGGAGGGACC   5580
TTTCTTTCCT CACAAGGGAC TTTTTTGTTC CATTATGCCT TGTTATGCAA TGGGCTCTAC   5640
AGCACCCTTT CCCACAGGTC AGAAATATTT CCCCAAGACA CAGGGAAATC GGTCCTAGCC   5700
TGGGGCCTGG GGATAGCTTG GAGTCCTGGC CCATGAACTT GATCCCTGCC CAGGTGTTTT   5760
```

-continued

| | | | | | | |
|---|---|---|---|---|---|---|
| CCGAGGGGCA | CTTGAGGCCC | AGTCTTTTCT | CAAGGCAGGT | GTAAGACACT | CAGAGGGAGA | 5820 |
| ACTGTACTGC | TGCCTCTTTC | CCACCTTCCT | CATCTCAATC | CTTGAGCGGC | AAGTTTGAAG | 5880 |
| TTCTTCTGGA | ACCATGCAAA | TCTGTCCTCC | TCATGCAATT | CCAAGGAGCT | TGCTGGCTCT | 5940 |
| GCAGCCACCT | CTGGGCCCCT | TCCAGCCTGC | CATGAATCAG | ATATCTTTCC | CAGAATCTGG | 6000 |
| GCGTTTCTGA | AGTTTTGGGG | AGAGCTGTTG | GGACTCATCC | AGTGCTCCAG | AAGGTGGACT | 6060 |
| TGCTTCTGGG | GGGTTTTAAA | GGAGCCTCCA | GGAGATATGC | TTAGCCAACC | ATGATGGATT | 6120 |
| TTACCCCAGC | TGGACTCGGC | AGCTCCAAGT | GGAATCCACG | TGCAGCTTCT | AGTCTGGGAA | 6180 |
| AGTCACCCAA | CCTAGCAGTT | GTCATGTGGG | TAACCTCAGG | CACCTCTAAG | CCTGTCCTGG | 6240 |
| AAGAAGGACC | AGCAGCCCCT | CCAGAACTCT | GCCCAGGACA | GCAGGTGCCT | GCTGGCTCTG | 6300 |
| GGTTTGGAAG | TTTGGGGTGG | GTAGGGGGTG | GTAAGTACTA | TATATGGCTC | TGGAAAACCA | 6360 |
| GCTGCTACTT | CCAAATCTAT | TGTCCATAAT | GGTTTCTTTC | TGAGGTTGCT | TCTTGGCCTC | 6420 |
| AGAGGACCCC | AGGGGATGTT | TGGAAATAGC | CTCTCTACCC | TTCTGGAGCA | TGGTTTACAA | 6480 |
| AAGCCAGCTG | ACTTCTGGAA | TTGTCTATGG | AGGACAGTTT | GGGTGTAGGT | TACTGATGTC | 6540 |
| TCAACTGAAT | AGCTTGTGTT | TTATAAGCTG | CTGTTGGCTA | TTATGCTGGG | GGAGTCTTTT | 6600 |
| TTTTTTATAT | TGTATTTTTG | TATGCCTTTT | GCAAAGTGGT | GTTAACTGTT | TTTGTACAAG | 6660 |
| GAAAAAAACT | CTTGGGGCAA | TTTCCTGTTG | CAAGGGTCTG | ATTTATTTTG | AAAGGCAAGT | 6720 |
| TCACCTGAAA | TTTTGTATTT | AGTTGTGATT | ACTGATTGCC | TGATTTTAAA | ATGTTGCCTT | 6780 |
| CTGGGACATC | TTCTAATAAA | AGATTTCTCA | AACATGTCAG | AGTGGGGCA | GCTTATGCCA | 6840 |
| CCTGAGTCCT | CCTCAACCAC | GGAAAACTAT | TCAGGGTAG | CCACAAGTGA | TCCAGAGGGC | 6900 |
| TGCACTTCTC | TAACCATGTT | GCTAACCTGG | TCATTCCACT | CTGGGTTCCT | GAAATGCCAT | 6960 |
| TTCAGACATG | TTGAAACAAT | GTAGGCTCAG | TACTCAGTGA | ACACGGAATT | C | 7011 |

( 2 ) INFORMATION FOR SEQ ID NO:43:

( i ) SEQUENCE CHARACTERISTICS:
        ( A ) LENGTH: 1604 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:43:

| | | | | | | |
|---|---|---|---|---|---|---|
| GAATTCCGGG | CGAGGGCCGG | GCAGGAGGAG | CGGGCGCGCG | GCGGGCGAGG | CTGGGACCCG | 60 |
| AGCGCGCTCA | CTTCGCCGCA | AAGTGCCAAC | TTCCCCTGGA | GTGCCGGGCG | CGCACCGTCC | 120 |
| GGGCGCGGGG | GAAAGAAAGG | CAGCGGGAAT | TTGAGATTTT | TGGGAAGAAA | GTCGGATTTC | 180 |
| CCCCGTCCCC | TTCCCCCTGT | TACTAATCCT | CATTAAAAAG | AAAAACAACA | ATAACTGCAA | 240 |
| ACTTGCTACC | ATCCCGTACG | TCCCCCACTC | CTGGCACCAT | GAAGGCGGCC | GTCGATCTCA | 300 |
| AGCCGACTCT | CACCATCATC | AAGACGGAAA | AAGTCGATCT | GGAGCTTTTC | CCCTCCCCGG | 360 |
| ATATGGAATG | TGCAGATGTC | CCACTATTAA | CTCCAAGCAG | CAAAGAAATG | ATGTCTCAAG | 420 |
| CATTAAAAGC | TACTTTCAGT | GGTTTCACTA | AAGAACAGCA | ACGACTGGGG | ATCCCAAAAG | 480 |
| ACCCCCGGCA | GTGGACAGAA | ACCCATGTTC | GGGACTGGGT | GATGTGGGCT | GTGAATGAAT | 540 |
| TCAGCCTGAA | AGGTGTAGAC | TTCCAGAAGT | TCTGTATGAA | TGGAGCAGCC | CTCTGCGCCC | 600 |
| TGGGTAAAGA | CTGCTTTCTC | GAGCTGGCCC | CAGACTTTGT | TGGGACATC | TTATGGGAAC | 660 |
| ATCTAGAGAT | CCTGCAGAAA | GAGGATGTGA | AACCATATCA | AGTTAATGGA | GTCAACCCAG | 720 |
| CCTATCCAGA | ATCCCGCTAT | ACCTCGGATT | ACTTCATTAG | CTATGGTATT | GAGCATGCCC | 780 |
| AGTGTGTTCC | ACCATCGGAG | TTCTCAGAGC | CCAGCTTCAT | CACAGAGTCC | TATCAGACGC | 840 |

| | | | | | |
|---|---|---|---|---|---|
| TCCATCCCAT | CAGCTCGGAA | GAGCTCCTCT | CCCTCAAGTA | TGAGAATGAC | TACCCCTCGG | 900
| TCATTCTCCG | AGACCCTCTC | CAGACAGACA | CCTTGCAGAA | TGACTACTTT | GCTATCAAAC | 960
| AAGAAGTCGT | CACCCCAGAC | AACATGTGCA | TGGGGAGGAC | CAGTCGTGGT | AAACTCGGGG | 1020
| GCCAGGACTC | TTTTGAAAGC | ATAGAGAGCT | ACGATAGTTG | TGATCGCCTC | ACCCAGTCCT | 1080
| GGAGCAGCCA | GTCATCTTTC | AACAGCCTGC | AGCGTGTTCC | CTCCTATGAC | AGCTTCGACT | 1140
| CAGAGGACTA | TCCGGCTGCC | CTGCCCAACC | ACAAGCCCAA | GGGCACCTTC | AAGGACTATG | 1200
| TGCGGGACCG | TGCTGACCTC | AATAAGGACA | AGCCTGTCAT | TCCTGCTGCT | GCCCTAGCTG | 1260
| GCTACACAGG | CAGTGGACCA | ATCCAGCTAT | GGCAGTTTCT | TCTGGAATTA | CTCACTGATA | 1320
| AATCCTGTCA | GTCTTTATC | AGCTGGACAG | GAGATGGCTG | GGAATTCAAA | CTTTCTGACC | 1380
| CAGATGAGGT | GGCCAGGAGA | TGGGGAAAGA | GGAAAAACAA | ACCTAAGATG | AATTATGAGA | 1440
| AACTGAGCCG | TGGCCTACGC | TACTATTACG | ACAAAAACAT | CATCCACAAG | ACAGCGGGGA | 1500
| AACGCTACGT | GTACCGCTTT | GTGTGTGACC | TGCAGAGCCT | GCTGGGGTAC | ACCCCTGAGG | 1560
| AGCTGCACGC | CATGCTGGAC | GTCAAGCCAG | ATGCCGACGA | GTGA | | 1604

(2) INFORMATION FOR SEQ ID NO:44:

(i) SEQUENCE CHARACTERISTICS:
(A) LENGTH: 3565 base pairs
(B) TYPE: nucleic acid
(C) STRANDEDNESS: double
(D) TOPOLOGY: linear (xi) SEQUENCE DESCRIPTION: SEQ ID NO:44:

| | | | | | |
|---|---|---|---|---|---|
| GCAGCCGGGC | GGCCGCAGAA | GCGCCCAGGC | CCGCGCGCCA | CCCCTCTGGC | GCCACCGTGG | 60
| TTGAGCCCGT | GACGTTTACA | CTCATTCATA | AAACGCTTGT | TATAAAAGCA | GTGGCTGCGG | 120
| CGCCTCGTAC | TCCAACCGCA | TCTGCAGCGA | GCAACTGAGA | AGCCAAGACT | GAGCCGGCGG | 180
| CCGCGGCGCA | GCGAACGAGC | AGTGACCGTG | CTCCTACCCA | GCTCTGCTTC | ACAGCGCCCA | 240
| CCTGTCTCCG | CCCCTCGGCC | CCTCGCCCGG | CTTTGCCTAA | CCGCCACGAT | GATGTTCTCG | 300
| GGCTTCAACG | CAGACTACGA | GGCGTCATCC | TCCCGCTGCA | GCAGCGCGTC | CCGGCCGGG | 360
| GATAGCCTCT | CTTACTACCA | CTCACCCGCA | GACTCCTTCT | CCAGCATGGG | CTCGCCTGTC | 420
| AACGCGCAGG | TAAGGCTGGC | TTCCCGTCGC | CGCGGGGCCG | GGGGCTTGGG | GTCGCGGAGG | 480
| AGGAGACACC | GGGCGGGACG | CTCCAGTAGA | TGAGTAGGGG | GCTCCCTTGT | GCCTGGAGGG | 540
| AGGCTGCCGT | GGCCGGAGCG | GTGCCGGCTC | GGGGGCTCGG | GACTTGCTCT | GAGCGCACGC | 600
| ACGCTTGCCA | TAGTAAGAAT | TGGTTCCCCC | TTCGGGAGGC | AGGTTCGTTC | TGAGCAACCT | 660
| CTGGTCTGCA | CTCCAGGACG | GATCTCTGAC | ATTAGCTGGA | GCAGACGTGT | CCCAAGCACA | 720
| AACTCGCTAA | CTAGAGCCTG | GCTTCTTCGG | GGAGGTGGCA | GAAAGCGGCA | ATCCCCCTC | 780
| CCCCGGCAGC | CTGGAGCACG | GAGGAGGGAT | GAGGGAGGAG | GGTGCAGCGG | GCGGGTGTGT | 840
| AAGGCAGTTT | CATTGATAAA | AAGCGAGTTC | ATTCTGGAGA | CTCCGGAGCG | GCGCCTGCGT | 900
| CAGCGCAGAC | GTCAGGGATA | TTTATAACAA | ACCCCCTTTC | AAGCAAGTGA | TGCTGAAGGG | 960
| ATAACGGGAA | CGCAGCGGCA | GGATGGAAGA | GACAGGCACT | GCGCTGCGGA | ATGCCTGGGA | 1020
| GGAAAAGGGG | GAGACCTTTC | ATCCAGGATG | AGGGACATTT | AAGATGAAAT | GTCCGTGGCA | 1080
| GGATCGTTTC | TCTTCACTGC | TGCATGCGGC | ACTGGAACT | CGCCCCACCT | GTGTCCGGAA | 1140
| CCTGCTCGCT | CACGTCGGCT | TTCCCCTTCT | GTTTTGTTCT | AGGACTTCTG | CACGGACCTG | 1200
| GCCGTCTCCA | GTGCCAACTT | CATTCCCACG | GTCACTGCCA | TCTCGACCAG | TCCGGACCTG | 1260

-continued

| | | | | | |
|---|---|---|---|---|---|
| CAGTGGCTGG | TGCAGCCCGC | CCTCGTCTCC | TCTGTGGCCC | CATCGCAGAC | CAGAGCCCCT | 1320 |
| CACCCTTTCG | GAGTCCCCGC | CCCCTCCGCT | GGGGCTTACT | CCAGGGCTGG | CGTTGTGAAG | 1380 |
| ACCATGACAG | GAGGCCGAGC | GCAGAGCATT | GGCAGGAGGG | GCAAGGTGGA | ACAGGTGAGG | 1440 |
| AACTCTAGCG | TACTCTTCCT | GGGAATGTGG | GGGCTGGGTG | GGAAGCAGCC | CCGGAGATGC | 1500 |
| AGGAGCCCAG | TACAGAGGAT | GAAGCCACTG | ATGGGGCTGG | CTGCACATCC | GTAACTGGGA | 1560 |
| GCCCTGGCTC | CAAGCCCATT | CCATCCCAAC | TCAGACTCTG | AGTCTCACCC | TAAGAAGTAC | 1620 |
| TCTCATAGTT | TCTTCCCTAA | GTTCTTACC | GCATGCTTTC | AGACTGGGCT | CTTCTTTGTT | 1680 |
| CTCTTGCTGA | GGATCTTATT | TTAAATGCAA | GTCACACCTA | TTCTGCAACT | GCAGGTCAGA | 1740 |
| AATGGTTTCA | CAGTGGGGTG | CCAGGAAGCA | GGGAAGCTGC | AGGAGCCAGT | TCTACTGGGG | 1800 |
| TGGGTGAATG | GAGGTGATGG | CAGACACTTT | TACTGAATGT | CGGTCTTTTT | TTGTGATTAT | 1860 |
| TCTAGTTATC | TCCAGAAGAA | GAAGAGAAAA | GGAGAATCCG | AAGGGAAAGG | AATAAGATGG | 1920 |
| CTGCAGCCAA | ATGCCGCAAC | CGGAGGAGGG | AGCTGACTGA | TACACTCCAA | GCGGTAGGTA | 1980 |
| CTCTGTGGGT | TGCTCCTTTT | TAAAACTTAA | GGGAAAGTTG | GAGATTGAGC | ATAAGGGCCC | 2040 |
| TTGAGTAAGA | CTGTGTCTTA | TGCTTTCCTT | TATCCCTCTG | TATACAGGAG | ACAGACCAAC | 2100 |
| TAGAAGATGA | GAAGTCTGCT | TTGCAGACCG | AGATTGCCAA | CCTGCTGAAG | GAGAAGGAAA | 2160 |
| AACTAGAGTT | CATCCTGGCA | GCTCACCGAC | CTGCCTGCAA | GATCCCTGAT | GACCTGGGCT | 2220 |
| TCCCAGAAGA | GATGTCTGTG | GCTTCCCTTG | ATCTGACTGG | GGGCCTGCCA | GAGGTTGCCA | 2280 |
| CCCCGGAGTC | TGAGGAGGCC | TTCACCCTGC | CTCTCCTCAA | TGACCCTGAG | CCCAAGCCCT | 2340 |
| CAGTGGAACC | TGTCAAGAGC | ATCAGCAGCA | TGGAGCTGAA | GACCGAGCCC | TTTGATGACT | 2400 |
| TCCTGTTCCC | AGCATCATCC | AGGCCCAGTG | GCTCTGAGAC | AGCCCGCTCC | GTGCCAGACA | 2460 |
| TGGACCTATC | TGGGTCCTTC | TATGCAGCAG | ACTGGGAGCC | TCTGCACAGT | GGCTCCCTGG | 2520 |
| GGATGGGGCC | CATGGCCACA | GAGCTGGAGC | CCCTGTGCAC | TCCGGTGGTC | ACCTGTACTC | 2580 |
| CCAGCTGCAC | TGCTTACACG | TCTTCCTTCG | TCTTCACCTA | CCCCGAGGCT | GACTCCTTCC | 2640 |
| CCAGCTGTGC | AGCTGCCCAC | CGCAAGGGCA | GCAGCAGCAA | TGAGCCTTCC | TCTGACTCGC | 2700 |
| TCAGCTCACC | CACGCTGCTG | GCCCTGTGAG | GGGGCAGGGA | AGGGGAGGCA | GCCGGCACCC | 2760 |
| ACAAGTGCCA | CTGCCCGAGC | TGGTGCATTA | CAGAGAGGAG | AAACACATCT | TCCCTAGAGG | 2820 |
| GTTCCTGTAG | ACCTAGGGAG | GACCTTATCT | GTGCGTGAAA | CACACCAGGC | TGTGGGCCTC | 2880 |
| AAGGACTTGA | AAGCATCCAT | GTGTGGACTC | AAGTCCTTAC | CTCTTCCGGA | GATGTAGCAA | 2940 |
| AACGCATGGA | GTGTGTATTG | TTCCCAGTGA | CACTTCAGAG | AGCTGGTAGT | TAGTAGCATG | 3000 |
| TTGAGCCAGG | CCTGGGTCTG | TGTCTCTTTT | CTCTTTCTCC | TTAGTCTTCT | CATAGCATTA | 3060 |
| ACTAATCTAT | TGGGTTCATT | ATTGGAATTA | ACCTGGTGCT | GGATATTTTC | AAATTGTATC | 3120 |
| TAGTGCAGCT | GATTTAACA | ATAACTACTG | TGTTCCTGGC | AATAGTGTGT | TCTGATTAGA | 3180 |
| AATGACCAAT | ATTATACTAA | GAAAAGATAC | GACTTTATTT | TCTGGTAGAT | AGAAATAAAT | 3240 |
| AGCTATATCC | ATGTACTGTA | GTTTTCTTC | AACATCAATG | TTCATTGTAA | TGTTACTGAT | 3300 |
| CATGCATTGT | TGAGGTGGTC | TGAATGTTCT | GACATTAACA | GTTTCCATG | AAAACGTTTT | 3360 |
| ATTGTGTTTT | TAATTTATTT | ATTAAGATGG | ATTCTCAGAT | ATTTATATTT | TTATTTTATT | 3420 |
| TTTTTCTACC | TTGAGGTCTT | TTGACATGTG | GAAAGTGAAT | TTGAATGAAA | AATTTAAGCA | 3480 |
| TTGTTTGCTT | ATTGTTCCAA | GACATTGTCA | ATAAAAGCAT | TTAAGTTGAA | TGCGACCAAC | 3540 |
| CTTGTGCTCT | TTTCATTCTG | GAAGT | | | | 3565 |

( 2 ) INFORMATION FOR SEQ ID NO:45:

( i ) SEQUENCE CHARACTERISTICS:
 ( A ) LENGTH: 3225 base pairs
 ( B ) TYPE: nucleic acid
 ( C ) STRANDEDNESS: double
 ( D ) TOPOLOGY: linear ( x i ) SEQUENCE DESCRIPTION: SEQ ID NO:45:

| | | | | | |
|---|---|---|---|---|---|
| GGCGGCAGCG | CCCTGCCGAC | GCCGGGGAGG | GACGCAGGCA | GGCGGCGGGC | AGCGGGAGGC | 60 |
| GGCACCCCGG | TGCTCCCCGC | GGCTCTCGGC | GGAGCCCGC | CGCCCGCCGC | GCCATGGCCC | 120 |
| GAAGACCCCG | GCACAGCATA | TATAGCAGTG | ACGAGGATGA | TGAGGACTTT | GAGATGTGTG | 180 |
| ACCATGACTA | TGATGGGCTG | CTTCCCAAGT | CTGGAAAGCG | TCACTTGGGG | AAAACAAGGT | 240 |
| GGACCCGGGA | AGAGGATGAA | AAACTGAAGA | AGCTGGTGGA | ACAGAATGGA | ACAGATGACT | 300 |
| GGAAAGTTAT | TGCCAATTAT | CTCCCGAATC | GAACAGATGT | GCAGTGCCAG | CACCGATGGC | 360 |
| AGAAAGTACT | AAACCCTGAG | CTCATCAAGG | GTCCTTGGAC | CAAAGAAGAA | GATCAGAGAG | 420 |
| TGATAGAGCT | TGTACAGAAA | TACGGTCCGA | AACGTTGGTC | TGTTATTGCC | AAGCACTTAA | 480 |
| AGGGGAGAAT | TGGAAAACAA | TGTAGGGAGA | GGTGGCATAA | CCACTTGAAT | CCAGAAGTTA | 540 |
| AGAAAACCTC | CTGGACAGAA | GAGGAAGACA | GAATTATTTA | CCAGGCACAC | AAGAGACTGG | 600 |
| GGAACAGATG | GGCAGAAATC | GCAAAGCTAC | TGCCTGGACG | AACTGATAAT | GCTATCAAGA | 660 |
| ACCACTGGAA | TTCTACAATG | CGTCGGAAGG | TCGAACAGGA | AGGTTATCTG | CAGGAGTCTT | 720 |
| CAAAAGCCAG | CCAGCCAGCA | GTGGCCACAA | GCTTCCAGAA | GAACAGTCAT | TTGATGGGTT | 780 |
| TTGCTCAGGC | TCCGCCTACA | GCTCAACTCC | CTGCCACTGG | CCAGCCCACT | GTTAACAACG | 840 |
| ACTATTCCTA | TTACCACATT | TCTGAAGCAC | AAAATGTCTC | CAGTCATGTT | CCATACCCTG | 900 |
| TAGCGTTACA | TGTAAATATA | GTCAATGTCC | CTCAGCCAGC | TGCCGCAGCC | ATTCAGAGAC | 960 |
| ACTATAATGA | TGAAGACCCT | GAGAAGGAAA | AGCGAATAAA | GGAATTAGAA | TTGCTCCTAA | 1020 |
| TGTCAACCGA | GAATGAGCTA | AAAGGACAGC | AGGTGCTACC | AACACAGAAC | CACACATGCA | 1080 |
| GCTACCCCGG | GTGGCACAGC | ACCACCATTG | CCGACCACAC | CAGACCTCAT | GGAGACAGTG | 1140 |
| CACCTGTTTC | CTGTTTGGGA | GAACACCACT | CCACTCCATC | TCTGCCAGCG | GATCCTGGCT | 1200 |
| CCCTACCTGA | AGAAAGCGCC | TCGCCAGCAA | GGTGCATGAT | CGTCCACCAG | GCACCATTC | 1260 |
| TGGATAATGT | TAAGAACCTC | TTAGAATTTG | CAGAAACACT | CCAATTTATA | GATTCTTTCT | 1320 |
| TAAACACTTC | CAGTAACCAT | GAAAACTCAG | ACTTGGAAAT | GCCTTCTTTA | ACTTCCACCC | 1380 |
| CCCTCATTGG | TCACAAATTG | ACTGTTACAA | CACCATTTCA | TAGAGACCAG | ACTGTGAAAA | 1440 |
| CTCAAAAGGA | AAATACTGTT | TTTAGAACCC | CAGCTATCAA | AAGGTCAATC | TTAGAAAGCT | 1500 |
| CTCCAAGAAC | TCCTACACCA | TTCAAACATG | CACTTGCAGC | TCAAGAAATT | AAATACGGTC | 1560 |
| CCCTGAAGAT | GCTACCTCAG | ACACCCTCTC | ATCTAGTAGA | AGATCTGCAG | GATGTGATCA | 1620 |
| AACAGGAATC | TGATGAATCT | GGATTTGTTG | CTGAGTTTCA | AGAAAATGGA | CCACCCTTAC | 1680 |
| TGAAGAAAAT | CAAACAAGAG | GTGGAATCTC | CAACTGATAA | ATCAGGAAAC | TTCTTCTGCT | 1740 |
| CACACCACTG | GGAAGGGGAC | AGTCTGAATA | CCCAACTGTT | CACGCAGACC | TCGCCTGTGC | 1800 |
| GAGATGCACC | GAATATTCTT | ACAAGCTCCG | TTTAATGGC | ACCAGCATCA | GAAGATGAAG | 1860 |
| ACAATGTTCT | CAAAGCATTT | ACAGTACCTA | AAAACAGGTC | CCTGGCGAGC | CCCTTGCAGC | 1920 |
| CTTGTAGCAG | TACCTGGGAA | CCTGCATCCT | GTGGAAAGAT | GGAGGAGCAG | ATGACATCTT | 1980 |
| CCAGTCAAGC | TCGTAAATAC | GTGAATGCAT | TCTCAGCCCG | GACGCTGGTC | ATGTGAGACA | 2040 |
| TTTCCAGAAA | AGCATTATGG | TTTTCAGAAC | AGTTCAAGTT | GACTTGGGAT | ATATCATTCC | 2100 |
| TCAACATGAA | ACTTTTCATG | AATGGGAGAA | GAACCTATTT | TTGTTGTGGT | ACAACAGTTG | 2160 |

| | | | | | | |
|---|---|---|---|---|---|---|
| AGAGCACGAC | CAAGTGCATT | TAGTTGAATG | AAGTCTTCTT | GGATTTCACC | CAACTAAAAG | 2220 |
| GATTTTTAAA | AATAAATAAC | AGTCTTACCT | AAATTATTAG | GTAATGAATT | GTAGCCAGTT | 2280 |
| GTTAATATCT | TAATGCAGAT | TTTTTAAAA | AAAACATAA | AATGATTTAT | CTGGTATTTT | 2340 |
| AAAGGATCCA | ACAGATCAGT | ATTTTTCCT | GTGATGGGTT | TTTTGAAATT | TGACACATTA | 2400 |
| AAAGGTACTC | CAGTATTTCA | CTTTTCTCGA | TCACTAAACA | TATGCATATA | TTTTAAAAA | 2460 |
| TCAGTAAAAG | CATTACTCTA | AGTGTAGACT | TAATACCATG | TGACATTTAA | TCCAGATTGT | 2520 |
| AAATGCTCAT | TTATGGTTAA | TGACATTGAA | GGTACATTTA | TTGTACCAAA | CCATTTTATG | 2580 |
| AGTTTTCTGT | TAGCTTGCTT | TAAAAATTAT | TACTGTAAGA | AATAGTTTTA | TAAAAATTA | 2640 |
| TATTTTTATT | CAGTAATTTA | ATTTGTAAA | TGCCAAATGA | AAAACGTTTT | TTGCTGCTAT | 2700 |
| GGTCTTAGCC | TGTAGACATG | CTGCTAGTAT | CAGAGGGGCA | GTAGAGCTTG | GACAGAAAGA | 2760 |
| AAAGAAACTT | GGTGTTAGGT | AATTGACTAT | GCACTAGTAT | TTCAGACTTT | TTAATTTTAT | 2820 |
| ATATATATAC | ATTTTTTTC | CTTCTGCAAT | ACATTTGAAA | ACTTGTTTGG | GAGACTCTGC | 2880 |
| ATTTTTTATT | GTGGTTTTTT | TGTTATTGTT | GGTTTATACA | AGCATGCGTT | GCACTTCTTT | 2940 |
| TTTGGGAGAT | GTGTGTTGTT | CATGTTCTAT | GTTTGTTTT | GTGTGTAGCC | TGACTGTTTT | 3000 |
| ATAATTTGGG | AGTTCTCGAT | TTGATCCGCA | TCCCCTGTGG | TTTCTAAGTG | TATGGTCTCA | 3060 |
| GAACTGTTGC | ATGGATCCTG | TGTTTGCAAC | TGGGGAGACA | GAAACTGTGG | TTGATAGCCA | 3120 |
| GTCACTGCCT | TAAGAACATT | TGATGCAAGA | TGGCCAGCAC | TGAACTTTTG | AGATATGACG | 3180 |
| GTGTACTTAC | TGCCTTGTAG | CAAAATAAAG | ATGTGCCCTT | ATTTT | | 3225 |

( 2 ) INFORMATION FOR SEQ ID NO:46:

( i ) SEQUENCE CHARACTERISTICS:
  ( A ) LENGTH: 2638 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:46:

| | | | | | | |
|---|---|---|---|---|---|---|
| GCTGACGCCT | TCGAGCGCGG | CCCGGGGCCC | GGAGCGGCCG | GAGCAGCCCG | GGTCCTGACC | 60 |
| CCGGCCCGGC | TCCCGCTCCG | GGCTCTGCCG | GCGGGCGGGC | GAGCGCGGCG | CGGTCCGGGC | 120 |
| CGGGGGATG | TCTCGGCGGA | CGCGCTGCGA | GGATCTGGAT | GAGCTGCACT | ACCAGGACAC | 180 |
| AGATTCAGAT | GTGCCGGAGC | AGAGGGATAG | CAAGTGCAAG | GTCAAATGGA | CCCATGAGGA | 240 |
| GGACGAGCAG | CTGAGGGCCC | TGGTGAGGCA | GTTGGACAG | CAGGACTGGA | AGTTCCTGGC | 300 |
| CAGCCACTTC | CCTAACCGCA | CTGACCAGCA | ATGCCAGTAC | AGGTGGCTGA | GAGTTTTGAA | 360 |
| TCCAGACCTT | GTCAAGGGGC | CATGGACCAA | AGAGGAAGAC | CAAAAAGTCA | TCGAGCTGGT | 420 |
| TAAGAAGTAT | GGCACAAAGC | AGTGGACACT | GATTGCCAAG | CACCTGAAGG | GCCGGCTGGG | 480 |
| GAAGCAGTGC | CGTGAACGCT | GGCACAACCA | CCTCAACCCT | GAGGTGAAGA | AGTCTTGCTG | 540 |
| GACCGAGGAG | GAGGACCGCA | TCATCTGCGA | GGCCCACAAG | GTGCTGGGCA | ACCGCTGGGC | 600 |
| CGAGATCGCC | AAGATGTTGC | CAGGGAGGAC | AGACAATGCT | GTGAAGAATC | ACTGGAACTC | 660 |
| TACCATCAAA | AGGAAGGTGG | ACACAGGAGG | CTTCTTGAGC | GAGTCCAAAG | ACTGCAAGCC | 720 |
| CCCAGTGTAC | TTGCTGCTGG | AGCTCGAGGA | CAAGGACGGC | CTCCAGAGTG | CCCAGCCCAC | 780 |
| GGAAGGCCAG | GGAAGTCTTC | TGACCAACTG | GCCCTCCGTC | CCTCCTACCA | TAAAGGAGGA | 840 |
| GGAAAACAGT | GAGGAGGAAC | TTGCAGCAGC | CACCACATCG | AAGGAACAGG | AGCCCATCGG | 900 |
| TACAGATCTG | GACGCAGTGC | GAACACCAGA | GCCCTTGGAG | GAATTCCCGA | AGCGTGAGGA | 960 |

| | | | | | |
|---|---|---|---|---|---|
| CCAGGAAGGC | TCCCCACCAG | AAACGAGCCT | GCCTTACAAG | TGGGTGGTGG | AGGCAGCTAA | 1020
| CCTCCTCATC | CCCGCTGTGG | GTTCTAGCCT | CTCTGAAGCC | CTGGACTTGA | TCGAGTCGGA | 1080
| CCCTGATGCT | TGGTGTGACC | TGAGTAAATT | TGACCTCCCT | GAGGAACCAT | CTGCAGAGGA | 1140
| CAGTATCAAC | AACAGCCTAG | TGCAGCTGCA | AGCGTCACAT | CAGCAGCAAG | TCCTGCCACC | 1200
| CCGCCAGCCT | TCCGCCCTGG | TGCCCAGTGT | GACCGAGTAC | CGCCTGGATG | CCACACCAT | 1260
| CTCAGACCTG | AGCCGGAGCA | GCCGGGGCGA | GCTGATCCCC | ATCTCCCCA | GCACTGAAGT | 1320
| CGGGGGCTCT | GGCATTGGCA | CACCGCCCTC | TGTGCTCAAG | CGGCAGAGGA | AGAGGCGTGT | 1380
| GGCTCTGTCC | CCTGTCACTG | AGAATAGCAC | CAGTCTGTCC | TTCCTGGATT | CCTGTAACAG | 1440
| CCTCACGCCC | AAGAGCACAC | CTGTTAAGAC | CCTGCCCTTC | TCGCCCTCCC | AGTTTCTGAA | 1500
| CTTCTGGAAC | AAACAGGACA | CATTGGAGCT | GGAGAGCCCC | TCGCTGACAT | CCACCCCAGT | 1560
| GTGCAGCCAG | AAGGTGGTGG | TCACCACACC | ACTGCACCGG | GACAAGACAC | CCTGCACCA | 1620
| GAAACATGCT | GCGTTTGTAA | CCCCAGATCA | GAAGTACTCC | ATGGACAACA | CTCCCCACAC | 1680
| GCCAACCCCG | TTCAAGAACG | CCCTGGAGAA | GTACGGACCC | CTGAAGCCCC | TGCCACAGAC | 1740
| CCCGCACCTG | GAGGAGGACT | TGAAGGAGGT | GCTGCGTTCT | GAGGCTGGCA | TCGAACTCAT | 1800
| CATCGAGGAC | GACATCAGGC | CCGAGAAGCA | GAAGAGGAAG | CCTGGGCTGC | GGCGGAGCCC | 1860
| CATCAAGAAA | GTCCGGAAGT | CTCTGGCTCT | TGACATTGTG | GATGAGGATG | TGAAGCTGAT | 1920
| GATGTCCACA | CTGCCCAAGT | CTCTATCCTT | GCCGACAACT | GCCCCTTCAA | ACTCTTCCAG | 1980
| CCTCACCCTG | TCAGGTATCA | AAGAAGACAA | CAGCTTGCTC | AACCAGGGCT | TCTTGCAGGC | 2040
| CAAGCCCGAG | AAGGCAGCAG | TGGCCCAGAA | GCCCCGAAGC | CACTTCACGA | CACCTGCCCC | 2100
| TATGTCCAGT | GCCTGGAAGA | CGGTGGCCTG | CGGGGGGACC | AGGGACCAGC | TTTTCATGCA | 2160
| GGAGAAAGCC | CGGCAGCTCC | TGGGCCGCCT | GAAGCCCAGC | CACACATCTC | GGACCCTCAT | 2220
| CTTGTCCTGA | GGTGTTGAGG | GTGTCACGAG | CCCATTCTCA | TGTTTACAGG | GGTTGTGGGG | 2280
| GCAGAGGGGG | TCTGTGAATC | TGAGAGTCAT | TCAGGTGACC | TCCTGCAGGG | AGCCTTCTGC | 2340
| CACCAGCCCC | TCCCCAGACT | CTCAGGTGGA | GGCAACAGGG | CCATGTGCTG | CCCTGTTGCC | 2400
| GAGCCCAGCT | GTGGGCGGCT | CCTGGTGCTA | ACAACAAAGT | TCCACTTCCA | GGTCTGCCTG | 2460
| GTTCCCTCCC | CAAGGCCACA | GGGAGCTCCG | TCAGCTTCTC | CCAAGCCCAC | GTCAGGCCTG | 2520
| GCCTCATCTC | AGACCCTGCT | TAGGATGGGG | GATGTGGCCA | GGGGTGCTCC | TGTGCTCACC | 2580
| CTCTCTTGGT | GCATTTTTTT | GGAAGAATAA | AATTGCCTCT | CTCTTTGAAA | AAAAAAA | 2638

( 2 ) INFORMATION FOR SEQ ID NO:47:

( i ) SEQUENCE CHARACTERISTICS:
        ( A ) LENGTH: 790 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:47:

| | | | | | |
|---|---|---|---|---|---|
| AGAATTTAGA | AGCAGGGAGA | TGTAATTAGA | GAATATGTCA | TTACCTAGAA | ATGAAGCCAC | 60
| AAAGTCTAAA | GTAAAGCAGT | TAGAAAGGAA | GTGGACAGAT | AAATAGATGA | TTAATGTATT | 120
| TAGTGTCATT | TATCTATACA | CTAAAACTTT | TATTCTGTGA | ATGCTTTTCC | TCAAATTCTT | 180
| CCCTGCAAAA | AGAAATAAAA | TATTACTAAG | GTAGCAACTC | ATTTTTTGA | AAATCCTTTA | 240
| TATTTAGGTG | CTCCAAATAC | TGCAGAATTA | AGGATTTGTC | GTGTAAACAA | GAATTGTGGA | 300
| AGTGTCAGAG | GAGGAGATGA | AATATTTCTA | CTTTGTGACA | AAGTTCAGAA | AGGTATTTAT | 360
| TTATTTCATT | GAATTTAGAA | TAAATTTTAG | ATTAATAGAT | GCAGTTACTT | TGTTTTCCCA | 420

| | | | | | |
|---|---|---|---|---|---|
| TTTTTTTTT | TTTGGTTTCT | TATTGACTAG | ATGACATAGA | AGTTCGTTTT | GTGTTGAACG | 480
| ATTGGGAAGC | AAAAGGCATC | TTTTCACAAG | CTGATGTACA | CCGTCAAGTA | GCCATTGTTT | 540
| TCAAAACTCC | ACCATATTGC | AAAGCTATCA | CAGAACCCGT | AACAGTAAAA | ATGCAGTTGC | 600
| GGAGACCTTC | TGACCAGGAA | GTTAGTGAAT | CTATGGATTT | TAGATATCTG | CCAGATGAAA | 660
| AAGGTATGAC | ATTTTGCTGG | TAATAATTTA | TATATTTCTT | GAAGTGGTCC | TGCTAATAAC | 720
| ATCTTCTTGT | AATATTCATT | TGAGTACAGT | TATGTATATT | CATAATTTAT | GTTTCTTTTC | 780
| CTGGAAGCTT | | | | | | 790

( 2 ) INFORMATION FOR SEQ ID NO:48:

( i ) SEQUENCE CHARACTERISTICS:
        ( A ) LENGTH: 2757 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:48:

| | | | | | |
|---|---|---|---|---|---|
| CTAGGCTTTT | GCAAAAAGCT | TCACGCTGCC | GCAAGCACTC | AGGGCGCAAG | GGCTGCTAAA | 60
| GGAAGCGGAA | CACGTAGAAA | GCCAGTCCGC | AGAAACGGTG | CTGACCCCGG | ATGAATGTCA | 120
| GCTACTGGGC | TATCTGGACA | AGGGAAAACG | CAAGCGCAAA | GAGAAAGCAG | TTCCTGTGCC | 180
| TTAAGAACAT | TAGAACCTTC | CTGTCCACCT | GCTGTGAGAA | GTTCGGCCTC | AAGCGGAGCG | 240
| AGCTCTTCGA | AGCCTTTGAC | CTCTTCGATG | TGCAGGATTT | TGGCAAGGTC | ATCTACACCC | 300
| TGTCTGCTCT | GTCCTGGACC | CCGATCGCCC | AGAACAGGGG | GATCATGCCC | TTCCCCACCG | 360
| AGGAGGAGAG | TGTAGGTGAT | GAAGACATCT | ACAGTGGCCT | GTCCGACCAG | ATCGACGACA | 420
| CGGTGGAGGA | GGATGAGGAC | CTGTATGACT | GCGTGGAGAA | TGAGGAGGCG | AAGGCGACG | 480
| AGATCTATGA | GGACCTCATG | CGCTCGGAGC | CCGTGTCCAT | GCCGCCCAAG | ATGACAGAGT | 540
| ATGACAAGCG | CTGCTGCTGC | CTGCGGGAGA | TCCAGCAGAC | GGAGGAGAAG | TACACTGACA | 600
| CGCTGGGCTC | CATCCAGCAG | CATTTCTTGA | AGCCCCTGCA | ACGGTTCCTG | AAACCTCAAG | 660
| ACATTGAGAT | CATCTTTATC | AACATTGAGG | ACCTGCTTCG | TGTTCATACT | CACTTCCTAA | 720
| AGGAGATGAA | GGAAGCCCTG | GGCACCCCTG | GCGCACCGAA | TCTCTACCAG | GTCTTCATCA | 780
| AATACAAGGA | GAGGTTCCTC | GTCTATGGCC | GCTACTGCAG | CCAGGTGGAG | TCAGCCAGCA | 840
| AACACCTGGA | CCGTGTGGCC | GCAGCCCGGG | AGGACGTGCA | GATGAAGCTG | GAGGAATGTT | 900
| CTCAGAGAGC | CAACAACGGG | AGGTTCACTG | CGCGACCTGC | TGATGGTGCC | TATGCAGCGA | 960
| GTTCTCAAAT | ATCACCTCCT | TCTCCAGGAG | CTGGTGAAAC | ACACGCAGGA | GGCGATGGAG | 1020
| CAAGGAAACT | GCGGCTGGCC | CTGGATGCCA | TGAGGGACCT | GGCTCAGTGC | GTGAACGAGG | 1080
| TCAAGCGAGA | CAACGAGACA | CTGCGACAGA | TCACCAATTT | CCAGCTGTCC | ATTGAGAACC | 1140
| TGGACCAGTC | TCTGGCTCAC | TATGGCCGGC | CCAAGATCGA | CGGGGAACTC | AAGATCACCT | 1200
| CGGTGGAACG | GCGCTCCAAG | ATGGACAGGT | ATGCCTTCCT | GCTCGACAAA | GCTCTACTCA | 1260
| TCTGTAAGCG | CAGGGGAGAC | TCCTATGACC | TCAAGGACTT | TGTAAACCTG | CACAGCTTCC | 1320
| AGGTTCGGGA | TGACTCTTCA | GGAGACCGAG | ACAACAAGAA | GTGGAGCCAC | ATGTTCCTCC | 1380
| TGATCGAGGA | CCAAGGTGCC | CAGGGCTATG | AGCTGTTCTT | CAAGACAAGA | GAATTGAAGA | 1440
| AGAAGTGGAT | GGAGCAGTTT | GAGATGGCCA | TCTCCAACAT | CTATCCGGAG | AATGCCACCG | 1500
| CCAACGGGCA | TGACTTCCAG | ATGTTCTCCT | TGAGGAGAC | CACATCCTGC | AAGGCCTGTC | 1560
| AGATGCTGCT | TAGAGGTACC | TTCTATCAGG | GCTACCGCTG | CCATCGGTGC | CGGGCATCTG | 1620

-continued

| | | | | | |
|---|---|---|---|---|---|
| CACACAAGGA | GTGTCTGGGG | AGGGTCCCTC | CATGTGGCCG | ACATGGGCAA | GATTTCCCAG | 1680
| GAACTATGAA | GAAGGACAAA | CTACATCGCA | GGGCTCAGGA | CAAAAGAGG | AATGAGCTGG | 1740
| GTCTGCCCAA | GATGGAGGTG | TTTCAGGAAT | ACTACGGGCT | TCCTCCACCC | CCTGGAGCCA | 1800
| TTGGACCCTT | TCTACGGCTC | AACCCTGGAG | ACATTGTGGA | GCTCACGAAG | GCTGAGGCTG | 1860
| AACAGAACTG | GTGGGAGGGC | AGAAATACAT | CTACTAATGA | AATTGGCTGG | TTTCCTTGTA | 1920
| ACAGGGTGAA | GCCCTATGTC | CATGGCCCTC | CTCAGGACCT | GTCTGTTCAT | CTCTGGTACG | 1980
| CAGGCCCCAT | GGAGCGGGCA | GGGGCAGAGA | GCATCCTGGC | CAACCGCTCG | GACGGGACTT | 2040
| TCTTGGTGCG | GCAGAGGGTG | AAGGATGCAG | CAGAATTTGC | CATCAGCATT | AAATATAACG | 2100
| TCGAGGTCAA | GCACACGGTT | AAAATCATGA | CAGCAGAAGG | ACTGTACCGG | ATCACAGAGA | 2160
| AAAAGGCTTT | CCGGGGGCTT | ACGGAGCTGG | TGGAGTTTTA | CCAGCAGAAC | TCTCTAAAGG | 2220
| ATTGCTTCAA | GTCTCTGGAC | ACCACCTTGC | AGTTCCCCTT | CAAGGAGCCT | GAAAAGAGAA | 2280
| CCATCAGCAG | GCCAGCAGTG | GGAAGCACAA | AGTATTTTGG | CACAGCCAAA | GCCCGCTATG | 2340
| ACTTCTGCGC | CCGTGACCGT | TCAGAGCTGT | CGCTCAAGGA | GGGTGACATC | ATCAAGATCC | 2400
| TTAACAAGAA | GGGACAGCAA | GGCTGGTGGC | GAGGGGAGAT | CTATGGCCGG | GTTGGCTGGT | 2460
| TCCCTGCCAA | CTACGTGGAG | GAAGATTATT | CTGAATACTG | CTGAGCCCTG | GTGCCTTGGC | 2520
| AGAGAGACGA | GAAACTCCAG | GCTCTGAGCC | CGGCGTGGCG | AGGCAGCGGA | CCAGGGCTG | 2580
| TGACAGCTCC | GGCGGGTGGA | GACTTTGGGA | TGGACTGGAG | GAGGCCAGCG | TCCAGCTGGC | 2640
| GGTGCTCCCG | GGATGTGCCC | TGACATGGTT | AATTTATAAC | ACCCCGATTT | TCCTCTTGGG | 2700
| TCCCCTCAAG | CAGACGGGGG | CTCAAGGGGG | TTACATTTAA | TAAAAGGATG | AAGATGG | 2757

( 2 ) INFORMATION FOR SEQ ID NO:49:

( i ) SEQUENCE CHARACTERISTICS:
        ( A ) LENGTH: 4175 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:49:

| | | | | | |
|---|---|---|---|---|---|
| TCCTCGTCGT | CTGTGGATTG | CTAAACCTGA | GTGGGAAGGG | GGGGGAAAAA | AAAAAGGGTG | 60
| GGTTGTTGTT | TTGTTTAAAA | AAAGAAAAAA | TCCCTTAAGT | GGATTTGTAC | CAGCGTGGAA | 120
| GATAACTGGG | GATTTTTGTT | GTTTGTTTTG | GGAATAGAAA | CTAAAAAATG | GAGACTGTAA | 180
| GTAGAAGCAG | CTTCCAGCCT | CATCCAGGAC | TGCAGAAGAC | CTTGGAACAG | TTTCATCTGA | 240
| GCTCTATGAG | CTCCCTGGGT | GGCCCTGCTG | CTTTCTCAGC | GCGATGGGCA | CAGGAGATGT | 300
| ACAAGAAAGA | CAATGGCAAA | GACCCAGCGG | AACCTGTACT | GCATCTGCCC | CCTATCCAGC | 360
| CCCCCCCGGT | GATGCCTGGT | CCCTTCTTCA | TGCCCTCGGA | CAGATCCACT | GAGAGGTGCG | 420
| AGACCATCCT | GGAAGGGGAA | ACCATCTCCT | GCTTCGTGGT | GGGTGGGGAA | AAGCGCCTTT | 480
| GCTTGCCCCA | GATCCTGAAC | TCGGTGCTCA | GGGACTTCTC | CCTGCAGCAG | ATCAATTCGG | 540
| TGTGCGATGA | GCTACACATT | TACTGCTCCA | GATGCACCGC | TGACCAGCTG | GAGATCCTCA | 600
| AAGTCATGGG | CATCTTGCCC | TTCTCTGCCC | CCTCCTGCGG | GCTGATCACT | AAAACTGATG | 660
| CTGAGAGGCT | TTGCAATGCC | TTGCTTTATG | GTGGCACCTA | TCCTCCCCAC | TGCAAGAAGG | 720
| AATTCTCTAG | CACGATTGAG | CTGGAGCTTA | CAGAGAAGAG | CTTCAAGGTG | TACCACGAGT | 780
| GCTTTGGGAA | GTGTAAGGGA | CTCCTGGTAC | CAGAGCTTTA | CAGTAACCCC | AGCGCAGCCT | 840
| GCATCCAGTG | CTTGGACTGC | AGGCTCATGT | ACCCGCCTCA | CAAATTTGTG | GTCCACTCTC | 900
| ACAAATCCCT | GGAAAACAGG | ACTTGCCACT | GGGGCTTTGA | CTCTGCAAAC | TGGAGGTCCT | 960

| | | | | | |
|---|---|---|---|---|---|
| ACATCCTCCT | TAGCCAGGAT | TACACTGGGA | AAGAGGAGAA | AGCTAGGCTG | GGCCAGCTCT | 1020
| TAGATGAAAT | GAAAGAAAAA | TTTGACTATA | ACAACAAATA | CAAGAGGAAA | GCCCCAGGA | 1080
| ACCGTGAGTC | TCCTAGAGTT | CAGCTCCGCC | GGACCAAAAT | GTTCAAGACA | ATGCTGTGGG | 1140
| ATCCAGCTGG | AGGTTCAGCG | GTACTGCAGC | GTCAGCCAGA | TGGAAATGAG | GTCCCTTCAG | 1200
| ATCCTCCTGC | TTCCAAGAAA | ACCAAAATAG | ACGACTCCGC | TTCCCAATCT | CCAGCTTCTA | 1260
| CTGAGAAGGA | AAAGCAGTCC | AGTTGGTTAC | GGTCCTTATC | CAGTTCATCT | AATAAGAGCA | 1320
| TTGGCTGTGT | CCATCCCCGT | CAGCGTCTCT | CAGCTTTCCG | GCCCTGGTCC | CCTGCTGTAT | 1380
| CAGCAAATGA | GAAAGAGCTC | TCAACCCATC | TTCCTGCATT | GATCCGAGAC | AGCAGTTTTT | 1440
| ACTCCTACAA | AAGCTTTGAG | AATGCTGTGG | CCCCCAACGT | GGCACTCGCA | CCTCCTGCCC | 1500
| AACAGAAAGT | TGTGAGCAAC | CCACCCTGTG | CCACAGTGGT | GTCCCGGAGC | AGCGAACCGC | 1560
| CGAGCAGCGC | TGCGCAGCCA | CGGAAAAGAA | AACATGCTGC | AGAAACCCCG | GCTGTCCCAG | 1620
| AGCCAGTGGC | CACGGTTACT | GCCCCTGAAG | AGGATAAGGA | ATCAGAAGCA | GAAATTGAAG | 1680
| TAGAGACCAG | GGAGGAATTC | ACCTCCTCCT | TATCCTCGCT | CTCCTCCCCA | TCCTTTACTT | 1740
| CATCCAGCTC | TGCAAAGGAC | ATGAGCTCAC | CTGGGATGCA | AGCCCAGTC | CCAGTCAACA | 1800
| GTTCATATGA | GGTTGCAGCA | CATTCTGACT | CTCACAGCAG | TGGGTTGGAA | GCTGAGCTGG | 1860
| AGCACCTAAG | GCAGGCCCTG | GACAGTGGCC | TAGATACAAA | AGAAGCCAAA | GAAAAATTCC | 1920
| TCCATGAAGT | TGTTAAAATG | AGAGTGAAGC | AGGAAGAGAA | GCTAAATGCT | GCCTTGCAAG | 1980
| CCAAACGCAG | CCTACATCAG | GAGCTGGAGT | TCCTCAGAGT | GGCAAAGAAG | GAGAAACTGA | 2040
| GAGAAGCAAC | GGAGGCAAAA | CGCAACTTAA | GGAAAGAGAT | TGAGCGTCTG | AGAGCTGAGA | 2100
| ATGAGAAGAA | AATGAAGGAA | GCAAACGAGT | CTCGGATACG | GCTAAAGAGG | GAACTGGAAC | 2160
| AAGCCAGGCA | GATCCGGGTT | TGCGACAAGG | GTTGTGAAGC | TGGCAGGCTT | CGGGCCAAGT | 2220
| ACTCTGCCCA | GATTGAGGAC | CTACAGGTTA | AGCTTCAGCA | TGCAGAGGCT | GACAGGGAGC | 2280
| AGCTCCGAGC | TGACCTGATG | CATGAGAGGG | AGGCTCGAGA | ACACTTGGAA | AAAGTAGTCA | 2340
| AGGAACTTCA | GGAACAGCTG | TGGCCTAAAT | CAAGCAGTCA | ATCCAGCAGT | GAAAACACAA | 2400
| CGAGCAACAT | GGAGAATTAA | ACCACGTCGT | CTAATACAAC | AGAATGACAT | ATATGCACAG | 2460
| TAAGGGAGGA | TGGGTGGGGT | ACGTGTGTAA | GTGCATGTGT | GAGTAGTTGT | GTCTTAACAC | 2520
| ACAGATCTAG | GAATATGGAT | TCTTATTAGT | TGGAAGGCAA | ATGTTACTCT | TTATAACAGA | 2580
| AGCACTGAAT | TACGCCTCTT | TTTTTTTCCA | ATCCATATAG | CACAACATCT | TACTGTGCCT | 2640
| ATAAAACACA | AATGTGTTTA | TAAACAAAAT | ACTTTAAGT | CCACAGCAAA | TTTTCTACTG | 2700
| GCAAACTCCA | AGCAAGCAGC | ATCCTCCAAC | TAGAATCAGA | GTAAAAGGCA | AGCATGGCAG | 2760
| TGTTTTCATG | TTGCCCTTCT | GCCTGTCGGA | ACATTTGGA | ATTTAAAAAC | AAACTTTTCT | 2820
| TATAAGCTAT | TTAAAGTAAT | TCATTACACA | GACTTGGTAT | TAAAAAAAAT | TAACAAGATT | 2880
| TTTTATAACG | AACCTTTAAA | AGCAAAACAA | AAACCTTCGA | TGCACAATTT | TTACGACTTG | 2940
| TTAAAGGCTT | TGGGATTCTT | ACTGCAGAAG | CCCTTGGTG | ATGATGCCAT | TTCATTAGCA | 3000
| GTTTTTTTA | ATCCTGTCCT | GTGGTTGTAT | GAGAATTTCA | GAGTGCTTTT | CAAAGTTGAT | 3060
| TTTTTTCCTT | AGAACAATC | ACCTTCATTT | CCTGTCCTGA | ACACAAGAAG | AAAGGAAGAT | 3120
| GCAGGACTGT | AAGGGCGTGG | GGGAGGGCAG | GAAGAGAAGA | TGGACGCTTT | GGAATTATAA | 3180
| ACCCAGCCTT | ACAGACTTCA | GTGTTTCAAA | TCACGCCATG | TTTTCTAAAG | ACGTCTTCAT | 3240
| TAATCGATGT | GTTCAAAAGA | CTCACTTCAT | CCAAGAGCAC | TTCAGCTTTA | GGAAAAGAAA | 3300
| GAAGGAAGTA | AAGGAAGGAA | ATGGATGACC | TGTTAAGTTG | GTTGAGAAAT | AAAGCAGAAG | 3360

```
ATGTGTTTTG AAGTCATTCT GAAATCTTCG CGTCAGCTTT CAGTTCTCTG GAAAACTCAT    3420
CTTTGTTGCA CCATCTTACC ATAGAATTCA GTATTTACCT ACTTCTATTC TGAACTGTTT    3480
GTCAGGATTT CTGTGCCCAA GGAGAGTGCA ACACCGCATT ATTGGATACT ACAGAAAAGA    3540
AAAACCACGT TTTTGCTGCT GTGAATAAGC CTACATCTTT TTTAAAAGAA AAACTTCTGT    3600
TTTTAAGAAT AGAAATTACT TTAATTTTGG GATCCGAGCC GCAGCCCTGG AATAGAAATG    3660
CAGCCTACCA TCACTCTGTC TTACTACCAT TGTTAGCGTC GTCGTTCATT TTTTTTTAAA    3720
CTGCACTTTG TCAGAACCTC ACTCTGCATT TTATTCCATA TTTTGGAAGT TTACAAGTTC    3780
AGCATTCTCG ATTCTGCTCT GCAGATGTTA AAATCATCAC CACCATTTTC CACCACGCGA    3840
CACCTCGGCC GTCATTTCCA TGTATGCAAA AGAAGAACTC AGTGGGTACA GAATGCTACC    3900
AAATACAAAG GCAGCAGAGC AGCGTGCTGC TGGTTGGGTT TCACAGCTGC GCTGCACGGC    3960
TGTGGCTGTC GAGGCTGGGA AGTGCTCAAA TACAGTTGGT GCTTACTGA ATGAGAGAGG    4020
AGTTATTTTC ACCCACACAC ACTCACCTCT GATACACTCA AGCTCAGTGA AAAGTTGATC    4080
TGGGGCTGCA GTTGTGCCTT CCAGCTCATT TTTCCTCTCA GCATCTTCTA TAGGCAATGC    4140
TGACACTTTT TTTTAAACC TTAAAGAATA AAAAG                                4175
```

( 2 ) INFORMATION FOR SEQ ID NO:50:

( i ) SEQUENCE CHARACTERISTICS:
        ( A ) LENGTH: 1364 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:50:

```
AAAATCAGGA ACTTGTGCTG GCCCTGCAAT GTCAAGGGAG GGGGCTCACC CAGGGCTCCT      60
GTAGCTCAGG GGGCAGGCCT GAGCCCTGCA CCCGCCCCAC GACCGTCCAG CCCCTGACGG     120
GCACCCCATC CTGAGGGGCT CTGCATTGGC CCCCACCGAG GCAGGGATC TGACCGACTC      180
GGAGCCCGGC TGGATGTTAC AGGCGTGCAA AATGGAAGGG TTTCCCCTCG TCCCCCCTCC     240
ATCAGAAGAC CTGGTGCCCT ATGACACGGA TCTATACCAA CGCCAAACGC ACGAGTATTA     300
CCCCTATCTC AGCAGTGATG GGGAGAGCCA TAGCGACCAT TACTGGGACT CCACCCCCA     360
CCACGTGCAC AGCGAGTTCG AGAGCTTCGC CGAGAACAAC TTCACGGAGC TCCAGAGCGT     420
GCAGCCCCCG CAGCTGCAGC AGCTCTACCG CCACATGGAG CTGGAGCAGA TGCACGTCCT     480
CGATACCCCC ATGGTGCCAC CCATCCCAG TCTTGGCCAC CAGGTCTCCT ACCTGCCCCG      540
GATGTGCCTC CAGTACCCAT CCCTGTCCCC AGCCCAGCCC AGCTCAGATG AGGAGGAGGG     600
CGAGCGGCAG AGCCCCCCAC TGGAGGTGTC TGACGGCGAG GCGGATGGCC TGGAGCCCGG     660
GCCTGGGCTC CTGCCTGGGG AGACAGGCAG CAAGAAGAAG ATCCGCCTGT ACCAGTTCCT     720
GTTGGACCTG CTCCGCAGCG GCGACATGAA GGACAGCATC TGGTGGGTGG ACAAGGACAA     780
GGGCACCTTC CAGTTCTCGT CCAAGCACAA GGAGGCGCTG GCGCACCGCT GGGGCATCCA     840
GAAGGGCAAC CGCAAGAAGA TGACCTACCA GAAGATGGCG CGCGCGCTGC GCAACTACGG     900
CAAGACGGGC GAGGTCAAGA AGGTGAAGAA GAAGCTCACC TACCAGTTCA GCGGCGAAGT     960
GCTGGGCCGC GGGGGCCTGG CCGAGCGGCG CCACCCGCCC CACTGAGCCC GCAGCCCCG     1020
CCGGCCCCGC CAGGCCTCCC CGCTGGCCAT AGCATTAAGC CCTCGCCCGG CCCGGACACA    1080
GGGAGGACGC TCCCGGGGCC CAGAGGCAGG ACTGTGGCGG CCGGGCTCC GTCACCCGCC     1140
CCTCCCCCCA CTCCAGGCCC CCTCCACATC CCGCTTCGCC TCCCTCCAGG ACTCCACCCC    1200
```

| | | | | | |
|---|---|---|---|---|---|
| GGCTCCCGAC | GCCAGCTGGG | CGTCAGACCC | ACCGGCAACC | TTGCAGAGGA | CGACCCGGGG | 1260 |
| TACTGCCTTG | GGAGTCTCAA | GTCCGTATGT | AAATCAGATC | TCCCCTCTCA | CCCCTCCCAC | 1320 |
| CCATTAACCT | CCTCCCAAAA | AACAAGTAAA | GTTATTCTCA | ATCC | | 1364 |

( 2 ) INFORMATION FOR SEQ ID NO:51:

( i ) SEQUENCE CHARACTERISTICS:
        ( A ) LENGTH: 1325 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

| | | | | | |
|---|---|---|---|---|---|
| GCAGTAGCAG | CGAGCAGCAG | AGTCCGCACG | CTCCGGCGAG | GGGCAGAAGA | GCGCGAGGGA | 60 |
| GCGCGGGGCA | GCAGAAGCGA | GAGCCGAGCG | CGGACCCAGC | CAGGACCCAC | AGCCCTCCCC | 120 |
| AGCTGCCCAG | GAAGAGCCCC | AGCCATGGAA | CACCAGCTCC | TGTGCTGCGA | AGTGGAAACC | 180 |
| ATCCGCCGCG | CGTACCCCGA | TGCCAACCTC | CTCAACGACC | GGGTGCTGCG | GCCATGCTG | 240 |
| AAGGCGGAGG | AGACCTGCGC | GCCCTCGGTG | TCCTACTTCA | AATGTGTGCA | GAAGGAGGTC | 300 |
| CTGCCGTCCA | TGCGGAAGAT | CGTCGCCACC | TGGATGCTGG | AGGTCTGCGA | GGAACAGAAG | 360 |
| TGCGAGGAGG | AGGTCTTCCC | GCTGGCCATG | AACTACCTGG | ACCGCTTCCT | GTCGCTGGAG | 420 |
| CCCGTGAAAA | AGAGCCGCCT | GCAGCTGCTG | GGGGCCACTT | GCATGTTCGT | GGCCTCTAAG | 480 |
| ATGAAGGAGA | CCATCCCCCT | GACGGCCGAG | AAGCTGTGCA | TCTACACCGA | CGGCTCCATC | 540 |
| CGGCCCGAGG | AGCTGCTGCA | AATGGAGCTG | CTCCTGGTGA | ACAAGCTCAA | GTGGAACCTG | 600 |
| GCCGCAATGA | CCCCGCACGA | TTTCATTGAA | CACTTCCTCT | CCAAAATGCC | AGAGGCGGAG | 660 |
| GAGAACAAAC | AGATCATCCG | CAAACACGCG | CAGACCTTCG | TTGCCTCTTG | TGCCACAGAT | 720 |
| GTGAAGTTCA | TTTCCAATCC | GCCCTCCATG | GTGGCAGCGG | GGAGCGTGGT | GGCCGCAGTG | 780 |
| CAAGGCCTGA | ACCTGAGGAG | CCCCAACAAC | TTCCTGTCCT | ACTACCGCCT | CACACGCTTC | 840 |
| CTCTCCAGAG | TGATCAAGTG | TGACCCAGAC | TGCCTCCGGG | CCTGCCAGGA | GCAGATCGAA | 900 |
| GCCCTGCTGG | AGTCAAGCCT | GCGCCAGGCC | CAGCAGAACA | TGGACCCCAA | GGCCGCCGAG | 960 |
| GAGGAGGAAG | AGGAGGAGGA | GGAGGTGGAC | CTGGCTTGCA | CACCCACCGA | CGTGCGGGAC | 1020 |
| GTGGACATCT | GAGGGGCCCA | GGCAGGCGGG | CGCCACCGCC | ACCCGCAGCG | AGGGCGGAGC | 1080 |
| CGGCCCCAGG | TGCTCCACAT | GACAGTCCCT | CCTCTCCGGA | GCATTTGAT | ACCAGAAGGG | 1140 |
| AAAGCTTCAT | TCTCCTTGTT | GTTGGTTGTT | TTTTCCTTTG | CTCTTTCCCC | CTTCCATCTC | 1200 |
| TGACTTAAGC | AAAAGAAAAA | GATTACCCAA | AAACTGTCTT | TAAAAGAGAG | AGAGAGAAAA | 1260 |
| AAAAAAAAAA | AAAAAAAAAA | AAAAAAAAAA | AAAAAAAAAA | AAAAAAAAAA | AAAAAAAAAA | 1320 |
| AAAAA | | | | | | 1325 |

( 2 ) INFORMATION FOR SEQ ID NO:52:

( i ) SEQUENCE CHARACTERISTICS:
        ( A ) LENGTH: 3036 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

| | | | | | |
|---|---|---|---|---|---|
| CTCCCCTTCA | GCTTCTCTTC | ACGCACTCCA | AGATCTAAAC | CGAGAATCGA | AACTAAGCTG | 60 |
| GGGTCCATGG | AGCCTGCACC | CGCCCGATCT | CCGAGGCCCC | AGCAGGACCC | CGCCCGGCCC | 120 |
| CAGGAGCCCA | CCATGCCTCC | CCCCGAGACC | CCCTCTGAAG | GCCGCCAGCC | CAGCCCCAGC | 180 |

-continued

| | | | | | |
|---|---|---|---|---|---|
| CCCAGCCCTA | CAGAGCGAGC | CCCCGCTTCG | GAGGAGGAGT | TCCAGTTTCT | GCGCTGCCAG | 240 |
| CAATGCCAGG | CGGAAGCCAA | GTGCCCGAAG | CTGCTGCCTT | GTCTGCACAC | GCTGTGCTCA | 300 |
| GGATGCCTGG | AGGCGTCGGG | CATGCAGTGC | CCCATCTGCC | AGGCGCCCTG | GCCCCTAGGT | 360 |
| GCAGACACAC | CCGCCCTGGA | TAACGTCTTT | TTCGAGAGTC | TGCAGCGGCG | CCTGTCGGTG | 420 |
| TACCGGCAGA | TTGTGGATGC | GCAGGCTGTG | TGCACCCGCT | GCAAAGAGTC | GGCCGACTTC | 480 |
| TGGTGCTTTG | AGTGCGAGCA | GCTCCTCTGC | GCCAAGTGCT | TCGAGGCACA | CCAGTGGTTC | 540 |
| CTCAAGCACG | AGGCCCGGCC | CCTAGCAGAG | CTGCGCAACC | AGTCGGTGCG | TGAGTTCCTG | 600 |
| GACGGCACCC | GCAAGACCAA | CAACATCTTC | TGCTCCAACC | CCAACCACCG | CACCCCTACG | 660 |
| CTGACCAGCA | TCTACTGCCG | AGGATGTTCC | AAGCCGCTGT | GCTGCTCGTG | CGCGCTCCTT | 720 |
| GACAGCAGCC | ACAGTGAGCT | CAAGTGCGAC | ATCAGCGCAG | AGATCCAGCA | GCGACAGGAG | 780 |
| GAGCTGGACG | CCATGACGCA | GGCGCTGCAG | GAGCAGGATA | GTGCCTTTGG | CGCGGTTCAC | 840 |
| GCGCAGATGC | ACGCGGCCGT | CGGCCAGCTG | GGCCGCGCGC | GTGCCGAGAC | CGAGGAGCTG | 900 |
| ATCCGCGAGC | GCGTGCGCCA | GGTGGTAGCT | CACGTGCGGG | CTCAGGAGCG | CGAGCTGCTG | 960 |
| GAGGCTGTGG | ACGCGCGGTA | CCAGCGCGAC | TACGAGGAGA | TGGCCAGTCG | GCTGGGCCGC | 1020 |
| CTGGATGCTG | TGCTGCAGCG | CATCCGCACG | GGCAGCGCGC | TGGTGCAGAG | GATGAAGTGC | 1080 |
| TACGCCTCGG | ACCAGGAGGT | GCTGGACATG | CACGGTTTCC | TGCGCCAGGC | GCTCTGCCGC | 1140 |
| CTGCGCCAGG | AGGAGCCCCA | GAGCCTGCAA | GCTGCCGTGC | GCACCGATGG | CTTCGACGAG | 1200 |
| TTCAAGGTGC | GCCTGCAGGA | CCTCAGCTCT | TGCATCACCC | AGGGGAAAGC | CATTGAGACC | 1260 |
| CAGAGCAGCA | GTTCTGAAGA | GATAGTGCCC | AGCCTCCCT | CGCCACCCCC | TCTACCCCGC | 1320 |
| ATCTACAAGC | CTTGCTTTGT | CTGTCAGGAC | AAGTCCTCAG | GCTACCACTA | TGGGGTCAGC | 1380 |
| GCCTGTGAGG | GCTGCAAGGG | CTTCTTCCGC | CGCAGCATCC | AGAAGAACAT | GGTGTACACG | 1440 |
| TGTCACCGGG | ACAAGAACTG | CATCATCAAC | AAGGTGACCC | GGAACCGCTG | CCAGTACTGC | 1500 |
| CGACTGCAGA | AGTGCTTTGA | AGTGGGCATG | TCCAAGGAGT | CTGTGAGAAA | CGACCGAAAC | 1560 |
| AAGAAGAAGA | AGGAGGTGCC | CAAGCCCGAG | TGCTCTGAGA | GCTACACGCT | GACGCCGGAG | 1620 |
| GTGGGGGAGC | TCATTGAGAA | GGTGCGCAAA | GCGCACCAGG | AAACCTTCCC | TGCCCTCTGC | 1680 |
| CAGCTGGGCA | AATACACTAC | GAACAACAGC | TCAGAACAAC | GTGTCTCTCT | GGACATTGAC | 1740 |
| CTCTGGGACA | AGTTCAGTGA | ACTCTCCACC | AAGTGCATCA | TTAAGACTGT | GGAGTTCGCC | 1800 |
| AAGCAGCTGC | CCGGCTTCAC | CACCCTCACC | ATCGCCGACC | AGATCACCCT | CCTCAAGGCT | 1860 |
| GCCTGCCTGG | ACATCCTGAT | CCTGCGGATC | TGCACGCGGT | ACACGCCCGA | GCAGGACACC | 1920 |
| ATGACCTTCT | CGGACGGGCT | GACCCTGAAC | CGGACCCAGA | TGCACAACGC | TGGCTTCGGC | 1980 |
| CCCCTCACCG | ACCTGGTCTT | TGCCTTCGCC | AACCAGCTGC | TGCCCCTGGA | GATGGATGAT | 2040 |
| GCGGAGACGG | GGCTGCTCAG | CGCCATCTGC | CTCATCTGCG | GAGACCGCCA | GGACCTGGAG | 2100 |
| CAGCCGGACC | GGGTGGACAT | GCTGCAGGAG | CCGCTGCTGG | AGGCGCTAAA | GGTCTACGTG | 2160 |
| CGGAAGCGGA | GGCCCAGCCG | CCCCCACATG | TTCCCCAAGA | TGCTAATGAA | GATTACTGAC | 2220 |
| CTGCGAAGCA | TCAGCGCCAA | GGGGGCTGAG | CGGGTGATCA | CGCTGAAGAT | GGAGATCCCG | 2280 |
| GGCTCCATGC | CGCCTCTCAT | CCAGGAAATG | TTGGAGAACT | CAGAGGGCCT | GGACACTCTG | 2340 |
| AGCGGACAGC | CGGGGGGTGG | GGGGCGGGAC | GGGGGTGGCC | TGGCCCCCCC | GCCAGGCAGC | 2400 |
| TGTAGCCCCA | GCCTCAGCCC | CAGCTCCAAC | AGAAGCAGCC | CGGCCACCCA | CTCCCCGTGA | 2460 |
| CCGCCCACGC | CACATGGACA | CAGCCCTCGC | CCTCCGCCCC | GGCTTTTCTC | TGCCTTTCTA | 2520 |
| CCGACCATGT | GACCCCGCAC | CAGCCCTGCC | CCCACCTGCC | CTCCCGGGCA | GTACTGGGGA | 2580 |

| | | | | | |
|---|---|---|---|---|---|
| CCTTCCCTGG | GGGACGGGGA | GGGAGGAGGC | AGCGACTCCT | TGGACAGAGG | CCTGGGCCCT | 2640
| CAGTGGACTG | CCTGCTCCCA | CAGCCTGGGC | TGACGTCAGA | GGCCGAGGCC | AGGAACTGAG | 2700
| TGAGGCCCCT | GGTCCTGGGT | CTCAGGATGG | GTCCTGGGGG | CCTCGTGTTC | ATCAAGACAC | 2760
| CCCTCTGCCC | AGCTCACCAC | ATCTTCATCA | CCAGCAAACG | CCAGGACTTG | GCTCCCCAT | 2820
| CCTCAGAACT | CACAAGCCAT | TGCTCCCCAG | CTGGGGAACC | TCAACCTCCC | CCCTGCCTCG | 2880
| GTTGGTGACA | GAGGGGGTGG | GACAGGGGCG | GGGGGTTCCC | CCTGTACATA | CCCTGCCATA | 2940
| CCAACCCCAG | GTATTAATTC | TCGCTGGTTT | TGTTTTTATT | TTAATTTTTT | TGTTTTGATT | 3000
| TTTTTAATAA | GAATTTTCAT | TTAAGCAAA | AAAAAA | | | 3036

(2) INFORMATION FOR SEQ ID NO:53:

( i ) SEQUENCE CHARACTERISTICS:
        ( A ) LENGTH: 4287 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

| | | | | | |
|---|---|---|---|---|---|
| CATAGAGCCA | GCGGGCGCGG | GCGGGACGGG | CGCCCCGCGG | CCGGACCCAG | CCAGGGCACC | 60
| ACGCTGCCCG | GCCCTGCGCC | GCCAGGCACT | TCTTTCCGGG | GCTCCTAGGG | ACGCCAGAAG | 120
| GAAGTCAACC | TCTGCTGCTT | CTCCTTGGCC | TGCGTTGGAC | CTTCCTTTTT | TTGTTGTTTT | 180
| TTTTTGTTTT | TCCCCTTTCT | TCCTTTTGAA | TTAACTGGCT | TCTTGGCTGG | ATGTTTTCAA | 240
| CTTCTTTCCT | GGCTGCGAAC | TTTTCCCCAA | TTGTTTTCCT | TTTACAACAG | GGGGAGAAAG | 300
| TGCTCTGTGG | TCCGAGGCGA | GCCGTGAAGT | TGCGTGTGCG | TGGCAGTGTG | CGTGGCAGGA | 360
| TGTGCGTGCG | TGTGTAACCC | GAGCCGCCCG | ATCTGTTTCG | ATCTGCGCCG | CGGAGCCCTC | 420
| CCTCAAGGCC | CGCTCCACCT | GCTGCGGTTA | CGCGGCGCTC | GTGGGTGTTC | GTGCCTCGGA | 480
| GCAGCTAACC | GGCGGGTGCT | GGGCGACGGT | GGAGGAGTAT | CGTCTCGCTG | CTGCCCGAGT | 540
| CAGGGCTGAG | TCACCCAGCT | GATGTAGACA | GTGGCTGCCT | TCCGAAGAGT | GCGTGTTTGC | 600
| ATGTGTGTGA | CTCTGCGGCT | GCTCAACTCC | CAACAAACCA | GAGGACCAGC | CACAAACTTA | 660
| ACCAACATCC | CCAAACCCGA | GTTCACAGAT | GTGGGAGAGC | TGTAGAACCC | TGAGTGTCAT | 720
| CGACTGGGCC | TTCTTATGAT | TGTTGTTTTA | AGATTAGCTG | AAGATCTCTG | AAACGCTGAA | 780
| TTTTCTGCAC | TGAGCGTTTT | GACAGAATTC | ATTGAGAGAA | CAGAGAACAT | GACAAGTACT | 840
| TCTAGCTCAG | CACTGCTCCA | ACTACTGAAG | CTGATTTTCA | AGGCTACTTA | AAAAAATCTG | 900
| CAGCGTACAT | TAATGGATTT | CTGTTGTGTT | TAAATTCTCC | ACAGATTGTA | TTGTAAATAT | 960
| TTTATGAAGT | AGAGCATATG | TATATATTTA | TATATACGTG | CACATACATT | AGTAGCACTA | 1020
| CCTTTGGAAG | TCTCAGCTCT | TGCTTTTCGG | GACTGAAGCC | AGTTTTGCAT | GATAAAGTG | 1080
| GCCTTGTTAC | GGGAGATAAT | TGTGTTCTGT | TGGGACTTTA | GACAAAACTC | ACCTGCAAAA | 1140
| AACTGACAGG | CATTAACTAC | TGGAACTTCC | AAATAATGTG | TTTGCTGATC | GTTTTACTCT | 1200
| TCGCATAAAT | ATTTTAGGAA | GTGTATGAGA | ATTTTGCCTT | CAGGAACTTT | TCTAACAGCC | 1260
| AAAGACAGAA | CTTAACCTCT | GCAAGCAAGA | TTCGTGGAAG | ATAGTCTCCA | CTTTTTAATG | 1320
| CACTAAGCAA | TCGGTTGCTA | GGAGCCCATC | CTGGGTCAGA | GGCCGATCCG | CAGAACCAGA | 1380
| ACGTTTTCCC | CTCCTGGACT | GTTAGTAACT | TAGTCTCCCT | CCTCCCCTAA | CCACCCCCGC | 1440
| CCCCCCCCAC | CCCCGCAGT | AATAAAGGCC | CCTGAACGTG | TATGTTGGTC | TCCCGGGAGC | 1500
| TGCTTGCTGA | AGATCCGCGC | CCCTGTCGCC | GTCTGGTAGG | AGCTGTTTGC | AGGGTCCTAA | 1560
| CTCAATCGGC | TTGTTGTGAT | GCGTATCCCC | GTAGATGCCA | GCACGAGCCG | CCGCTTCACG | 1620

```
CCGCCTTCCA CCGCGCTGAG CCCAGGCAAG ATGAGCGAGG CGTTGCCGCT GGGCGCCCCG    1680
GACGCCGGCG CTGCCCTGGC CGGCAAGCTG AGGAGCGGCG ACCGCAGCAT GGTGGAGGTG    1740
CTGGCCGACC ACCCGGGCGA GCTGGTGCGC ACCGACAGCC CCAACTTCCT CTGCTCCGTG    1800
CTGCCTACGC ACTGGCGCTG CAACAAGACC CTGCCCATCG CTTTCAAGGT GGTGGCCCTA    1860
GGGGATGTTC CAGATGGCAC TCTGGTCACT GTGATGGCTG GCAATGATGA AAACTACTCG    1920
GCTGAGCTGA GAAATGCTAC CGCAGCCATG AAGAACCAGG TTGCAAGATT TAATGACCTC    1980
AGGTTTGTCG GTCGAAGTGG AAGAGGGAAA AGCTTCACTC TGACCATCAC TGTCTTCACA    2040
AACCCACCGC AAGTCGCCAC CTACCACAGA GCCATCAAAA TCACAGTGGA TGGGCCCCGA    2100
GAACCTCGAA ATCGTACTGA AAGCACTCC ACAATGCCAG ACTCACCTGT GGATGTGAAG    2160
ACGCAATCTA GGCTGACTCC TCCAACAATG CCACCTCCCC CAACTACTCA AGGAGCTCCA    2220
AGAACCAGTT CATTTACACC GACAACGTTA ACTAATGGCA CGAGCCATTC TCCTACAGCC    2280
TTGAATGGCG CCCCCTCACC ACCCAATGGC TTCAGCAATG GGCCTTCCTC TTCTTCCTCC    2340
TCCTCTCTGG CTAATCAACA GCTGCCCCCA GCCTGTGGTG CCAGGCAACT CAGCAAGCTG    2400
AAAAGGTTCC TTACTACCCT GCAGCAGTTT GGCAATGACA TTTCACCCGA GATAGGAGAA    2460
AGAGTTCGCA CCCTCGTTCT GGGACTAGTG AACTCCACTT TGACAATTGA AGAATTTCAT    2520
TCCAAACTGC AAGAAGCTAC TAACTTCCCA CTGAGACCTT TTGTCATCCC ATTTTTGAAG    2580
GCCAACTTGC CCCTGCTGCA GCGTGAGCTC CTCCACTGCG CAAGACTGGC CAAACAGAAC    2640
CCTGCCCAGT ACCTCGCCCA GCATGAACAG CTGCTTCTGG ATGCCAGCAC CACCTCACCT    2700
GTTGACTCCT CAGAGCTGCT TCTCGATGTG AACGAAAACG GAAGAGGCG AACTCCAGAC    2760
AGAACCAAAG AAAATGGCTT TGACAGAGAG CCTTTGCACT CAGAACATCC AAGCAAGCGA    2820
CCATGCACTA TTAGCCCAGG CCAGCGGTAC AGTCCAAATA ACGGCTTATC CTACCAGCCC    2880
AATGGCCTGC CTCACCCTAC CCCACCTCCA CCTCAGCATT ACCGTTTGGA TGATATGGCC    2940
ATTGCCCACC ACTACAGGGA CTCCTATCGA CACCCCAGCC ACAGGGACCT CAGGGACAGA    3000
AACAGACCTA TGGGGTTGCA TGGCACACGT CAAGAAGAAA TGATTGATCA CAGACTAACA    3060
GACAGAGAAT GGGCAGAAGA GTGGAAACAT CTTGACCATC TGTTAAACTG CATAATGGAC    3120
ATGGTAGAAA AAACAAGGCG ATCTCTCACC GTACTAAGGC GGTGTCAAGA AGCAGACCGG    3180
GAAGAATTGA ATTACTGGAT CCGGCGGTAC AGTGACGCCG AGGACTTAAA AAAAGGTGGC    3240
GGCAGTAGCA GCAGCCACTC TAGGCAGCAG AGTCCCGTCA ACCCAGACCC AGTTGCACTA    3300
GACGCGCATC GGGAATTCCT TCACAGGCCT GCGTCTGGAT ACGTGCCAGA GGAGATCTGG    3360
AAGAAAGCTG AGGAGGCCGT CAATGAGGTG AAGCGCCAGG CGATGACGGA GCTGCAGAAG    3420
GCCGTGTCTG AGGCGGAGCG GAAAGCCCAC GACATGATCA ACAGAGAG GGCCAAGATG    3480
GAGCGCACGG TCGCCGAGGC CAAACGGCAG GCGGCGGAGG ACGCACTGGC AGTTATCAAT    3540
CAGCAGGAGG ATTCAAGCGA GAGTTGCTGG AATTGTGGCC GTAAAGCGAG TGAAACCTGC    3600
AGTGGCTGTA ACACAGCCCG ATACTGTGGC TCATTTTGCC AGCACAAAGA CTGGGAGAAG    3660
CACCATCACA TCTGTGGACA GACCCTGCAG GCCCAGCAGC AGGGAGACAC ACCTGCAGTC    3720
AGCTCCTCTG TCACGCCCAA CAGCGGGGCT GGGAGCCCGA TGGACACACC ACCAGCAGCC    3780
ACTCCGAGGT CAACCACCCC GGGAACCCCT TCCACCATAG ACAACCCC TCGCTAGACG    3840
TGAACTCAGA ACTGTCGGAG GAAAGACAAC ACAACCAACG CGAAACCAAT TCCTCATCCT    3900
CAGATGCTCA AAGTTGTTTT TTTGTTTGT TTGTTTATTA GATGAATTAT CCTATTTCAG    3960
TACTTCAGCA AGAGAGAACC TAACTGTATC TTGAGGTGGT AGTAAAACAC AGAGGGCCAG    4020
```

-continued

```
TAACGGGTCG TAATGACTTA TTGTGGATAA CAAAGATATC TTTTCTTTAG AGAACTGAAA    4080

AGAGAGCAGA GAATATAACA TGAAATGATA GATTTGACCT CCTCCCTGTT ATTTTCAAGT    4140

AGCTGGGATT TTAAACTAGA TGACCTCATT AACCGATGCT TTACCAAACA GCAAACCAAG    4200

AGATTGCTAA TTGCTGTTGA AAGCAAAAAT GCTAATATTA AAAGTCACAA TGTTCTTTAT    4260

ATACAATAAT GGAAAAAAAA AAAAAAA                                        4287
```

( 2 ) INFORMATION FOR SEQ ID NO:54:

( i ) SEQUENCE CHARACTERISTICS:
        ( A ) LENGTH: 2952 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:54:

```
ACGCGCCGCG TGCCCGGCCG CGCCCAGCAG GGTTTCCAGG CCTGAGGTGC CCGCCCTGGC      60

CCCAGGAGAA TGAACCAGCC GCAGAGGATG GCGCCTGTGG GCACAGACAA GGAGCTCAGT     120

GACCTCCTGG ACTTCAGCAT GATGTTCCCG CTGCCTGTCA CCAACGGGAA GGGCCGGCCC     180

GCCTCCCTGG CCGGGGCGCA GTTCGGAGGT TCAGGTCTTG AGGACCGGCC CAGCTCAGGC     240

TCCTGGGGCA GCGGCGACCA GAGCAGCTCC TCCTTTGACC CCAGCCGGAC CTTCAGCGAG     300

GGCACCCACT TCACTGAGTC GCACAGCAGC CTCTCTTCAT CCACATTCCT GGGACCGGGA     360

CTCGGAGGCA AGAGCGGTGA GCGGGGCGCC TATGCCTCCT TCGGGAGAGA CGCAGGCGTG     420

GGCGGCCTGA CTCAGGCTGG CTTCCTGTCA GGCGAGCTGG CCCTCAACAG CCCCGGGCCC     480

CTGTCCCCTT CGGGCATGAA GGGGACCTCC CAGTACTACC CCTCCTACTC CGGCAGCTCC     540

CGGCGGAGAG CGGCAGACGG CAGCCTAGAC ACGCAGCCCA AGAAGGTCCG GAAGGTCCCG     600

CCGGGTCTTC CATCCTCGGT GTACCCACCC AGCTCAGGTG AGGACTACGG CAGGGATGCC     660

ACCGCCTACC CGTCCGCCAA GACCCCCAGC AGCACCTATC CCGCCCCCTT CTACGTGGCA     720

GATGGCAGCC TGCACCCCTC AGCCGAGCTC TGGAGTCCCC CGGGCCAGGC GGGCTTCGGG     780

CCCATGCTGG GTGGGGGCTC ATCCCGCTG CCCCTCCCGC CGGTAGCGG CCCGGTGGGC     840

AGCAGTGGAA GCAGCAGCAC GTTTGGTGGC CTGCACCAGC ACGAGCGTAT GGGCTACCAG     900

CTGCATGGAG CAGAGGTGAA CGGTGGGCTC CCATCTGCAT CCTCCTTCTC CTCAGCCCCC     960

GGAGCCACGT ACGGCGGCGT CTCCAGCCAC ACGCCGCCTG TCAGCGGGGC CGACAGCCTC    1020

CTGGGCTCCC GAGGGACCAC AGCTGGCAGC TCCGGGGATG CCCTCGGCAA AGCACTGGCC    1080

TCGATCTACT CCCCGGATCA CTCAAGCAAT AACTTCTCGT CCAGCCCTTC TACCCCCGTG    1140

GGCTCCCCCC AGGGCCTGGC AGGAACGTCA CAGTGGCCTC GAGCAGGAGC CCCCGGTGCC    1200

TTATCGCCCA GCTACGACGG GGGTCTCCAC GGCCTGCAGA GTAAGATAGA AGACCACCTG    1260

GACGAGGCCA TCCACGTGCT CCGCAGCCAC GCCGTGGGCA CAGCGGCGA CATGCACACG    1320

CTGCTGCCTG CCACGGGGC GCTGGCCTCA GGTTTCACCG CCCCATGTC ACTGGGCGGG    1380

CGGCACGCAG GCCTGGTTGG AGGCAGCCAC CCCGAGGACG GCCTCGCAGG CAGCACCAGC    1440

CTCATGCACA ACCACGCGGC CCTCCCCAGC CAGCCAGGCA CCCTCCCTGA CCTGTCTCGG    1500

CCTCCCGACT CCTACAGTGG TTTTGAGTAT CCGAGGAGCC AGGAGGAGG AACCCACAGA    1560

CCCCCAGCTG ATGCGGCTGG ACAACATGCT GTTAGCGGAA GGCGTGGCGG GGCCTGAGAA    1620

GGGCGGAGGG TCGGCGGCAG CGGCGGCAGC GGCGGCGGCT TCTGGAGGGG CAGGTTCAGA    1680

CAACTCAGTG GAGCATTCAG ATTACAGAGC CAAACTCTCA CAGATCAGAC AAATCTACCA    1740
```

| | | | | | |
|---|---|---|---|---|---|
| TACGGAGCTG | GAGAAATACG | AGCAGGCCTG | CAACGAGTTC | ACCACCCACG | TGATGAATCT | 1800 |
| CCTGCGAGAC | GAAAGCCGGA | CCAGGCCCAT | CTCCCCAAAG | GAGATTGAGC | GGATGGTCAG | 1860 |
| CATCATCCAC | CGCAAGTTCA | GCTCCATCCA | GATGCAGCTC | AAGCAGAGCA | CGTGCGAGGC | 1920 |
| GGTGATGATC | CTGCGTTCCC | GATTTCTGGA | TGCGCGGCGG | AAGAGACGGA | ATTTCAACAA | 1980 |
| GCAAGCGACA | GAAATCCTGA | ATGAATATTT | CTATTCCCAT | CTCAGCAACC | CTTACCCCAG | 2040 |
| TGAGGAAGCC | AAAGAGGAGT | TAGCCAAGAA | GTGTGGCATC | ACAGTCTCCC | AGGTATCAAA | 2100 |
| CTGGTTTGGA | AATAAGCGAA | TCCGGTACAA | GAAGAACATA | GGTAAATTTC | AAGAGGAAGC | 2160 |
| CAATATTTAT | GCTGCCAAAA | CAGCTGTCAC | TGCTACCAAT | GTGTCAGCCC | ATGGAAGCCA | 2220 |
| AGCTAACTCG | CCCTCAACTC | CCAACTCGGC | TGGTTCTTCC | AGTTCTTTTA | ACATGTCAAA | 2280 |
| CTCTGGAGAT | TTGTTCATGA | GCGTGCAGTC | ACTCAATGGG | GATTCTTACC | AAGGGGCCCA | 2340 |
| GGTTGGAGCC | AACGTGCAAT | CACAGGTGGA | TACCCTTCGC | CATGTTATCA | GCCAGACAGG | 2400 |
| AGGATACAGT | GATGGACTCG | CAGCCAGTCA | GATGTACAGT | CCGCAGGGCA | TCAGTGCTAA | 2460 |
| TGGAGGTTGG | CAGGATGCTA | CTACCCCTTC | ATCAGTGACC | TCCCCTACAG | AAGGCCCTGG | 2520 |
| CAGTGTTCAC | TCTGATACCT | CCAACTGATC | TCCAGCAAT | CGCATCCGG | CTGACCCTCT | 2580 |
| GCCCCAGTTG | GGGCAGGGGC | AGGAGGGAGG | GTTTCTCTCC | CAAAGCTGAA | GCGGTCAGAC | 2640 |
| TGGAGGTCGA | AGCAATCAGC | AAACACAATA | AGAGTCTCCT | TCTCTTCTCT | TCTTTGGGAT | 2700 |
| GCTATTTCAG | CCAATCTGGA | CACTTCTTTA | TACTCTCTTC | CCTTTTTTTT | CTGGGTAGAA | 2760 |
| GCCACCCTTC | CCTGCCTCCA | GCTGTCAGCC | TGGTTTTCGT | CATCTTCCCT | GCCCCTGTGC | 2820 |
| CTCTGTCCTA | GACTTCCCGG | GGTCCCCGCC | CTCTCTCATA | TCACTGAAGG | ATATTTTCAA | 2880 |
| CAATTAGAGG | AATTTAAAGA | GGAAAAAAAT | TACAAAGAAA | ATAATAAAAG | TGTTTGTACG | 2940 |
| TTTTCAAAAA | AA | | | | | 2952 |

( 2 ) INFORMATION FOR SEQ ID NO:55:

( i ) SEQUENCE CHARACTERISTICS:
        ( A ) LENGTH: 14255 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

| | | | | | |
|---|---|---|---|---|---|
| GCGGCGGCGG | CGGCGGGAAG | CAGCGGGGCT | GGGGTTCCAG | GGGGAGCGGC | CGCCGCCTCA | 60 |
| GCAGCCTCCT | CGTCGTCCGC | CTCGTCTTCG | TCTTCGTCAT | CGTCCTCAGC | CTCTTCAGGG | 120 |
| CCGGCCCTGC | TCCGGGTGGG | CCCGGGCTTC | GACGCGGCGC | TGCAGGTCTC | GGCCGCCATC | 180 |
| GGCACCAACC | TGCGCCGGTT | CCGGGCCGTG | TTTGGGGAGA | GCGGCGGGGG | AGGCGGCAGC | 240 |
| GGAGAGGATG | AGCAATTCTT | AGGTTTTGGC | TCAGATGAAG | AAGTCAGAGT | GCGAAGTCCC | 300 |
| ACAAGGTCTC | CTTCAGTTAA | AACTAGTCCT | CGAAAACCTC | GTGGGAGACC | TAGAAGTGGC | 360 |
| TCTGACCGAA | ATTCAGCTAT | CCTCTCAGAT | CCATCTGTGT | TTTCCCCTCT | AAATAAATCA | 420 |
| GAGACCAAAT | CTGGAGATAA | GATCAAGAAG | AAAGATTCTA | AAGTATAGA | AAGAAGAGA | 480 |
| GGAAGACCTC | CCACCTTCCC | TGGAGTAAAA | ATCAAAATAA | CACATGGAAA | GGACATTTCA | 540 |
| GAGTTACCAA | AGGGAAACAA | AGAAGATAGC | CTGAAAAAAA | TTAAAGGAC | ACCTTCTGCT | 600 |
| ACGTTTCAGC | AAGCCACAAA | GATTAAAAAA | TTAAGAGCAG | GTAAACTCTC | TCCTCTCAAG | 660 |
| TCTAAGTTTA | AGACAGGGAA | GCTTCAAATA | GGAAGGAAGG | GGGTACAAAT | TGTACGACGG | 720 |
| AGAGGAAGGC | CTCCATCAAC | AGAAAGGATA | AAGACCCCTT | CGGGTCTCCT | CATTAATTCT | 780 |
| GAACTGGAAA | AGCCCCAGAA | AGTCCGGAAA | GACAAGGAAG | GAACACCTCC | ACTTACAAAA | 840 |

```
GAAGATAAGA CAGTTGTCAG ACAAAGCCCT CGAAGGATTA AGCCAGTTAG GATTATTCCT      900
TCTTCAAAAA GGACAGATGC AACCATTGCT AAGCAACTCT TACAGAGGGC AAAAAAGGGG      960
GCTCAAAAGA AAATTGAAAA AGAAGCAGCT CAGCTGCAGG GAAGAAAGGT GAAGACACAG     1020
GTCAAAAATA TTCGACAGTT CATCATGCCT GTTGTCAGTG CTATCTCCTC GCGGATCATT     1080
AAGACCCCTC GGCGGTTTAT AGAGGATGAG GATTATGACC CTCCAATTAA AATTGCCCGA     1140
TTAGAGTCTA CACCGAATAG TAGATTCAGT GCCCCGTCCT GTGGATCTTC TGAAAAATCA     1200
AGTGCAGCTT CTCAGCACTC CTCTCAAATG TCTTCAGACT CCTCTCGATC TAGTAGCCCC     1260
AGTGTTGATA CCTCCACAGA CTCTCAGGCT TCTGAGGAGA TTCAGGTACT TCCTGAGGAG     1320
CGGAGCGATA CCCCTGAAGT TCATCCTCCA CTGCCCATTT CCCAGTCCCC AGAAAATGAG     1380
AGTAATGATA GGAGAAGCAG AAGGTATTCA GTGTCGGAGA GAAGTTTTGG ATCTAGAACG     1440
ACGAAAAAAT TATCAACTCT ACAAAGTGCC CCCCAGCAGG AGACCTCCTC GTCTCCACCT     1500
CCACCTCTGC TGACTCCACC GCCACCACTG CAGCCAGCCT CCAGTATCTC TGACCACACA     1560
CCTTGGCTTA TGCCTCCAAC AATCCCCTTA GCATCACCAT TTTTGCCTGC TTCCACTGCT     1620
CCTATGCAAG GGAAGCGAAA ATCTATTTTG CGAGAACCGA CATTTAGGTG GACTTCTTTA     1680
AAGCATTCTA GGTCAGAGCC ACAATACTTT TCCTCAGCAA AGTATGCCAA AGAAGGTCTT     1740
ATTCGCAAAC CAATATTTGA TAATTTCCGA CCCCCTCCAC TAACTCCCGA GGACGTTGGC     1800
TTTGCATCTG GTTTTCTGC ATCTGGTACC GCTGCTTCAG CCCGATTGTT TTCGCCACTC      1860
CATTCTGGAA CAAGGTTTGA TATGCACAAA AGGAGCCCTC TTCTGAGAGC TCCAAGATTT     1920
ACTCCAAGTG AGGCTCACTC TAGAATATTT GAGTCTGTAA CCTTGCCTAG TAATCGAACT     1980
TCTGCTGGAA CATCTTCTTC AGGAGTATCC AATAGAAAAA GGAAAGAAA AGTGTTTAGT      2040
CCTATTCGAT CTGAACCAAG ATCTCCTTCT CACTCCATGA GGACAAGAAG TGGAAGGCTT     2100
AGTAGTTCTG AGCTCTCACC TCTCACCCCC CCGTCTTCTG TCTCTTCCTC GTTAAGCATT     2160
TCTGTTAGTC CTCTTGCCAC TAGTGCCTTA AACCCAACTT TTACTTTTCC TTCTCATTCC     2220
CTGACTCAGT CTGGGGAATC TGCAGAGAAA AATCAGAGAC CAAGGAAGCA GACTAGTGCT     2280
CCGGCAGAGC CATTTTCATC AAGTAGTCCT ACTCCTCTCT TCCCTTGGTT TACCCCAGGC     2340
TCTCAGACTG AAAGAGGGAG AAATAAAGAC AAGGCCCCCG AGGAGCTGTC CAAAGATCGA     2400
GATGCTGACA AGAGCGTGGA GAAGGACAAG AGTAGAGAGA GAGACCGGGA GAGAGAAAAG     2460
GAGAATAAGC GGGAGTCAAG GAAAGAGAAA AGGAAAAAGG GATCAGAAAT TCAGAGTAGT     2520
TCTGCTTTGT ATCCTGTGGG TAGGGTTTCC AAAGAGAAGG TTGTTGGTGA AGATGTTGCC     2580
ACTTCATCTT CTGCCAAAAA AGCAACAGGG CGGAAGAAGT CTTCATCACA TGATTCTGGG     2640
ACTGATATTA CTTCTGTGAC TCTTGGGGAT ACAACAGCTG TCAAAACCAA AATACTTATA     2700
AAGAAAGGGA GAGGAAATCT GGAAAAAACC AACTTGGACC TCGGCCCAAC TGCCCCATCC     2760
CTGGAGAAGG AGAAACCCT CTGCCTTTCC ACTCCTTCAT CTAGCACTGT TAAACATTCC      2820
ACTTCCTCCA TAGGCTCCAT GTTGGCTCAG GCAGACAAGC TTCCAATGAC TGACAAGAGG     2880
GTTGCCAGCC TCCTAAAAAA GGCCAAAGCT CAGCTCTGCA AGATTGAGAA GAGTAAGAGT     2940
CTTAAACAAA CCGACCAGCC CAAAGCACAG GGTCAAGAAA GTGACTCATC AGAGACCTCT     3000
GTGCGAGGAC CCCGGATTAA ACATGTCTGC AGAAGAGCAG CTGTTGCCCT TGGCCGAAAA     3060
CGAGCTGTGT TTCCTGATGA CATGCCCACC CTGAGTGCCT TACCATGGGA AGAACGAGAA     3120
AAGATTTTGT CTTCCATGGG GAATGATGAC AAGTCATCAA TTGCTGGCTC AGAAGATGCT     3180
GAACCTCTTG CTCCACCCAT CAAACCAATT AAACCTGTCA CTAGAAACAA GGCACCCCAG     3240
```

| | | | | | | |
|---|---|---|---|---|---|---|
| GAACCTCCAG | TAAAGAAAGG | ACGTCGATCG | AGGCGGTGTG | GGCAGTGTCC | CGGCTGCCAG | 3300 |
| GTGCCTGAGG | ACTGTGGTGT | TTGTACTAAT | TGCTTAGATA | AGCCCAAGTT | TGGTGGTCGC | 3360 |
| AATATAAAGA | AGCAGTGCTG | CAAGATGAGA | AAATGTCAGA | ATCTACAATG | GATGCCTTCC | 3420 |
| AAAGCCTACC | TGCAGAAGCA | AGCTAAAGCT | GTGAAAAAGA | AAGAGAAAAA | GTCTAAGACC | 3480 |
| AGTGAAAAGA | AAGACAGCAA | AGAGAGCAGT | GTTGTGAAGA | ACGTGGTGGA | CTCTAGTCAG | 3540 |
| AAACCTACCC | CATCAGCAAG | AGAGGATCCT | GCCCCAAAGA | AAAGCAGTAG | TGAGCCTCCT | 3600 |
| CCACGAAAGC | CCGTCGAGGA | AAAGAGTGAA | GAAGGGAATG | TCTCGGCCCC | TGGGCCTGAA | 3660 |
| TCCAAACAGG | CCACCACTCC | AGCTTCCAGG | AAGTCAAGCA | AGCAGGTCTC | CAGCCAGCA | 3720 |
| CTGGTCATCC | CGCCTCAGCC | ACCTACTACA | GGACCGCCAA | GAAAGAAGT | TCCCAAAACC | 3780 |
| ACTCCTAGTG | AGCCCAAGAA | AAAGCAGCCT | CCACCACCAG | AATCAGGTCC | AGAGCAGAGC | 3840 |
| AAACAGAAAA | AAGTGGCTCC | CCGCCCAAGT | ATCCCTGTAA | ACAAAAACC | AAAAGAAAAG | 3900 |
| GAAAAACCAC | CTCCGGTCAA | TAAGCAGGAG | AATGCAGGCA | CTTTGAACAT | CCTCAGCACT | 3960 |
| CTCTCCAATG | GCAATAGTTC | TAAGCAAAAA | ATTCCAGCAG | ATGGAGTCCA | CAGGATCAGA | 4020 |
| GTGGACTTTA | AGGAGGATTG | TGAAGCAGAA | AATGTGTGGG | AGATGGGAGG | CTTAGGAATC | 4080 |
| TTGACTTCTG | TTCCTATAAC | ACCCAGGGTG | GTTTGCTTTC | TCTGTGCCAG | TAGTGGGCAT | 4140 |
| GTAGAGTTTG | TGTATTGCCA | AGTCTGTTGT | GAGCCCTTCC | ACAAGTTTTG | TTTAGAGGAG | 4200 |
| AACGAGCGCC | CTCTGGAGGA | CCAGCTGGAA | AATTGGTGTT | GTCGTCGTTG | CAAATTCTGT | 4260 |
| CACGTTTGTG | GAAGGCAACA | TCAGGCTACA | AAGCAGCTGC | TGGAGTGTAA | TAAGTGCCGA | 4320 |
| AACAGCTATC | ACCCTGAGTG | CCTGGGACCA | AACTACCCA | CCAAACCCAC | AAAGAAGAAG | 4380 |
| AAAGTCTGGA | TCTGTACCAA | GTGTGTTCGC | TGTAAGAGCT | GTGGATCCAC | AACTCCAGGC | 4440 |
| AAAGGGTGGG | ATGCACAGTG | GTCTCATGAT | TTCTCACTGT | GTCATGATTG | CGCCAAGCTC | 4500 |
| TTTGCTAAAG | GAAACTTCTG | CCCTCTCTGT | GACAAATGTT | ATGATGATGA | TGACTATGAG | 4560 |
| AGTAAGATGA | TGCAATGTGG | AAAGTGTGAT | CGCTGGGTCC | ATTCCAAATG | TGAGAATCTT | 4620 |
| TCAGGTACAG | AAGATGAGAT | GTATGAGATT | CTATCTAATC | TGCCAGAAAG | TGTGGCCTAC | 4680 |
| ACTTGTGTGA | ACTGTACTGA | GCGGCACCCT | GCAGAGTGGC | GACTGGCCCT | TGAAAAAGAG | 4740 |
| CTGCAGATTT | CTCTGAAGCA | AGTTCTGACA | GCTTTGTTGA | ATTCTCGGAC | TACCAGCCAT | 4800 |
| TTGCTACGCT | ACCGGCAGGC | TGCCAAGCCT | CCAGACTTAA | ATCCCGAGAC | AGAGGAGAGT | 4860 |
| ATACCTTCCC | GCAGCTCCCC | CGAAGGACCT | GATCCACCAG | TTCTTACTGA | GGTCAGCAAA | 4920 |
| CAGGATGATC | AGCAGCCTTT | AGATCTAGAA | GGAGTCAAGA | GGAAGATGGA | CCAAGGGAAT | 4980 |
| TACACATCTG | TGTTGGAGTT | CAGTGATGAT | ATTGTGAAGA | TCATTCAAGC | AGCCATTAAT | 5040 |
| TCAGATGGAG | GACAGCCAGA | AATTAAAAAA | GCCAACAGCA | TGGTCAAGTC | CTTCTTCATT | 5100 |
| CGGCAAATGG | AACGTGTTTT | TCCATGGTTC | AGTGTCAAAA | AGTCCAGGTT | TTGGGAGCCA | 5160 |
| AATAAAGTAT | CAAGCAACAG | TGGGATGTTA | CCAAACGCAG | TGCTTCCACC | TTCACTTGAC | 5220 |
| CATAATTATG | CTCAGTGGCA | GGAGCGAGAG | GAAAACAGCC | ACACTGAGCA | GCCTCCTTTA | 5280 |
| ATGAAGAAAA | TCATTCCAGC | TCCCAAACCC | AAAGGTCCTG | GAGAACCAGA | CTCACCAACT | 5340 |
| CCTCTGCATC | CTCCTACACC | ACCAATTTTG | AGTACTGATA | GGAGTCGAGA | AGACAGTCCA | 5400 |
| GAGCTGAACC | CACCCCCAGG | CATAGAAGAC | AATAGACAGT | GTGCGTTATG | TTTGACTTAT | 5460 |
| GGTGATGACA | GTGCTAATGA | TGCTGGTCGT | TTACTATATA | TTGGCCAAAA | TGAGTGGACA | 5520 |
| CATGTAAATT | GTGCTTTGTG | GTCAGCGGAA | GTGTTTGAAG | ATGATGACGG | ATCACTAAAG | 5580 |
| AATGTGCATA | TGGCTGTGAT | CAGGGGCAAG | CAGCTGAGAT | GTGAATTCTG | CCAAAAGCCA | 5640 |

```
GGAGCCACCG TGGGTTGCTG TCTCACATCC TGCACCAGCA ACTATCACTT CATGTGTTCC     5700
CGAGCCAAGA ACTGTGTCTT TCTGGATGAT AAAAAAGTAT ATTGCCAACG ACATCGGGAT     5760
TTGATCAAAG GCGAAGTGGT TCCTGAGAAT GGATTTGAAG TTTTCAGAAG AGTGTTTGTG     5820
GACTTTGAAG GAATCAGCTT GAGAAGGAAG TTTCTCAATG GCTTGGAACC AGAAAATATC     5880
CACATGATGA TTGGGTCTAT GACAATCGAC TGCTTAGGAA TTCTAAATGA TCTCTCCGAC     5940
TGTGAAGATA AGCTCTTTCC TATTGGATAT CAGTGTTCCA GGGTATACTG GAGCACCACA     6000
GATGCTCGCA AGCGCTGTGT ATATACATGC AAGATAGTGG AGTGCCGTCC TCCAGTCGTA     6060
GAGCCGGATA TCAACAGCAC TGTTGAACAT GATGAAAACA GGACCATTGC CCATAGTCCA     6120
ACATCTTTTA CAGAAAGTTC ATCAAAAGAG AGTCAAAACA CAGCTGAAAT TATAAGTCCT     6180
CCATCACCAG ACCGACCTCC TCATTCACAA ACCTCTGGCT CCTGTTATTA TCATGTCATC     6240
TCAAAGGTCC CCAGGATTCG AACACCCAGT TATTCTCCAA CACAGAGATC CCCTGGCTGT     6300
CGACCGTTGC CTTCTGCAGG AAGTCCTACC CCAACCACTC ATGAAATAGT CACAGTAGGT     6360
GATCCTTTAC TCTCCTCTGG ACTTCGAAGC ATTGGCTCCA GGCGTCACAG TACCTCTTCC     6420
TTATCACCCC AGCGGTCCAA ACTCCGGATA ATGTCTCCAA TGAGAACTGG GAATACTTAC     6480
TCTAGGAATA ATGTTCCTC AGTCTCCACC ACCGGGACCG CTACTGATCT TGAATCAAGT      6540
GCCAAAGTAG TTGATCATGT CTTAGGGCCA CTGAATTCAA GTACTAGTTT AGGGCAAAAC     6600
ACTTCCACCT CTTCAAATTT GCAAAGGACA GTGGTTACTG TAGGCAATAA AAACAGTCAC     6660
TTGGATGGAT CTTCATCTTC AGAAATGAAG CAGTCCAGTG CTTCAGACTT GGTGTCCAAG     6720
AGCTCCTCTT TAAAGGGAGA GAAGACCAAA GTGCTGAGTT CCAAGAGCTC AGAGGGATCT     6780
GCACATAATG TGGCTTACCC TGGAATTCCT AAACTGGCCC CACAGGTTCA TAACACAACA     6840
TCTAGAGAAC TGAATGTTAG TAAAATCGGC TCCTTTGCTG AACCCTCTTC AGTGTCGTTT     6900
TCTTCTAAAG AGGCCCTCTC CTTCCCACAC CTCCATTTGA GAGGGCAAAG GAATGATCGA     6960
GACCAACACA CAGATTCTAC CCAATCAGCA AACTCCTCTC CAGATGAAGA TACTGAAGTC     7020
AAAACCTTGA AGCTATCTGG AATGAGCAAC AGATCATCCA TTATCAACGA ACATATGGGA     7080
TCTAGTTCCA GAGATAGGAG ACAGAAAGGG AAAAAATCCT GTAAAGAAAC TTTCAAAGAA     7140
AAGCATTCCA GTAAATCTTT TTTGGAACCT GGTCAGGTGA CAACTGGTGA GGAAGGAAAC     7200
TTGAAGCCAG AGTTTATGGA TGAGGTTTTG ACTCCTGAGT ATATGGGCCA ACGACCATGT     7260
AACAATGTTT CTTCTGATAA GATTGGTGAT AAAGGCCTTT CTATGCCAGG AGTCCCCAAA     7320
GCTCCACCCA TGCAAGTAGA AGGATCTGCC AAGGAATTAC AGGCACCACG GAAACGCACA     7380
GTCAAAGTGA CACTGACACC TCTAAAAATG GAAAATGAGA GTCAATCCAA AAATGCCCTG     7440
AAAGAAAGTA GTCCTGCTTC CCCTTTGCAA ATAGAGTCAA CATCTCCCAC AGAACCAATT     7500
TCAGCCTCTG AAAATCCAGG AGATGGTCCA GTGGCCCAAC CAAGCCCCAA TAATACCTCA     7560
TGCCAGGATT CTCAAAGTAA CAACTATCAG AATCTTCCAG TACAGGACAG AAACCTAATG     7620
CTTCCAGATG GCCCCAAACC TCAGGAGGAT GGCTCTTTTA AAGGAGGTA TCCCCGTCGC      7680
AGTGCCCGTG CACGTTCTAA CATGTTTTTT GGGCTTACCC CACTCTATGG AGTAAGATCC     7740
TATGGTGAAG AAGACATTCC ATTCTACAGC AGCTCAACTG GAAGAAGCG AGGCAAGAGA      7800
TCAGCTGAAG GACAGGTGGA TGGGGCCGAT GACTTAAGCA CTTCAGATGA AGACGACTTA     7860
TACTATTACA ACTTCACTAG AACAGTGATT TCTTCAGGTG GAGAGGAACG ACTGGCATCC     7920
CATAATTTAT TTCGGGAGGA GGAACAGTGT GATCTTCCAA AAATCTCACA GTTGGATGGT     7980
GTTGATGATG GGACAGAGAG TGATACTAGT GTCACAGCCA CAACAAGGAA AAGCAGCCAG     8040
```

```
ATTCCAAAAA GAAATGGTAA AGAAAATGGA ACAGAGAACT TAAAGATTGA TAGACCTGAA      8100
GATGCTGGGG AGAAAGAACA TGTCACTAAG AGTTCTGTTG GCCACAAAAA TGAGCCAAAG      8160
ATGGATAACT GCCATTCTGT AAGCAGAGTT AAAACACAGG GACAAGATTC CTTGGAAGCT      8220
CAGCTCAGCT CATTGGAGTC AAGCCGCAGA GTCCACACAA GTACCCCTC CGACAAAAAT       8280
TTACTGGACA CCTATAATAC TGAGCTCCTG AAATCAGATT CAGACAATAA CAACAGTGAT      8340
GACTGTGGGA ATATCCTGCC TTCAGACATT ATGGACTTTG TACTAAAGAA TACTCCATCC      8400
ATGCAGGCTT TGGGTGAGAG CCCAGAGTCA TCTTCATCAG AACTCCTGAA TCTTGGTGAA      8460
GGATTGGGTC TTGACAGTAA TCGTGAAAAA GACATGGGTC TTTTTGAAGT ATTTTCTCAG      8520
CAGCTGCCTA CAACAGAACC TGTGGATAGT AGTGTCTCTT CCTCTATCTC AGCAGAGGAA      8580
CAGTTTGAGT TGCCTCTAGA GCTACCATCT GATCTGTCTG TCTTGACCAC CCGGAGTCCC     8640
ACTGTCCCCA GCCAGAATCC CAGTAGACTA GCTGTTATCT CAGACTCAGG GGAGAAGAGA      8700
GTAACCATCA CAGAAAAATC TGTAGCCTCC TCTGAAAGTG ACCCAGCACT GCTGAGCCCA      8760
GGAGTAGATC CAACTCCTGA AGGCCACATG ACTCCTGATC ATTTTATCCA AGGACACATG      8820
GATGCAGACC ACATCTCTAG CCCTCCTTGT GGTTCAGTAG AGCAAGGTCA TGGCAACAAT      8880
CAGGATTTAA CTAGGAACAG TAGCACCCCT GGCCTTCAGG TACCTGTTTC CCCAACTGTT      8940
CCCATCCAGA ACCAGAAGTA TGTGCCCAAT TCTACTGATA GTCCTGGCCC GTCTCAGATT      9000
TCCAATGCAG CTGTCCAGAC CACTCCACCC CACCTGAAGC CAGCCACTGA GAAACTCATA      9060
GTTGTTAACC AGAACATGCA GCCACTTTAT GTTCTCCAAA CTCTTCCAAA TGGAGTGACC      9120
CAAAAAATCC AATTGACCTC TTCTGTTAGT CTACACCCA GTGTGATGGA GACAAATACT       9180
TCAGTATTGG GACCCATGGG AGGTGGTCTC ACCCTTACCA CAGGACTAAA TCCAAGCTTG      9240
CCAACTTCTC AATCTTTGTT CCCTTCTGCT AGCAAAGGAT TGCTACCCAT GTCTCATCAC      9300
CAGCACTTAC ATTCCTTCCC TGCAGCTACT CAAAGTAGTT TCCCACCAAA CATCAGCAAT      9360
CCTCCTTCAG GCCTGCTTAT TGGGGTTCAG CCTCCTCCGG ATCCCAACT TTTGGTTTCA       9420
GAATCCAGCC AGAGGACAGA CCTCAGTACC ACAGTAGCCA CTCCATCCTC TGGACTCAAG      9480
AAAAGACCCA TATCTCGTCT ACAGACCCGA AAGAATAAAA AACTTGCTCC CTCTAGTACC      9540
CCTTCAAACA TTGCCCCTTC TGATGTGGTT CTAATATGA CATTGATTAA CTTCACACCC       9600
TCCCAGCTTC CTAATCATCC AAGTCTGTTA GATTGGGGT CACTTAATAC TTCATCTCAC       9660
CGAACTGTCC CCAACATCAT AAAAAGATCT AAATCTAGCA TCATGTATTT TGAACCGGCA      9720
CCCCTGTTAC CACAGAGTGT GGGAGGAACT GCTGCCACAG CGGCAGGCAC ATCAACAATA      9780
AGCCAGGATA CTAGCCACCT CACATCAGGG TCTGTGTCTG GCTTGGCATC CAGTTCCTCT      9840
GTCTTGAATG TTGTATCCAT GCAAACTACC ACAACCCCTA CAAGTAGTGC GTCAGTTCCA      9900
GGACACGTCA CCTTAACCAA CCCAAGGTTG CTTGGTACCC CAGATATTGG CTCAATAAGC      9960
AATCTTTTAA TCAAAGCTAG CCAGCAGAGC CTGGGGATTC AGGACCAGCC TGTGGCTTTA     10020
CCGCCAAGTT CAGGAATGTT TCCACAACTG GGACATCAC AGACCCCCTC TACTGCTGCA      10080
ATAACAGCGG CATCTAGCAT CTGTGTGCTC CCCTCCACTC AGACTACGGG CATAACAGCC     10140
GCTTCACCTT CTGGGGAAGC AGACGAACAC TATCAGCTTC AGCATGTGAA CCAGCTCCTT     10200
GCCAGCAAAA CTGGGATTCA TTCTTCCCAG CGTGATCTTG ATTCTGCTTC AGGGCCCCAG     10260
GTATCCAACT TTACCCAGAC GGTAGACGCT CCTAATAGCA TGGGACTGGA GCAGAACAAG     10320
GCTTTATCCT CAGCTGTGCA AGCCAGCCCC ACCTCTCCTG GGGTTCTCC ATCCTCTCCA      10380
TCTTCTGGAC AGCGGTCAGC AAGCCCTTCA GTGCCGGGTC CCACTAAACC CAAACCAAAA     10440
```

```
ACCAAACGGT TTCAGCTGCC TCTAGACAAA GGGAATGGCA AGAAGCACAA TGTTTCCCAT    10500
TTGCGGACCA GTTCTTCTGA AGCACACATT CCAGACCAAG AAACGACATC CCTGACCTCA    10560
GGCACAGGGA CTCCAGGAGC AGAGGCTGAG CAGCAGGATA CAGCTAGCGT GGAGCAGTCC    10620
TCCCAGAAGG AGTGTGGGCA ACCTGCAGGG CAAGTCGCTG TTCTTCCGGA AGTTCAGGTG    10680
ACCCAAAATC CAGCAAATGA ACAAGAAAGT GCAGAACCTA AAACAGTGGA AGAAGAGGAA    10740
AGTAATTTCA GCTCCCCACT GATGCTTTGG CTTCAGCAAG AACAAAAGCG AAGGAAAGC    10800
ATTACTGAGA AAAAACCCAA GAAAGGACTT GTTTTTGAAA TTTCCAGTGA TGATGGCTTT    10860
CAGATCTGTG CAGAAAGTAT TGAAGATGCC TGGAAGTCAT TGACAGATAA AGTCCAGGAA    10920
GCTCGATCAA ATGCCCGCCT AAAGCAGCTC TCATTTGCAG GTGTTAACGG TTTGAGGATG    10980
CTGGGGATTC TCCATGATGC AGTTGTGTTC CTCATTGAGC AGCTGTCTGG TGCCAAGCAC    11040
TGTCGAAATT ACAAATTCCG TTTCCACAAG CCAGAGGAGG CCAATGAACC CCCCTTGAAC    11100
CCTCACGGCT CAGCCAGGGC TGAAGTCCAC CTCAGGAAGT CAGCATTTGA CATGTTTAAC    11160
TTCCTGGCTT CTAAACATCG TCAGCCTCCT GAATACAACC CAATGATGA AGAAGAGGAG    11220
GAGGTACAGC TGAAGTCAGC TCGGAGGGCA ACTAGCATGG ATCTGCCAAT GCCCATGCGC    11280
TTCCGGCACT TAAAAAGAC TTCTAAGGAG GCAGTTGGTG TCTACAGGTC TCCCATCCAT    11340
GGCCGGGGTC TTTTCTGTAA GAGAAACATT GATGCAGGTG AGATGGTGAT TGAGTATGCC    11400
GGCAACGTCA TCCGCTCCAT CCAGACTGAC AAGCGGGAAA AGTATTACGA CAGCAAGGGC    11460
ATTGGTTGCT ATATGTTCCG AATTGATGAC TCAGAGGTAG TGGATGCCAC CATGCATGGA    11520
AATGCTGCAC GCTTCATCAA TCACTCGTGT GAGCCTAACT GCTATTCTCG GGTCATCAAT    11580
ATTGATGGGC AGAAGCACAT TGTCATCTTT GCCATGCGTA AGATCTACCG AGGAGAGGAA    11640
CTCACTTACG ACTATAAGTT CCCCATTGAG GATGCCAGCA ACAAGCTGCC CTGCAACTGT    11700
GGCGCCAAGA AATGCCGGAA GTTCCTAAAC TAAAGCTGCT CTTCTCCCCC AGTGTTGGAG    11760
TGCAAGGAGG CGGGGCCATC CAAAGCAACG CTGAAGGCCT TTTCCAGCAG CTGGGAGCTC    11820
CCGGATTGCG TGGCACAGCT GAGGGGCCTC TGTGATGGCT GAGCTCTCTT ATGTCCTATA    11880
CTCACATCAG ACATGTGATC ATAGTCCCAG AGACAGAGTT GAGGTCTCGA AGAAAAGATC    11940
CATGATCGGC TTTCTCCTGG GGCCCCTCCA ATTGTTTACT GTTAGAAAGT GGGAATGGGG    12000
TCCCTAGCAG ACTTGCCTGG AAGGAGCCTA TTATAGAGGG TTGGTTATGT TGGGAGATTG    12060
GGCCTGAATT TCTCCACAGA AATAAGTTGC CATCCTCAGG TTGGCCCTTT CCCAAGCACT    12120
GTAAGTGAGT GGGTCAGCCA AAGCCCCAAA TGGAGGGTTG GTTAGATTCC TGACAGTTTG    12180
CCAGCCAGCC GCCACCTACA GCGTCTGTCG AACAAACAGA GGTCTGGTGG TTTTCCCTAC    12240
TGTCCTCCCA CTCGAGAGTT CACTTCTGGT TGGGAGACAG GATTCCTAGC ACCTCCGGTG    12300
TCAAAAGGCT GTCATGGGGT TGTGCCAATT AATTACCAAA CATTGAGCCT GCAGGCTTTG    12360
AGTGGGAGTG TTGCCCCCAG GAGCCTTATC TCAGCCAATT ACCTTCTTG ACAGTAGGAG    12420
CGGCTTCCCT CTCCCATTCC CTCTTCACTC CCTTTTCTTC CTTTCCCCTG TCTTCATGCC    12480
ACTGCTTTCC CATGCTTCTT TCGGTTGTAG GGGAGACTGA CTGCCTGCTC AAGGACACTC    12540
CCTGCTGGGC ATAGGATGTG CCTGCAAAAA GTTCCCTGAG CCTGTAAGCA CTCCAGGTGG    12600
GGAAGTGGAC AGGAGCCATT GGTCATAACC AGACAGAATT TGGAAACATT TTCATAAAGC    12660
TCCATGGAGA GTTTTAAAGA AACATATGTA GCATGATTTT GTAGGAGAGG AAAAAGATTA    12720
TTTAAATAGG ATTTAAATCA TGCAACAACG AGAGTATCAC AGCCAGGATG ACCCTTGGGT    12780
CCCATTCCTA AGACATGGTT ACTTTATTTT CCCCTTGTTA AGACATAGGA AGACTTAATT    12840
```

| | | | | | | |
|---|---|---|---|---|---|---|
| TTTAAACGGT | CAGTGTCCAG | TTGAAGGCAG | AACACTAATC | AGATTTCAAG | GCCCACAACT | 12900 |
| TGGGGACTAG | ACCACCTTAT | GTTGAGGGAA | CTCTGCCACC | TGCGTGCAAC | CCACAGCTAA | 12960 |
| AGTAAATTCA | ATGACACTAC | TGCCCTGATT | ACTCCTTAGG | ATGTGGTCAA | AACAGCATCA | 13020 |
| AATGTTTCTT | CTCTTCCTTT | CCCCAAGACA | GAGTCCTGAA | CCTGTTAAAT | TAAGTCATTG | 13080 |
| GATTTACTC | TGTTCTGTTT | ACAGTTTACT | ATTTAAGGTT | TTATAAATGT | AAATATATTT | 13140 |
| TGTATATTTT | TCTATGAGAA | GCACTTCATA | GGGAGAAGCA | CTTATGACAA | GGCTATTTTT | 13200 |
| TAAACCGCGG | TATTATCCTA | ATTTAAAAGA | AGATCGGTTT | TTAATAATTT | TTTATTTTCA | 13260 |
| TAGGATGAAG | TTAGAGAAAA | TATTCAGCTG | TACACACAAA | GTCTGGTTTT | TCCTGCCCAA | 13320 |
| CTTCCCCCTG | GAAGGTGTAC | TTTTTGTTGT | TTAATGTGTA | GCTTGTTTGT | GCCCTGTTGA | 13380 |
| CATAAATGTT | TCCTGGGTTT | GCTCTTTGAC | AATAAATGGA | GAAGGAAGGT | CACCCAACTC | 13440 |
| CATTGGGCCA | CTCCCCTCCT | TCCCTATTG | AAGCTCCTCA | AAAGGCTACA | GTAATATCTT | 13500 |
| GATACAACAG | ATTCTCTTCT | TTCCCGCCTC | TCTCCTTTCC | GGCGCAACTT | CCAGAGTGGT | 13560 |
| GGGAGACGGC | AATCTTTACA | TTTCCCTCAT | CTTTCTTACT | TCAGAGTTAG | CAAACAACAA | 13620 |
| GTTGAATGGC | AACTTGACAT | TTTTGCATCA | CCATCTGCCT | CATAGGCCAC | TCTTTCCTTT | 13680 |
| CCCTCTGCCC | ACCAAGTCCT | CATATCTGCA | GAGAACCCAT | TGATCACCTT | GTGCCCTCTT | 13740 |
| TTGGGGCAGC | CTGTTGAAAC | TGAAGCACAG | TCTGACCACT | CACGATAAAG | CAGATTTTCT | 13800 |
| CTGCCTCTGC | CACAAGGTTT | CAGAGTAGTG | TAGTCCAAGT | AGAGGGTGGG | GCACCCTTTT | 13860 |
| CTCGCCGCAA | GAAGCCCATT | CCTATGGAAG | TCTAGCAAAG | CAATACGACT | CAGCCCAGCA | 13920 |
| CTCTCTGCCC | CAGGACTCAT | GGCTCTGCTG | TGCCTTCCAT | CCTGGGCTCC | CTTCTCTCCT | 13980 |
| GTGACCTTAA | GAACTTTGTC | TGGTGGCTTT | GCTGGAACAT | TGTCACTGTT | TTCACTGTCA | 14040 |
| TGCAGGGAGC | CCAGCACTGT | GGCCAGGATG | GCAGAGACTT | CCTTGTCATC | ATGGAGAAGT | 14100 |
| GCCAGCAGGG | GACTGGGAAA | AGCACTCTAC | CCAGACCTCA | CCTCCCTTCC | TCCTTTTGCC | 14160 |
| CATGAACAAG | ATGCAGTGGC | CCTAGGGGTT | CCACTAGTGT | CTGCTTTCCT | TTATTATTGC | 14220 |
| ACTGTGTGAG | GTTTTTTTGT | AAATCCTTGT | ATTCC | | | 14255 |

ANTISENSE OLIGONUCLEOTIDES TARGETING COOPERATING ONCOGENES

REFERENCE TO GOVERNMENT GRANT

The invention described herein was supported in part by National Institutes of Health grant CA 56309. The United States Government has certain rights in the invention.

FIELD OF THE INVENTION

The invention relates to antisense oligonucleotides, in particular to antisense oligonucleotides to oncogenes, and the use of such oligonucleotides to inhibit proliferation of neoplastic cells.

BACKGROUND OF THE INVENTION

Proto-oncogenes are normal cellular genes the alteration of which engenders a transforming allele or "oncogene" Damage to one or more proto-oncogenes has with some consistency been found in a variety of human malignancies, causing changes in gene expression or in the gene product itself. Some of the more consistent correlations between disease occurrence and alterations in proto-oncogene expression or gene product include the following. The list is representative, not exhaustive.

| Proto-Oncogenes and Human Tumors | | |
|---|---|---|
| Proto-Oncogene | Neoplasm(s) | Lesion |
| abl | Chronic myelogenous leukemia; lymphoma | Translocation |
| erbB-1 | Squamous cell and lung carcinoma; astrocytoma; glioblastoma; leukemia | Amplification |
| erbB-2 | Adenocarcinoma of breast, ovary and stomach | Amplification |
| fos | osteoblastoma | Overexpression |
| gip | Carcinoma of ovary and adrenal gland | Point mutations |
| gsp | Adenoma of pituitary gland; carcinoma of thyroid | Point mutations |
| kit | leukemia and lymphoma | |
| myc | Burkitt's lymphoma; leukemia; carcinoma of lung, breast and cervix; myeloma; neuropithelioma | Translocation Amplification |
| myb | leukemia, lymphoma, melanoma, colorectal carcinoma; neuroectodermal tumors | |
| L-myc | Carcinoma of lung | Amplification |
| N-myc | Neuroectodermal tumors (neuroblastoma and neuroepithelioma); small cell carcinoma of lung | Amplification |
| neu | breast and ovarian carcinoma | Amplification |
| H-ras and/or K-ras | Carcinoma of colon, lung, prostate, bladder, breast, thyroid and pancreas; melanoma; acute myelogenous and lymphoblastic leukemia; carcinoma of thyroid | point mutations |
| N-ras | Carcinoma of genitourinary tract and thyroid; melanoma; leukemia | Point mutations |
| ret | Carcinoma of thyroid | Rearrangement |
| ros | Astrocytoma | ? |
| K-sam | Carcinoma of stomach | Amplification |
| sis | Astrocytoma | ? |
| src | Carcinoma of colon | ? |
| trk | Carcinoma of thyroid | Rearrangement |

As may be appreciated from the above table, a large number and variety of human tumors contain consistent point mutations in ras proto-oncogenes. Chromosomal translocations also contribute to tumorigenesis by activating proto-oncogenes to oncogenes, e.g., the translocation of c-abl to the BCR locus to form the hybrid oncogene bcr-abl which has been correlated with the occurrence of Philadelphia chromosome-positive leukemias. Other tumors carry abnormally amplified domains of DNA that can include proto-oncogenes and magnify their expression (Alitalo & Schwab, Adv. Cancer Res. 47, 235–282, 1986). The potential of proto-oncogenes to participate in tumorigenesis arises from the fact that their protein products are relays in the biochemical circuitry that governs the phenotype of vertebrate cells (Bishop, Cell 64, 235–248, 1991).

The three biochemical mechanisms by which proto-oncogenes act were recently reviewed by Bishop, id. The first mechanism is by phosphorylation of proteins at serine, threonine or tyrosine residues. The immediate role of the proto-oncogene product may be induction of the phosphorylation (as with some growth factors) or catalysis itself (as with the receptors for some growth factors). The second mechanism of proto-oncogene action is transmission of signals by GTPases (Bourne et al., Nature, 348, 125–131, 1990. The ras family of oncogenes encode a variety of GTPase. Moreover, at least some heterotrimeric G proteins can also transform cells when suitably mutant in their α subunits. The corresponding proto-oncogenes are known as gsp (stimulatory G proteins) and gip (inhibitory G proteins). The third mechanism of proto-oncogene action consists of control of transcription from DNA. A variety of transcription factors, discussed below, are encoded by proto-oncogenes.

Oncogenes/proto-oncogenes are broadly subdivided into two major groups: nuclear and cytoplasmic. This distinction is of course based upon the cellular location of the encoded proteins and/or their place of action, but has also acquired a broader meaning in relationship to the model of tumorigenic conversion of primary embryo fibroblasts that is based on the cooperation between the cytoplasmic oncogene c-ras and the nuclear oncogene c-myc (Land et al., Nature 304, 602–606, 1983).

The proto-oncogenes which encode proteins localized in the nucleus participate in the regulation of the proliferation of mammalian cells. They are believed to be directly involved in the regulation of gene expression that leads to cell proliferation, division, and differentiation. Many of these proteins are able to bind DNA. Studies have shown that transient expression of nuclear protein-encoding proto-oncogenes is required for cells to traverse specific points in the cell cycle.

Nuclear proto-oncogenes which comprise transcription factors include, for example, erbA, evi-1, gli-1, maf, lyl-1, ets-1, ets-2, fos, jun, myb, myc, rel, vav, ski, and spi-1. The indicated genes may in some cases comprise a group of variants identified under a common name. For example, the jun family includes at least three distinct genes—c-jun, c-jun-B and c-jun-D. Antisense oligonucleotides hybridizable to the relevant mRNA may be prepared, based upon reported cDNA sequences. The following is a partial listing of references reporting DNAs for the indicated proto-oncogenes and/or reports of inhibition of cell proliferation with antisense oligonucleotides specific for the targeted genes:

- c-myc—Gazin et al., *EMBO J.* 3:383–387, 1984 (cDNA); Wickstrom et al., *Proc. Natl. Acad. Sci. USA* 85, 1028–1032 (1988); Loke et al., *Clin. Res.* 36(3), 443A (1988); Holt et al., *Cell. Biol.* 8, 963–973 (1988); Yokoyama et al., *Proc. Natl. Acad. Sci. USA* 84, 7363–7367 (1987); Harel-Bellan et al., *J. Immunol.* 140, 2431–2435 (1988) (inhibition of growth of leukemic cells by antisense oligonucleotides);

- L-myc—Kaye et al., *Mol. Cel.Biol.* 8:186–195, 1988 (cDNA);

- N-myc—Ibson & Rabbitts, *Oncogene* 2:399–402, 1988 (cDNA);

- c-jun—Hattori et al., *Proc. Natl. Acad. Sci. USA* 85:9148–9152, 1988 (cDNA);

- c-fos—van Straaten et al., Proc. Natl. Acad. Sci. USA 80:3183–3187, 1983 (cDNA); Nercola et al., *Biochem. Biophys. Res. Comm.* 147, 288–294 (1987); Groger et al., *Proc. Am. Assoc. Caner Res.* 29, 439 (1988) (inhibition of growth of transformed cells by antisense oligonucleotide);

- c-myb—Majello et al., *Proc. Natl. Acad. Sci. USA* 83:9636–9640, 1986 (cDNA);

- B-myb—Nomura et al., *Nucl. Acid Res.* 16:11075–11090, 1988 (cDNA);

- cyclin D1 (also known as bcl-1)—Xiong et al., Cell 65. 601–699, 1991 (cDNA).

The following is a partial listing of nuclear oncogenes, formed by translocation events. Each citation reports the relevant cDNA sequence. The oncogenes are established or purported transcriptional factors.

PML/RARα—Kakizura et al., *Cell*, 66:663–674, 1991;

DEK/CAN—von Linden et al., *Mol. Cell. Biol.*, 12: 1687–1697, 1992;

AML1/MTG8—Miyoshi et al., *EMBO J.* 12:2715–2721, 1993;

E2A/prl—Nouse et al., *Cell*, 60: 535–545, 1990; Kamps et al., *Cell*, 60: 547–555 1990;

ALL-1/AF-4—Gu et al., *Cell* 71: 701–708, 1992.

Nucleotide sequences of various other oncogenes/-proto-oncogenes are disclosed in International Patent Application WO 94/00473, the entire disclosure of which is incorporated herein by reference.

Certain of the nuclear oncogenes/proto-oncogenes code for proteins with DNA-binding activity. The nuclear proto-oncogenes comprising the jun family (c-jun, jun-B and jun-D), c-myb, the proto-oncogenes comprising the c-ets family (c-ets-1 and c-ets-2), and c-myc, recognize specific nucleotide core sequences.

The proto-oncogene c-jun, which encodes the transcription activator protein AP-1, has been shown to bind to a specific heptameric consensus sequence TGACTCA (Bohmann et al., *Science* 238, 1386–1392, 1987; Angel et al., *Nature* 332, 166–1711, 1988). Jun-B has extensive amino acid sequence similarity to c-jun in the region that encodes the DNA-binding domain and, as expected, binds to the same DNA consensus sequence (Nakageppu et al., *Cell* 5, 907–915, 1988); jun-D, the third number of this family, behaves similarly (Nakageppu et al., 1988). The proteins encoded by c-ets-1 and c-ets-2 genes bind to a 14-base pair sequence from the oncogene-responsive domain of the polyoma enhancer, in which the ACTTCCT appears to be the essential portion of the domain (Wasylyk et al., *Nature* 346,191–193, 1990). The DNA-binding activity also appears to be localized at the carboxy-terminal region of the c-ets-encoded protein (Wasylyk et al., 1990).

c-Myb encodes a protein that binds to a specific core sequence (pyAACG/TG) (Biedenkapp et al., *Nature* bv3351, 835–837, 1988). The DNA-binding activity of c-myb, unlike that of the c-jun and c-ets gene families, is localized in the amino-terminal portion of the protein (Klempnauer and Sippel, 1987). The c-fos product has been shown to bind nonspecifically to DNA (Renz et al., *Nucleic Acid Res.* 15, 277–292, 1987); however, when complexed to c-jun encoded proteins, the c-fos product has a marked stimulatory effect on their binding to AP-1 sites (Chiu et al., *Cell* 59, 979–986, 1988; Halazonetis et al., *Cell* 55, 917–924, 1988). The human c-myc protein is a DNA-binding protein exhibiting a high nonspecific activity for double-stranded DNA (Persson et al., *Science* 225, 718–721, 1984; Watt et al., *Mol. Cell. Biol.* 5, 448–456, 1985). Recently, it has been shown that a purified carboxyl terminal fragment of human c-myc binds in vitro in a sequence-specific manner to the sequence CACGTG (Blackwell et al., *Science* 250, 1149–1151, 1990).

c-Myb up-regulates the expression of reporter genes linked to myb-binding sites (Weston and Bishop, *Cell* 58, 85–93, 1989; Sakura et al., *Proc. Natl. Acad. Sci. U.S.A.* 86, 5758–5762, 1989) and the cellular gene MIM-1, whose expression is promyelocytic-specific, appears to be directly regulated by c-myb and contains myb-binding sites in the 5' flanking region (Ness et al., *Cell* 59, 1115–1125, 1989). The MYB protein binds to DNA by virtue of an N-terminal region that contains a triple repeat.

The CD34 antigen defines a subset of hematopoietic progenitor cells with self-renewal capacity and the ability to reconstitute hematopoiesis in irradiated primates and marrow-ablated humans. The c-myb gene plays a fundamental role in hematopoiesis, most likely through its transcriptional regulator function. The MYB protein transactivates the CD34 promotor via specific interaction with multiple MYB binding sites in the 5' flanking region of the CD34 antigen gene and induces expression of the endogenous CD34 mRNA in rodent fibroblasts, directly demonstrating that c-myb regulates the expression of the CD34 antigen (Melotti o et al., *J. Exp. Med.* 179, 1023–1028, 1994).

It has been suggested that c-ets-1 and c-ets-2 transactivate the expression of reporter genes linked to c-ets binding sites; the c-ets binding domain is contiguous with the AP-1 binding site in the polyoma (Py) enhancer; this association generates a responsive element that is highly stimulated by the concomitant expression of c-jun and c-ets (Wasylyk et al., 1990). The c-rel gene is also a regulator of transcription.

ErbA is another nuclear oncogene whose protein product binds nucleic acid. It codes for a thyroid hormone receptor, a member of the class of steroid hormone receptors. Upon binding its ligand, asteroid receptor activates expression of particular target genes by binding to its specific response element in a promotor or enhancer. These receptors, such as erbA, are therefore transcription factors that respond to binding particular ligands.

Cytoplasmic oncogenes/proto-oncogenes include members of the ras and raf families of oncogenes, as well as various protein kinase types, most notably the protein tyrosine kinases.

The ras gene family members are found expressed in human cancers more often than any other oncogene. Three ras genes have been characterized, designated c-H-ras, c-K-ras and c-N-ras. The three genes all encode proteins of 21,000 daltons molecular weight generally known as p21$^{ras}$. These proteins are very homologous in amino acid sequence differing primarily at their C terminii. The cDNA sequences for each of the H-, K-and N-ras genes have been reported (Capon et al., *Nature* 302, 33–37, 1983; Kahn et al., *Anticancer Res.* 7, 639–652, 1987; Hall & Brown, *Nucl. Acid Res.* 13, 5255–5268, 1985).

The p21$^{ras}$ proteins belong to a family of signal-transducing monomeric proteins with GTP-binding activity and appear to play a central role in signal transduction pathways (Bourne et al., *Nature* 348:125 (1990-)). The IL-2, IL-3, CSF-1, GM-CSF, EGF, SCF and PDGF receptors (Satoh et al., *Proc. Natl. Acad. Sci. USA* 88:3314 (1991); Duronio et al., *Proc. Natl. Acad. Sci. USA* 89:1587 (1992); Satoh et al., *Proc. Natl. Acad. Sci. USA* 87:5993 (1990); Satoh et al., *Proc. Natl. Acad. Sci. USA* 87:7926 (1990; Gibbs et al., *J. Biol. Chem.* 265:20437 (1990)), and several oncogene products with constitutively enhanced tyrosine kinase activity (fms, src, abl, bcr-abl) (Gibbs et al., *J. Biol. Chem.* 265:20437 (1990); Smith et al., *Nature* 320:540 (1986); Mandanas et al., *Blood* 80 (Suppl.1):14a (1992)), activate p21$^{ras}$ proteins.

The p21$^{ras}$ proteins bind guanine nucleotides with high affinity and hydrolyze GTP with low catalytic efficiency. p21$^{ras}$ is activated by the replacement of GDP by GTP, a process that is catalyzed by a guanine nucleotide-releasing factor. In the GTP form, p21$^{ras}$ proteins serve as signal transducers (Smith et al., *Nature* 320:540 (1986); Trahey and McCormick *Science* 238:542 (1987)) but are inactive in the GDP-bound form.

In mammalian cells two proteins, p120 rasGTPase activating protein ("rasGAP" or "p120-GAP") and NF-1, inactivate p21$^{ras}$ (Bollag and McCormick, *Annu. Rev. Cell. Biol.* 7:601 (1992)) by inducing a 100-fold increase of the intrinsically low GTPase activity of p21$^{ras}$, which converts the active GTP-bound form to the inactive GDP-bound form by stimulation GTP-GDP exchange (Trahey and McCormick, *Science* 238:542 (1987)). The active p21$^{ras}$-GTP-bound form of p21$^{ras}$ is inactivated by an intrinsic GTPase activity that is catalyzed by the carboxylterminus domain of p120-GAP (Marshall et al., *EMBO (Eur. Mol. Biol. Organ) J.* 8:1105 (1989)).

It has been shown that p21$^{ras}$ plays an important role in the formation of normal and leukemic hematopoietic colonies (Skorski et al., *J. Exp. Med.* 175:743, 1992), and that p120-GAP is an inhibitor of p21$^{ras}$. A decrease in the GTPase activity observed in the activated ras oncogene product is believed to be responsible for its transforming activity (Seeburg et al., *Nature* 312:71, 1984). Thus, the binding of GTP with the diminished capacity to hydrolyze it would maintain the protein in a constitutively active state, thus sending a continuous signal to the cell along the mitogenic pathway.

The raf proto-oncogene codes a protein-serine/threonine kinase. The activity of this enzyme is induced by direct or indirect action of diverse cell surface receptors, cytoplasmic protein tyrosine kinases, and ras (Morrison et al., *Proc. Natl. Acad. Sci. USA* 85, 8855–8859, 1988; Morrison et al., *Cell* 58, 649–657, 1988). The cDNA sequence for the c-raf gene has been reported (Bonner et al., *Nucl. Acid Res.* 14, 1009–1015, 1986).

The protein tyrosine kinases encompass a large diverse group of oncogenes and proto-oncogenes which encode proteins which catalyze the transfer of a phosphate residue from a nucleoside triphosphate to the side chain of a tyrosine residue in a protein. The transforming potential of protein tyrosine kinases is activated by N-terminal or C-terminal rearrangements. These alterations may remove down-regulating domains of the protein and result in the constitutive activation of what is normally a conditionally regulated enzyme activity. Thus, when suitably mutated (or, in some instances, anomalously expressed), protein tyrosine kinases themselves become transforming proteins, acting through unwanted phosphorylation of their diverse substrates. Further, protein tyrosine kinases can be vehicles for transformation by disturbances elsewhere in signalling pathways., e.g., constitutive production of growth factors that act through protein tyrosine kinase receptors (Aaronson & Pierce, *Cancer Cells* 2, 212–214, 1990) and the effects of phosphatases, which play crucial roles in governing the activity of protein tyrosine kinases (Hunter, *Cell* 58, 1013–1016, 1989).

One type of tyrosine protein kinase comprises the transmembrane protein kinases which span the plasma membrane. They contain large extracellular and cytoplasmic domains. One such category comprises the EGF family of growth factor receptors. The receptor has intrinsic tyrosine kinase activity that is activated by the binding of its ligand. EGF-1 is expressed in breast cancers and glioblastomas. EGF$_2$ is found expressed in neuroblastomas. The cDNA sequence corresponding to the former is reported by Helin et al., *Cell* 70, 337–350 (1992).

Further examples of the tyrosine kinase growth factor receptor family include erbB, fms, ros, kit, met, trk and neu oncogenes. Expression of met has been found in gastric carcinomas. The cDNA sequence of c-kit was reported by Vandenbark et al., *Oncogene* 7, 1259–1266 (1992).

Another type of tyrosine kinases includes a large number of nonintegral membrane-associated protein tyrosine kinases. The protein product of v-src, the prototype of this family, is associated with the plasma membrane but does not traverse the membrane. Oncogenic p60$^{v-src}$ encoded in Rous sarcoma virus and its cellular homolog p60$^{c-src}$, are membrane-localized phosphoproteins that possess protein tyrosine kinase activity. The cDNA sequence of the normal cellular homologue, the proto-oncogene c-src, has been reported (Braeuninger et al., *Proc. Natl. Acad. Sci. USA* 88, 10411–10415, 1991). Normal p60$^{c-src}$ is tightly regulated in its kinase activity relative to p60$^{v-src}$ and generally is not oncogenic. Mutations in p60$^{c-src}$ that elevate its kinase activity also activate its oncogenic potential. It has been suggested that p60$^{v-src}$ and p60$^{c-src}$ associate with complexes containing p120-GAP and provide a biochemical link between these kinases and p120-GAP/ras traduction pathways (Brott et al., *Proc. Natl. Acad. Sci. USA* 88, 755–759, 1991).

Other members of the tyrosine kinase family include fes, abl, fgr and yes. All of these proto-oncogene products are homologous in their tyrosine kinase domains. The tyrosine kinase domains as in the growth factor receptor tyrosine kinase family, is responsible for catalyzing the transfer of phosphate groups from ATP to tyrosine residues during auto-phosphorylation or transphosphorylation of target molecules.

The aberrant expression of a nonintegral membrane associated tyrosine kinase is best illustrated by the abl proto-oncogene, the cDNA sequence of which is reported by Shtivelman et al., *Cell* 47, 277–284 (1986). Aberrant expression of abl results from the c-abl gene's translocation from the long arm of chromosome 9 to the breakpoint cluster region (bcr) on chromosome 22, resulting in the formation of bcr-abl hybrid genes. The break occurs near the end of the long arm of chromosome 9 (band 9q34) and in the upper half of chromosome 22 (band 22q11). The chimeric message is in turn translated into a larger chimeric abl protein (210 kDa) that has increased tyrosine kinase activity (Konopka et al., *Cell* 37, 1035 (1984); Kloetzer et al., *Virology* 140, 230 (1985); Konopka et al., *Proc. Natl. Acad. Sci. U.S.A.* 82, 1810 (1985)). The 210 kDa protein is considerably larger than the normal human abl protein of 145 kDa, and has a very high tyrosine kinase activity. The cDNA sequences of the various bcr-abl oncogenes have been reported: Shtivelman et al., *Cell* 47, 277 (1986); Mes-Masson et al., *Proc. Natl. Acad. Sci. USA* 83, 9768–9772 (1986); Fainstein et al., *Nature* 330, 386–388 (1987).

Molecular strategies are being developed to downregulate unwanted gene expression, including oncogene expression. One such strategy involves inhibiting gene expression with oligonucleotides complementary in sequence to ther messenger RNA of a deleterious target gene. The so-called "antisense" oligonucleotides have been proposed as anti-cancer agents, by targeting various oncogenes or proto-oncogenes. See, for example, U.S. Pat. No. 5,098,890 (c-myb antisense for treating hematologic neoplasms, including use in bone marrow purging); international Patent Application WO 91/93260 (c-abl antisense for treating myeloproliferative disorders); International Patent Application W092/19252 and Ratajczak et al., *Proc. Natl. Acad. Sci. USA* 89, 1710–1714 (1992) (c-kit for inhibiting malignant hematopoietic cell proliferation); International Patent Application W092/20348 and Melani et al., *Cancer Res.* 51; 2897–2901 (1991) (c-myb antisense for inhibiting proliferation of colon cancer cells); international Patent Application WO93/09789 (c-myb antisense for inhibiting malignant melanoma cell proliferation); International Patent Application WO92/22303 and Szcylick et al., *Science* 253, 562–565 (1991) (bcr-abl antisense for inhibiting leukemia cell proliferation); and U.S. Pat. No. 5,087,617 which describes bone marrow purging and in vivo therapy using antisense oligonucleotides to a variety of oncogenes of proto-oncogenes. The entire disclosure of each of the aforementioned references is incorporated by reference herein.

Growing evidence suggests that cancer arises through a multistep process which involves activation of proto-oncogenes and loss of function of tumor suppressor genes (Fearon et al., *Cell* 61, 759 (1991). Oncogene cooperation was originally demonstrated in vitro (Murray et al., *Cell* 33, 749 (1983); Thompson et al., *Cell* 56, 917 (1989); Stasser et al., *Nature* 348 (1990)) and subsequently validated in vivo using transgenic mouse models (Adams et al., *Science* 254, 1161 (1991)). Chronic myelogenous leukemia (CML) illustrates well the concept of a multistep process in human malignancies, because the clinical course consists of two well-defined stages, i.e., a relatively indolent and long lasting chronic phase, and a terminal, more aggressive blast crisis (Kantarjan et al., *Blood* 82, 691 (1993)). At the genetic level, the predominant abnormality of the chronic phase is the Philadelphia chromosome ($Ph^1$) translocation resulting in the formation of the bcr-abl oncogene.

Some studies have indicated that specific combinations of oncogenes are able to cooperate to induce a transformed phenotype, and that oncogene products which act in the nucleus cooperate best with those that act in the cytoplasm. These studies have been recently reviewed by Hunter, *Cell* 64, 249–270 (1991).

Despite evidence of cooperation of nuclear and cytoplasmic oncogenes in transformation, there is no suggestion that simultaneous inhibition of both oncogene types can result in enhanced antitumor effect. Moreover, while antisense oligonucleotides have been indicated as being useful for the treatment of cancer, it has not been heretofore suggested to adopt multiple antisense oligonucleotides specific for diverse oncogenes to provide enhanced antineoplastic effect.

SUMMARY OF THE INVENTION

According to the present invention, a composition is provided comprising at least one first antisense oligonucleotide specific for a cytoplasmic oncogene or proto-oncogene and at least one second antisense oligonucleotide specific for a nuclear oncogene or proto-oncogene. According to one preferred embodiment of the invention, the first antisense oligonucleotide is specific for a ras or raf gene. According to another preferred embodiment, the first antisense oligonucleotide is specific for a gene which codes for a protein tyrosine kinase.

The second antisense oligonucleotide is, according to one aspect of the invention, specific for a nuclear oncogene or proto-oncogene which encodes a transcriptional factor.

According to one embodiment, each of the first and second oligonucleotides has a nucleotide sequence capable of forming a stable duplex with a portion of an mRNA transcript of a cytoplasmic oncogene/proto-oncogene, or with an mRNA transcript of a nuclear/oncogene or proto-oncogene, respectively.

Each oligonucleotide is generally at least an 8-mer oligonucleotide, that is, the oligonucleotide is an oligomer containing at least 8 nucleotide residues, more preferably at least about 12 nucleotides. The preferred maximum size of the oligonucleotide is about 60 nucleotides, more preferably about 50 nucleotides, most preferably about 40 nucleotides. The oligomer is preferably an oligodeoxynucleotide. While oligonucleotides smaller than 12-mers may be utilized, they are statistically more likely to hybridize with non-targeted sequences, and for this reason may be less specific. In addition, a single mismatch may destabilize the hybrid. While oligonucleotides larger than 40-mers may be utilized, uptake may become somewhat more difficult without specialized vehicles or oligonucleotide carriers. Moreover, partial matching of long sequences may lead to non-specific hybridization, and non-specific effects. Most preferably, the oligonucleotide is a 15- to 40-mer oligodeoxynucleotide, more advantageously an 18- to 30-mer.

While in principle oligonucleotides having a sequence complementary to any region of the target mRNA find utility in the present invention, preferred are oligonucleotides capable of forming a stable duplex with a portion of the transcript lying within about 50 nucleotides (preferably within about 40 nucleotides) upstream (the 5' direction), or about 50 (preferably 40) nucleotides downstream (the 3' direction) from the translation initiation codon of the target mRNA. Also preferred are oligonucleotides which are capable of forming a stable duplex with a portion of the target mRNA transcript including the translation initiation codon.

The invention is also a method for inhibiting the proliferation of neoplastic cells, comprising contacting such cells with a proliferation-inhibiting effective amount of at least one first antisense oligonucleotide specific for a cytoplasmic oncogene/proto-oncogene and at least one second antisense oligonucleotide specific for a nuclear oncogene/proto-oncogene.

The invention also provides a method for treating neoplastic disease comprising administering to a patient in need of such treatment an effective amount of at least one first antisense oligonucleotide specific for a cytoplasmic oncogene/proto-oncogene and at least one second antisense oligonucleotide specific for a nuclear oncogene/proto-oncogene.

In yet another embodiment, the invention is a method for purging bone marrow of neoplastic cells such as leukemic cells, or solid tumor cells which have metastasized to the bone marrow. Bone marrow cells aspirated from an individual afflicted with a neoplastic disease are treated with an effective amount of at least one first antisense oligonucleotide specific for a cytoplasmic oncogene/proto-oncogene and at least one second antisense oligonucleotide specific for a nuclear oncogene/proto-oncogene. The thus-treated cells are then returned to the body of the afflicted individual.

According to another embodiment, the invention is an artificially-constructed gene comprising a first promotor segment and a segment containing DNA of a cytoplasmic oncogene or proto-oncogene DNA, and a second promotor segment and a segment containing DNA of a nuclear oncogene or proto-oncogene. The oncogene/-proto-oncogene DNA-containing segments are in inverted orientation such that transcription of the artificially-constructed gene produces RNA complementary to an mRNA transcript of the cytoplasmic oncogene or proto-oncogene and RNA complementary to an mRNA transcript of the nuclear oncogene or proto-oncogene. The gene may be introduced into target cells to inhibit the proliferation of those cells. The artificially-constructed gene may be introduced into the target cells by, for example, transfection, transduction with a viral vector, or microinjection.

Definitions

By "proto-oncogene" is meant a normal, cellular human gene, the alteration of which gives rise to a transforming allele or "oncogene".

By "oncogene" is meant a human gene in a host cell which is responsible, in whole or in part, for the neoplastic transformation of the host cell.

By "cytoplasmic oncogene" or "cytoplasmic proto-oncogene" is meant an oncogene/proto-oncogene the encoded protein of which is localized primarily in the cell cytoplasm.

By "nuclear oncogene" or "nuclear proto-oncogene" is meant an oncogene or proto-oncogene the encoded protein of which is localized primarily in the cell nucleus.

By "protein tyrosine kinase" is meant an enzyme which catalyzes the transfer of a phosphate residue form a nucleoside triphosphate to the side chain of a tyrosine amino acid residue in a protein.

By "transcriptional factor" is meant the product of a nuclear oncogene or proto-oncogene which binds a target DNA segment to activate transcription of another gene.

An "antisense oligonucleotide specific for" a targeted oncogene or proto-oncogene is meant an oligonucleotide having a sequence (i) capable of forming a stable triplex with a portion of the targeted oncogene, or (ii) capable of forming a stable duplex with a portion of an mRNA transcript of the targeted oncogene.

The term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions, such as Watson-Crick type of base pairing, Hoogsteen or reverse Hoogsteen types of base pairing, or the like. Usually, monomers are linked by phosphodiester bonds or analogs thereof to form oligonucleotides ranging in size from a few monomeric units, e.g., 3–4, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate, and the like, as more fully described below. As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g., described generally by Scheit, Nucleotide Analogs (John Wiley, New York, 1980). Such analogs include synthetic nucleosides designed to enhance binding properties, e.g., duplex or triplex stability, specificity, or the like.

The term "phosphorothioate oligonucleotide" means an oligonucleotide wherein one or more of the internucleotide linkages is a phosphorothioate group,

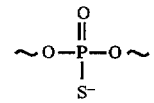

as opposed to the phosphodiester group

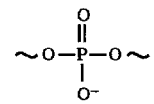

which is characteristic of unmodified oligonucleotides.

By "alkylphosphonate oligonucleoside" is meant an oligonucleotide wherein one or more of the internucleotide linkages is an alkylphosphonate group,

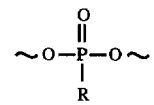

wherein R is an alkyl group, preferably methyl or ethyl.

The term "modified oligonucleotide" is meant an oligonucleotide containing one or more modified monomers and/or linkages to enhance the stability or uptake of the oligonucleotide.

"Stability" in reference to duplex or triplex formation roughly means how tightly an antisense oligonucleotide binds to its intended target sequence; more precisely, it means the free energy of formation of the duplex or triplex under physiological conditions. Melting temperature under a standard set of conditions, e.g., as described below, is a convenient measure of duplex and/or triplex stability. Preferably, antisense oligonucleotides of the invention are selected that have melting temperatures of at least 50° C. under the standard conditions set forth below; thus, under physiological conditions and the preferred concentrations, duplex or triplex formation will be substantially favored over the state in which the antisense oligonucleotide and its target are dissociated. It is understood that a stable duplex or triplex may in some embodiments include mismatches between base pairs and/or among base triplets in the case of triplexes. Preferably, antisense oligonucleotides of the invention form perfectly matched duplexes and/or triplexes with their target polynucleotides.

The term "downstream" when used in reference to a direction along a nucleotide sequence means the direction. Similarly, the term "upstream" means the 3'→5' direction.

The term "targeted oncogene (or proto-oncogene) mRNA transcript" means the presently known mRNA transcript of the targeted oncogene (or proto-oncogene) and all variations thereof, or any further transcripts which may be elucidated.

The term "[S]ODN" means phosphorothioate oligodeoxynucleotide.

DETAILED DESCRIPTION OF THE INVENTION

Figure 1A:
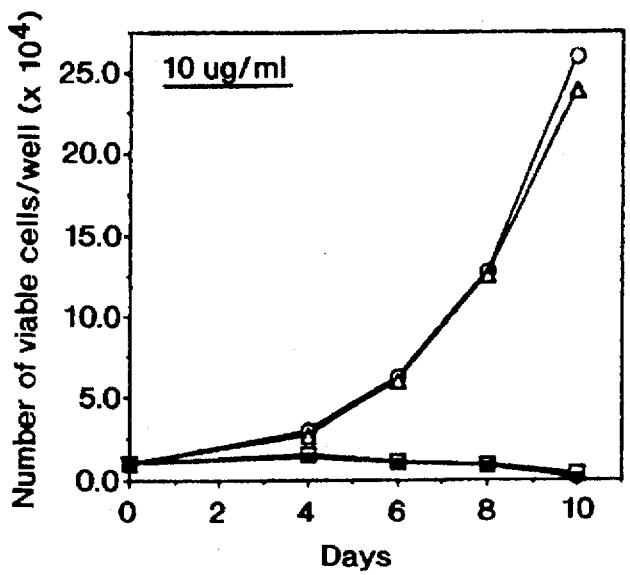
FIGS. 1A, 1B and 1C contain the results of cell proliferation assays demonstrating the effects of various oligonucleotides on the proliferation of chronic myelogenous leukemia (BV173) cells at final oligonucleotide concentrations of 10 (FIG. 1A), 5 (FIG. 1B) and 2.5 (FIG. 1C) µg/ml: (○) control; (△) b2/a2 plus c-myc sense; (□) b2/a2 antisense; (■) c-myc antisense, (●) b2/a2 and c-myc antisense.

According to the present invention, at least one antisense oligonucleotide specific for at least one cytoplasmic oncogene or proto-oncogene, is administered to a patient with at least one antisense oligonucleotide specific for a nuclear oncogene or proto-oncogene, preferably an antisense oligonucleotide specific for a transcriptional factor. The two antisense oligonucleotides may be administered by any of the routes described hereinafter. While it is preferred that the two agents be administered simultaneously, such as in the form of a single pharmaceutical composition, the two agents may be administered separately, in sequence. While it is presently preferred that both oligonucleotides are administered through the same route, they may be administered through different routes.

The antisense oligonuclerotide pair may comprise, for example, antisense oligonucleotides specific to any of the nuclear and cytoplasmic oncogenes/proto-oncogenes disclosed herein. Thus, for example, the targeted cytoplasmic gene may comprise c-erbB, c-fms, c-ras, c-kit, c-met, c-trk, c-neu, c-src, c-fes, c-abl, bcr-abl, c-fgr, or c-yes. Combinations of antisense oligonucleotides specific for the same or different cytoplasmic genes may be utilized. The targeted nuclear gene may comprise, for example, c-erbA, c-evi-1, c-gli-1, c-maf, c-lyl-1, c-ets, c-fos, c-jun, c-myb, c-myc, b-myb, N-myc, L-myc, c-rel, c-vav, c-ski, c-spi or cyclin D1. Combinations of antisense oligonucleotides specific for the same or different nuclear genes may be utilized. It should be appreciated that in the aforesaid listings, the indicated gene may comprise a group of variants identified under a common name, e.g., "c-jun" includes the specific genes c-jun, c-jun-B and c-jun-D.

According to one preferred embodiment of the invention, the therapeutic combination comprises one or more antisense oligonucleotides specific for a ras gene in combination with one or more antisense oligonucleotides specific for a myc gene. By "ras" is meant any of the family of ras genes, such as N-ras, c-ras or H-ras. Similarly, by "myc" is meant any of the family of myc genes, such as c-myc, L-myc and N-myc, and by "jun" is meant any of the family of jun genes such as c-jun, c-junB and c-junD. The protein tyrosine kinases encoded by src, kit, bcr-abl, fms, and the receptor type kinases (insulin, IGF-1, EGF, etc.), all converge on RAS, which in turn binds RAF, which in turn activates MAP-kinase, which in turn phosphorylates nuclear effectors such as myc. The RAS protein also activates jun, which is in turn a regulator of all growth. A combination of antisense oligonucleotides specific for ras and myc genes is thus believed particularly useful against neoplastic disorders, e.g., CML, characterized by activated (i.e., oncogenic) protein tyrosine kinases. The combination may be used also, for example, for the treatment of epithelial tumors, such as tumors of the breast, prostate, colon, pancrease and gastric tract.

According to another preferred embodiment of the invention, the therapeutic combination comprises one or more antisense oligonucleotides specific for a raf oncogene in combination with one or more antisense oligonucleotides specific for a jun gene. The combination is used for the treatment of the aforesaid tumors of epithelial origin. In yet another preferred embodiment; ras or raf antisense oligonucleotides are combined with myc antisense oligonucleotides, particularly c-myc, for the treatment of leukemia, particularly Ph$^1$-positive leukemias. Other combinations may be adopted for treatment of yet other neoplastic diseases.

The following oncogene or proto-oncogene nucleotide sequences are set forth herein:

| | | |
|---|---|---|
| c-jun | SEQ ID NO:13 | |
| c-H-ras | SEQ ID NO:14 | |
| c-K-ras | SEQ ID NO:15 | |
| c-N-ras | SEQ ID NO:16 | |
| c-raf | SEQ ID NO:17 | |
| EGF-1 | SEQ ID NO:18 | |
| c-fms | SEQ ID NO:19 | |
| c-ros | SEQ ID NO:20 | |
| c-kit | SEQ ID NO:21 | |
| c-met | SEQ ID NO:22 | |
| c-trk | SEQ ID NO:23 | |
| c-src1 | SEQ ID NO:24 | |
| c-src2 | SEQ ID NO:25 | |
| c-src3 | SEQ ID NO:26 | |
| c-src4 | SEQ ID NO:27 | |
| c-src5 | SEQ ID NO:28 | |
| c-src6 | SEQ ID NO:29 | |
| c-src7 | SEQ ID NO:30 | |
| c-src8 | SEQ ID NO:31 | |
| c-src9 | SEQ ID NO:32 | |
| c-src10 | SEQ ID NO:33 | |
| c-src11 | SEQ ID NO:34 | |
| c-abl | SEQ ID NO:35 | |
| bcr-abl | SEQ ID NO:36 | (b2a2 genotype) |
| bcr-abl | SEQ ID NO:37 | (b3a2 genotype) |
| bcr-abl | SEQ ID NO:38 | (b1a2 genotype) |
| c-fgr | SEQ ID NO:39 | |
| c-yes | SEQ ID NO:40 | |
| c-myc | SEQ ID NO:41 | |
| L-myc | SEQ ID NO:42 | |
| c-ets | SEQ ID NO:43 | |
| c-fos | SEQ ID NO:44 | |
| c-myb | SEQ ID NO:45 | |
| B-myb | SEQ ID NO:46 | |
| c-rel | SEQ ID NO:47 | |
| c-yav | SEQ ID NO:48 | |
| c-ski | SEQ ID NO:49 | |
| c-spi | SEQ ID NO:50 | |
| cyclin D1 | SEQ ID NO:51 | |
| PML/RARα | SEQ ID NO:52 | |
| AML1/MTG8 | SEQ ID NO:53 | |
| E2A/prl | SEQ ID NO:54 | |
| ALL-1/AF-4 | SEQ ID NO:55. | |

In the practice of the present invention, target oncogene/ proto-oncogene polynucleotides may be single-stranded or double-stranded DNA or RNA; however, single-stranded DNA or RNA targets are preferred. It is understood that the target to which the oncogene/-proto-oncogene antisense oligonucleotides of the invention are directed include allelic forms of the targeted gene and mRNA. There is substantial guidance in the literature for selecting particular sequences for antisense oligonucleotides given a knowledge of the sequence of the target polynucleotide, e.g., Peyman and Ulmann, *Chemical Reviews*, 90:543–584, 1990; Crooke, *Ann. Rev. Pharmacal. Toxicol.*, 32:329–376 (1992); and Zamecnik and Stephenson, *Proc. Natl. Acad. Sci.*, 75:280–284 (1974). Preferably, the sequences of antisense compounds are selected such that the G-C content is at least 60%. Preferred mRNA targets include the 5' cap site, tRNA primer binding site, the initiation codon site, the mRNA donor splice site, and the mRNA acceptor splice site, e.g., Goodchild et al., U.S. Pat. No. 4,806,463.

Where the target polynucleotide comprises an mRNA transcript, oligonucleotides complementary to and hybridizable with any portion of the transcript are, in principle, effective for inhibiting translation, and capable of inducing the effects herein described. It is believed that translation is most effectively inhibited by blocking the mRNA at a site at or near the initiation codon. Thus, oligonucleotides complementary to the 5'-region of mRNA transcript are preferred. Oligonucleotides complementary to the oncogene/proto-oncogene mRNA, including the initiation codon (the first codon at the 5' end of the translated portion of the transcript), or codons adjacent the initiation codon, are preferred.

While antisense oligomers complementary to the 5'-region of the oncogene/proto-oncogene mRNA transcripts are preferred, particularly the region including the initiation codon, it should be appreciated that useful antisense oligomers are not limited to those oligomers complementary to the sequences found in the translated portion of the mRNA transcript, but also includes oligomers complementary to nucleotide sequences contained in, or extending into, the 5'- and 3'-untranslated regions.

Antisense oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like.

Antisense compounds of the invention may also contain pendent groups or moieties, either as part of or separate from the basic repeat unit of the polymer, to enhance specificity, nuclease resistance, delivery, or other property related to efficacy, e.g., cholesterol moieties, duplex intercalators such as acridine, poly-L-lysine, "end-capping" with one or more nuclease-resistant linkage groups such as phosphorothioate, and the like.

For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Non-ionic oligonucleotides such as these are characterized by increased resistance to nuclease hydrolysis and/or increased cellular uptake, while retaining the ability to form stable complexes with complementary nucleic acid sequences. The alkylphosphonates, in particular, are stable to nuclease cleavage and soluble in lipid. The preparation of alkylphosphonate oligonucleosides is disclosed in Tso et al., U.S. Pat. No. 4,469,863.

Preferably, nuclease resistance is conferred on the antisense compounds of the invention by providing nuclease-resistant internucleosidic linkages. Many such linkages are known in the art, e.g., phosphorothioate: Zon and Geiser, *Anti-Cancer Drug Design*, 6:539–568 (1991); Stec et al., U.S. Pat. No. 5,151,510; Hirschbein, U.S. Pat. No. 5,166, 387; Bergot, U.S. Pat. No. 5,183,885; phosphorodithioates:

Marshall et al., *Science*, 259:1564–1570 (1993); Caruthers and Nielsen, International application PCT/US89/02293; phosphoramidates, e.g., —OP(=O)(NR$^1$R$^2$)—O— with R$^1$ and R$^2$ hydrogen or $C_1$–$C_3$ alkyl; Jager et al., *Biochemistry*, 27:7237–7246 (1988); Froehler et al., International application PCT/US90/03138; peptide nucleic acids: Nielsen et al., *Anti-Cancer Drug Design*, 8:53–63 (1993), International application PCT/EP92/01220; methylphosphonates: Miller et al., U.S. Pat. No. 4,507,433, Ts' o et al., U.S. Pat. No. 4,469,863; Miller et al., U.S. Pat. 4,757,055; and P-chiral linkages of various types, especially phosphorothioates, Stec et al., European patent application 506,242 (1992) and Lesnikowski, *Bioorganic Chemistry*, 21:127–155 (1993). Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl ($C_1$–$C_6$)- or diphenylsilyl, sulfamate ester, and the like. Such linkages and methods for introducing them into oligonucleotides are described in many references, e.g., reviewed generally by Peyman and Ulmann, *Chemical Reviews* 90:543–584 (1990); Milligan et al., *J. Med. Chem.*, 36:1923–1937 (1993); Matteucci et al., International application PCT/US91/06855.

Resistance to nuclease digestion may also be achieved by modifying the internucleotide linkage at both the 5' and 3' termini with phosphoroamidites according to the procedure of Dagle et al., Nucl. Acids Res. 18, 4751–4757 (1990).

Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., *Proc. Natl. Acad. Sci.*, 86, 3474–3478 (1989)).

It is understood that in addition to the preferred linkage groups, compounds of the invention may comprise additional modifications, e.g., boronated bases, Spielvogel et al., 5,130,302; cholesterol moieties, Shea et al., *Nucleic Acids Research*, 18:3777–3783 (1990) or Letsinger et al., *Proc. Natl. Acad. Sci.*, 86:6553–6556 (1989); and 5-propynyl modification of pyrimidines, Froehler et al., *Tetrahedron Lett.*, 33:5307–5310 (1992).

Preferably, antisense compounds of the invention are synthesized by conventional means on commercially available automated DNA synthesizers, e.g., an Applied Biosystems (Foster City, Calif.) model 380B, 392 or 394 DNA/RNA synthesizer. Preferably, phosphoramidite chemistry is employed, e.g., as disclosed in the following references: Beaucage and Iyer, Tetrahedron, 48:2223–2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g., whether ribose or deoxyribose nucleosides are employed), base modifications (e.g., methylated cytosine, and the like) in order to maximize, or otherwise regulate, triplex stability as desired in particular embodiments, e.g., Roberts et al., *Proc. Natl. Acad. Sci.*, 88:9397–9401 (1991); Roberts et al., *Science*, 58:1463–1466 (1992); Distefano et al., *Proc. Natl. Acad. Sci.*, 90:1179–1183 (1993); Mergny et al., *Bio-chemistry*, 30:9791–9798 (1992); Cheng et al., *J. Am. Chem. Soc.*, 114:4465–4474 (1992); Beal and Dervan, *Nucleic Acids Research*, 20:2773–2776 (1992); Beal and Dervan, *J. Am. Chem. Soc.*, 114:4976–4982; Giovannangeli et al., *Proc. Natl. Acad. Sci.*, 89:8631–8635 (1992); Moser and Dervan, *Science*, 238:645–650 (1987); McShan et al., *J. Biol. Chem.*, 267:5712–5721 (1992); Yoon et al., *Proc. Natl. Acad. Sci.*, 89:3840–3844 (1992); and Blume et al., *Nucleic Acids Research*, 20:1777–1784 (1992).

The length of the oligonucleotide moieties is sufficiently large to ensure that specific binding will take place only at the desired target polynucleotide and not at other fortuitous sites, as explained in many references, e.g., Rosenberg et al., International application PCT/US92/05305; or Szostak et al., *Meth. Enzymol*, 68:419–429 (1979). The upper range of the length is determined by several factors, including the inconvenience and expense of synthesizing and purifying oligomers greater than about 30–40 nucleotides in length, the greater tolerance of longer oligonucleotides for mismatches than shorter oligonucleotides, whether modifications to enhance binding or specificity are present, whether duplex or triplex binding is desired, and the like. Usually, antisense compounds of the invention have lengths in the range of about 12 to 60 nucleotides. More preferably, antisense compounds of the invention have lengths in the range of about 15 to 40 nucleotides; and most preferably, they have lengths in the range of about 18 to 30 nucleotides.

In general, the antisense oligonucleotides used in the practice of the present invention will have a sequence which is completely complementary to a selected portion of the target polynucleotide. Absolute complementarity is not however required, particularly in larger oligomers. Thus, reference herein to a "nucleotide sequence complementary to" a target polynucleotide does not necessarily mean a sequence having 100% complementarity with the target segment. In general, any oligonucleotide having sufficient complementarity to form a stable duplex with the target (e.g. an oncogene mRNA) that is, an oligonucleotide which is "hybridizable", is suitable. Stable duplex formation depends on the sequence and length of the hybridizing oligonucleotide and the degree of complementarity with the target polynucleotide. Generally, the larger the hybridizing oligomer, the more mismatches may be tolerated. More than one mismatch probably will not be tolerated for antisense oligomers of less than about 21 nucleotides. One skilled in the art may readily determine the degree of mismatching which may be tolerated between any given antisense oligomer and the target sequence, based upon the melting point, and therefore the thermal stability, of the resulting duplex.

Preferably, the thermal stability of hybrids formed by the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0–2.0 μM. Typical conditions are as follows: 150 mM NaCl and 10mM $MgCl_2$ in a 10 mM sodium phosphate buffer (pH 7.0) or in a 10mM Tris-HCl buffer (pH 7.0). Data for melting curves are accumulated by heating a sample of the antisense oligonucleotide/target polynucleotide complex from room temperature to about 85°–° C. As the temperature of the sample increases, absorbance of 260 nm light is monitored at 1° C. intervals, e.g., using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. The pharmaceutical carrier may comprise a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For water soluble formulations, the pharmaceutical composition preferably includes a buffer such as a phosphate buffer, or other organic acid salt, preferably at a pH of between about 7 and 8. For formulations containing weakly soluble antisense compounds, micro-emulsions may be employed, for example by using a nonionic surfactant such as polysorbate 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g., Remington's Pharmaceutical Science, latest edition (Mack Publishing Company, Easton, Pa.).

Antisense compounds of the invention include the pharmaceutically acceptable salts thereof, including those of alkaline earths, e.g., sodium or magnesium, ammonium or $NX_4^+$, wherein X is $C_1-C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in with a suitable cation such as $Na^+$, $NH_4^+$, or the like.

The antisense oligonucleotides are preferably administered parenterally, most preferably intravenously. The vehicle is designed accordingly. Alternatively, oligonucleotide may be administered subcutaneously via controlled release dosage forms.

In addition to administration with conventional carriers, the antisense oligonucleotides may be administered by a variety of specialized oligonucleotide delivery techniques. Sustained release systems suitable for use with the pharmaceutical compositions of the invention include semipermeable polymer matrices in the form of films, microcapsules, or the like, comprising polylactides; copolymers of L-glutamic acid and gamma-ethyl-L-glutamate, poly(2-hydroxyethyl methacrylate), and like materials, e.g., Rosenberg et al., International application PCT/US92/05305.

The oligonucleotides may be encapsulated in liposomes for therapeutic delivery, as described for example in Liposome Technology, Vol. II, Incorporation of Drugs, Proteins, and Genetic Material, CRC Press. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature.

The oligonucleotides may be conjugated to poly(L-lysine) to increase cell penetration. Such conjugates are described by Lemaitre et al., Proc. Natl. Acad. Sci. USA, 84, 648–652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride. This procedure converts the 3'-terminal ribose ring into a morpholine structure antisense oligomers.

Antisense compounds of the invention also include conjugates of such oligonucleotides with appropriate ligand-binding molecules. The oligonucleotides may be conjugated for therapeutic administration to ligand-binding molecules which recognize cell-surface molecules, such as according to International Patent Application WO 91/04753. The ligand-binding molecule may comprise, for example, an antibody against a cell surface antigen, an antibody against a cell surface receptor, a growth factor having a corresponding cell surface receptor, an antibody to such a growth factor, or an antibody which recognizes a complex of a growth factor and its receptor. Methods for conjugating ligand-binding molecules to oligonucleotides are detailed in WO 91/04753.

In particular, the growth factor to which the antisense oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. The preparation of transferrin complexes as carriers of oligonucleotide uptake into cells is described by Wagner et al., Proc. Natl. Acad. Sci. USA 87, 3410–3414 (1990). Inhibition of leukemia cell proliferation by transferrin receptor-mediated uptake of c-myb antisense oligonucleotides conjugated to transferrin has been demonstrated by Citro et al., Proc. Natl. Acad. Sci. USA., 89, 7031–7035 (1992). Cellular delivery of folate-macromolecule conjugates via folate receptor endocytosis, including delivery of an antisense oligonucleotide, is described by Low et al., U.S. Pat. No. 5,108,921. Also see, Leamon et al., Proc. Natl. Acad. Sci. 88, 5572 (1991).

A preferred method of administration of oligonucleotides comprises either systemic or regional perfusion, as is appropriate. According to a method of regional perfusion, the afferent and efferent vessels supplying the extremity containing the lesion are isolated and connected to a low-flow perfusion pump in continuity with an oxygenator and a heat exchanger. The iliac vessels may be used for perfusion of the lower extremity. The axillary vessels are cannulated high in the axilla for upper extremity lesions. Oligonucleotide is added to the perfusion circuit, and the perfusion is continued for an appropriate time period, e.g., one hour. Perfusion rates of from 100 to 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher doses of chemotherapeutic agent than would otherwise be tolerated upon infusion into the arterial or venous systemic circulation.

For systemic infusion, the oligonucleotides are preferably delivered via a central venous catheter, which is connected to an appropriate continuous infusion device. Indwelling catheters provide long term access to the intravenous circulation for frequent administration of drugs over extended time periods. They are generally surgically inserted into the external cephalic or internal jugular vein under general or local anesthesia. The subclavian vein is another common site of catheterization. The infuser pump may be external, or may form part of an entirely implantable central venous system such as the INFUSAPORT system available from Infusaid Corp., Norwood, Mass. and the PORT-A-CATH system available from Pharmacia Laboratories, Piscataway, N.J. These devices are implanted into a subcutaneous pocket under local anesthesia. A catheter, connected to the pump injection port, is threaded through the subclavian vein to the superior vena cava. The implant contains a supply of oligonucleotide in a reservoir which may be replenished as needed by injection of additional drug from a hypodermic needle through a self-sealing diaphragm in the reservoir. Completely implantable infusers are preferred, as they are generally well accepted by patients because of the convenience, ease of maintenance and cosmetic advantage of such devices.

As an alternative to treatment with exogenous oligonucleotides, antisense polynucleotide synthesis may be induced in situ by local treatment of the targeted neoplastic cells with a vector containing an artificially-constructed gene comprising transcriptional promotors and targeted oncogene/proto-oncogene DNA in inverted orientation. The DNA for insertion into the artificial gene in inverted orientation comprises cDNA which may be prepared, for example, by reverse transcriptase polymerase chain reaction from RNA using primers derived from the published target oncogene/proto-oncogene cDNA sequences.

A first DNA segment for insertion contains cDNA of a cytoplasmic oncogene/proto-oncogene. A second DNA segment for insertion contains cDNA of a nuclear oncogene/proto-oncogene. The two segments are under control of corresponding first and second promotor segments. Upon transcription, the inverted oncogene/proto-oncogene segments, which are complementary to the corresponding targeted oncogene/proto-oncogenes, are produced in situ in the targeted cell. The endogenously produced RNAs hybridize to the relevant oncogene/proto-oncogene mRNAs, resulting in interference with oncogene function and inhibition of the proliferation of the targeted cell.

The promotor segments of the artificially-constructed gene serve as signals conferring expression of the inverted oncogene/proto-oncogene sequences which lie downstream thereof. Each promotor will include all of the signals necessary for initiating transcription of the relevant downstream sequence. Each promotor may be of any origin as long as it specifies a rate of transcription which will produce sufficient antisense mRNA to inhibit the expression of the target oncogene/proto-oncogene, and therefore the proliferation of the targeted cells. Preferably, a highly efficient promotor such as a viral promotor is employed. Other sources of potent promotors include cellular genes that are expressed at high levels. The promotor segment may comprise a constitutive or a regulatable promotor.

The artificial gene may be introduced by any of the methods described in U.S. Pat. No. 4,740,463, incorporated herein by reference. One technique is transfection; which can be done by several different methods. One method of transfection involves the addition of DEAE-dextran to increase the uptake of the naked DNA molecules by a recipient cell. See McCutchin, J. H. and Pagano, J. S., *J. Natl. Cancer Inst.* 41, 351–7 (1968). Another method of transfection is the calcium phosphate precipitation technique which depends upon the addition of $Ca^{++}$ to a phosphate-containing DNA solution. The resulting precipitate apparently includes DNA in association with calcium phosphate crystals. These crystals settle onto a cell monolayer; the resulting apposition of crystals and cell surface appears to lead to uptake of the DNA. A small proportion of the DNA taken up becomes expressed in a transfectant, as well as in its clonal descendants. See Graham, F. L. and van der Eb, A. J., *Virology* 52, 456–467 (1973) and *Virology* 54, 536–539 (1973).

Transfection may also be carried out by cationic phospholipid-mediated delivery. In particular, polycationic liposomes can be formed from N-[1-( 2,3-di-oleyloxy) propyl]-N,N,N-trimethylammonium chloride (DOT-MA). See Felgner et al., *Proc. Natl. Acad. Sci.*, 84, 7413–7417 (1987) (DNA-transfection); Malone et al., *Proc. Natl. Acad. Sci.*, 86, 6077–6081 (1989) (RNA-transfection).

Alternatively, the artificially-constructed gene can be introduced in to cells, in vitro or in vivo, via a transducing viral vector. See Tabin et al., *Mol. Cel. Biol.* 2,426–436 (1982). Use of a retrovirus, for example, will infect a variety of cells and cause the artificial gene to be inserted into the genome of infected cells. Such infection could either be accomplished with the aid of a helper retrovirus, which would allow the virus to spread through the organism, or the antisense retrovirus could be produced in a helper-free system, such as Ψ2 like cells (See Mann et al., *Cell* 33, 153–160, 1983) that package amphotropic viruses. A helper-free virus might be employed to minimize spread throughout the organism. Viral vectors in addition to retroviruses can also be employed, such as papovaviruses, SV40–like viruses, or papilloma viruses. The use of retroviruses for gene transfer has been reviewed by Eglitis and Anderson, *BioTechniques* 6, 608–614 (1988).

Vesicle fusion could also be employed to deliver the artificial gene. Vesicle fusion may be physically targeted to the malignant cells if the vesicle were approximately designed to be taken up by those cells. Such a delivery system would be expected to have a lower efficiency of integration and expression of the artificial gene delivered, but would have a higher specificity than a retroviral vector. A strategy of targeted vesicles containing papilloma virus or retrovirus DNA molecules might provide a method for increasing the efficiency of expression of targeted molecules.

Particulate systems and polymers for in vitro and in vivo delivery of polynucleotides were extensively reviewed by Felgner in *Advanced Drug Delivery Reviews* 5, 163–187

(1990). Techniques for direct delivery of purified genes in vivo, without the use of retroviruses, has been reviewed by Felgner in *Nature* 349, 351–352 (1991). Such methods of direct delivery of polynucleotides may be utilized for local delivery of either exogenous oncogene antisense oligonucleotide or artificially-constructed genes producing oncogene antisense oligonucleotide in situ.

Recently, Wolf et al. demonstrated that direct injection of non-replicating gene sequences in a non-viral vehicle is possible. See *Science*, 247, 1465–1468 (1990). DNA injected directly into mouse muscle did not integrate into the host genome, and plasmid essentially identical to the starting material was recovered from the muscle months after injection. Interestingly, no special delivery system is required. Simple saline or sucrose solutions are sufficient to delivery DNA and RNA.

The antisense oligonucleotides may be used as the primary therapeutic for the treatment of the disease state, or may be used in with non-oligonucleotide agents. In particular, the antisense oligonucleotides may find utility as bone marrow purging agents in the treatment of leukemias or cancers which have metastasized to the bone marrow. High dose chemotherapy coupled with autologous bone marrow rescue involves removing a portion of the patient's bone marrow, treating the patient with conventional chemotherapy or radiation to substantially destroy the remaining malignant bone marrow cells, treating the stored bone marrow with an agent to eradicate neoplastic cells, and returning the treated cells to the patient. The treated cells, when returned to the patient, may be stimulated by various known hematopoietic growth factors to repopulate the bone marrow with cells which do not carry the oncogenic transcript.

According to a method for bone marrow purging, bone marrow is harvested from a donor by standard operating room procedures from the iliac bones of the donor. Methods of aspirating bone marrow from donors are well-known in the art. Examples of apparatus and processes for aspirating bone marrow from donors are disclosed in U.S. Pat. Nos. 4,481,946 and 4,486,188. Sufficient marrow is withdrawn so that the recipient, who is either the donor (autologous transplant) or another individual (allogeneic transplant), may receive from about $4\times10^8$ to about $8\times10^8$ processed marrow cells per kg of bodyweight. This generally requires aspiration of about 750 to about 1000 ml of marrow. The aspirated marrow is filtered until a single cell suspension, known to those skilled in the art as a "buffy coat" preparation, is obtained. This suspension of leukocytes is treated with the relevant antisense oligonucleotides in a suitable carrier, advantageously in a concentration of about 50–200 µg/ml. Alternatively, the leucocyte suspension may be stored in liquid nitrogen using standard procedures known to those skilled in the art until purging is carried out. The purged marrow can be stored frozen in liquid nitrogen until ready for use. Methods of freezing bone marrow and biological substances are disclosed, for example, in U.S. Pat. Nos. 4,107,937 and 4,117,881.

Other methods of preparing bone marrow for treatment with antisense oligonucleotide may be utilized, which methods may result in even more purified preparations of hematopoietic cells than the aforesaid buffy coat preparation.

While hematopoietic growth factors are typically added to the aspirated marrow or buffy coat preparation to stimulate growth of hematopoietic neoplasms, the amount of growth factor added in the practice of the present invention should be limited to only what is necessary to sustain the normal cell population. If too much growth factor is added, differential sensitivity to antisense inhibition as between normal and leukemic cells in the aspirated marrow may be lost. One skilled in the art may readily determine the appropriate amount of growth factor. Growth factors, if used, may include, for example, IL-3 and granulocyte macrophage colony stimulating factor (GM-CSF). The recombinant human versions of such growth factors are advantageously employed.

After treatment with the antisense oligonucleotides, the cells to be transferred are washed with autologous plasma or buffer to remove unincorporated oligomer. The washed cells are then infused back into the patient. Other methods for bone marrow purging utilizing antisense oligonucleotide are disclosed in U.S. Pat. No. 5,087,617.

According to a preferred treatment regimen for bone marrow purging, the aspirated bone marrow is contacted daily or twice daily for approximately one to four days with an amount of antisense oligonucleotides effective to overcome the malignant phenotype.

For systemic or regional in vivo administration, the amount of antisense oligonucleotides may vary depending on the nature and extent of the neoplasm, the particular oligonucleotides utilized, and other factors. The actual dosage administered may take into account the size and weight of the patient, whether the nature of the treatment is prophylactic or therapeutic in nature, the age, health and sex of the patient, the route of administration, whether the treatment is regional or systemic, and other factors. Intercellular concentrations of from about 1 to about 200 µg/ml at the target polynucleotide may be employed, preferably from about 10 µg/ml to about 100 µg/ml. The patient should receive a sufficient daily dosage of antisense oligonucleotide to achieve these intercellular concentrations of combined oligonucleotides. The daily combined oligonucleotide dosage combination of nuclear and cytoplasmic oncogene/ proto-oncogene-targetting oligonucleotides may range from about 25 mg to about 2 grams per day, with at least about 250 mg being preferred. An effective human continuous intravenous infusion dosage, based upon animal studies employing antisense oligonucleotides targeting other genes in antileukemic therapy, is about 0.4 mg/kg/day. Greater or lesser amounts of oligonucleotide may be administered, as required. Those skilled in the art should be readily able to derive appropriate dosages and schedules of administration to suit the specific circumstance and needs of the patient. It is believed that a course of treatment may advantageously comprise infusion of the recommended daily dose as a continuous intravenous infusion over 7 days. The oligonucleotides may be given for a period of from about 3 to about 28 days, more preferably from about 7 to about 10 days. Those skilled in the art should readily be able to determine the optimal dosage in each case. For modified oligonucleotides, such as phosphorothioate oligonucleotides, which have a half life of from 24 to 48 hours, the treatment regimen may comprise dosing on alternate days.

The ratio of the amounts of cytoplasmic gene-specific to nuclear gene-specific antisense oligonucleotide may vary over a broad range. Preferably, the ratio varies from about 10:1 to about 1:10, by weight, more preferably from about 4:1 to about 1:4, most preferably from about 3:1 to about 1:3. According to one preferred embodiment of the invention, the two oligonucleotides are present in approximately equal amounts, by weight. Of course, it may be appreciated that where plural cytoplasmic oncogene-specific oligonucleotides and/or plural nuclear oncogene-specific oligonucleotides are utilized, the total weight of lo all such compounds is considered with respect to the aforementioned preferred cytoplasmic/nuclear antisense ratio.

For ex vivo antineoplastic application, such as, for example, in bone marrow purging, the antisense oligonucleotides may be administered in amounts effective to kill neoplastic cells. Such amounts may vary depending on the extent to which malignant cells may arise in or have metastasized to the bone marrow, the particular oligonucleotide utilized, the relative sensitivity of the neoplastic cells to the oligonucleotide, and other factors. Total oligonucleotide concentrations from about 10 to 200 µg/ml per $10^5$ cells may be employed, preferably from about 40 to 150 µg/ml per $10^5$ cells. Supplemental dosing of the same or lesser amounts of oligonucleotide are advantageous to optimize the treatment. Thus, for purging bone marrow containing $2\times10^7$ cell per ml of marrow volume, dosages of from about 2 to 40 mg antisense per ml of marrow may be effectively utilized, preferably from about 8 to 24 mg/ml. Greater or lesser amounts of oligonucleotide may be employed.

The effectiveness of the treatment may be assessed by routine methods which are used for determining whether or not remission has occurred. Such methods generally depend upon some of morphological, cytochemical, cytogenetic, immunologic and molecular analyses. In addition, remission can be assessed genetically by probing the level of expression of one or more relevant oncogenes. The reverse transcriptase polymerase chain reaction methodology can be used to detect even very low numbers of mRNA transcript. For example, RT-PCR has been used to detect and genotype the three known bcr-abl fusion sequences in $Ph^1$ leukemias. See PCT/US9-2/05035 and Kawasaki et al., *Proc. Natl. Acad. Sci. USA* 85, 5698–5702 (1988).

Typically, therapeutic success is assessed by the decrease and the extent of the primary and any metastatic diseases lesions. For solid tumors, decreasing tumor size is the primary indicia of successful treatment. Neighboring tissues should be biopsied to determine the extent to which metastasis has occurred. Tissue biopsy methods are known to those skilled in the art. For non-solid tumors, i.e. the leukemias, treatment is monitored primarily by histological examination of the bone marrow for surviving leukemic cells. However, a significant number of leukemic cells may still exist when marrow examination provides normal results. For this reason, more recent methods for detecting leukemic cells have focused on detecting the presence of the gene for the relevant oncogene, or its corresponding mRNA, in cells of the bone marrow as a more sensitive test. See, for example, the following U.S. Pat. Nos. 4,681,840, 4,857,466 and 4,874,853. The presence of even a few copies of the target oncogene can be effectively detected by amplification using reverse transcriptase polymerase chain reaction technology. For a detailed discussion of such methods, see for example, *Cancer: Principles & Practice of Oncology*, edited by V. T. DeVita, S. Hellman and S. A. Rosenberg, J. B. Lippincott Company, Philadelphia, Pa. (3rd ed., 1989). Methods for diagnosing and monitoring the progress of neoplastic disorders vary depending upon the nature of the particular disease.

An antileukemic treatment plan is proposed as follows. Antisense oligonucleotides (phosphorothioate 24-mer) are administered as a 24-hour continuous intravenous infusion over 7 days. Each oligonucleotide is placed in 5% dextrose water and given at a daily dose ranging from about 0.30 to about 2 mg/kg/day. The dosage may be escalated as needed. Bone marrow aspiration/biopsy is conducted 7, 14 and 21 days after the first cycle of therapy. The patient is evaluated for response on day 21. Additional cycles of therapy may be performed. For such additional cycles of therapy, a bone marrow biopsy will be performed 21 days after the initiation of therapy. Complete remission is determined by the presence of all of the following for a period of at least 4 weeks: (1) a white count below 10,000/mm³ with granulocytes >1,000/mm³; (2) platelet count of $\geq$100,000/mm³; (3) absence of leukemic blasts from the peripheral blood; (4) a cellularity of bone marrow biopsy of $\geq$20%, with maturation of all cell lines; (5)$\geq$5% blasts in the bone marrow; (6) the absence of detectable Auer rods; (7) the absence of organomegaly; (8) the absence of extramedullary leukemia, such as central nervous system or soft tissue involvement.

According to one preferred embodiment, the invention comprises in vivo or ex vivo treatment of $Ph^1$-positive leukemias, that is, leukemias characterized by the chromosomal abnormality known as the Philadelphia or $Ph^1$ chromosome. At the molecular level, the most notable feature is the translocation of the proto-oncogene c-abl from the long arm of chromosome 9 to the breakpoint cluster region (bcr) on chromosome 22, resulting in the formation of bcr-abl hybrid genes. The break occurs near the end of the long arm of chromosome 9 (band 9q34) and in the upper half of chromosome 22 (band 22q11).

The c-abl proto-oncogene normally encodes a protein with tyrosine kinase activity. This activity is augmented in cells carrying bcr-abl hybrid genes. The gene located at the breakpoint on chromosome 22 is called bcr because the break in chromosome 22 in CML occurs in a very small 5.8-kilobase (kb) segment (breakpoint cluster region) of the gene on chromosome 22. Two alternative first exons of the c-abl oncogene exist, namely exon 1a and exon 1b, which are spliced to the common splice acceptor site, exon 2. As a result of this configuration, at least two major c-abl messages are transcribed, differing in their 5' regions. (Shtivelman et al., *Cell* 47, 277 (1986); Bernards et al., *Mol. Cell. Biol.* 7, 3231 (1987); Fainstein et al., *Oncogene*4, 1477–1481 (1989)). If exon 1b is used, the mRNA is 7.0 kb. If exon 1a is used, the mRNA is 6.0 kb. Each of exons 1a and 1b are preceded by a transcriptional promoter. The 9;22 translocation in CML results in the abnormal juxtaposition of abl sequences adjacent to bcr sequences. The fusion leads to an 8.5 kb chimeric mRNA consisting of 5' BCR sequences and 3' abl sequences. The chimeric message is in turn translated into a larger chimeric abl protein (210 kDa) that has increased tyrosine kinase activity (Konopka et al., *Cell* 37, 1035 (1984); Kloetzer et al., *Virology*140, 230 (1985).

Two major types of bcr-abl translocations are known, characterized by two different bcr-abl junctions. One translocation is between bcr exon 2 and abl exon 2, while another translocation is between bcr exon 3 and the same abl exon 2 (Shtivelman et al., *Cell* 47, 277–284 (1986)). The two types of junction have been referred to as the "L-6" (or "b2a2") and "K-28" (or "b3a2") junctions, respectively. The alternative splicing from two bcr-abl exons to the abl coding sequence results in two different bcr-abl fusion proteins, one including the 25 amino acids encoded by bcr exon 3 and one which lacks those amino acids. One or both of these junctions is detected in $Ph^1$-positive CML patients (Shtivelman et al., *Blood* 69, 971 (1986)).

A significant portion of acute lymphocytic leukemia (ALL) patients carry $Ph^1$ chromosomes in their leukemic cells. $Ph^1$-positive ALL is generally regarded as being less responsive to chemotherapeutic treatment than $Ph^1$-negative forms of ALL. This is particularly true of children with $Ph^1$-positive ALL.

Approximately one half of $Ph^1$-positive individuals afflicted with ALL express either of the two major bcr-abl junctions, L-6 or K-28. The remainder have bcr-abl genes characterized by a junction formed by the fusion of bcr exon 1 and c-abl exon 2 ("bla2" junction). See Fainstein et al., Nature 330, 386-388 (1987).

Clinically, CML invariably progresses from the chronic phase into the blast crisis. In chronic phase CML, the increase in mature and immature myeloid elements in bone marrow and peripheral blood is the most characteristic feature (Koeffler et al., N. Engl. J. Med. 304, 201 (1981)). Kinetic studies indicate that these abnormal cells do not proliferate or mature faster than their normal counterparts. Instead, the basic defect underlying the exuberant granulopoiesis in CML appears to reside in the expansion of the myeloid progenitor cell pool in bone marrow and peripheral blood. Id. Nevertheless, the generation of terminally differentiated cells indicates that the process of hematopoiesis retains some normal features. In contrast, during blastic transformation, the leukemic cells exhibit a marked degree of differentiation arrest with a "blast" phenotype (Rosenthal et al., Am. J. Med. 63, 542 (1977)). The onset of the blastic transformation or "blast crisis" limits the therapeutic options available. The disease-free period, and consequently survival, is generally brief. Typically it is less than about four months.

According to a preferred embodiment of the practice of the present invention, phi-positive leukemias are treated, either in vivo or ex vivo, with a combination of antisense oligonucleotides. Preferably, the oligonucleotides comprise at least one bcr-abl-specific antisense oligonucleotide, and at least one antisense oligonucleotide specific for a nuclear oncogene or proto-oncogene.

Preferably, the bcr-abl antisense oligonucleotide is complementary to a position of the bcr-abl mRNA corresponding to the breakpoint junction between the bcr-derived and abl-derived portions of the mRNA. By "abl-derived portion" is meant that portion of the bcr-abl RNA transcript which results from the transcription of the abl coding sequence which is translocated to the bcr coding sequence in the chromosomal translocation event giving rise to formation of the $Ph^1$ chromosome. Similarly, by "bcr-derived portion" of the bcr-abl transcript is meant that portion which results from the transcription of the bcr coding sequence which is juxtaposed to c-abl. This ensures specific hybridization to bcr-abl transcripts. Most preferably, the antisense molecule is complementary to a target mRNA sequence containing an about equal number of abl-derived nucleotides and bcr-derived nucleotides, that is, an about equal number of nucleotides on either side flanking the translocation breakpoint. Preferred antisense oligonucleotides complementary to the bcr-abl b1a2, b2a2 and b3a2 junctions are disclosed in International Patent Application W092/22303, the disclosure of which is incorporated herein by reference.

The practice of the present invention is illustrated by the following non-limiting examples. Combinations of nuclear and cytoplasmic oligonucleotides were more effective than either oligonucleotide alone.

EXAMPLE 1

Effect of bcr-abl and c-myc Antisense Oligonucleotides on BV-173 Cells

A. Phosphorothioate Oligodeoxynucleotides

Phosphorothioate oligodeoxynucleotides ([S]ODNs) were synthesized on an Applied Biosystems model 390Z automated synthesizer. The sequence of the b2/a2 bcr-abl antisense [S]ODN CGCTGAAGGG CTTCTTCCTT ATTGAT (SEQ ID NO:1) was complementary to a 26-nucleotide segment of the bcr-abl mRNA transcript spanning thirteen nucleotides upstream and downstream of the c-abl exon 2 and BCR exon 2 breakpoint junction. The sequence of the c-myc antisense [S]ODN TTGGTGAAGC TAACGTTGAG GGGCAT (SEQ ID NO:3) was complementary to the first 26 nucleotides of the mRNA transcript beginning from the translation initiation codon. Corresponding sense oligonucleotides had the sequences ATCAATAAGG AAGAAGCCCT TCAGCG (bcr-abl, SEQ ID NO:2) and ATGCCCCTCA ACGTTAGCTT CACCAA (c-myc, SEQ ID NO:4).

B. Cell Proliferation Assay

Figure 1B:
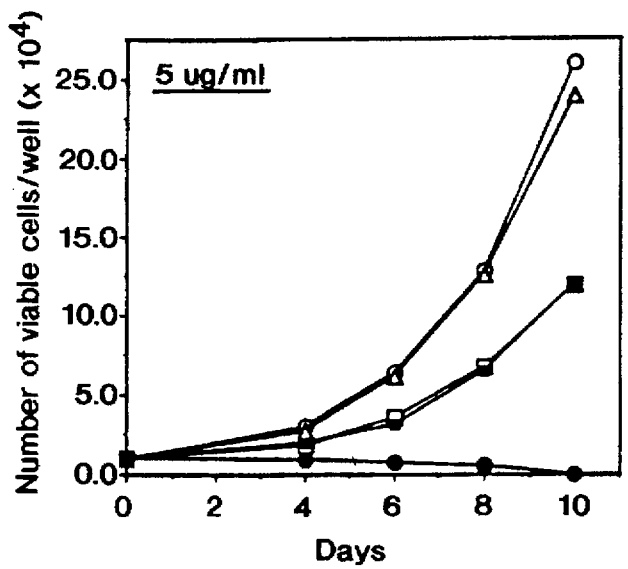
Figure 1C:
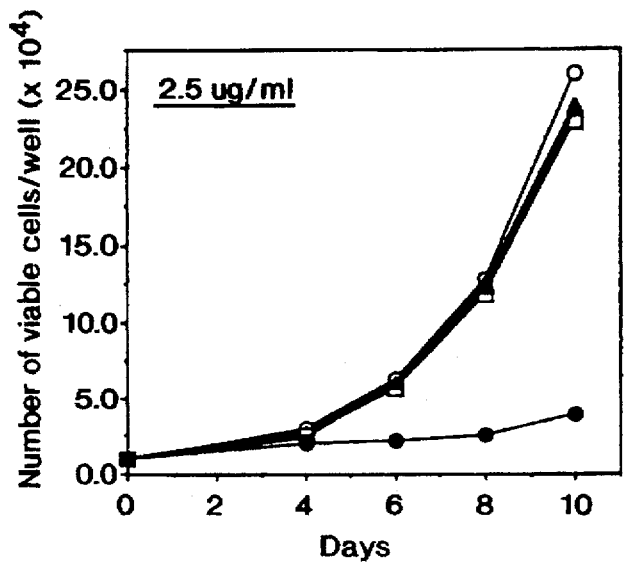

Chronic myelogenous leukemia (BV173) cells ($10^4$/100 µl/well) were placed in 96-well culture plates in RPMI medium supplemented with 10% fetal bovine serum, L-glutamine, and penicillin/streptomycin. For the protein studies and cell cycle analysis described below, $5 \times 10^6$ BV173 cells/20 ml of medium were placed in 175 $cm^2$ LUX tissue culture flasks (Nunc, Inc., Naperville, Ill.). Sense or antisense [S] ODNs were added at the beginning of culture and again (at 50% of the initial dose) 24 and 48 hours later. The final concentrations of [S] ODNs are indicated in FIG. 1A (10 µg/ml), FIG. 1B (5 µg/ml) and FIG. 1C (2.5 µg/ml). Control cells were left untreated. Cells in 96-well plates were counted in Trypan blue on days +4,+6 and +8. Cells in flasks were centrifuged on HISTOPAQUE-1077, washed, counted and used for further studies. The results are shown in FIGS. 1A–1C: (○) control; (Δ) b2/a2 plus c-myc sense; (□) b2/a2 antisense; (■) c-myc antisense, (●) b2/a2 and c-myc antisense.

C. Protein Analysis

Figure 2:
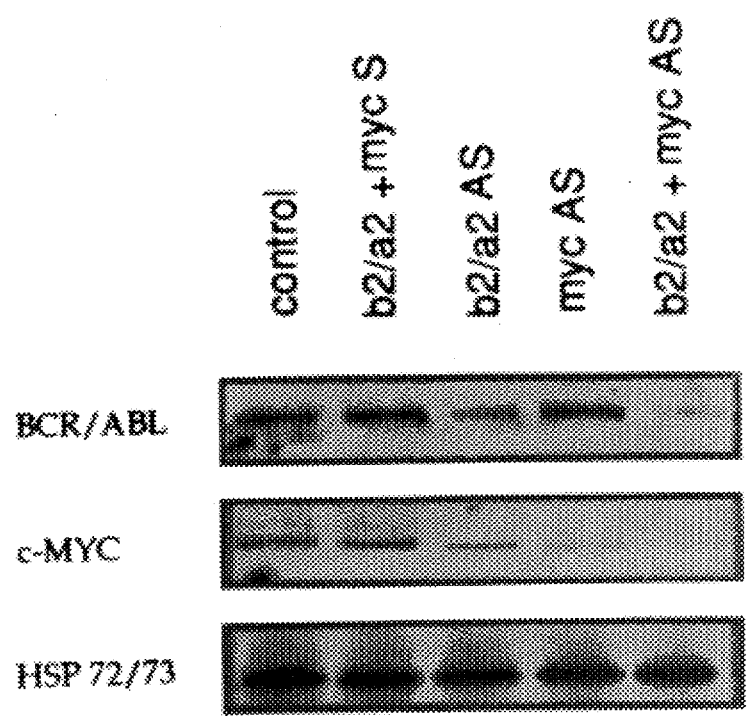
FIG. 2 is a Western blot of total cellular protein from BV173 cells after 72 hours incubation with 10 µg/ml of the above oligonucleotides, treated with anti-ABL, anti-c-MYC or anti-heat shock protein (HSP) 72/73 antibody.
Figure 3A:
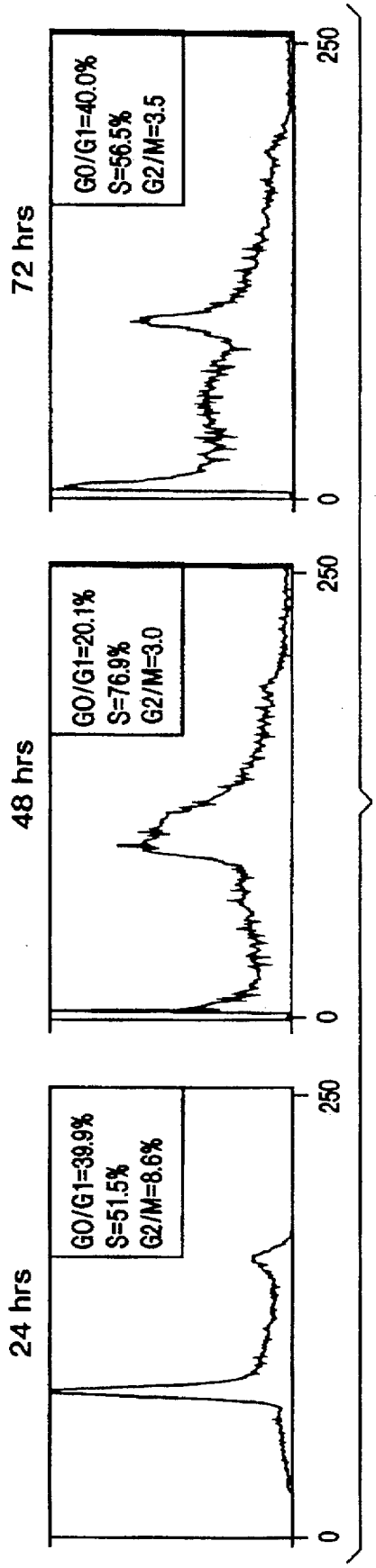
FIGS. 3A–3D comprise the results of flow cytometry DNA content analysis of BV173 cells incubated for 24, 48, and 72 hours in the presence of the following antisense [S]ODNs: 3A, b2/a2 10 µg/ml; 3B, c-myc 10 µg/ml, 3C, b2/a2 2.5 µg/ml; 3D, b2/a2+c-myc 2.5 µg/ml.
Figure 3B:
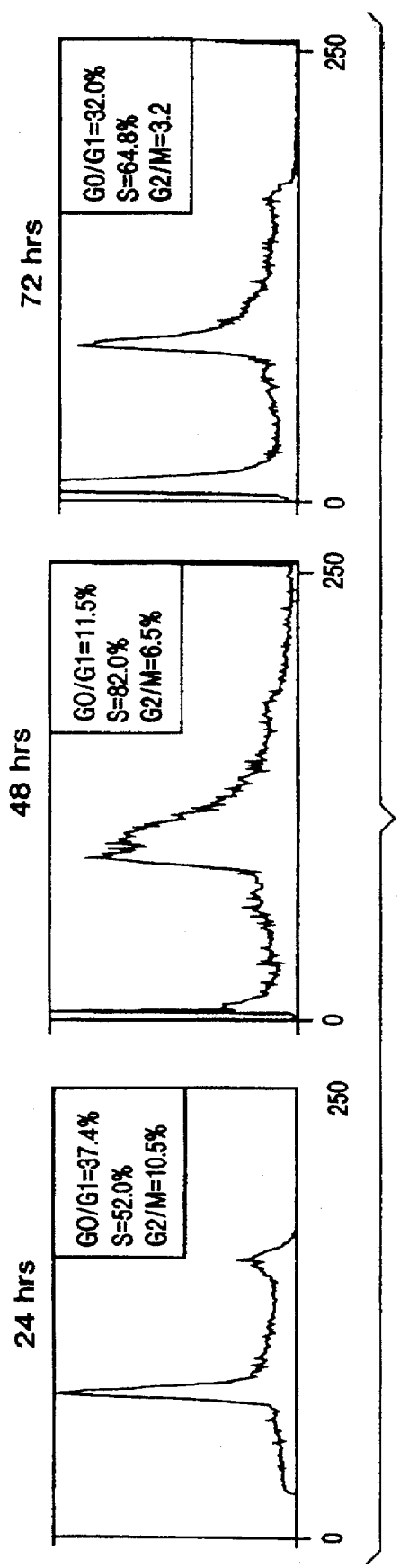
Figure 3C:
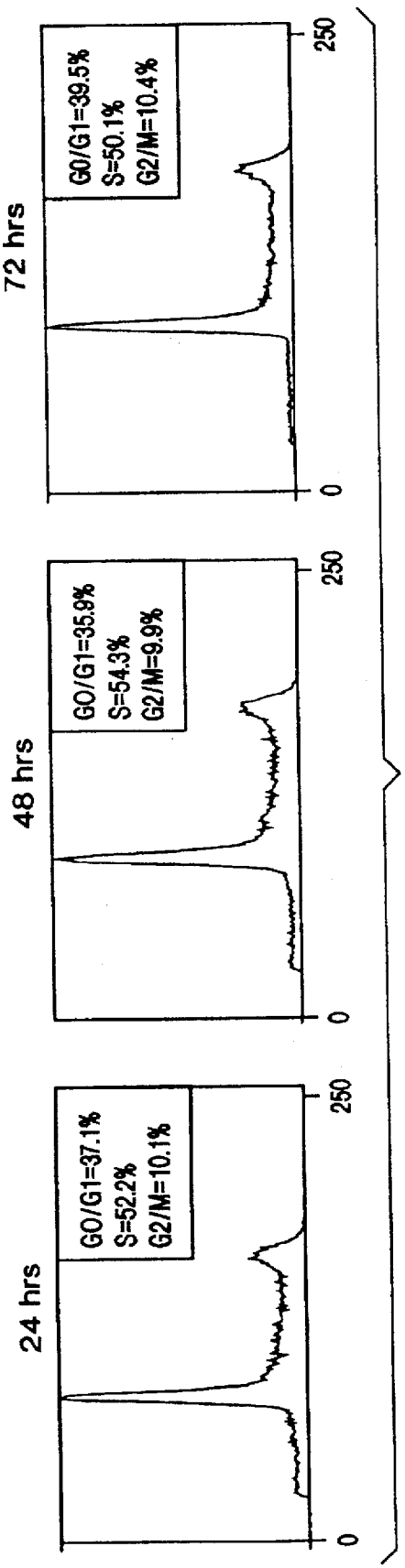
Figure 3D:
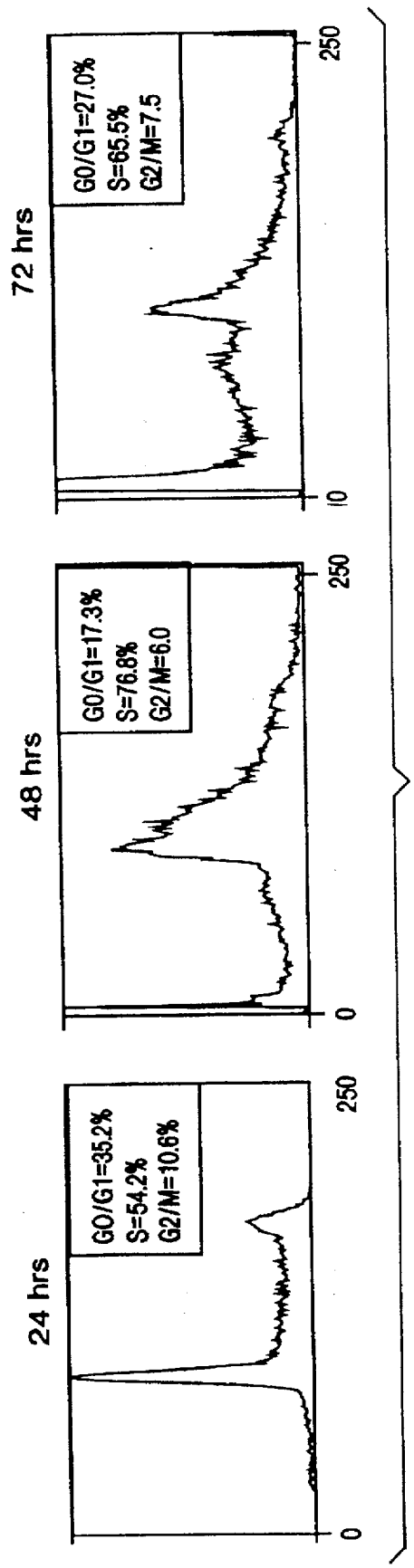

In this experiment, total cellular proteins were isolated from BV 173 cells after 72 hours of incubation without [S] ODNs (control), or with 10 µg/ml of the above indicated [S] ODNs and analyzed by SDS-PAGE and Western blotting for the expression of indicated proteins. Accordingly, $10^6$ cells were solubilized in RIPA lysis buffer containing 10% deoxycholate, 2% NP-40, 0.2% SDS, and 10% glycerol, in Tris-buffered saline, pH 7.2. Proteins were separated on 7.5% SDS-PAGE and transferred to nitrocellulose (MCI, Westboro, Mass.). Filters were blocked in 0.5% gelatin in TBS and then incubated with murine monoclonal anti-ABL antibody (gift of Dr. R. Arlinghaus, M. D. Anderson Medical Center, Houston, Tex.), murine monoclonal anti-c-MYC antibody (Oncogene Science Inc., Uniondale, N.J.), and murine monoclonal anti-HSP 72/72 (Oncogene Science). Filters were washed 5 times with 0.2% TWEEN 0.25% NP-40 in TBS buffer and blotted with anti-murine polyclonal antibody linked to horseradish peroxidase (Amersham Corp., Arlington Heights, Ill.). Proteins were detected using the ECL Western blotting system (Amersham). The results are shown in FIG. 2.

D. Cell Cycle Analysis

After incubation for 24, 48, and 72 hours in the presence of antisense [S] ODNs (b2/a2, 10 µg/ml; c-myc 10 µg/ml; b2/a2, 2.5 µg/ml; b2/a2+c-myc, 2.5 µg/ml), DNA content of BV173 cells was determined by flow cytometry. Cells ($10^6$) were fixed in 70% ethanol for 15 minutes at 4° C., washed and incubated in 1 ml of PBS+0.1% NP-40+1 mg/ml of DNAse-free RNAse (Boehringer Mannheim Co., Indianapolis, Ind.) for 10 minutes at room temperature. Propidium iodide (5 µg/ml) was added and cells were analyzed by the EPICS PROFILE analyzer (Coulter). The results are shown in FIGS. 3A–3D for the following concentrations of the following antisense [S] ODNs : 3A, b2/a2 10 µg/ml; 3B, c-myc 1 µg/ml, 3C, b2/a2 2.5 µg/ml; 3D, b2/a2+c-myc 2.5 µg/ml.

E. Discussion

In vitro proliferation of Philadelphia[1]-positive BV173 cells which carry the bcr exon 2-abl exon 2 (b2/a2) junction was completely inhibited in the presence of b2/a2 or c-myc antisense oligodeoxynucleotides at a concentration of 10 µg/ml each (FIG. 1A–1C), whereas the [S] ODNs inhibited proliferation at a 2-and 4-fold lower final concentration, i.e., concentrations at which the individual [S] ODNs were nearly or completely ineffective (FIG. 1A–1C). Sense [S] ODNs were non-inhibitory at any concentration tested.

Inhibition of BV173 cell proliferation by b2/a2 or c-myc antisense [S] ODNs was accompanied by a down-regulation of bcr/abl and c-MYC protein levels, respectively (FIG. 2). Expression of MYC protein was also partially inhibited by b2/a2 antisense [S] ODNs, which might rest in a functional linkage between bcr/abl and c-myc. The combined treatment with b2/a2+c-myc antisense [S] ODNs downregulated both BCR/ABL and c-MYC protein expression. In this case downregulation of c-MYC proteins appears more pronounced than that obtained using the individual antisense [S] ODNs.

Analysis of cellular DNA content (cell cycle distribution) by flow cytometry revealed that treatment with b2/a2 or c-myc antisense [S] ODNs, as well as with the of both antisense [S] ODNs at concentrations affecting their proliferation, led after 48 and 72 hours to accumulation of cells in S phase of the cell cycle, concomitant with a decrease in the proportion of G1 and G2 cells, and with the appearance of cells with fractional DNA content (FIGS. 3A–3D). The changes in the cell cycle, when analyzed in light of the suppressed cell proliferation by antisense [S] ODNs treatment (FIGS. 1A–1C), indicate a dramatically slowed cell progression through S phase. The cells with fractional DNA content are typical of cells dying by mode of apoptosis. The degraded, low molecular weight DNA from apoptotic cells is generally extracted prior to and during the staining procedure. Such cells, as well as apoptotic bodies, stain with much lower intensity with DNA fluorochromes, representing a "sub-G1" cell population on the DNA frequency histograms. This population is very heterogeneous with respect to DNA content, both after 48 and 72 hours (FIGS. 3A–3D), which indicates different degrees of DNA degradation in individual cells. This in turn is suggestive that cell death in these cultures was asynchronous.

The apoptotic mode of cell death, and the asynchrony of apoptosis, were confirmed by observation of cell morphology following differential staining of DNA and protein (data not shown). The changes characteristic of apoptosis, involving cell shrinkage, chromatin condensation, fragmentation of nuclei, hyperchromicity of chromatin, and shedding of apoptotic bodies, were observed in all cultures treated with b2/a2, c-myc or of both antisense [S] ODNs. After 48, and especially after 72 hours, there were numerous very late apoptotic cells in these cultures, containing very little, or almost no stainable DNA.

Thus, the flow cytometric data indicate that exposure of cells to b2/a2 or c-myc antisense [S] ODNs, or to both of these [S] ODNs, while not precluding cell entrance into S phase, does prevent cell progression through the S phase.

EXAMPLE 2

Effect of bcr-abl and c-myc Antisense Oligonucleotides on Growth of CML Blast Crisis Patient Cells Bone marrow cells collected from CML patients in blast crisis were suspended ($10^5$ cells/0.4 ml) in Iscove's modified Dulbecco medium supplemented with 2% of human AB serum, Hepes buffer, L-glutamine and peni/strepto. The cells were treated in liquid culture for 5 days with bcr-abl, or c-myc, or bcr-abl+c-myc sense (S) or antisense (AS) [S] ODNs (80 µg/ml added on day 0, 40 µg/ml on day+1, and 40 µg/ml on day+2). The [S] ODNs doses were equally divided in the case of combination in liquid culture for 5 days. Then the cells were plated in methylcellulose and the colonies and clusters were counted after 7–12 days of incubation. The results shown in Table 1 represent mean±standard deviation from two experiments, each performed in duplicate.

TABLE 1

Synergistic effect of bcr/abl + c-myc antisense [S]ODNs on the growth of CML-BC cells

| PATIENT | [S]ODNs bcr/abl | [S]ODNs c-myc | COLONIES mean ± SD |
|---|---|---|---|
| A (b2/a2) | — | — | 1365 ± 219 |
|  | S | S | 1259 ± 85 |
|  | AS | — | 274 ± 31 |
|  | — | AS | 245 ± 26 |
|  | AS | AS | 73 ± 21[a] |
| B (b3/a2) | — | — | 954 ± 85 |
|  | S | S | 974 ± 42 |
|  | AS | — | 488 ± 18 |
|  | — | AS | 451 ± 9 |
|  | AS | AS | 162 ± 38[b] |
| C (b2/a2) | — | — | 129 ± 16 |
|  | S | S | 140 ± 40 |
|  | AS | — | 56 ± 5 |
|  | — | AS | 51 ± 5 |
|  | AS | AS | 22 ± 6[c] |

[a] $p = 0.017$, and $p = 0.019$ in comparison to bcr-abl AS, and c-myc AS group, respectively.
[b] $p = 0.008$, and $p = 0.009$ in comparison to bcr-abl AS, and c-myc AS group, respectively.
[c] $p < 0.001$ in comparison to bcr-abl AS, and c-myc AS group.

EXAMPLE 3

In Vivo Effect of bcr-abl and c-myc Antisense Oligonucleotides

The antileukemic effects of bcr-abl and c-myc ODNs, alone and in combination, were assessed in vivo as follows.

A. Leukemic Cell Assay-4 Weeks Post-Transplantation of Leukemic Cells

Immunodeficient SCID mice (males 8–10 weeks old, 20–22 g) were injected intravenously with $10^6$ BV173 cells, a regimen that produces a disease process reminiscent of that in humans. Seven days later, mice were systemically injected for 12 consecutive days with 1 mg/day/mouse of b2/a2 sense+c-myc sense (6 days each, every other day), b2/a2 antisense, c-myc antisense or b2/a2+c-myc antisense (6 days each, every other day). Control mice were injected with diluent only. Four weeks after leukemia implantation, peripheral blood (PBL), spleen (SPL), and bone marrow (BMC) from one mouse per group were analyzed to assess the disease process. Leukemia growth in the mice was analyzed by assessing the tissues for CD10+cells by immunocytometry and for clonogenic growth in methylcellulose as described by Skorski et al., Proc. Natl. Acad. Sci. USA 91:4504 (1994). Immunofluorescence assay (sensitivity $10^{-2}$) did not detect CD10+leukemic cells, whereas colony assay (sensitivity $10^{-3}$) revealed several clonogenic leukemia cells in BMC suspensions of control and sense [S] ODNs -treated mice, but none from cell suspensions of mice treated with antisense [S] ODNs either individually or in combination (not shown). RT-PCR amplification of bcr-abl transcripts present in the total RNA isolated from bone marrow and spleen, followed by Southern blot hybridization, revealed a relatively strong signal from amplification products of RNA isolated from control and sense [S] ODNs -treated mice, but only a weak signal in RNA derived from tissue of mice treated with individual ODNs, and a nearly undetectable signal in RNA from the mouse treated with both b2/a2+c-myc antisense [S] ODNs (not shown). Equal amounts of β-actin transcript were detected in RNA samples from each tissue.

B. Leukemic Cell Assay—8 Weeks Post-Transplantation of Leukemic Cells

Mice were inoculated intravenously with $10^6$ BV173 cells and 7 days later, injected i.v. with sense (S) or antisense (AS) [S] ODNs (1 mg/mouse/day) for 12 consecutive days. In the group (b2/a2+c-myc) [S] ODNs were injected every other day. Control mice were injected with diluent only. Leukemia growth in the mice was analyzed on day 56 by assessing peripheral blood leukocytes (PBL), spleen (SPL), and bone marrow cells (BMC) for CD10+cells by immunocytometry and for clonogenic growth in methylcellulose. The results are given in Table 2. Numbers show individual results obtained from 3 mice (A, B and C). NT=not tested.

TABLE 2

Presence of CD10+ and leukemia clonogenic cells in SCID mice injected with BV173 cells and treated with bcr-abl (b2/a2) and/or c-myc [S]ODNs.

| Treatment | Groups | % CD10-positive cells | | | Leukemic colonies/ $10^5$ cells | | |
|---|---|---|---|---|---|---|---|
| | | PBL | SPL | BMC | PBL | SPL | BMC |
| Control | A | 1.4 | 6.1 | 24.9 | 19 | 559 | 2519 |
| | B | 0 | 4.9 | 11.6 | 7 | 252 | 1579 |
| | C | 0 | 5.0 | 7.4 | 2 | 258 | 1166 |
| b2/a2 S + | A | NT | 6.3 | 38.5 | NT | 588 | 3005 |
| c-myc S | B | 0 | 6.5 | 10.4 | 4 | 239 | 1389 |
| | C | 0 | 4.2 | 7.0 | 0 | 194 | 1214 |
| b2/a2 AS | A | 0 | 0 | 0 | 0 | 5 | 4 |
| | B | 0 | 0 | 0 | 0 | 5 | 9 |
| | C | 0 | 0 | 0 | 0 | 9 | 19 |
| c-myc AS | A | 0 | 0 | 0 | 0 | 13 | 20 |
| | B | 0 | 0 | 0 | 0 | 8 | 37 |
| | C | 0 | 0 | 0 | 0 | 4 | 22 |
| b2/a2 AS + | A | 0 | 0 | 0 | 0 | 0 | 0 |
| c-myc AS | B | 0 | 0 | 0 | 0 | 0 | 1 |
| | C | 0 | 0 | 0 | 0 | 0 | 0 |

Immunofluorescence assay detected CD10+cells in peripheral blood (only one mouse positive), spleen and bone marrow of control and sense [S] ODNs treated mice, but not in the corresponding tissues of the mice treated with antisense ODNs (Table 2). The more sensitive clonogenic assay revealed several leukemic colonies in peripheral blood, and abundant colonies in spleen and bone marrow of control and sense [S] ODNs treated mice. In contrast, cell suspensions of c-myc or b2/a2 antisense-treated mice contained far fewer malignant clonogenic cells (Table 2). Only one of the mice treated with both b2/a2+c-myc antisense ODNs contained detectable clonogenic leukemic cells.

C. Scoring of Superficial Liver Metastases

Superficial liver metastases were scored in mice treated as described in part A., above. The result are described in Table 3, below. Numbers indicate visible liver metastases. Scoring of superficial liver metastases was consistent with immunofluorescence and clonogenic assays. Numerous metastatic nodules were visible on the surface of livers from control and sense-treated mice, several on the livers of mice treated with single antisense, and none on the organs from mice treated with both antisense [S] ODNs.

TABLE 3

Superficial metastases in the liver of SCID mice injected with BV173 cells and treated with b2/a2, c-myc or b2/a2 + c-myc antisense (AS or sense (S) [S]ODNs)

| Treatment Groups | Number of Metastases |
|---|---|
| Control | 89, 54, 88 |
| b2/a2 + c-myc S | 156, 107, 61 |
| b2/a2 AS | 12, 10, 8 |
| c-myc AS | 15, 15, 4 |
| b2/a2 AS + c-myc AS | 0, 0, 0 |

D. Detection of bcr-abl Transcripts by Reverse Transcriptase-Polymerase Chain Reaction Cells were collected separately from various organs of [S] ODNs treated SCID mice, 56 days after leukemia implantation. Total RNA was extracted from $10^6$ cells (Chromczynski et al., *Anal. Biochem.* 162, 156 (1987)), and divided into two portions. A 3' primer of ABL exon 2, 3' primer of β-actin, 5' primer of BCR exon 2, 5' primer for β-actin, and ABL and β-actin probes recognizing amplified transcripts were all prepared according to published sequences (Szczylik et al., *Science* 253, 562 (1991); Skorski et al., *J. Clin. Invest.* 92, 194 (1993); Caracciolo et al., ibid 85, 55 (1990)). One cell sample was reverse transcribed using 400 U of Moloney murine leukemia virus reverse-transcriptase (Bethesda Research Laboratories, Gaithersburg, MD) and 0.1 μg of 3'-end primer of abl exon 2 for 1 hour at 37° C. The second sample was reverse transcribed using the β-actin 3' primer. Resulting cDNA fragments were amplified with 5U Taq polymerase (Perkin Elmer Cetus, Norwalk, CT) in the presence of 5' primer of either BCR exon 2 or β-actin, generating 257-bp and 209-bp fragments of bcr-abl and β-actin, respectively, during 50 cycles of PCR (Chromczynski et al., *Anal. Biochem* 162; 156 (1987)). Reaction products were electrophoresed, transferred and hybridized, using the appropriate probes (c-abl or β-actin). Blots were exposed 24 hours (bcr-abl) and 2 hours (β-actin).

Figure 4:
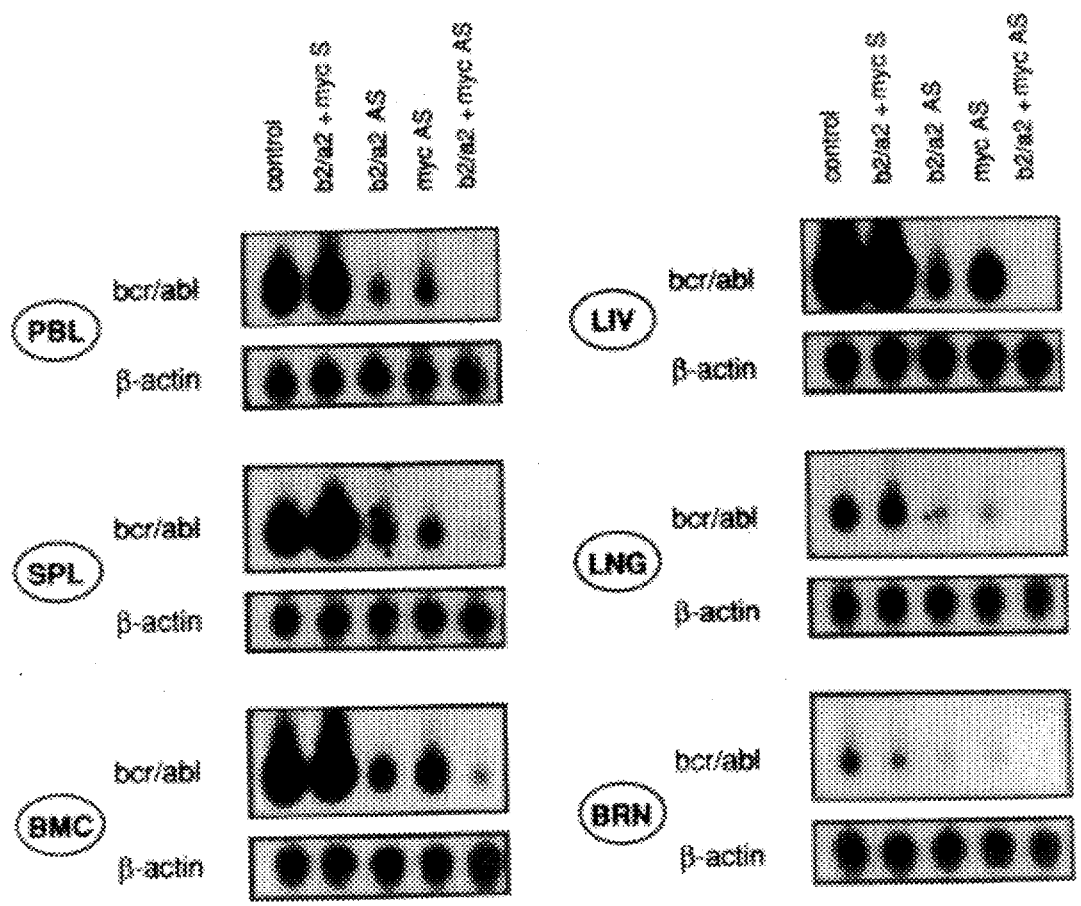
FIG. 4 contains a series of blots of the RT-PCR amplification of bcr-abl and β-actin RNA from total RNA extracted from various organs of BV173-transplanted SCID mice 56 days post transplantation. Seven days post transplantation the, mice were systemically injected for 12 consecutive days with 1 mg/day/mouse of b2/a2 sense+c-myc sense (6 days each, every other day), b2/a2 antisense, c-myc antisense or b2/a2+c-myc antisense (6 days each, every other day). Control mice were injected with diluent only. (PBL= peripheral blood lymphocyte; SPL=spleen; BMC=bone marrow cell; LIV=liver; LNG=lung; and BRN=brain).

The results are shown in FIG. 4, indicating detection of bcr-abl transcripts by RT-PCR in RNA from tissues of [S]ODN treated (b2/a2+c-myc sense (S); b2/a2 antisense (AS); c-myc AS; or b2/a2+c-myc (AS) or untreated (control) leukemic SCID mice. The blot is representative of three different experiments using three mice/group (PBL= peripheral blood lymphocyte; SPL=spleen; BMC=bone marrow cell; LIV=liver; LNG =lung; and BRN=brain).

RT-PCR amplification of bcr-abl transcripts in RNA isolated from various tissues of control and sense [S] ODNs -treated animals (three mice/group) revealed bcr-abl transcripts in each of these tissues. Bcr-abl transcripts were also detected in all tissues except brain of mice treated with single antisense [S] ODNs, but the signal was much weaker than observed with control and sense [S] ODNs -treated mouse tissues. Even weaker signals were detected in the RNA isolated from all the organs except brain of mice injected with b2/a2 +c-myc antisense [S] ODNs, suggesting that the leukemic cell load in mice treated with [S] ODNs in was reduced as compared with that of mice treated with individual ODNs. Equal amounts of β-actin detected in each group of organs indicated the integrity and equal loading of the amplified products.

E. Quantitative RT-PCR Detection of bcr-abl Transcripts

To confirm that the differences in the intensity of the bcr-abl bands corresponding to tissues of single versus combined antisense [S] ODNs -treated mice reflected the difference in amounts of bcr-abl transcript in the tissues, quantitative RT-PCR (Qt/RT-PCR) was performed using the same amount of RNA isolated from bone marrow cells of b2/a2 and b2/a2+c-myc antisense [S]ODN-treated mice, in the presence of increasing amounts of RNA from K562 cells (b3/a2) as a source of competitive bcr-abl RNA, and using optimal concentrations of primers. Integrity of the isolated RNA was confirmed by RT-PCR which detected similar amounts of β-actin transcript. Accordingly, various amounts (zero, 0.1 ng, 1 ng, 10 ng, 100 ng) of total RNA isolated from K562 (b3/a2 junction) cells were added as a source of competitive bcr-abl-containing RNA to the same amount of total RNA isolated from $10^6$ BMC obtained from b2/a2 AS or b2/a2 AS+c-myc AS-treated mice. Southern blot analysis of RT-PCR amplification products was performed.

Figure 5:
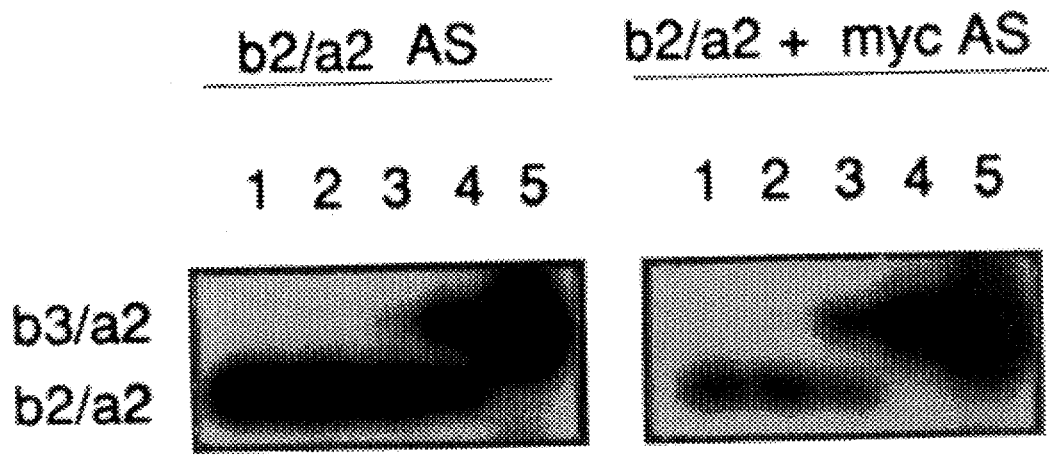
FIG. 5 presents the results of quantitative RT-PCR of bcr-abl transcripts in RNA isolated from bone marrow cells of b2/a2 antisense and b2/a2+c-myc antisense [S]ODN-treated mice, in the presence of increasing amounts of RNA from K562 cells (b3/a2) as a source of competitive bcr-abl RNA (lane 1, no K562 RNA; lane 2, 0.1 ng; lane 3, 1 ng; lane 4, 10 ng; lane 5, 100 ng).

The results of the assay appear in FIG. 5 (lane 1, no K562 RNA; lane 2, 0.1 ng; lane 3, 1 ng; lane 4, 10 ng; lane 5, 100 ng) The blot of FIG. 5 is representative of two different experiments.

The analysis detected the b2/a2 fragment from BV173 RNA contaminating mouse BMC (FIG. 5, lower band) RNA, and the b3/a2 fragment from the K562 RNA (FIG. 5, upper band) added as competitor.

The analysis revealed competitive blocking of the b2/a2 transcript (from BV173 cells present in the tissue) at lower K562 RNA concentrations when bone marrow cells were isolated from mice injected with both b2/a2 and c-myc antisense [S] ODNs as compared to those receiving only one antisense [S] ODNs (FIG. 5). This indicates the lower amounts of bcr-abl transcripts in bone marrow cell RNA from the combined versus single antisense ODN-treated mice. These results are consistent with those obtained by nonquantitative RT-PCR, immunofluorescence, and clonogenic assays, and by assessment of liver metastases.

F. Leukemic Cell Assay—20 Weeks Post-Transplantation of Leukemic Cells

Two other b2/a2+c-myc antisense [S]ODN-treated mice (mice D and E) were subjected to leukemic cell assay 20 weeks after leukemia implantation. At this point, all mice treated with individual [S] ODNs were dead. Leukemic colonies were counted after 9-day culture in methylcellulose. The intensity of the RT-PCR band was evaluated after blotting with a junction-specific $[\gamma^{32}P]$-labelled probe and exposing the filters for different times. The assay results, set forth in Table 4, revealed different degrees of disease process as reflected by the tumor load of the two mice: (−) not detectable after 7-day exposure; (+) visible after 7-day exposure; (++) visible after 24 h exposure; (+++) visible after 1 hour exposure. The abbreviations in Table 4 are the same as in FIG. 4:

G. Survival of Leukemic Cell-Transplanted Mice

Figure 6:
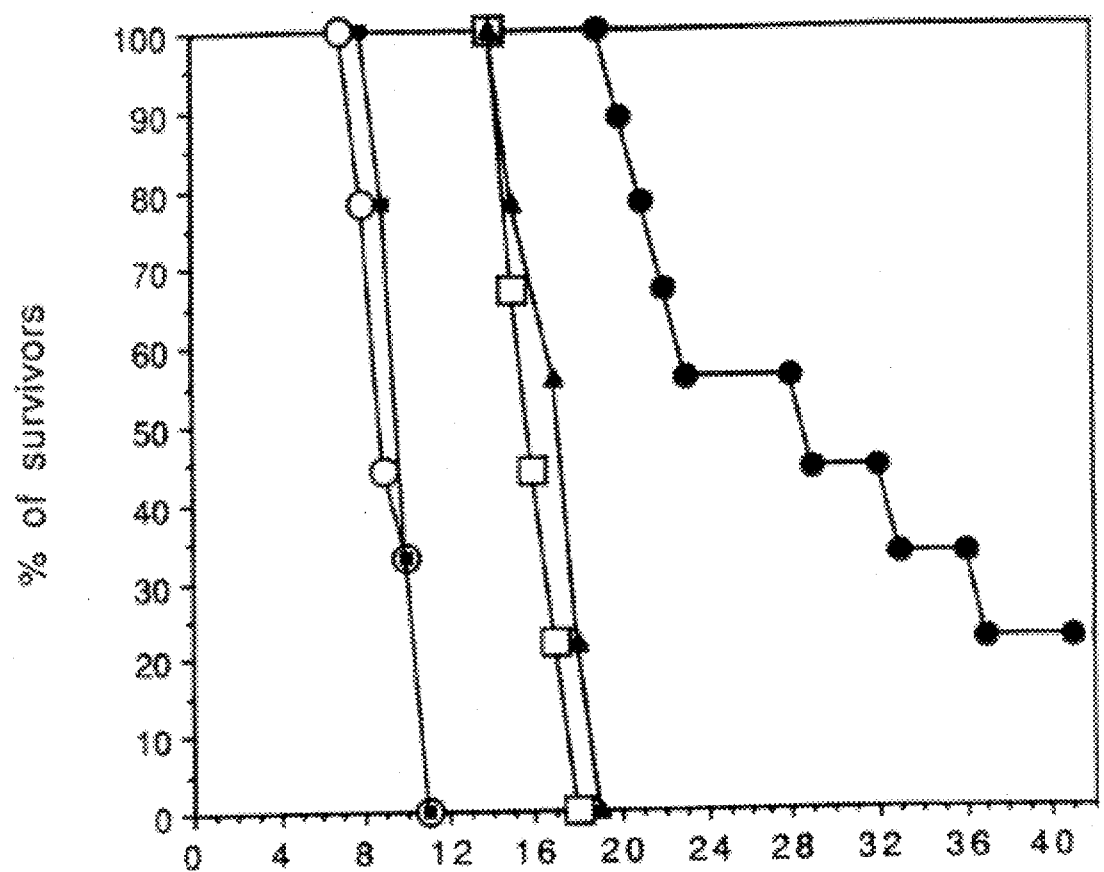
FIG. 6 is a plot of the survival of BV173-transplanted SCID mice treated with sense, single antisense and dual antisense [S]ODNs: b2/a2 S+c-myc S (■); b2/a2 AS (▲), c-myc AS (□); or b2/a2 AS c-myc AS (●). Control mice (○) received diluent only.

Differences in the survival of control, sense, single antisense and dual antisense [S]ODN treated mice are summarized in FIG. 6: b2/a2 S+c-myc S (■); b2/a2 AS (▲), c-myc AS (□); or b2/a2 AS c-myc AS (●). Control mice (○) received diluent only. All nine control and nine sense [S]ODN-treated mice died with diffuse leukemia, as confirmed by necropsy, 7–10 weeks after i.v. injection of $10^6$ BV173 leukemia cells (median survival time 7.7±0.8 and 8.3±0.5 weeks, respectively). In contrast, the nine b2/a2 antisense [S] ODNs - and nine c-myc antisense [S] ODNs -treated mice died after 14–18 and 14–19 weeks, respectively, of leukemia growth (median survival time 14.7±0.8 and 14.8±0.9 weeks, respectively; p<0.001 compared with control groups). Seven of nine mice treated with both antisense [S] ODNs survived significantly longer (median survival time 26.0±5.4 weeks; p<0.001 compared to mice treated with either antisense ODNs). Two remaining mice were still alive 41 weeks after injection of leukemic cells, but one of them had minimal residual disease as revealed by RT-PCR detection of bcr-abl transcripts in peripheral blood (not shown).

Figures 7A, 7B:
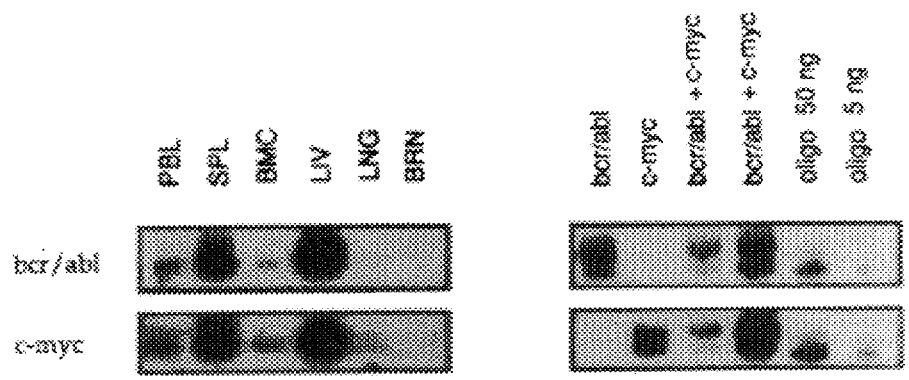
FIG. 7A presents the results of a hybridization assay detecting bcr-abl (b2/a2) and c-myc antisense [S]ODNs in various tissues of antisense-treated SCID mice 24 hours after conclusion of a 1 mg/day/12 consecutive day treatment with b2/a2 and c-myc antisense [S]ODN.
FIG. 7B presents the results of a hybridization assay detecting bcr-abl (b2/a2) and c-myc antisense [S]ODNs in CD10+BV173 cells isolated from bone marrow and spleen suspensions of mice treated in accordance with FIG. 7A. Standard 26-mer antisense [S]ODNs (50 ng and 5 ng) were run as controls.

H. Detection of Intact [S]ODN in Mouse Tissues and Leukemic Cells Infiltrating Bone Marrow and Spleen SCID mice were injected (1 mg/day/12 consecutive days) with b2/a2+c-myc AS [S] ODNs . Twenty-four hours after the last injection, DNA obtained from $10^6$ cells of various tissues was electrophoresed and intracellular [S] ODNs were detected by specific hybridization with complementary oligoprobes. The [S]ODN detection results are shown in FIG. 7A. For detection of intact [S] ODNs in BV173 cells infiltrating mouse tissues, leukemic SCID mice were injected (1 mg/day/12 consecutive days) with bcr-abl, c-myc, or bcr-abl+c-myc AS [S] ODNs . Twenty-four hours after the last injection, CD10+BV173 were isolated by immunosorting from bone marrow and spleen cell suspensions. After DNA isolation, intracellular [S] ODNs were detected as described previously (Ratajczak et al., *Proc. Natl. Acad. Sci. USA* 89, 11823 (1993); Kitajima et al. *Science* 258, 1792 (1992); Higgins et al., *PNAS* 90, 9901 (1993); Skorski et al., *PNAS* 91, 4504 (1994); Huiya et al., ibid 31, 4499 (1994)). Standard 26-met antisense [S] ODNs were run as controls. The results are shown in FIG. 7B.

The leukemia suppressive effects of antisense [S] ODNs correlated well with their detection in all organs examined except brain, although blot hybridization of tissue DNA isolated 1 day after the last injection showed highest ODNs concentrations in liver and spleen (FIG. 7A). [S] ODNs were still detectable in these organs 7 days after the last injection (not shown). Intact b2/a2 and c-myc, antisense [S] ODNs

TABLE 4

Leukemia growth in SCID mice 20 weeks after injection of $10^6$ BV 173 cells and treatment with b2/a2 + c-myc antisense [S]ODNs

| Mice | Leukemic colonies/$10^5$ cell | | | bcr/abl mRNA levels | | | | | | Liver metas tases |
|---|---|---|---|---|---|---|---|---|---|---|
| | PBL | SPL | BMC | PBL | SPL | BMC | LIV | LNG | BRN | |
| D | 0 | 2 | 236 | − | + | ++ | + | + | − | 0 |
| E | 53 | 283 | 2387 | + | +++ | +++ | +++ | + | + | 23 | were simultaneously detected in vivo in leukemic cells infiltrating bone marrow and spleen of SCID mice one day after completion of the injection protocol, by immunosorting of CD10+cells and Southern blot hybridization of the isolated DNA with oligomer probes complementary to with c-myc or bcr-abl antisense [S] ODNs (FIG. 7B).

EXAMPLE 4

Effect of c-raf and c-myc Antisense Oligonucleotides on BV173 Cells

A. Phosphorothioate Oligodeoxynucleotides

The following phosphorothioate oligodeoxynucleotides ([S] ODNs) were synthesized on an Applied Biosystems model 390Z automated synthesizer. The sequence of each antisense [S]ODN was complementary to the first 26 nucleotides of the mRNA transcript of the indicated oncogene, beginning from the translation initiation codon.

c-myc (AS) TTGGTGAAGC TAACGTTGAG GGGCAT (SEQ ID NO:3)
c-myc (S) ATGCCCCTCA ACGTTAGCTT CACCAA (SEQ ID NO:4)
c-raf (AS) GGTGAGGGAG CGGGAGGCGG TCACAT (SEQ ID NO:5)
c-raf (S) ATGTGACCGC CTCCCGCTCC CTCACC (SEQ ID NO:6)

B. Cell Proliferation Assay

Figure 8:
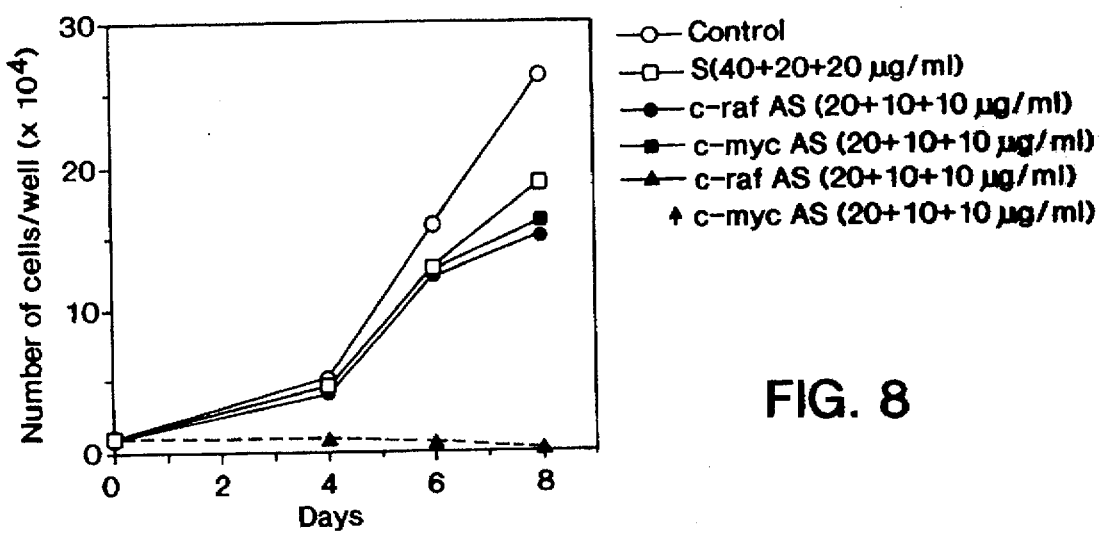
FIG. 8 contains the results of cell proliferation assays demonstrating the effectiveness of the combination of c-raf and c-myc antisense oligonucleotides on BV173 cells. Cells were treated with the indicated concentrations of oligonucleotides at the beginning of culture and again (at 50% of the initial dose) 24 and 48 hours later. Control wells received no oligomer. Sense oligonucleotide-treated cells received equal mixtures of c-raf and c-myc sense oligonucleotides. (○) control; (□) c-raf plus c-myc sense; (●) c-raf antisense; (■) c-myc antisense; (△) c-raf and c-myc antisense.

BV173 cells (10⁴/100 µl/well) were placed in 96-well culture plates in RPMI medium supplemented with 10% fetal bovine serum, L-glutamine, and penicillin/streptomycin. Sense or antisense [S] ODNs were added at the beginning of culture (20 µg/ml) and again (at 50% of the initial dose) 24 and 48 hours later. Control wells received no oligomer. Sense oligonucleotide-treated cells received equal mixtures of c-raf and c-myc sense oligonucleotides. Cells in 96-well plates were counted in Trypan blue on days oncogenes. +4,+6 and +8. The oligonucleotide dosages and results appear in FIG. 8: (O) control; (□) c-raf plus c-myc sense; (●) c-raf antisense; (m) c-myc antisense, (▲) c-tar and c-myc antisense. The results indicate that the c-raf and c-myc antisense oligonucleotides acted synergistically in inhibiting leukemic cell proliferation.

EXAMPLE 5

Effect of ras and c-myc Antisense Oligonucleotides on BV173 Cells

Figure 9:
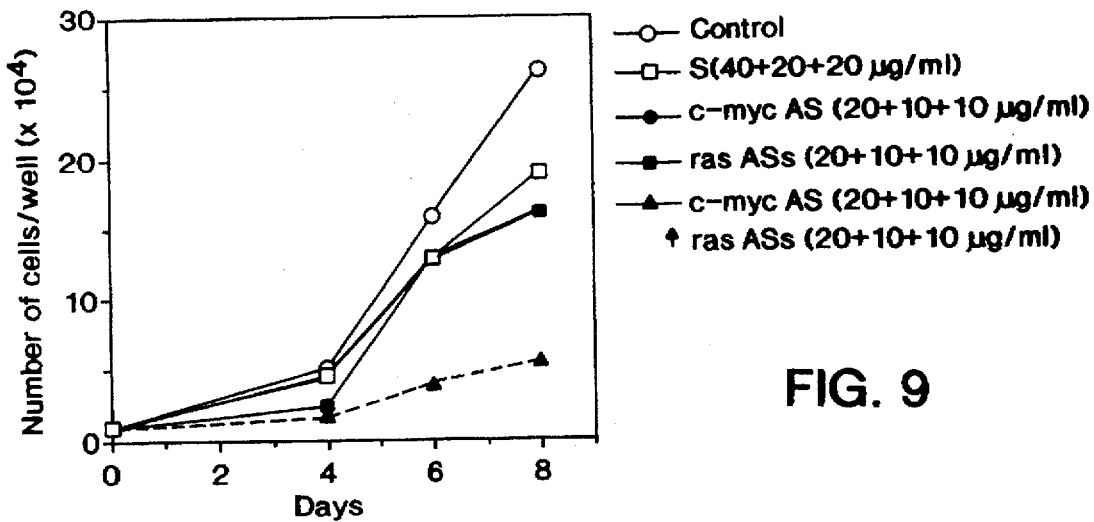
FIG. 9 is similar to FIG. 8 except that ras oligonucleotides were substituted for c-raf oligonucleotides. The ras oligonucleotide-treated cells received an equal mixture of a combination of N-, K-, and H-ras oligonucleotides. The oligonucleotide dosages appear in the figure. (○) control; (□) ras plus c-myc sense; (●) c-myc antisense; (■) ras antisense, (▲) ras and c-myc antisense.

The following phosphorothioate oligodeoxynucleotides ([S] ODNs) were synthesized:

N-ras (AS) CACCACCAGT TTGTACTCAG TCAT (SEQ ID NO:7)
N-ras (S) ATGACTGAGT ACAAACTGGT GGTG (SEQ ID NO:8)
K-ras (AS) TACCACAAGT TTATATTCAG TCAT (SEQ ID NO:9)
K-ras (S) ATGACTGAAT ATAAACTTGT GGTA (SEQ ID NO:10)
H-ras (AS) CACCACCAGC TTATATTCCG TCAT (SEQ ID NO:11)
H-ras (S) ATGACGGAAT ATAAGCTGGT GGTG (SEQ ID NO:12). The sequence of each antisense [S]ODN was complementary to the first 24 nucleotides of the mRNA transcript of the indicated oncogene, beginning from the translation initiation codon. A cell proliferation assay according to the procedure of Example 4 was carried out, using ras and c-myc sense and antisense oligonucleotides. For ras oligonucleotide-treated cells, the cells received an equal mixture of a of the above N- , K-, and H-ras oligonucleotides. The oligonucleotide dosages and results appear in FIG. 9: (O) control; (□) c-ras plus c-myc sense; (●) c-myc antisense; (■) ras antisense, (▲) ras and c-myc antisense. The results indicate that the c-ras and c-myc antisense oligonucleotides acted synergistically in inhibiting leukemic cell proliferation.

Comparative Example 5

Effect of ras and raf Antisense Oligonucleotides on BV173 Cells

Figure 10:
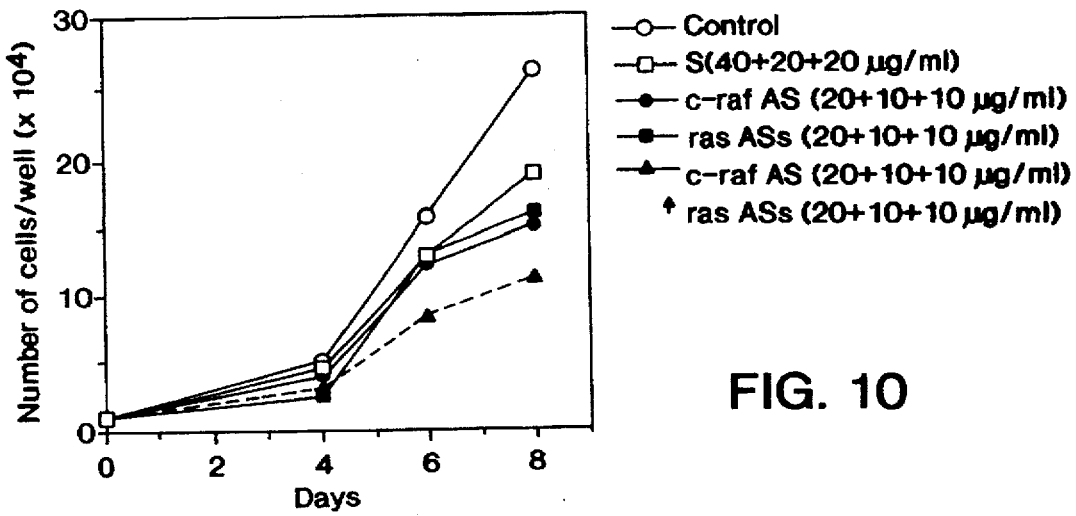
FIG. 10 is similar to FIG. 9, except that c-raf oligonucleotides were substituted for c-myc oligonucleotides. (○) control; (□) c-raf plus ras sense; (●) c-raf antisense; (■) ras antisense; (▲) c-raf and ras antisense.

The procedure of Example 5 was repeated except that the c-raf oligonucleotides SEQ ID NO:5 (sense) and SEQ ID NO:6 (antisense) were substituted for the corresponding c-myc oligonucleotides. The results are shown in FIG. 10: (O) control; (□) c-raf plus ras sense; (●) c-tar antisense; (■) ras antisense, (▲) c-raf and ras antisense. The effect of antisense oligonucleotides to c-raf and ras, which are both cytoplasmic oncogenes, was not synergistic, suggesting that synergism requires antisense to at least one cytoplasmic oncogene and at least one nuclear oncogene.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

We claim:

1. A composition comprising at least one first antisense oligonucleotide specific for a cytoplasmic oncogene or proto-oncogene selected from the group consisting of ras genes, raf genes, EGF-1, c-fms, c-ros, c-kit, c-met, c-trk, c-src, c-abl, bcr-abl, c-fgr and c-yes and at least one second antisense oligonucleotide specific for a nuclear oncogene or proto-oncogene selected from the group consisting of myc genes, jun genes, c-ets, c-fos, c-myb, B-myb, c-rel, c-vav, c-ski, c-spi, cyclin D1, PML/RARα, AML1/MTG8, E2A/prl and ALL-1/AF-4.

2. The composition according to claim 1 wherein the first antisense oligonucleotide is specific for an oncogene or proto-oncogene which encodes a protein tyrosine kinase.

3. The composition according to claim 1 wherein the first antisense oligonucleotide is specific for bcr-abl.

4. The composition according to claim 1 wherein the first antisense oligonucleotide is specific for a cytoplasmic oncogene or proto-oncogene selected from the group consisting of ras and raf genes.

5. The composition according to claim 1 wherein the second antisense oligonucleotide is specific for an oncogene or proto-oncogene which encodes a transcriptional factor.

6. The composition according to claim 1 wherein the second antisense oligonucleotide is specific for a myc gene.

7. The composition according to claim 1 wherein the first antisense oligonucleotide is specific for a ras or raf gene, and the second antisense oligonucleotide is specific for a myc gene or a jun gene.

8. The composition according to claim 1 wherein the first antisense oligonucleotide forms a stable duplex with a portion of an mRNA transcript of a cytoplasmic oncogene or proto-oncogene, and the second antisense oligonucleotide forms a stable duplex with a portion of an mRNA transcript of a nuclear oncogene or proto-oncogene.

9. The composition according to claim 1 further comprising a pharmaceutically acceptable carrier.

10. The composition according to claim 3 wherein the second antisense oligonucleotide is specific for c-myc.

11. The composition according to claim 8 wherein the first antisense oligonucleotide forms a stable duplex with a portion of an mRNA transcript lying within about 50 nucleotides of the translation initiation codon of the cytoplasmic oncogene or proto-oncogene mRNA, and the second antisense oligonucleotide forms a stable duplex with a portion of an mRNA transcript lying within about 50 nucleotides of the translation initiation codon of the nuclear oncogene or proto-oncogene mRNA.

12. The composition according to claim 8 wherein the oligonucleotides comprise from 12-mers to 50-mers.

* * * * *